(12) United States Patent
Ericsson et al.

(10) Patent No.: US 8,008,481 B2
(45) Date of Patent: Aug. 30, 2011

(54) INDAZOLE COMPOUNDS

(76) Inventors: Anna M. Ericsson, Shrewsbury, MA (US); Andrew Burchat, Shrewsbury, MA (US); Kristine E. Frank, Worcester, MA (US); David J. Calderwood, Framingham, MA (US); Lily K. Abbott, Brighton, MA (US); Maria A. Argiriadi, Wayland, MA (US); David W. Borhani, Worcester, MA (US); Kevin P. Cusack, Holden, MA (US); Richard W. Dixon, Jefferson, MA (US); Thomas D. Gordon, Medway, MA (US); Kelly D. Mullen, Charlton, MA (US); Robert V. Talanian, Harvard, MA (US); Xiaoyun Wu, Westborough, MA (US); Xiaolei Zhang, Ashland, MA (US); Lu Wang, Northborough, MA (US); Biqin Li, Northborough, MA (US); Claude E. Barberis, Hillsborough, NJ (US); Neil Wishart, Jefferson, MA (US)

( * ) Notice: Subject to any disclaimer, the term of this patent is extended or adjusted under 35 U.S.C. 154(b) by 903 days.

(21) Appl. No.: 11/731,950

(22) Filed: Apr. 2, 2007

(65) Prior Publication Data
US 2007/0282101 A1    Dec. 6, 2007

Related U.S. Application Data

(60) Provisional application No. 60/788,553, filed on Mar. 31, 2006.

(51) Int. Cl.
*C07D 409/14* (2006.01)
*C07D 413/14* (2006.01)

(52) U.S. Cl. ........ 544/119; 544/371; 544/405; 546/199; 546/275.7; 548/126; 548/159

(58) Field of Classification Search .................. None
See application file for complete search history.

(56) References Cited

U.S. PATENT DOCUMENTS

| | | | |
|---|---|---|---|
| 4,999,356 | A | 3/1991 | Stupczewski |
| 5,444,038 | A | 8/1995 | James et al. |
| 6,492,383 | B1 | 12/2002 | Munchhof et al. |
| 2004/0038023 | A1 | 2/2004 | Hartley et al. |
| 2004/0077877 | A1 | 4/2004 | Bhagwat et al. |
| 2004/0097575 | A1 | 5/2004 | Doherty et al. |
| 2004/0167122 | A1 | 8/2004 | Bernotas et al. |
| 2005/0038023 | A1 | 2/2005 | Bebbington et al. |
| 2005/0054626 | A1 | 3/2005 | Carter et al. |
| 2005/0054651 | A1 | 3/2005 | Natarajan et al. |
| 2005/0054697 | A1 | 3/2005 | Yager et al. |
| 2005/0090529 | A1 | 4/2005 | McAlpine et al. |
| 2005/0101602 | A1 | 5/2005 | Basha et al. |
| 2005/0101617 | A1 | 5/2005 | Wallace et al. |
| 2005/0107386 | A1 | 5/2005 | Narla et al. |
| 2005/0119276 | A1 | 6/2005 | Harnish et al. |
| 2005/0119324 | A1 | 6/2005 | Harnish et al. |
| 2006/0074102 | A1 | 4/2006 | Cusack et al. |

FOREIGN PATENT DOCUMENTS

| | | |
|---|---|---|
| EP | 1 105 120 | 3/2005 |
| EP | 1 510 516 | 3/2005 |
| EP | 1 514 869 | 3/2005 |
| EP | 1105120 | 3/2005 |
| EP | 1510516 | 3/2005 |
| EP | 1514869 | 3/2005 |
| WO | WO 2004/021999 | 3/2004 |
| WO | WO 2005/011681 | 2/2005 |
| WO | WO 2005/012280 | 2/2005 |
| WO | WO 2005/014554 | 2/2005 |
| WO | WO 2005/014558 | 2/2005 |
| WO | WO 2005/016862 | 2/2005 |
| WO | WO 2005/016892 | 2/2005 |
| WO | WO 2005/021554 | 3/2005 |
| WO | WO 2005/023761 | 3/2005 |
| WO | WO 2005/026129 | 3/2005 |
| WO | WO 2005/026130 | 3/2005 |
| WO | WO 2005/028445 | 3/2005 |
| WO | WO 2005/030206 | 4/2005 |
| WO | WO 2005/035514 | 4/2005 |
| WO | WO 2005/042530 | 5/2005 |
| WO | WO 2005/046683 | 5/2005 |

*Primary Examiner* — Kamal Saeed
(74) *Attorney, Agent, or Firm* — Gayle O'Brien; Susan L. Steele

(57) ABSTRACT

Novel compounds of Formula (I) or pharmaceutically acceptable salts, prodrugs and biologically active metabolites thereof of Formula (I)

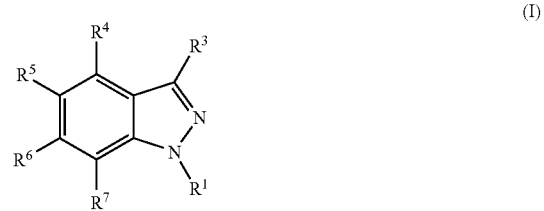

wherein the substituents are as defined herein, which are useful as therapeutic agents.

8 Claims, No Drawings

INDAZOLE COMPOUNDS

This Application claims benefit of U.S. Application No. 60/788,553, filed Mar. 31, 2006 the entire contents of which are incorporated herein by reference.

BACKGROUND OF THE INVENTION

Protein phosphorylation, at specific amino acid residues, is important for the regulation of many cellular processes including cell cycle progression and division, signal transduction, and apoptosis. The phosphorylation is usually a transfer reaction of the terminal phosphate group from ATP to the protein substrate. The specific structure in the target substrate to which the phosphate is transferred is a tyrosine, serine or threonine residue. Since these amino acid residues are the target structures for the phosphoryl transfer, and since most kinases target either tyrosine or both serine and threonine, these protein kinase enzymes are commonly referred to as tyrosine kinases or serine/threonine (S/T) kinases. The phosphorylation reactions, and counteracting phosphatase reactions, on the tyrosine, serine and threonine residues are involved in many cellular processes that underlie responses to diverse intracellular signals, regulation of cellular functions, and activation or deactivation of cellular processes. A cascade of protein kinases often function in intracellular signal transduction. Protein kinases can be found integrated into the plasma membrane, as cytoplasmic enzymes or localized in the nucleus, often as components of enzyme complexes. In many instances, these protein kinases are an essential element of enzyme and structural protein complexes that determine where and when a cellular process occurs within a cell. Given the importance and diversity of protein kinase function, it is not surprising that phosphorylation events are required in cellular processes associated with many diseases such as cancer, diabetes, inflammation, and hypertension.

The identification of effective small molecules that specifically inhibit protein kinases involved in abnormal or inappropriate cell proliferation, signaling, differentiation, protein production, or metabolism is therefore desirable. The identification of methods and compounds that specifically inhibit the function of kinases that are involved in immune modulation or proliferative disorders is particularly desirable.

The present invention provides novel compounds that inhibit one or more receptor, or non-receptor, tyrosine or S/T kinase.

SUMMARY OF THE INVENTION

The present invention provides a compound of Formula (I)

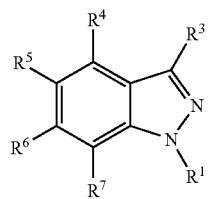

(I)

wherein
$R^1$ is selected from the group consisting of H, benzyl substituted with $OCH_3$, optionally substituted $(C_1-C_3)$alkyl, pyrimidine substituted with $NH_2$ and amino$(C_1-C_3)$alkyl;

$R^3$ is selected from the group consisting of H, halogen, $NH_2$, OH, COOH, —C(O)—NH—$CH_2$—C(O)—$OCH_3$, —NH—$CH_2$-phenyl, —C(O)-pyridinyl, —NH—C(O)-cyclobutyl and —NH—C(O)-phenyl wherein phenyl is optionally substituted with either $N(CH_3)_2$ or $OCH_3$; or $R^3$ is selected from the optionally substituted group consisting of $(C_1-C_6)$alkyl, benzo[b]thienyl, 2,3-dihydrobenzofuranyl, indolyl, isoquinolinyl, morpholinyl, naphthyl, phenyl, piperazinyl, pyrazolyl, pyridinyl, pyrimidinyl, pyrrolyl, quinolinyl and thienyl;
  wherein the substituent is selected from one or more $CH_3$, $NH_2$, Cl, F, dimethylamino, OH, $CH_2OH$, —C(O)$NH_2$, COOH, $CF_3$, isopropyl, $OCF_3$, $OCH_3$, —O—$CH_2$-phenyl, CN, $OCH_2CH_3$, —NH—C(O)-cyclobutyl, —NH—C(O)-phenyl, NH—C(O)—$CH_3$, $NHC(O)CH_3$, $N(CH_3)_2$, $S(O)_2CH_3$ and C(O)NH-phenyl; or $R^3$ is —C(O)—$NY^{100}$—$(C(Y^{100})_2)_x$—$R^a$ wherein
  x is 0, 1, 2 or 3;
  $Y^{100}$ is independently H or $(C_1-C_3)$alkyl; and
  $R^a$ is —C(O)—$CH_3$ or is selected from the optionally substituted group $(C_1-C_3)$alkyl, amino, aminoalkyl, benzimidazolyl, benzo[b]thienyl, benzotriazolyl, biphenyl, 1,3-dihydrobenzimidazolyl, 1,3-dihydrobenzimidazolyl-2-one, imidazolyl, indolyl, naphthyl, phenyl, pyrazolyl, pyridinyl, pyrimidinyl, tetrahydropyranyl and thiazolyl; or $R^3$ is A-B wherein A is connected to the indazole and
  A is selected from the group consisting of —C≡C, —C≡C-phenyl, indazolyl, phenyl, pyridinyl and thienyl;
  B is selected from the group consisting of benzyloxy, morpholinyl, phenyl, thienyl, t-butyl, —NH—C(O)-cyclobutyl and —NH—C(O)-phenyl;

$R^4$ is H or $NH_2$;

$R^5$ is selected from the group consisting of H, $NH_2$, $NO_2$, halo; or $R^5$ is selected from the optionally substituted group consisting of benzimidazolyl, 3,4-dihydrobenzo[1,4]thiazinyl, benzyloxyphenyl, furo[3,2-c]pyridine, indazolyl, indolyl, isoquinolinyl, phenyl, pyrazolo[3,4-d]pyrimidine, pyrazinyl, pyrazolyl, pyridinyl, pyrrolo[2,3-b]pyridinyl, pyrrolo[2,3-c]pyridinyl, pyrrolo[2,3-d]pyridinyl, pyrimidinyl, pyrrolo[3,2-d]pyridine, pyrrolo[2,3-d]pyrimidinyl, pyridinyl, pyrrolyl, quinolinyl, quinazolinyl, thienyl, thieno[2,3-c]pyridinyl, thieno[2,3-d]pyrimidine, thieno[3,2-c]pyridine, 7-azaindolinyl and 7-azaindolyl; or $R^5$ is —C(O)—$R^b$; wherein
  $R^b$ is selected from the group consisting of OH, $(C_1-C_3)$ alkoxy, phenyl, optionally substituted piperidinyl, optionally substituted pyridinyl and optionally substituted pyrrolidinyl; or
  $R^b$ is D-E wherein D is attached to the C(O) and
    D is selected from the group consisting of piperidinyl and pyrrolidinyl;
    E is selected from the group consisting of pyridinyl and pyrimidinylaminemethyl;

$R^5$ is —C(O)—NH—$(CH_2)_a$—$R^c$; wherein
  a is 0, 1, 2 or 3;
  $R^c$ is —$CONH_2$ or
  $R^c$ is selected from the optionally substituted group consisting of benzimidazolyl, benzothiazolyl, benzo[b]thiophenyl, dimethylamino, fluorene, imidazolyl, indanyl, indazolyl, isoxazolyl, oxazolyl, phenyl, piperidinyl, pyrazolyl, pyridinyl, quinazolinyl, thiadiazolyl and 1,2,4-triazolyl; or
  $R^c$ is $J^{100}$-$J^{200}$ wherein $J^{100}$ is attached to $(CH_2)_x$ and J$^{100}$ is selected from the optionally substituted group consisting of isoxazolyl, piperazinyl, pyrazolyl pyridinyl, and phenyl; and J$^{200}$ is selected from the group consisting of benzimidazolyl, benzoxazolyl, cyclohexyl, furanyl, imidazo[1,2-a]pyridinyl, indolyl, isoxazolyl, —NH—C(O)-phenyl, phenoxy and optionally substituted phenyl;

R$^5$ is —NH—C(O)—(CH$_2$)$_n$—R$^d$; wherein
n is 0 to 3;
R$^d$ is —C(CH$_3$)$_2$—CH$_2$—C(O)—CH$_3$; or
R$^d$ is selected from the optionally substituted group of (C$_1$-C$_2$)alkoxy, alkylamino, benzimidazolyl, benzo[1,3]dioxazolyl, benzo[1,2,5]oxadiazolyl, benzotriazolyl, benzo[b]thienyl, benzofuranyl, benzyloxy, cyclopropyl, cyclohexyl, chromenyl, dimethylamino, furanyl, hexahydropyrimidinyl, imidazolyl, imidazo[2,1-b]thiazolyl, imidazo[2,1-b]thiazolyl, imidazolidinyl, indolyl, isoxazolyl, morpholinyl, phenyl, piperazinyl, piperidinyl, pyrazinyl, pyrazolyl, pyrazolo[1,5-a]pyrimidinyl, pyridazinyl, pyridinyl, pyrimidinyl, pyrrolidinyl, pyrrolyl, quinolinyl, quinoxalinyl, tetrahydrobenzofuranyl, tetrahydrofuranyl, thiazolyl, thieno[2,3-d]pyrimidinyl, thienyl, 2,3-dihydrothiazolo[3,2-a]pyrimidine, —S-pyrimidinyl, —O-phenyl, —O—Si(CH$_3$)$_2$—C(CH$_3$)$_3$, —NH—S(O)$_2$-phenyl, —NH—C(O)—NH$_2$, 1,2,3,4-tetrahydronaphthyridinyl or N(CH$_3$)$_2$; or R$^d$ is M-Q wherein M is attached to the (CH$_2$)$_n$ and
M is selected from the group consisting of optionally substituted methylene, cyclopropylidene, optionally substituted isoxazolyl, phenyl, pyrazolyl, —NH—C(O) and optionally substituted 1,3,5-triazinyl;
Q is selected from the group consisting of furanyl, morpholinyl, phenyl, phenylamine and optionally substituted 1,3,4-thiadiazolyl;

R$^5$ is —NH—CH$_2$—C(Y$^{200}$)$_2$—R$^e$ wherein Y$^{200}$ is independently H or (C$_1$-C$_3$)alkyl and R$^e$ is selected from the optionally substituted group of (C$_1$-C$_6$)alkoxy, imidazolyl, phenyl, piperidinyl, pyrrolidinyl and 1,2,3,4-tetrahydro[1,8]naphthyridine; or R$^5$ is —NH—C(O)—N(R$^f$)$_2$ wherein R$^f$ is independently H or optionally substituted (C$_1$-C$_3$)alkyl; or R$^5$ is —NH—(C(O))$_m$—NY$^{300}$—(CH$_2$)$_p$—R$^g$; wherein
m is 0, 1 or 2;
Y$^{300}$ is H or optionally substituted (C$_1$-C$_3$)alkyl;
p is 1 or 2; and
R$^g$ is selected from the optionally substituted group of amino, (C$_1$-C$_2$)alkoxy, benzo[1,3]dioxazolyl, benzothiazolyl, benzo[1,4]oxazinyl, benzo[1,2,5]thiadiazolyl, imidazol[1,2-a]pyridinyl, imidazolyl, isoxazolyl, morpholinyl, oxazolyl, phenyl, piperidinyl, pyrazinyl, pyrazolyl, pyridinyl, pyrrolyl, tetrahydropyranyl, thiazolyl and triazolyl; or
R$^g$ is W—X wherein W is attached to the (CH$_2$)$_p$ and
W is thiazolyl and X is thienyl;

R$^5$ is —NH—S(O)$_2$R$^h$ wherein R$^h$ is selected from the group of optionally substituted benzo[1,2,5]oxodiazolyl, benzo[1,2,5]thiadiazolyl, imidazolyl, isoxazolyl, oxazolyl, benzo[1,4]oxazinyl, pyrazolyl, phenyl, quinolinyl, thiazolyl, thienyl and thienyl; or
R$^h$ is T-U wherein T is attached to the S(O)$_2$ and
T is phenyl or thienyl;
U is selected from the group consisting of pyridinyl, optionally substituted thiazolyl and —NH-pyrimidinyl wherein the pyrimidinyl can be optionally substituted; or R$^5$ is —N(Y$^{400}$)—R$^i$ wherein
Y$^{400}$ is H or Y$^{400}$ is selected from the optionally substituted group consisting of (C$_1$-C$_3$)alkyl, amino(C$_1$-C$_3$)alkyl and pyridinylmethyl; and
R$^i$ is selected from the optionally substituted group of (C$_1$-C$_3$)alkyl, 6-azaindolyl cyclobutenyl, phenyl, purinyl, pyrazinyl, pyrazolo[1,5-a]pyrimidine, pyridazinyl, pyridinyl, pyrimidinyl, pyrrolo[2,3-c]pyridinyl, pyrrolo[2,3-b]pyrimidinyl, pyrrolo[3,2-d]pyrimidinyl, pyrrolo[3,4-b]pyrimidinyl, pyrrolo[2,3-d]pyrimidinyl, quinazolinyl, thieno[3,2-d]pyrimidinyl, thieno[3,2-b]pyridinyl, and triazinyl; or
R$^i$ is V—W wherein V is attached to the nitrogen and
V is a bond or is selected from the optionally substituted group consisting of isoquinolinyl, pyridinyl, pyrimidinyl and pyrrolo[3,2-d]pyrimidinyl;
W is selected from the optionally substituted group consisting of (C$_1$-C$_3$)alkyl, alkoxyalkyl, cyclopentyl, morpholinyl, phenyl, pyrimidinyl, pyrrolidinyl, thieno[3,2-b]pyridinyl, —NH-phenyl, —NH—CH$_2$—CH$_2$—N(CH$_3$)$_2$, —NH—NH$_2$, NH—C(O)—CH$_3$, CH$_2$-phenyl, NH—C(O)-furanyl, S-isopropyl, S-naphthyl, S-phenyl and S—CH$_2$—CH$_2$—NH$_2$; or R$^5$ is Z$^{100}$-Z$^{200}$ wherein Z$^{100}$ is attached to the indazole and
Z$^{100}$ is selected from the group consisting of butyl, ethyl, indazolyl, optionally substituted phenyl, optionally substituted pyridinyl, optionally substituted pyrimidinyl, pyrrolo[3,2-d]pyrimidinyl and optionally substituted thienyl;
Z$^{200}$ is selected from the group consisting of —C(O)—NH—CH$_2$CH$_2$—NH$_2$, NH$_2$, —NH—C(O)-thienyl, —NH—C(O)—CH(CH$_3$)$_2$, —NH—C(O)—CH$_3$, —NH—C(O)C(CH$_3$)$_3$, —NH—C(O)—NH-furanyl, —NH—C(O)—NH-phenyl, benzo[b]thienyl, morpholinylethyl, phenyl, piperazinyl, piperidinyl, pyrazolyl and tetrazolyl; or R$^5$ is —NH—C(O)—Y$^{500}$—C(O)—R$^k$; wherein
Y$^{500}$ is optionally substituted (C$_1$-C$_3$)alkyl; and
R$^k$ is H or R$^k$ is selected from the optionally substituted group consisting of phenyl, phenylamino and thienyl; or R$^5$ is —NH—C(O)—(CH$_2$)$_y$—NH-T-R$^m$; wherein
y is 1 or 2;
T is C(O) or S(O)$_2$; and
R$^m$ is selected from the group consisting of furanyl, phenyl and thienyl;

R$^6$ is H or R$^6$ is selected from the optionally substituted group consisting of (C$_1$)alkoxy, (C$_1$-C$_3$)alkyl, benzo[b]thienyl, —NH-pyrimidinyl, —NH—S(O)$_2$-phenyl-NH-pyrimidinyl, —NH—C(O)-benzo[b]thienyl, pyrrolo[2,3-b]pyrimidinyl and pyridinyl; and R$^7$ is selected from the group consisting of H, halo, NH$_2$, or R$^7$ is selected from optionally substituted group consisting of (C$_2$-C$_5$)alkenyl, (C$_2$-C$_5$)alkynyl, aminoalkynyl, benzofuranyl, benzothiazolyl, benzo[b]thienyl, furanyl, indolyl, isoquinolinyl, naphthyl, phenyl, phenylalkyl, phenyl(C$_2$-C$_5$)alkenyl, phenyl(C$_2$-C$_5$)alkynyl, piperidinyl, pyridinyl, pyrimidinyl, pyrrolyl, quinolinyl, quinoxalinyl, thieno[2,3-b]pyridinyl, thienyl, —NH—S(O)$_2$—CH$_3$, —NH—C(O)—CH$_3$, —NH—C(O)-phenyl, —C(O)—NH—CH$_2$-phenyl and —C(O)—NH-phenyl; or R$^7$ is Y—Z wherein Y is attached to the indazole; and
Y is benzo[b]thienyl or thienyl; and
Z is selected from the group consisting of phenyl, thienyl, CH$_2$NHCH$_2$CH$_2$-morpholinyl and substituted piperazinyl; or $R^7$ is —C(O)—NH—(CH$_2$)$_r$-phenyl wherein r is 0 or 1 and the phenyl is optionally substituted;

provided that the compound is not

[Structure: indazole with $R^5$, $R^3$, $R^7$ substituents and N-CH$_2$-phenyl bearing $R^{100}$ and $R^{200}$]

wherein
$R^3$ is selected from the group consisting of H, OH and COOH;
$R^5$ is H or NO$_2$;
$R^7$ is H or NH$_2$
$R^{100}$ is OCH$_3$ and
$R^{200}$ is H or —C(O)—OCH$_3$;
provided that the compound is not

[Structure: indazole with $R^5$, $R^3$, and N-propyl-NH$_2$ substituent]

wherein
$R^3$ is NH$_2$ or phenyl; and
$R^5$ is H or NO$_2$;
provided that the compound is not

[Structure: 3-phenyl-indazole with R, $R^1$, $R^7$ substituents]

wherein
$R^1$ is H, methyl or propyl;
$R^7$ is H, F or methyl; and
R is H, methyl, OH, NH, or OCH$_3$;
provided that the compound is not

[Structure: indazole with $R^3$ substituent]

wherein $R^3$ is selected from the group consisting of I, Br, COOH, NH$_2$, thienyl, pyridinyl, pyrrolyl, —C(O)—NH—CH—(CH$_2$OH)$_2$, —C(O)—NH—CH$_2$—X$^{100}$,

[Structures: 3,5-dimethylphenyl; 2,4,5-trimethylphenyl; 2,6-diisopropyl-4-(pentan-3-yl)-ethoxyphenyl; and benzene-1,3,5-tricarboxylic acid]

wherein X$^{100}$ is pyridinyl or phenyl optionally substituted with methyl;
provided that the compound is not

[Structure: indazole with $R^5$, $R^6$, $R^7$, $R^3$ substituents]

wherein
$R^3$ is morpholinyl or 4-methylpiperazinyl;
$R^c$ is H, Cl or NO$_2$;
$R^6$ is H or Cl and
$R^7$ is H, Cl or NO$_2$;
provided that the compound is not

[Structure: indazole-3-carboxamide with $R^5$, $R^6$, $L^{100}$, CH$_2$-X$^{200}$ substituents]

wherein
$R^6$ is H, methyl or OCH$_3$;
$R^6$ is H or OCH$_3$;
$L^{100}$ is H or isopropyl; and
$X^{200}$ is phenyl or 4-chlorophenyl;
provided that the compound is not

[Structure: 3-amido-indazole with $R^1$, X$^{300}$ substituents]

wherein
R¹ is H or CH₃ and X³⁰⁰ is benzyl, phenyl, 2-aminophenyl or 2-hydroxyphenyl; and
provided that the compound is not

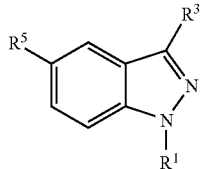

wherein
R¹ is H, CH₂OH, methyl, phenyl or 4-methoxybenzyl;
R³ is H, I, pyridinyl or

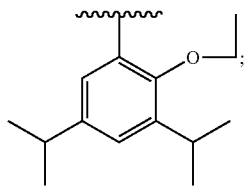

and
R⁵ is H, Br, F, C(OH), —C(O)—OCH₂CH₃ or —NH—C(O)—NH-benzyl.

In a second embodiment, the invention provides compounds or pharmaceutically acceptable salts thereof according to any of the foregoing inventions wherein
R¹ is H or pyrimidinyl substituted with NH₂;
R³ is selected from the group consisting of H, CH₃, OH, Cl, benzo[b]thienyl, 2,3-dihydrobenzofuranyl, indolyl, naphthyl, phenyl, pyrazolyl, pyridinyl, pyrimidinyl, pyrrolyl, quinolinyl, thienyl, —NH—C(O)-cyclobutyl and —NH—C(O)-phenyl; wherein
the indolyl is optionally substituted with CH₃;
the naphthyl is optionally substituted with OCH₃ or OH; and
the phenyl optionally substituted with one or more substituents selected from the group consisting of CH₃, NH₂, Cl, F, N(CH₃)₂, OH, CH₂OH, C(O)NH₂, COOH, CF₃, OCF₃, OCH₃, CN, OCH₂CH₃, NHC(O)CH₃, —S(O)₂CH₃ and —C(O)—NH-pheny; or
R³ is —C(O)—NY¹⁰⁰—(C(Y¹⁰⁰)₂)ₓ—Rᵃ wherein
x is 0 or 1;
Y¹⁰⁰ is H;
Rᵃ is selected from the optionally substituted group consisting of benzo[b]thienyl, benzimidazolyl, 1,3-dihydrobenzimidazolyl-2-one, benzotriazolyl, biphenyl, 1,3-dihydrobenzimidazolyl, indolyl, naphthyl and phenyl; wherein
the naphthyl is substituted with OH or OCH₃;
the phenyl is optionally substituted with one or more Cl, F, OH, CH₂OH, CH₂CH₂OH, COOH, C(O)NH₂, N(CH₃)₂ or methyl; or
R³ is A-B wherein
A is selected from the group consisting of —C≡C, —C≡C-phenyl, phenyl and thienyl; and
B is selected from the group consisting of benzyloxy, phenyl, thienyl, —NH—C(O)-cyclobutyl and —NH—C(O)-phenyl;

R⁴ is H;
R⁵ is pyridinyl substituted with C(O)H, CH₂OH, SCH₂CH₂NH₂ or NH₂; or
R⁵ is selected from the group consisting of

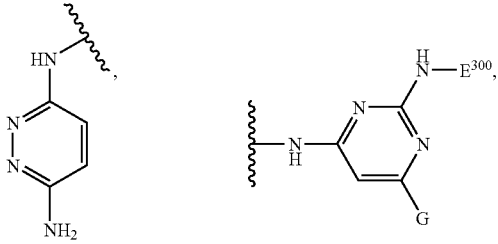

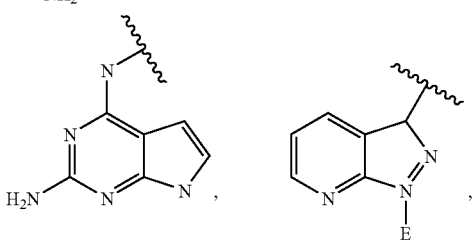

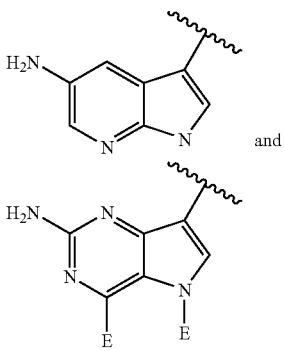

wherein
E is selected from the group consisting of H, OH, CH₃, —CH₂CH₂NH₂, CH₂CH₂CH₂OH, CH₂CH₂OCH₃, CH₂CH₂CH₂NH₂, CH₂C(O)OH, CH₂CH₂C(O)OH, CH₂CH₂C(O)NH₂, CH₂CH₂C(O)OCH₃, CH₂CH₂CH₂OCH₃, NHCH₂CH₂CH₃, CH₂CH₂C(O)NH(CH₃), CH₂CH₂C(O)N(CH₃)₂, C(O)NHCH₂CH₂NH(CH₃), NHCH₂CH₂OCH₃, NHCH₂CH₂OH, NHCH₂CH₂N(CH₃)₂, isopropyl, CH₂C(O)NH₂, CH₂CH(CH₃)C(O)OH, CH₂CH₂CH₂C(O)OH, CH₂CH(CH₃)C(O)OCH₃, CH₂CH₂CH₂CH₂NH₂, CH₂CH₂CH₂C(O)NH₂, N(CH₃)₂, morpholinylethyl, piperidinylethyl,

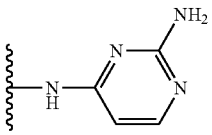

and 4-methylpiperazinylcyclohexyl;
E³⁰⁰ is H or CH₂CH₂OCH₃;
G is selected from the group consisting of H, Cl, NH₂, CH₂CH₂C(O)NHCH₂CH₂NH₂, C(O)NH₂, C(O)NHCH₂CH₂NH₂, C(O)NHCH₂CH₂N(CH₃)₂, CH₂CH₂NH₂, CH₂CH₂CH₂NH₂, CH₂CH₂C(O)OH, CH₂C(O)NH₂, NHCH₂CH₂N(CH₃)₂, NHCH₂CH₂-pyridinyl and NHCH₂CH₂NH₂; or $R^5$ is —C(O)—NH—(CH$_2$)$_a$—R$^c$ wherein
a is 0
R$^c$ is benzimidazolyl or fluorene substituted with oxo; or
R$^c$ is J$^{100}$-J$^{200}$ wherein
J$^{100}$ is selected from the group consisting of pyrazolyl, pyridinyl, piperazinyl and phenyl;
wherein
the phenyl is optionally substituted with one or more substituents selected from the group consisting of F, OH and OCH$_3$;
the piperazinyl is substituted with methyl; and
J$^{200}$ is selected from the group consisting of benzoxazolyl, benzimidazolyl, furanyl, imidazo[1,2-a]pyridinyl and 1,8a-dihydroimidazo[1,2-a]pyridinyl; or
R$^5$ is —NH—C(O)—(CH$_2$)$_n$—R$^d$ wherein
n is 0, 1 or 2; and
R$^d$ is benzimidazolyl, benzo[b]thienyl, imidazolyl, phenyl or pyrazolo[1,5-a]pyrimidinyl;
wherein
the phenyl is substituted with NO$_2$;
R$^5$ is —NH—(C(O))$_m$—NY$^{300}$—(CH$_2$)$_p$—R$^g$ wherein
m is 2;
Y$^{300}$ is H;
p is 1; and
R$^g$ is benzo[1,3]dioxazolyl; or
R$^5$ is —N(Y$^{400}$)—R$^i$ wherein
Y$^{400}$ is selected from H, CH$_2$CH$_2$CH$_2$OH, CH$_2$CH$_2$NH$_2$ or pyridinylmethyl;
R$^i$ is V—W wherein
V is a bond or pyrimidinyl; and
W is pyrimidinyl substituted with NH$_2$ or pyrrolidinyl substituted with OH; or
R$^5$ is Z$^{100}$-Z$^{200}$ wherein
Z$^{100}$ is thienyl or pyridinyl substituted with CH$_3$ and Z$^{200}$ is thienyl or NH—C(O)-furanyl;
R$^6$ is selected from the group consisting of H, pyrrolo[2,3-b]pyrimidinyl and

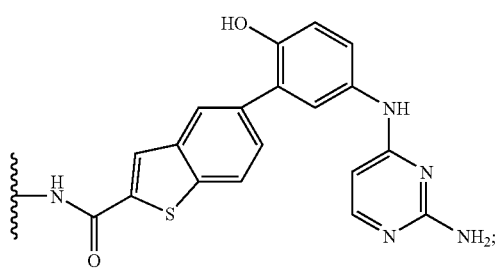

and
R$^7$ is selected from the optionally substituted group consisting of H, Br, Cl, I, benzofuranyl, benzo[b]thienyl, furanyl, indolyl, naphthyl, phenyl, pyridinyl, pyrrolyl, quinolinyl, quinoxalinyl, thieno[2,3-b]pyridinyl, thienyl, —CH=CH-phenyl, —C≡C-phenyl, —C(O)—NH—CH$_2$-phenyl and —C(O)—NH-phenyl wherein
the naphthyl is optionally substituted with OH or OCH$_3$;
the benzo[b]thienyl is optionally substituted with OH, CH$_3$, OCH$_3$, N(CH$_3$)$_2$, OH, CH$_2$=CHNHCH$_3$, CH$_2$NH$_2$, CH$_2$CH$_2$NH$_2$ or CH$_2$NHCH$_2$CH$_2$N(CH$_3$)$_2$;
the indolyl is substituted with C(O)N(CH(CH$_3$)$_2$)$_2$, CH$_2$OH, CH$_2$C(O)NH$_2$, COOH, C(O)NH$_2$, N(CH$_3$)$_2$ or S(O)$_2$CH$_3$; and
the phenyl is optionally substituted with one or more substituents selected from the group consisting of Cl, F, CH$_3$, CH$_2$OH, CN, —C(O)NH$_2$, OH, OCH$_3$, N(CH$_3$)$_2$, NH—C(O)CH$_3$, —NH—S(O)$_2$—CH$_3$;
the thienyl is substituted with CH$_2$OH; or
R$^7$ is Y—Z wherein
Y is benzo[b]thienyl or thienyl; and
Z is selected from the optionally substituted group consisting of CH=CHNHCH$_3$, NHCH$_3$, CH$_2$NH$_2$, CH$_2$CH$_2$NH$_2$, CH$_2$NHCH$_3$, CH$_2$NHCH$_2$CH$_2$N(CH$_3$)$_2$, N(CH$_3$)$_2$, CH$_2$NHCH$_2$CH$_2$-morpholinyl, benzo[b]thienyl, morpholinylmethyl, piperazinylmethylphenyl and thienyl; or
R$^7$ is —C(O)—NH—(CH$_2$)$_r$-phenyl wherein
r is 0 or 1;
the phenyl is optionally substituted with NH$_2$.
In a third embodiment, the invention provides compounds or pharmaceutically acceptable salts thereof according to any of the foregoing inventions wherein R$^1$ is H or pyrimidinyl substituted with NH$_2$;
R$^3$ is selected from the group consisting of H, CH$_3$, OH, Cl, benzo[b]thienyl, 2,3-dihydrobenzofuranyl, indolyl, naphthyl, phenyl, pyrazolyl, pyridinyl, pyrimidinyl, pyrrolyl, quinolinyl, thienyl, —NH—C(O)-cyclobutyl and —NH—C(O)-phenyl; wherein
the indolyl is optionally substituted with CH$_3$;
the naphthyl is optionally substituted with OH; and
the phenyl optionally substituted with one or more substituents selected from the group consisting of OH, F, CH$_3$, CF$_3$, CN, —C(O)NH$_2$, NH$_2$, NHC(O)CH$_3$, OCH$_3$, OCF$_3$, OCH$_2$CH$_3$, N(CH$_3$)$_2$, —C(O)—NH-phenyl and —S(O)$_2$CH$_3$; or
R$^3$ is —C(O)—NY$^{100}$—(C(Y$^{100}$)$_2$)$_x$—R$^a$ wherein
Y$^{100}$ is H;
x is 0;
R$^a$ is selected from the optionally substituted group consisting of benzimidazolyl, 1,3-dihydrobenzimidazolyl-2-one, benzotriazolyl, biphenyl, indolyl, naphthyl and phenyl; wherein
the naphthyl is substituted with OH or OCH$_3$;
the phenyl is optionally substituted with one or more Cl, F, OH, CH$_2$OH, CH$_2$CH$_2$OH, C(O)NH$_2$, N(CH$_3$)$_2$ or methyl; or
R$^3$ is A-B wherein
A is selected from the group consisting of phenyl and thienyl; and
B is selected from the group consisting of benzyloxy, phenyl, thienyl, —NH—C(O)-cyclobutyl and —NH—C(O)-phenyl;
R$^5$ is pyridinyl substituted with NH$_2$; or
R$^5$ is selected from the group consisting of

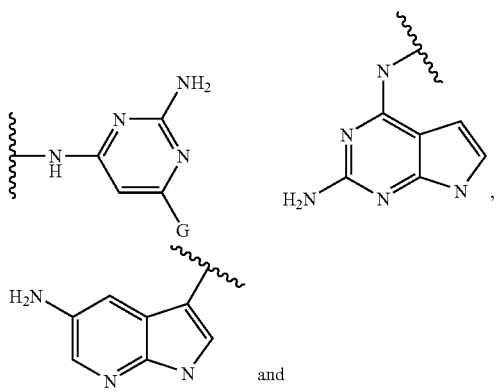

-continued

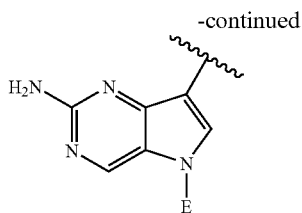

wherein
E is selected from the group consisting of H, CH$_3$, CH$_2$C(O)OH, CH$_2$CH$_2$CH$_2$OH, CH$_2$CH$_2$CH$_2$NH$_2$, CH$_2$CH$_2$C(O)OH, CH$_2$CH$_2$C(O)NH$_2$, CH$_2$CH$_2$C(O)OCH$_3$, CH$_2$CH$_2$CH$_2$OCH$_3$, NHCH$_2$CH$_2$CH$_3$, CH$_2$CH$_2$C(O)NH(CH$_3$), NHCH$_2$CH$_2$OCH$_3$, NHCH$_2$CH$_2$OH, isopropyl, CH$_2$C(O)NH$_2$, CH$_2$CH(CH$_3$)C(O)OH, morpholinylethyl, piperidinylethyl, CH$_2$CH$_2$CH$_2$C(O)OH, CH$_2$CH(CH$_3$)C(O)OCH$_3$, CH$_2$CH$_2$NH$_2$, CH$_2$CH$_2$CH$_2$NH$_2$, CH$_2$CH$_2$C(O)NH$_2$, CH$_2$CH$_2$C(O)N(CH$_3$)$_2$, and N(CH$_3$)$_2$; and
G is selected from the group consisting of H, NH$_2$, Cl, CH$_2$CH$_2$C(O)NHCH$_2$CH$_2$NH$_2$, C(O)NHCH$_2$CH$_2$NH$_2$, C(O)NHCH$_2$CH$_2$N(CH$_3$)$_2$, NHCH$_2$CH$_2$N(CH$_3$)$_2$, NHCH$_2$CH$_2$NH$_2$, CH$_2$CH$_2$NH$_2$, CH$_2$CH$_2$CH$_2$NH$_2$, CH$_2$CH$_2$C(O)OH, CH$_2$CH$_2$C(O)NH$_2$ and NHCH$_2$CH$_2$-pyridinyl;
R$^5$ is —C(O)—NH—(CH$_2$)$_a$—R$^c$ wherein
a is 0;
R$^c$ is J$^{100}$-J$^{200}$ wherein
J$^{100}$ is pyrazolyl or phenyl wherein the phenyl is optionally substituted with OCH$_3$; and
J$^{200}$ is benzoxazolyl, benzimidazolyl, furanyl, imidazo[1,2-a]pyridinyl or 1,8a-dihydroimidazo[1,2-a]pyridinyl; or
R$^5$ is —NH—C(O)—(CH$_2$)$_n$—R$^d$ wherein
n is 0, 1 or 2; and
R$^d$ is selected from the group consisting of benzimidazolyl, benzo[b]thieny, imidazolyl and pyrazolo[1,5-a]pyrimidinyl;
R$^5$ is —N(Y$^{400}$)—R$^i$ wherein
Y$^{400}$ is selected from H, CH$_2$CH$_2$CH$_2$OH, CH$_2$CH$_2$NH$_2$ or pyridinylmethyl;
R$^i$ is V—W wherein
V is a bond or pyrimidinyl and W is pyrimidinyl substituted with NH$_2$ or pyrrolidinyl substituted with OH;
R$^5$ is Z$^{100}$-Z$^{200}$ wherein
Z$^{100}$ is thienyl;
Z$^{200}$ is thienyl;
R$^6$ is H or

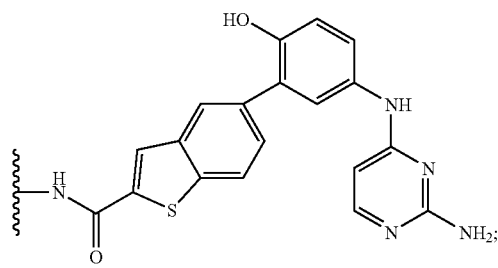

and
R$^7$ is selected from the optionally substituted group consisting of H, benzofuranyl, benzo[b]thienyl, furanyl, indolyl, naphthyl, quinolinyl, phenyl, pyrrolyl, quinoxalinyl, thienyl, thieno[2,3-b]pyridinyl, —CH═CH-phenyl, —C≡C-phenyl, —C(O)—NH—CH$_2$-phenyl and —C(O)—NH-phenyl wherein
the benzo[b]thienyl is optionally substituted with OH, CH$_3$, OCH$_3$, N(CH$_3$)$_2$, CH$_2$═CHNHCH$_3$, CH$_2$NH$_2$, CH$_2$CH$_2$NH$_2$ or CH$_2$NHCH$_2$CH$_2$N(CH$_3$)$_2$;
the indolyl is substituted with methyl, CN, C(O)H, CH$_2$CH$_2$CH$_2$NH$_2$, CH$_2$NHCH$_2$CH═CH$_2$, C(O)CH$_3$, C(O)OCH$_3$, OCH$_3$, C(O)N(CH(CH$_3$)$_2$)$_2$, CH$_2$OH, CH$_2$C(O)NH$_2$, C(O)NH$_2$, CH$_2$NHCH$_2$CH$_2$N(CH$_3$)$_2$ or piperidinylmethyl; and
the phenyl is optionally substituted with one or more substituents selected from the group consisting of Cl, F, CH$_3$, CH$_2$OH, CN, —C(O)NH$_2$, OH, OCH$_3$, N(CH$_3$)$_2$ and —NH—S(O)$_2$—CH$_3$; or
R$^7$ is Y—Z wherein
Y is benzo[b]thienyl or thienyl; and
Z is selected from the optionally substituted group consisting of CH═CHNHCH$_3$, NHCH$_3$, CH$_2$NH$_2$, CH$_2$CH$_2$NH$_2$, CH$_2$NHCH$_3$, CH$_2$NHCH$_2$CH$_2$N(CH$_3$)$_2$, N(CH$_3$)$_2$, CH$_2$NHCH$_2$CH$_2$-morpholinyl, benzo[b]thienyl, morpholinylmethyl and piperazinylmethyl; wherein
the piperazinyl is optionally substituted with methyl.
In a fourth embodiment, the invention provides compounds or pharmaceutically acceptable salts thereof according to any of the foregoing inventions wherein R$^1$ and R$^4$ are H;
R$^3$ is selected from the optionally substituted group consisting of H, OH, 2,3-dihydrobenzofuranyl, naphthyl, pyrazolyl and pyrrolyl; wherein
R$^3$ is —C(O)—NY$^{100}$—(C(Y$^{100}$)$_2$)$_x$—R$^a$ wherein
Y$^{100}$ is H;
x is 0;
R$^a$ is selected from the optionally substituted group consisting of naphthyl and phenyl; wherein
the naphthyl is optionally substituted with OH;
the phenyl is optionally substituted with OH; or
R$^3$ is selected from the group consisting of —NH—C(O)-cyclobutyl and —NH—C(O)-phenyl;
R$^3$ is A-B wherein
A is selected from the group consisting of phenyl and thienyl; and
B is selected from the group consisting of benzyloxy, phenyl and thienyl;
R$^5$ is selected from the group consisting of

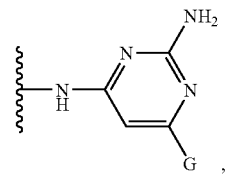
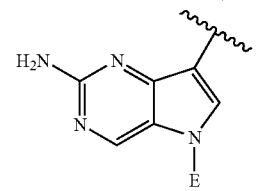
and wherein
E is selected from the group consisting of H, CH$_2$C(O)NH$_2$, CH$_2$CH(CH$_3$)C(O)OCH$_3$, CH$_2$CH$_2$CH$_2$OH, CH$_2$CH$_2$C(O)OCH$_3$, CH$_2$CH$_2$CH$_2$OCH$_3$, CH$_2$CH$_2$NH$_2$, CH$_2$CH$_2$CH$_2$NH$_2$, CH$_2$CH$_2$C(O)OH, CH$_2$CH$_2$C(O)NH$_2$, CH$_2$CH$_2$CH$_2$CH$_2$NH$_2$, CH$_2$CH$_2$CH$_2$OCH$_3$, CH$_2$CH$_2$CH$_2$C(O)OH, CH$_2$CH$_2$CH$_2$C(O)NH$_2$, CH$_2$CH(CH$_3$)C(O)OH, CH$_2$CH$_2$C(O)NH(CH$_3$), CH$_2$CH$_2$C(O)N(CH$_3$)$_2$, N(CH$_3$)$_2$, isopropyl, morpholinylethyl and piperidinylethyl; and G is H, NH$_2$ or NHCH$_2$CH$_2$-pyridinyl or R$^5$ is —C(O)—NH—(CH$_2$)$_a$—R$^c$ wherein
 a is 0
 R$^c$ is J$^{100}$-J$^{200}$ wherein
  J$^{100}$ is phenyl optionally substituted with OCH$_3$ and
  J$^{200}$ is imidazo[1,2-a]pyridinyl or 1,8a-dihydroimidazo[1,2-a]pyridinyl; or R$^5$ is —NH—C(O)—(CH$_2$)$_n$—R$^d$ wherein
 n is 2 and R$^d$ is imidazolyl; or R$^5$ is Z$^{100}$-Z$^{200}$ wherein
 Z$^{100}$ is thienyl;
 Z$^{200}$ is thienyl;

R$^6$ is H or

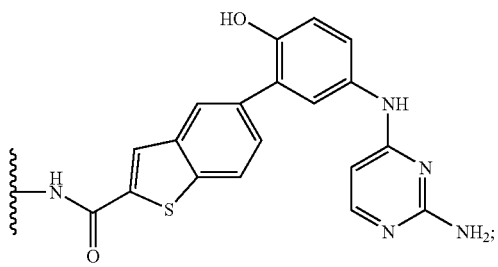

and

R$^7$ is selected from the optionally substituted group consisting of H, benzofuranyl, benzo[b]thienyl, indolyl, naphthyl, quinolinyl, CH═CH-phenyl, —C≡C-phenyl, —C(O)—NH—CH$_2$-phenyl and —C(O)—NH-phenyl wherein
 the benzo[b]thienyl is optionally substituted with OH, CH$_3$, OCH$_3$, N(CH$_3$)$_2$, CH$_2$═CH$_2$NHCH$_3$, CH$_2$NH$_2$, CH$_2$CH$_2$NH$_2$, CH$_2$NHCH$_2$CH$_2$N(CH$_3$)$_2$, piperidinylmethyl or CH$_2$NHCH$_2$N(CH$_3$)$_2$; and
 the indolyl is optionally substituted with methyl, CN, C(O)H, CH$_2$CH$_2$CH$_2$NH$_2$, CH$_2$NHCH$_2$CH═CH$_2$, C(O)CH$_3$, C(O)OCH$_3$, or OCH$_3$; methyl, CN, C(O)H, CH$_2$CH$_2$CH$_2$NH$_2$, CH$_2$NHCH$_2$CH═CH$_2$, C(O)CH$_3$, C(O)OCH$_3$, or OCH$_3$
 the phenyl is optionally substituted with one or more substituents selected from the group consisting of OH and OCH$_3$; or R$^7$ is Y—Z wherein
 Y is benzo[b]thienyl or thienyl; and
 Z is selected from the group consisting of CH═CHNHCH$_3$, NHCH$_3$, CH$_2$NH$_2$, CH$_2$CH$_2$NH$_2$, CH$_2$NHCH$_3$, CH$_2$NHCH$_2$CH$_2$N(CH$_3$)$_2$, N(CH$_3$)$_2$, CH$_2$NHCH$_2$CH$_2$-morpholinyl, benzo[b]thienyl, morpholinylmethyl and piperazinylmethyl;
  wherein the piperazinyl is optionally substituted with methyl.

In a fifth embodiment, the invention provides compounds or pharmaceutically acceptable salts thereof according to any of the foregoing inventions wherein R$^1$ and R$^4$ are H;

R$^3$ is selected from the group consisting of H, OH, 2,3-dihydrobenzofuranyl, pyrrolyl and optionally substituted napthyl; or R$^3$ is —C(O)—NY$^{100}$—(C(Y$^{100}$)$_2$)$_x$—R$^a$ wherein
 Y$^{100}$ is H;
 x is 0; and
 R$^a$ is phenyl substituted with OH;

R$^5$ is

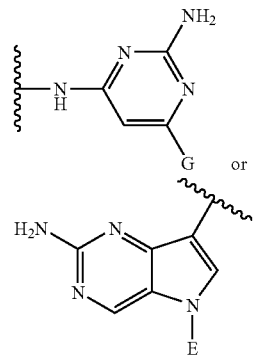

wherein

E is selected from the group consisting of H, CH$_2$C(O)NH$_2$, CH$_2$CH$_2$NH$_2$, CH$_2$CH$_2$CH$_2$NH$_2$, CH$_2$CH$_2$CH$_2$CH$_2$NH$_2$, CH$_2$CH$_2$CH$_2$OCH$_3$, CH$_2$CH$_2$CH$_2$OH, CH$_2$CH$_2$C(O)OH, CH$_2$CH$_2$CH$_2$C(O)OH, CH$_2$CH$_2$C(O)NH$_2$, CH$_2$CH$_2$CH$_2$C(O)NH$_2$, CH$_2$CH(CH$_3$)C(O)OCH$_3$, CH$_2$CH(CH$_3$)C(O)OH, CH$_2$CH$_2$C(O)OCH$_3$, CH$_2$CH$_2$C(O)NH(CH$_3$), CH$_2$CH$_2$C(O)N(CH$_3$)$_2$, N(CH$_3$)$_2$, isopropyl, morpholinylethyl and piperidinylethyl; and G is H, NH$_2$ or NHCH$_2$CH$_2$-pyridinyl or R$^5$ is —C(O)—NH—(CH$_2$)$_a$—R$^c$ wherein
 a is 0; and
 R$^c$ is J$^{100}$-J$^{200}$ wherein
  J$^{100}$ is phenyl and J$^{200}$ is 1,8a-dihydroimidazo[1,2a]pyridinyl; or R$^5$ is —NH—C(O)—(CH$_2$)$_n$—R$^d$ wherein
 n is 2 and R$^d$ is imidazolyl; or R$^5$ is Z$^{100}$-Z$^{200}$ wherein
 Z$^{100}$ is thienyl and Z$^{200}$ is thienyl;

R$^6$ is H or

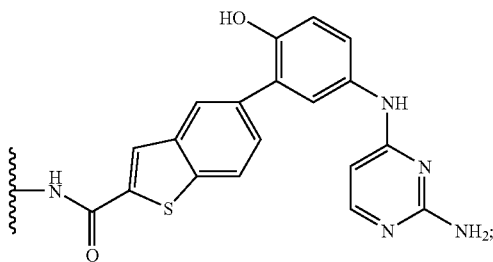

and

R$^7$ is selected from the optionally substituted group consisting of H, —CH═CH-phenyl, —C≡C-phenyl, benzofuranyl, benzo[b]thienyl, indolyl, quinolinyl, naphthyl, —C(O)—NH—CH$_2$-phenyl and —C(O)—NH-phenyl;
 wherein the naphthyl is optionally substituted with OH, C(O)H or OCH$_3$:
 the benzo[b]thienyl optionally substituted with OH, CH$_3$, OCH$_3$, CH$_2$═CH$_3$—NHCH$_3$, CH$_2$NH$_2$, CH$_2$CH$_2$NH$_2$, CH$_2$NHCH$_2$CH$_2$N(CH$_3$)$_2$, N(CH$_3$)$_2$ or piperidinylmethyl;

the indolyl is optionally substituted with methyl, CN, C(O)
H, CH$_2$CH$_2$CH$_2$NH$_2$, CH$_2$NHCH$_2$CH=CH$_2$, C(O)
CH$_3$, C(O)OCH$_3$, or OCH$_3$;
the phenyl is optionally substituted with OH or OCH$_3$; or
R$^7$ is Y—Z wherein
Y is benzo[b]thienyl; and
Z is selected from the group consisting of
CH$_2$NHCH$_2$CH$_2$-morpholinyl, morpholinylmethyl and
piperazinylmethyl wherein the piperazinyl is optionally
substituted with methyl.

In a sixth embodiment, the invention provides compounds or pharmaceutically acceptable salts thereof according to any of the foregoing inventions wherein R$^1$, R$^3$, R$^4$ and R$^6$ are H;
R$^5$ is

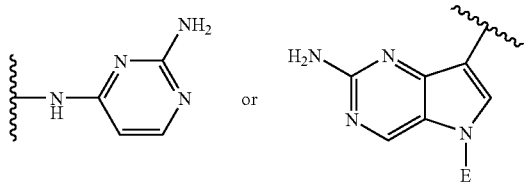

wherein
E is selected from the group consisting of H,
—CH$_2$CH$_2$NH$_2$, CH$_2$CH$_2$CH$_2$NH$_2$, CH$_2$CH$_2$CH$_2$OH,
CH$_2$CH$_2$C(O)OH and CH$_2$CH$_2$C(O)NH$_2$; and
R$^7$ is selected from the group consisting of benzo[b]thienyl,
indolyl, —C(O)—NH—CH$_2$-phenyl and —C(O)—NH-phenyl wherein
the benzo[b]theinyl is optionally substituted by piperidinylmethyl;
the indolyl is optionally substituted by CN, methyl or C(O)H.

In a seventh embodiment, the invention provides compounds or pharmaceutically acceptable salts thereof according to any of the foregoing inventions wherein R$^1$, R$^3$, R$^4$ and R$^6$ are H;
R$^5$ is

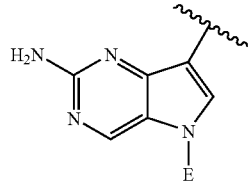

wherein
E is H; and
R$^7$ is —C(O)—NH—CH$_2$-phenyl or —C(O)—NH-phenyl.

In an eighth embodiment, the invention provides compounds or pharmaceutically acceptable salts thereof according to any of the foregoing inventions wherein R$^1$, R$^3$, R$^4$ and R$^6$ are H;
R$^5$ is

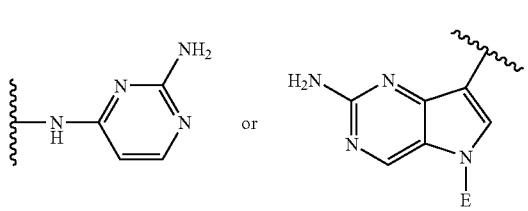

wherein
E is selected from the group consisting of H,
—CH$_2$CH$_2$NH$_2$, CH$_2$CH$_2$CH$_2$NH$_2$, CH$_2$CH$_2$CH$_2$OH,
CH$_2$CH$_2$C(O)OH and CH$_2$CH$_2$C(O)NH$_2$; and
R$^7$ is benzo[b]thienyl or indolyl wherein
the benzo[b]theinyl is optionally substituted by piperidinylmethyl;
the indolyl is optionally substituted by CN, methyl or C(O)H;

In a ninth embodiment, the invention provides compounds or pharmaceutically acceptable salts thereof according to any of the foregoing inventions wherein wherein R$^1$, R$^3$, R$^4$ and R$^6$ are H;
R$^5$ is

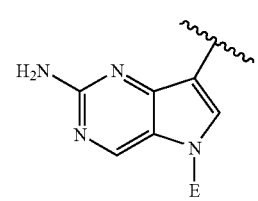

wherein
E is selected from the group consisting of —CH$_2$CH$_2$NH$_2$,
CH$_2$CH$_2$CH$_2$NH$_2$, CH$_2$CH$_2$CH$_2$OH, CH$_2$CH$_2$C(O)OH
and CH$_2$CH$_2$C(O)NH$_2$; and
R$^7$ is benzo[b]thienyl.

DETAILED DESCRIPTION OF THE INVENTION

Protein Kinases

Protein kinases are a broad and diverse class, of over 500 enzymes, that include growth factors receptors, signal transduction intermediates, apoptosis related kinases and cyclin dependent kinases. Many can function as oncogenes. They are responsible for the transfer of a phosphate group to specific tyrosine, serine or threonine amino acid residues, and are broadly classified as tyrosine and S/T kinases as a result of their substrate specificity.

Serine/Threonine Kinases

S/T kinases are a large sub-family of protein kinases that specifically transfer a phosphate group to a terminal hydroxyl moiety of specific serine or threonine residues (Hanks et al., (1988) *Science*, 241: 42-52). A number of S/T kinase family members are involved in inflammatory signaling, tumor growth or cellular transformation. For example, the mitogen-activated protein kinases (MAPKs) are S/T kinases that act as intermediates within the signaling cascades of Toll like receptors (TLRs), such as TLR4, growth/survival factors, such as EGF, and death receptors, such as the TNF receptor. Activation of MAPKs, such as extracellular signal-regulated kinases (ERK1-2), p38α, c-Jun N-terminal kinase (JNK) or MAP-KAP-K2 (MK2) have been shown to transduce signaling in cells, such as macrophages, resulting in the production and secretion of pro-inflammatory cytokines, such as TNF.

TPL-2 is a S/T kinase which is homologous to a subfamily of kinases called MAP kinase kinase kinases (MAP3K) in its catalytic domain (Salmeron, et al., (1996) *EMBO J.*, 15, 817-826) and is >90% identical to the proto-oncogene product of human COT (Aoki et al., (1993) *J. Biol. Chem.*, 268, 22723-22732). TPL-2 was originally identified, in a C-terminally deleted form, as the product of an oncogene associated with Moloney murine leukemia virus-induced T cell lymphomas in rats (Patriotis, et al., (1993) *Proc. Natl. Acad. Sci. USA* 90, 2251-2255). TPL-2 is also highly homologous to the kinase NIK, which has been shown to regulate the inducible degradation of IκB-α (Malinin et al., (1997) *Nature,* 385, 540-544; WO 97/37016; May and Ghosh, (1998) *Immunol. Today,* 19, 80-88). TPL-2 is essential for the activation of a MAP2K (MEK1-2), which in turn activate a MAPK (extracellular signal-regulated kinase, ERK1-2) in macrophages stimulated by TLR agonists, such as lipopolysachharide (LPS). TPL-2 plays a crucial role in the regulation of LPS-induced TNF, IL-1β and COX-2 induced prostaglandin-E2 production in macrophages (Tsichlis et al, (2000), *Cell,* 103, 1071; Tsichlis et al, (2002), *EMBO J,* 21, 4831-4840). The expression of COT/TPL-2 in various tumors (Tsanisi et al., (2000), *Int J Mol Med,* 5, 583) and the defect in TNF production observed in COT knockout mice (Tsichlis et al, (2000), *Cell,* 103, 1071) suggests that inhibition of COT may be a useful approach in the treatment of cancer, inflammation or other diseases mediated by pro-inflammatory cytokines.

MK2 (MAPKAP-K2) is an S/T kinase critically involved in inflammatory processes. MK2 is a substrate for the MAPK p38 (Stokoe et al., (1992), *EMBO J.,* 11, 3985-3994; Ben-Levy et al., (1995), *EMBO J.,* 14, 5920-5930). Activation of MK2 in immune cells results in an array of cellular responses including cytokine production, proliferation and activation. Knockout mice defective in MK2 production are healthy and fertile but fail to produce cytokines such as tumor necrosis factor (TNF) in response to inflammatory stimuli (Kotlyarov et al., (1999), *Nat. Cell Biol,* 1, 94-97.). MK2 may alter gene expression by phosphorylation of mRNA-binding proteins (Winzen et al., (1999), *EMBO J.,* 18, 4969-4980; Lasa et al., (2000), *Mol. Cell. Biol.,* 20, 4265-4274; Rousseau et al., (2002), *EMBO J.,* 21, 6505-6514; Bollig et al., (2003), *Biochem. Biophys. Res. Commun,* 301, 665-670; Tran et al., (2003), *Mol. Cell. Biol.,* 23, 7177-7188.), Chrestensen, C. A. et al. *J. Biol. Chem.* 2004, 279, 10176-10184 and Stoecklin, G. et al. *EMBO J.* 2004, 23, 1313-1324) transcription factors (Heidenreich et al., (1999), *J. Biol. Chem.,* 274, 14434-14443) or other proteins (Stokoe et al, (1992), *FEBS Lett.,* 313, 307-313; Sutherland et al., (1993), *Eur. J. Biochem.,* 217, 715-722; Werz et al, (2000), *Proc. Natl. Acad. Sci._USA,* 97, 5261-5266). The defect in TNF production in MK2 knockouts suggests that the antiinflammatory effect of p38 MAPK inhibitors may be largely due to blockade of activation of MK2. Inhibitors of MK2 may be effective treatments of inflammation or other diseases mediated by pro-inflammatory cytokines.

Protein Tyrosine Kinases.

Protein tyrosine kinases (PTKs) are enzymes that catalyse the phosphorylation of specific tyrosine residues in cellular proteins. This post-translational modification of these substrate proteins, often enzymes themselves, acts as a molecular switch regulating cell proliferation, activation or differentiation (for review, see Schlessinger and Ulrich, 1992, *Neuron* 9:383-391). Aberrant or excessive PTK activity has been observed in many disease states including benign and malignant proliferative disorders as well as diseases resulting from inappropriate activation of the immune system (e.g. autoimmune disorders), allograft rejection, and graft vs. host disease. In addition, endothelial-cell specific receptor PTKs such as KDR and Tie-2 mediate the angiogenic process, and are thus involved in supporting the progression of cancers and other diseases involving inappropriate vascularization (e.g., diabetic retinopathy, choroidal neovascularization due to age-related macular degeneration, psoriasis, arthritis, retinopathy of prematurity, and infantile hemangiomas).

Tyrosine kinases can be of the receptor-type (having extracellular, transmembrane and intracellular domains) or the non-receptor type (being wholly intracellular).

Receptor Tyrosine Kinases (RTKs). The RTKs comprise a large family of transmembrane receptors with diverse biological activities. At present, at least nineteen (19) distinct RTK subfamilies have been identified. The receptor tyrosine kinase (RTK) family includes receptors that are crucial for the growth and differentiation of a variety of cell types (Yarden and Ullrich, *Ann. Rev. Biochem.* 57:433-478, 1988; Ullrich and Schlessinger, *Cell* 61:243-254, 1990). The intrinsic function of RTKs is activated upon ligand binding, which results in phosphorylation of the receptor and multiple cellular substrates, and subsequently in a variety of cellular responses (Ullrich & Schlessinger, 1990, *Cell* 61:203-212). Thus, receptor tyrosine kinase mediated signal transduction is initiated by extracellular interaction with a specific growth factor (ligand), typically followed by receptor dimerization, stimulation of the intrinsic protein tyrosine kinase activity and receptor trans-phosphorylation. Binding sites are thereby created for intracellular signal transduction molecules and lead to the formation of complexes with a spectrum of cytoplasmic signaling molecules that facilitate the appropriate cellular response (e.g., cell division, differentiation, metabolic effects, and changes in the extracellular microenvironment; see Schiessinger and Ullrich, 1992, *Neuron* 9:1-20).

Non-Receptor Tyrosine Kinases. Non-receptor tyrosine kinases represent a collection of cellular enzymes that lack extracellular and transmembrane sequences. Over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. The Src subfamily of non-receptor tyrosine kinases is comprised of the largest number of PTKs and include Src, Yes, Fyn, Lyn, Lck, Blk, Hck, Fgr and Yrk. The Src subfamily of enzymes has been linked to oncogenesis and immune responses. A more detailed discussion of non-receptor tyrosine kinases is provided in Bohlen, 1993, *Oncogene* 8:2025-2031, which is incorporated herein by reference.

Many of the kinases, whether a receptor or non-receptor tyrosine kinase or a S/T kinase have been found to be involved in cellular signaling pathways involved in numerous pathogenic conditions, including immunomodulation, inflammation, or proliferative disorders such as cancer.

In a related aspect the invention provides a method for inhibiting COT in a human subject suffering from a disorder in which COT activity is detrimental, comprising administering to the human subject a compound of Formula (I) such that COT activity in the human subject is inhibited and treatment is achieved.

In another related aspect the invention provides a method for inhibiting MK2 in a human subject suffering from a disorder in which MK2 activity is detrimental, comprising administering to the human subject a compound of Formula (I) such that MK2 activity in the human subject is inhibited and treatment is achieved.

A compound of formula (I) or a salt thereof or pharmaceutical compositions containing a therapeutically effective amount thereof is useful in the treatment of a disorder selected from the group comprising rheumatoid arthritis, osteoarthritis, juvenile chronic arthritis, Lyme arthritis, psoriatic arthritis, reactive arthritis, and septic arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection (including but not limited to bone marrow and solid organ rejection), acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia areata, seronegative arthopathy, arthropathy, Reiter's disease, psoriatic arthropathy, ulcerative colitic arthropathy, enteropathic synovitis, chlamydia, yersinia and salmonella associated arthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinaemia), dilated cardiomyopathy, female infertility, ovarian failure, premature ovarian failure, fibrotic lung disease, chronic wound healing, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasculitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjögren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci (GBS) infection, mental disorders (e.g., depression and schizophrenia), Th2 Type and Th1 Type mediated diseases, and cancers such as lung, breast, stomach, bladder, colon, pancreas, ovarian, prostate and rectal cancer and hematopoietic malignancies (leukemia and lymphoma), and hematopoietic malignancies (leukemia and lymphoma), and diseases involving inappropriate vascularization for example diabetic retinopathy, retinopathy of prematurity, choroidal neovascularization due to age-related macular degeneration, and infantile hemangiomas in human beings. In addition, such compounds may be useful in the treatment of disorders such as edema, ascites, effusions, and exudates, including for example macular edema, cerebral edema, acute lung injury, adult respiratory distress syndrome (ARDS), proliferative disorders such as restenosis, fibrotic disorders such as hepatic cirrhosis and atherosclerosis, mesangial cell proliferative disorders such as glomerulonephritis, diabetic nephropathy, malignant nephrosclerosis, thrombotic microangiopathy syndromes, and glomerulopathies, myocardial angiogenesis, coronary and cerebral collaterals, ischemic limb angiogenesis, ischemia/reperfusion injury, peptic ulcer Helicobacter related diseases, virally-induced angiogenic disorders, Crow-Fukase syndrome (POEMS), preeclampsia, menometrorrhagia, cat scratch fever, rubeosis, neovascular glaucoma and retinopathies such as those associated with diabetic retinopathy, retinopathy of prematurity, or age-related macular degeneration. In addition, these compounds can be used as active agents against solid tumors, malignant ascites, von Hippel Lindau disease, hematopoietic cancers and hyperproliferative disorders such as thyroid hyperplasia (especially Grave's disease), and cysts (such as hypervascularity of ovarian stroma characteristic of polycystic ovarian syndrome (Stein-Leventhal syndrome) and polycystic kidney disease since such diseases require a proliferation of blood vessel cells for growth and/or metastasis.

Compounds of formula (I) of the invention can be used alone or in combination with another therapeutic agent to treat such diseases. It should be understood that the compounds of the invention can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the compound of the present invention. The additional agent also can be an agent that imparts a beneficial attribute to the therapeutic composition e.g., an agent which effects the viscosity of the composition.

It should further be understood that the combinations that are to be included within this invention are those combinations useful for their intended purpose. The agents set forth below are illustrative for purposes and not intended to be limited. The combinations, which are part of this invention, can be the compounds of the present invention and at least one additional agent selected from the lists below. The combination can also include more than one additional agent, e.g., two or three additional agents if the combination is such that the formed composition can perform its intended function.

Preferred combinations are non-steroidal anti-inflammatory drug(s) also referred to as NSAIDS which include drugs like ibuprofen. Other preferred combinations are corticosteroids including prednisolone; the well known side-effects of steroid use can be reduced or even eliminated by tapering the steroid dose required when treating patients in combination with the anti-IL-18 antibodies of this invention. Non-limiting examples of therapeutic agents for rheumatoid arthritis with which a compound of formula (I) of the invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-12, IL-15, IL-16, IL-21, IL-23, interferons, EMAP-II, GM-CSF, FGF, and PDGF. Antibodies of the invention, or antigen binding portions thereof, can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the autoimmune and subsequent inflammatory cascade; preferred examples include TNF antagonists like chimeric, humanized or human TNF antibodies, D2E7 (HUMIRA™), (PCT Publication No. WO 97/29131), CA2 (REMICADE™), CDP 571, and soluble p55 or p75 TNF receptors, derivatives, thereof, (p75TNFR1gG (ENBREL™) or p55TNFR1gG (Lenercept), and also TNFα converting enzyme (TACE) inhibitors; similarly IL-1 inhibitors (Interleukin-1-converting enzyme inhibitors, IL-1RA etc.) may be effective for the same reason. Other preferred combinations include Interleukin 11. Yet another preferred combination are other key players of the autoimmune response which may act parallel to, dependent on or in concert with IL-18 function; especially preferred are IL-12 antagonists including IL-12 antibodies or soluble IL-12 receptors, or IL-12 binding proteins. It has been shown that IL-12 and IL-18 have overlapping but distinct functions and a combination of antagonists to both may be most effective. Yet another preferred combination are non-depleting anti-CD4 inhibitors. Yet other preferred combinations include antagonists of the co-stimulatory pathway CD80 (B7.1) or CD86 (B7.2) including antibodies, soluble receptors or antagonistic ligands.

A compound of formula (I) of the invention may also be combined with agents, such as methotrexate, 6-MP, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g. IRAK family, NIK, IKK family, p38 or other MAP kinase inhibitors), IL-1β converting enzyme inhibitors, TNTFα converting enzyme (TACE) inhibitors, T-cell signalling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors and the derivatives p75TNFRIgG (Enbrel™ and p55TNFRIgG (Lenercept)), sIL-1RI, sIL-1RII, sIL-6R), antiinflammatory cytokines (e.g. IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, human recombinant, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl, misoprostol, naproxen sodium, omeprazole, cyclophosphamide, rituximab, IL-1 TRAP, MRA, CTLA4-IG, IL-18 BP, anti-IL-12, Anti-IL15, BIRB-796, SCIO-469, VX-702, AMG-548, VX-740, Roflumilast, IC-485, CDC-801, and Mesopram. Preferred combinations include methotrexate or leflunomide and in moderate or severe rheumatoid arthritis cases, cyclosporine and anti-TNF antibodies as noted above.

Non-limiting examples of therapeutic agents for inflammatory bowel disease with which a compound of formula (I) of the invention can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signalling by proinflammatory cytokines such as TNFα or IL-1 (e.g. IRAK, NIK, IKK, p38 or MAP kinase inhibitors); IL-1β converting enzyme inhibitors; TNFα converting enzyme inhibitors; T-cell signalling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-11, IL-13 and TGFβ). Preferred examples of therapeutic agents for Crohn's disease in which a compound of formula (I) can be combined include the following: TNF antagonists, for example, anti-TNF antibodies, D2E7 (PCT Publication No. WO 97/29131; HUMIRA™), CA2 (REMICADE™), CDP 571, TNFR-Ig constructs, (p75TNFRIgG (ENBREL™) and p55TNFRIgG (LENERCEPT™)) inhibitors and PDE4 inhibitors. A compound of formula (I) can be combined with corticosteroids, for example, budenoside and dexamethasone; sulfasalazine, 5-aminosalicylic acid; olsalazine; and agents which interfere with synthesis or action of proinflammatory cytokines such as UL-1, for example, IL-1β converting enzyme inhibitors and IL-1ra; T cell signaling inhibitors, for example, tyrosine kinase inhibitors 6-mercaptopurines; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which a compound of formula (I) can be combined include the following: corticosteroids; prednisolone; methylprednisolone; azathioprine; cyclophosphamide; cyclosporine; methotrexate; 4-aminopyridine; tizanidine; interferon-β1a (AVONEX; Biogen); interferon-β1b (BETASERON; Chiron/Berlex); interferon (α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE; Teva Pharmaceutical Industries, Inc.); hyperbaric oxygen; intravenous immunoglobulin; clabribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of formula (I) can be combined with antibodies to cell surface molecules such as CD2, CD3, CD4, CD8, CD19, CD20, CD25, CD28, CD30, CD40, CD45, CD69, CD80, CD86, CD90 or their ligands. A compound of formula (I) may also be combined with agents, such as methotrexate, cyclosporine, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-13 and TGFβ).

Preferred examples of therapeutic agents for multiple sclerosis in which a compound of formula (I) can be combined to include interferon-β for example, IFNβ1a and IFNβ1b; copaxone, corticosteroids, caspase inhibitors, for example inhibitors of caspase-1, IL-1 inhibitors, TNF inhibitors, and antibodies to CD40 ligand and CD80.

A compound of formula (I) may also be combined with agents, such as alemtuzumab, dronabinol, Unimed, daclizumab, mitoxantrone, xaliproden hydrochloride, fampridine, glatiramer acetate, natalizumab, sinnabidol, a-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist) MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists, IL4 agonists.

Non-limiting examples of therapeutic agents for Angina with which a compound of formula (I) of the invention can be combined include the following: aspirin, nitroglycerin, isosorbide mononitrate, metoprolol succinate, atenolol, metoprolol tartrate, amlodipine besylate, diltiazem hydrochloride, isosorbide dinitrate, clopidogrel bisulfate, nifedipine, atorvastatin calcium, potassium chloride, furosemide, simvastatin, verapamil HCl, digoxin, propranolol hydrochloride, carvedilol, lisinopril, spironolactone, hydrochlorothiazide, enalapril maleate, nadolol, ramipril, enoxaparin sodium, heparin sodium, valsartan, sotalol hydrochloride, fenofibrate, ezetimibe, bumetanide, losartan potassium, lisinopril/hydrochlorothiazide, felodipine, captopril, bisoprolol fumarate.

Non-limiting examples of therapeutic agents for Ankylosing Spondylitis with which a compound of formula (I) can be combined include the following: ibuprofen, diclofenac and misoprostol, naproxen, meloxicam, indomethacin, diclofenac, celecoxib, rofecoxib, Sulfasalazine, Methotrexate, azathioprine, minocyclin, prednisone, etanercept, infliximab.

Non-limiting examples of therapeutic agents for Asthma with which a compound of formula (I) can be combined include the following: albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, methylprednisolone, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin HCl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, metaproterenol sulfate.

Non-limiting examples of therapeutic agents for COPD with which a compound of formula (I) can be combined include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, Cilomilast, Roflumilast.

Non-limiting examples of therapeutic agents for HCV with which a compound of formula (I) can be combined include the following: Interferon-alpha-2a, Interferon-alpha-2b, Interferon-alpha con1, Interferon-alpha-n1, Pegylated interferon-alpha-2a, Pegylated interferon-alpha-2b, ribavirin, Peginterferon alfa-2b+ribavirin, Ursodeoxycholic Acid, Glycyrrhizic Acid, Thymalfasin, Maxamine, VX-497 and any compounds that are used to treat HCV through intervention with the following targets: HCV polymerase, HCV protease, HCV helicase, HCV IRES (internal ribosome entry site).

Non-limiting examples of therapeutic agents for Idiopathic Pulmonary Fibrosis with which a compound of formula (I) can be combined include the following: prednisone, azathioprine, albuterol, colchicine, albuterol sulfate, digoxin, gamma interferon, methylprednisolone sod succ, lorazepam, furosemide, lisinopril, nitroglycerin, spironolactone, cyclophosphamide, ipratropium bromide, actinomycin d, alteplase, fluticasone propionate, levofloxacin, metaproterenol sulfate, morphine sulfate, oxycodone HCl, potassium chloride, triamcinolone acetonide, tacrolimus anhydrous, calcium, interferon-alpha, methotrexate, mycophenolate mofetil, Interferon-gamma-1β.

Non-limiting examples of therapeutic agents for Myocardial Infarction with which a compound of formula (I) can be combined include the following: aspirin, nitroglycerin, metoprolol tartrate, enoxaparin sodium, heparin sodium, clopidogrel bisulfate, carvedilol, atenolol, morphine sulfate, metoprolol succinate, warfarin sodium, lisinopril, isosorbide mononitrate, digoxin, furosemide, simvastatin, ramipril, tenecteplase, enalapril maleate, torsemide, retavase, losartan potassium, quinapril HCl/mag carb, bumetanide, alteplase, enalaprilat, amiodarone hydrochloride, tirofiban HCl m-hydrate, diltiazem hydrochloride, captopril, irbesartan, valsartan, propranolol hydrochloride, fosinopril sodium, lidocaine hydrochloride, eptifibatide, cefazolin sodium, atropine sulfate, aminocaproic acid, spironolactone, interferon, sotalol hydrochloride, potassium chloride, docusate sodium, dobutamine HCl, alprazolam, pravastatin sodium, atorvastatin calcium, midazolam hydrochloride, meperidine hydrochloride, isosorbide dinitrate, epinephrine, dopamine hydrochloride, bivalirudin, rosuvastatin, ezetimibe/simvastatin, avasimibe, cariporide.

Non-limiting examples of therapeutic agents for Psoriasis with which a compound of formula (I) can be combined include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine.

Non-limiting examples of therapeutic agents for Psoriatic Arthritis with which a compound of formula (I) can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, efalizumab.

Non-limiting examples of therapeutic agents for Restenosis with which a compound of formula (I) can be combined include the following: sirolimus, paclitaxel, everolimus, tacrolimus, ABT-578, acetaminophen.

Non-limiting examples of therapeutic agents for Sciatica with which a compound of formula (I) can be combined include the following: hydrocodone bitartrate/apap, rofecoxib, cyclobenzaprine HCl, methylprednisolone, naproxen, ibuprofen, oxycodone HCl/acetaminophen, celecoxib, valdecoxib, methylprednisolone acetate, prednisone, codeine phosphate/apap, tramadol HCl/acetaminophen, metaxalone, meloxicam, methocarbamol, lidocaine hydrochloride, diclofenac sodium, gabapentin, dexamethasone, carisoprodol, ketorolac tromethamine, indomethacin, acetaminophen, diazepam, nabumetone, oxycodone HCl, tizanidine HCl, diclofenac sodium/misoprostol, propoxyphene napsylate/apap, asa/oxycod/oxycodone ter, ibuprofen/hydrocodone bit, tramadol HCl, etodolac, propoxyphene HCl, amitriptyline HCl, carisoprodol/codeine phos/asa, morphine sulfate, multivitamins, naproxen sodium, orphenadrine citrate, temazepam.

Preferred examples of therapeutic agents for SLE (Lupus) in which a compound of formula (I) include the following: NSAIDS, for example, diclofenac, naproxen, ibuprofen, piroxicam, indomethacin; COX2 inhibitors, for example, Celecoxib, rofecoxib, valdecoxib; anti-malarials, for example, hydroxychloroquine; Steroids, for example, prednisone, prednisolone, budenoside, dexamethasone; Cytotoxics, for example, azathioprine, cyclophosphamide, mycophenolate mofetil, methotrexate; inhibitors of PDE4 or purine synthesis inhibitor, for example Cellcept. A compound of formula (I) may also be combined with agents such as sulfasalazine, 5-aminosalicylic acid, olsalazine, Imuran and agents which interfere with synthesis, production or action of proinflammatory cytokines such as IL-1, for example, caspase inhibitors like IL-1β converting enzyme inhibitors and IL-1ra. A compound of formula (I) may also be used with T cell signaling inhibitors, for example, tyrosine kinase inhibitors; or molecules that target T cell activation molecules, for example, CTLA4-IgG or anti-B7 family antibodies, anti-PD-1 family antibodies. A compound of formula (I) can be combined with UL-11 or anti-cytokine antibodies, for example, fonotolizumab (anti-IFNg antibody), or anti-receptor receptor antibodies, for example, anti-IL-6 receptor antibody and antibodies to B-cell surface molecules. A compound of formula (I) may also be used with LJP 394 (abetimus), agents that deplete or inactivate B-cells, for example, Rituximab (anti-CD20 antibody), lymphostat-B (anti-BlyS antibody), TNF antagonists, for example, anti-TNF antibodies, D2E7 (PCT Publication No. WO 97/29131; HUMIRA™), CA2 (REMICADE™), CDP 571, TNFR-Ig constructs, (p75TNFRIgG (ENBREL™) and p55TNFRIgG (LENERCEPT™)).

In this invention, the following definitions are applicable:

A "therapeutically effective amount" is an amount of a compound of Formula I or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

"Physiologically acceptable salts" refers to those salts which retain the biological effectiveness and properties of the free bases and which are obtained by reaction with inorganic acids, for example, hydrochloric acid, hydrobromic acid, sulfuric acid, nitric acid, and phosphoric acid or organic acids such as sulfonic acid, carboxylic acid, organic phosphoric acid, methanesulfonic acid, ethanesulfonic acid, p-toluenesulfonic acid, citric acid, fumaric acid, maleic acid, succinic acid, benzoic acid, salicylic acid, lactic acid, tartaric acid (e.g. (+) or (−)-tartaric acid or mixtures thereof), amino acids (e.g. (+) or (−)-amino acids or mixtures thereof), and the like. These salts can be prepared by methods known to those skilled in the art.

Certain compounds of formula I which have acidic substituents may exist as salts with pharmaceutically acceptable bases. The present invention includes such salts. Examples of such salts include sodium salts, potassium salts, lysine salts and arginine salts. These salts may be prepared by methods known to those skilled in the art.

Certain compounds of formula I and their salts may exist in more than one crystal form and the present invention includes each crystal form and mixtures thereof.

Certain compounds of formula I and their salts may also exist in the form of solvates, for example hydrates, and the present invention includes each solvate and mixtures thereof.

Certain compounds of formula I may contain one or more chiral centers, and exist in different optically active forms. When compounds of formula I contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of formula I contains more than one chiral center it may exist in diastereoisomeric forms. The diastereoisomeric pairs may be separated by methods known to those skilled in the art, for example chromatography or crystallization and the individual enantiomers within each pair may be separated as described above. The present invention includes each diastereoisomer of compounds of formula I and mixtures thereof.

Certain compounds of formula I may exist in different tautomeric forms or as different geometric isomers, and the present invention includes each tautomer and/or geometric isomer of compounds of formula I and mixtures thereof.

Certain compounds of formula I may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of formula I and mixtures thereof.

Certain compounds of formula I may exist in zwitterionic form and the present invention includes each zwitterionic form of compounds of formula I and mixtures thereof.

As used herein the term "pro-drug" refers to an agent which is converted into the parent drug in vivo by some physiological chemical process (e.g., a prodrug on being brought to the physiological pH is converted to the desired drug form). Pro-drugs are often useful because, in some situations, they may be easier to administer than the parent drug. They may, for instance, be bioavailable by oral administration whereas the parent drug is not. The prodrug may also have improved solubility in pharmacological compositions over the parent drug. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to carboxylic acid substituents (e.g., —$CH_2$)C(O)H or a moiety that contains a carboxylic acid) wherein the free hydrogen is replaced by ($C_1$-$C_4$)alkyl, ($C_2$-$C_{12}$)alkanoyloxymethyl, ($C_4$-$C_9$)1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)-alkylcarbamoyl-($C_1$-$C_2$)alkyl and piperidino-, pyrrolidino- or morpholino($C_2$-$C_3$) alkyl.

Other exemplary pro-drugs release an alcohol of Formula I wherein the free hydrogen of the hydroxyl substituent (e.g., $R^1$ contains hydroxyl) is replaced by ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylamino-methyl, succinoyl, ($C_1$-$C_6$)alkanoyl, α-amino($C_1$-$C_4$)alkanoyl, arylactyl and α-aminoacyl, or α-aminoacyl-α-aminoacyl wherein said α-aminoacyl moieties are independently any of the naturally occurring L-amino acids found in proteins, P(O)(OH)$_2$, —P(O)(O($C_1$-$C_6$)alkyl)$_2$ or glycosyl (the radical resulting from detachment of the hydroxyl of the hemiacetal of a carbohydrate).

Heteroaromatic groups, as used herein, include heteroaryl ring systems (e.g., for purposes of exemplification, which should not be construed as limiting the scope of this invention: thienyl, pyridyl, pyrazole, isoxazolyl, thiadiazolyl, oxadiazolyl, indazolyl, furans, pyrroles, imidazoles, pyrazoles, triazoles, pyrimidines, pyrazines, thiazoles, isothiazoles, oxazolyl or tetrazoles) and heteroaryl ring systems in which a carbocyclic aromatic ring, carbocyclic non-aromatic ring or heteroaryl ring is fused to one or more other heteroaryl rings (e.g., for purposes of exemplification, which should not be construed as limiting the scope of this invention: benzo(b) thienyl, benzimidazolyl, benzoxazolyl, benzothiazolyl, benzothiadiazolyl, benzoxadiazolyl, indole, tetrahydroindole, azaindole, indazole, quinoline, imidazopyridine, quinazoline purine, pyrrolo[2,3-d]pyrimidine, pyrazolo[3,4-d]pyrimidine) and their N-oxides. Substituted heteroaryl groups are preferably substituted with one or more substituents each independently selected from the group consisting of halogen, hydroxy, alkyl, alkoxy, alkyl-O—C(O)—, alkoxyalkyl, a heterocycloalkyl group, optionally substituted phenyl, nitro, amino, mono-substituted amino or di-substituted amino.

The term "heterocyclic" or "heterocyclyl", as used herein, include aromatic and non-aromatic, ring systems, including, but not limited to, monocyclic, bicyclic and tricyclic rings, which can be completely saturated or which can contain one or more units of unsaturation and have 3 to 12 atoms including at least one heteroatom, such as nitrogen, oxygen, or sulfur. For purposes of exemplification, which should not be construed as limiting the scope of this invention: azaindole, azetidinyls furans, imidazoles, imidazopyridine, indole, isoxazoles, isothiazoles, oxadiazoles, oxazoles, piperazines, piperidines, pyrans, pyrazines, pyrazoles, pyridines, pyrimidines, pyrroles, pyrrolidines, quinolines, quinazolines, triazoles, thiazoles, tetrahydroindole, tetrazoles, thiadiazoles, thienyls, thiomorpholinos or triazles.

When the term "substituted heterocyclic" (or heterocyclyl) is used, what is meant is that the heterocyclic group is substituted with one or more substituents that can be made by one of ordinary skill in the art and results in a molecule that is a kinase inhibitor. For purposes of exemplification, which should not be construed as limiting the scope of this invention, preferred substituents for the heterocyclyls of this invention are each independently selected from the optionally substituted group consisting of alkenyl, alkoxy, alkoxyalkoxy, alkoxyalkyl, alkoxycarbonyl, alkoxycarbonylheterocycloalkoxy, alkyl, alkylcarbonyl, alkylester, alkyl-O—C(O)—, alkyl-heterocyclyl, alkyl-cycloalkyl, alkyl-nitrile, alkynyl, amido groups, amino, aminoalkyl, aminocarbonyl, carbonitrile, carbonylalkoxy, carboxamido, $CF_3$, CN, —C(O)OH, —C(O)H, —C(O)—)(CH$_3$)$_3$, —OH, —C(O)O-alkyl, —C(O)O-cycloalkyl, —C(O)O-heterocyclyl, —C(O)-alkyl, —C(O)-cycloalkyl, —C(O)-heterocyclyl, cycloalkyl, dialkylaminoalkoxy, dialkylaminocarbonylalkoxy, dialkylaminocarbonyl, halogen, heterocyclyl, a heterocycloalkyl group, heterocyclyloxy, hydroxy, hydroxyalkyl, nitro, $NO_2$, $OCF_3$, oxo, phenyl, —$SO_2CH_3$, —$SO_2CR_3$, tetrazolyl, thienylalkoxy, trifluoromethylcarbonylamino, trifluoromethylsulfonamido, heterocyclylalkoxy, heterocyclyl-S(O)$_p$, cycloalkyl-S(O)$_p$, alkyl-S—, heterocyclyl-S, heterocycloalkyl, cycloalkylalkyl, heterocycolthio, cycloalkylthio, —$Z^{105}$—C(O)N(R)$_2$, —$Z^{105}$—N(R)—C(O)—$Z^{200}$, —$Z^{105}$—N(R)—S(O)$_2$—$Z^{200}$, —$Z^{105}$—N(R)—C(O)—N(R)—$Z^{200}$, —N(R)—C(O)R, —N(R)—C(O) OR, OR—C(O)-heterocyclyl-OR, $R_c$ and —$CH_2OR_c$;

where $R_c$ for each occurrence is independently hydrogen, optionally substituted alkyl, optionally substituted aryl, —(C$_1$-C$_6$)—NR$_d$R$_e$, -E-(CH$_2$)$_t$—NR$_d$R$_e$, -E-(CH$_2$)$_t$—O-alkyl, -E-(CH$_2$)$_t$—S-alkyl, or -E-(CH$_2$)$_t$—OH
wherein t is an integer from about 1 to about 6;
$Z^{105}$ for each occurrence is independently a covalent bond, alkyl, alkenyl or alkynyl; and
$Z^{200}$ for each occurrence is independently selected from an optionally substituted group selected from the group consisting of alkyl, alkenyl, alkynyl, phenyl, alkyl-phenyl, alkenyl-phenyl or alkynyl-phenyl;

E is a direct bond, O, S, S(O), S(O)$_2$, or NR$_f$, wherein R$_f$ is H or alkyl and R$_d$ and R$_e$ are independently H, alkyl, alkanoyl or SO$_2$-alkyl; or R$_d$, R$_e$ and the nitrogen atom to which they are attached together form a five- or six-membered heterocyclic ring.

An "heterocycloalkyl" group, as used herein, is a heterocyclic group that is linked to a compound by an aliphatic group having from one to about eight carbon atoms. For example, a preferred heterocycloalkyl group is an imidazolylethyl group.

As used herein, "aliphatic" or "an aliphatic group" or notations such as "(C$_0$-C$_8$)" include straight chained or branched hydrocarbons which are completely saturated or which contain one or more units of unsaturation, and, thus, includes alkyl, alkenyl, alkynyl and hydrocarbons comprising a mixture of single, double and triple bonds. When the group is a C$_0$ it means that the moiety is not present or in other words, it is a bond. As used herein, "alkyl" means C$_1$-C$_8$ and includes straight chained or branched hydrocarbons which are completely saturated. Preferred alkyls are methyl, ethyl, propyl, butyl, pentyl, hexyl and isomers thereof. As used herein, "alkenyl" and "alkynyl" means C$_2$-C$_8$ and includes straight chained or branched hydrocarbons which contain one or more units of unsaturation, one or more double bonds for alkenyl and one or more triple bonds for alkynyl.

As used herein, aromatic groups (or aryl groups) include aromatic carbocyclic ring systems (e.g. phenyl and cyclopentyldienyl) and fused polycyclic aromatic ring systems (e.g. naphthyl, biphenylenyl and 1,2,3,4-tetrahydronaphthyl).

As used herein, cycloalkyl means C$_3$-C$_{12}$ monocyclic or multicyclic (e.g., bicyclic, tricyclic, etc.) hydrocarbons which is completely saturated or has one or more unsaturated bonds but does not amount to an aromatic group. Preferred examples of a cycloalkyl group are cyclopropyl, cyclobutyl, cyclopentyl, cyclopentenyl, cyclohexyl and cyclohexenyl.

As used herein, amido group means —NHC(=O)—.
As used herein, acyloxy groups are —OC(O)R.
As used herein, many moieties or substituents are termed as being either "substituted" or "optionally substituted". When a moiety is modified by one of these terms, it denotes that any portion of the moiety that is known to one skilled in the art as being available for substitution can be substituted, which includes one or more substituents, where if more than one substituent then each substituent is independently selected. Such means for substitution are well-known in the art and/or taught by the instant disclosure. For purposes of exemplification, which should not be construed as limiting the scope of this invention, some examples of groups that are substituents are: alkenyl groups, alkoxy group (which itself can be substituted, such as —O—C$_1$-C$_6$-alkyl-OR, —O—C$_1$-C$_6$-alkyl-N(R)$_2$, and OCF$_3$), alkoxyalkoxy, alkoxycarbonyl, alkoxycarbonylpiperidinylalkoxy, alkyl groups (which itself can also be substituted, such as —C$_1$-C$_6$-alkyl-OR, —C$_1$-C$_6$-alkyl-N(R)$_2$, and —CF$_3$), alkylamino, alkylcarbonyl, alkylester, alkylnitrile, alkylsulfonyl, amino, aminoalkoxy, CF$_3$, COH, COOH, CN, cycloalkyl, dialkylamino, dialkylaminoalkoxy, dialkylaminocarbonyl, dialkylaminocarbonylalkoxy, dialkylaminosulfonyl, esters (—C(O)—OR, where R is groups such as alkyl, heterocycloalkyl (which can be substituted), heterocyclyl, etc., which can be substituted), halogen or halo group (F, Cl, Br, I), hydroxy, morpholinoalkoxy, morpholinoalkyl, nitro, oxo, OCF$_3$, optionally substituted phenyl, S(O)$_2$CH$_3$, S(O)$_2$CF$_3$, and sulfonyl, N-alkylamino or N,N-dialkylamino (in which the alkyl groups can also be substituted).

Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

For any compound used in a method of the present invention, the therapeutically effective dose can be estimated initially from cellular assays. For example, a dose can be formulated in cellular and animal models to achieve a circulating concentration range that includes the $IC_{50}$ as determined in cellular assays (i.e., the concentration of the test compound which achieves a half-maximal inhibition of a given protein kinase activity). In some cases it is appropriate to determine the $IC_{50}$ in the presence of 3 to 5% serum albumin since such a determination approximates the binding effects of plasma protein on the compound. Such information can be used to more accurately determine useful doses in humans. Further, the most preferred compounds for systemic administration effectively inhibit protein kinase signaling in intact cells at levels that are safely achievable in plasma.

A therapeutically effective dose refers to that amount of a compound of Formula I or a combination of two or more such compounds, which inhibits, totally or partially, the progression of a condition or alleviates, at least partially, one or more symptoms of the condition. A therapeutically effective amount can also be an amount which is prophylactically effective. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art. The exact formulation, route of administration and dosage can be chosen by the individual physician in view of the patient's condition. (See e.g. Fingl et al., 1975, in "The Pharmacological Basis of Therapeutics", Ch. 1 p 1). In the treatment of crises, the administration of an acute bolus or an infusion approaching the MTD may be required to obtain a rapid response.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g. the concentration necessary to achieve 50-90% inhibition of protein kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10-90% of the time, preferably between 30-90% and most preferably between 50-90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

In some formulations it may be beneficial to use the compounds of the present invention in the form of particles of very small size, for example as obtained by fluid energy milling.

The use of compounds of the present invention in the manufacture of pharmaceutical compositions is illustrated by the following description. In this description the term "active compound" denotes any compound of the invention but particularly any compound which is the final product of one of the preceding Examples.

a) Capsules

In the preparation of capsules, 10 parts by weight of active compound and 240 parts by weight of lactose can be de-aggregated and blended. The mixture can be filled into hard gelatin capsules, each capsule containing a unit dose or part of a unit dose of active compound.

b) Tablets

Tablets can be prepared, for example, from the following ingredients.

| | Parts by weight |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch can be de-aggregated, blended and the resulting mixture can be granulated with a solution of the polyvinyl-pyrrolidone in ethanol. The dry granulate can be blended with the magnesium stearate and the rest of the starch. The mixture is then compressed in a tabletting machine to give tablets each containing a unit dose or a part of a unit dose of active compound.

c) Enteric Coated Tablets

Tablets can be prepared by the method described in (b) above. The tablets can be enteric coated in a conventional manner using a solution of 20% cellulose acetate phthalate and 3% diethyl phthalate in ethanol:dichloromethane (1:1).

d) Suppositories

In the preparation of suppositories, for example, 100 parts by weight of active compound can be incorporated in 1300 parts by weight of triglyceride suppository base and the mixture formed into suppositories each containing a therapeutically effective amount of active ingredient.

In the compositions of the present invention the active compound may, if desired, be associated with other compatible pharmacologically active ingredients. For example, the compounds of this invention can be administered in combination with another therapeutic agent that is known to treat a disease or condition described herein. For example, with one or more additional pharmaceutical agents that inhibit or prevent the production of VEGF or angiopoietins, attenuate intracellular responses to VEGF or angiopoietins, block intracellular signal transduction, inhibit vascular hyperpermeability, reduce inflammation, or inhibit or prevent the formation of edema or neovascularization. The compounds of the invention can be administered prior to, subsequent to or simultaneously with the additional pharmaceutical agent, whichever course of administration is appropriate. The additional pharmaceutical agents include, but are not limited to any of the agents, for examples, described in pages 20-28. The compounds of the invention and the additional pharmaceutical agents act either additively or synergistically. Thus, the administration of such a combination of substances that inhibit angiogenesis, vascular hyperpermeability and/or inhibit the formation of edema can provide greater relief from the deletrious effects of a hyperproliferative disorder, angiogenesis, vascular hyperpermeability or edema than the administration of either substance alone. In the treatment of malignant disorders combinations with antiproliferative or cytotoxic chemotherapies or radiation are included in the scope of the present invention.

The present invention also comprises the use of a compound of formula I as a medicament.

A further aspect of the present invention provides the use of a compound of formula I or a salt thereof in the manufacture of a medicament for treating vascular hyperpermeability, angiogenesis-dependent disorders, proliferative diseases and/or disorders of the immune system in mammals, particularly human beings.

The present invention also provides a method of treating vascular hyperpermeability, inappropriate neovascularization, proliferative diseases and/or disorders of the immune system which comprises the administration of a therapeutically effective amount of a compound of formula I to a mammal, particularly a human being, in need thereof.

The contents of all references, patents and published patent applications, in their entirety, cited throughout this application are incorporated herein by reference.

Assays for Screening Compounds of Formula (I)
Enzyme Assays

The in vitro potency of compounds in inhibiting one or more of the protein kinases discussed herein or described in the art may be determined by the procedures detailed below.

The potency of compounds can be determined by the amount of inhibition of the phosphorylation of an exogenous substrate (e.g., a synthetic peptide (Z. Songyang et al., *Nature*. 373:536-539) by a test compound relative to control. Homogenous time-resolved fluorescence (HTRF) in vitro kinase assay (see Mathis, G., *HTRF(R) Technology*. J Biomol Screen, 1999. 4(6): p. 309-314, the contents of which are incorporated in its entirety herein by reference):

Purified enzymes (available from commercial sources) were mixed with different amounts of N-biotinylated substrates or GST-tagged substrates (see table) at varying concentrations of inhibitor in different reaction buffers (40 μL final volume, see table). The kinase reaction was initiated by addition of ATP (0.01-0.1 mM final conc.) in a black 96-half-well plate (Perkin Elmer). After 50-60 minutes incubation at room temperature, the reaction was quenched by addition of EDTA (final conc. 100 mM) and developed by addition of revelation reagents (final approximate concentrations: 30 mM HEPES, pH7.0, 0.06% BSA, 0.006% Tween-20, 0.24 M KF, varying amounts of donor europium labeled antibodies and acceptor streptavidin labeled allophycocyanin (SAXL) or anti-GST-XL which are specific to the enzyme reactions. (see table). The developed reaction was incubated in the dark either at room temperature for 10 min, or at 4° C. overnight (see table), then read in a time-resolved fluorescence detector (Discovery, Perkin Elmer or Rubystar, BMG) at 620 nm and 665 nm simultaneously. A 337 nm nitrogen laser was used for excitation. The ratio between the signal of 620 nm and 665 nm was used to calculate the $IC_{50}$.

Specific detailed reaction conditions for the various enzymes are included below:

| Enzyme | Construct/Mw | Substrate | Assay Buffer | Enzyme Conc. (ng/well) | Substrate Conc. (μM) | ATP Conc. (mM) | DMSO Conc. (%) | Reaction Time (min) | Detection condition | Comments |
|---|---|---|---|---|---|---|---|---|---|---|
| Akt1 | NA/56 kD | Biotin-Bad-peptide | Akt Buffer | 0.12 | 4 | 0.1 | 5 | 50 | 13.6 ng/well Anti-P-BAD-Eu; 0.17 μg/well SAXL | Develop at 4° C. overnight |
| B-Raf | Flag-B-Raf (446-766)/ 37.3 kD | GST-Unactive MEK1 (UBI) | COT Buffer | 30 | 0.15 | 0.1 | 5 | 60 | 14 ng/well Anti-P-MEK-Eu; 0.75 μg/well anti-GST-XL | Develop at 4° C. overnight |
| Casine Kinase II (Calbiochem) | Human recombinant/ 130 kDa | Biotin-IκBα-peptide | CKII buffer | 60 | 0.5 | 0.1 | 5 | 60 | 13.6 ng/well Anti-P-IκBα-Eu; 0.34 μg/well SAXL | Develop at 4° C. overnight |
| CDK2/ Cyclin A (UBI) | C-His CDK2; N-GST Cyclin A/110 kD | Biotin-MBP protein (UBI) | MK2 buffer | 1.335 | 0.1 | 0.1 | 5 | 60 | 15 ng/well Anti-P-MBP-Eu; 0.34 μg/well SAXL | Develop at 4° C. overnight |
| CHK1 | CHK1(1-289)-His6/33.8 kD | Biotin-cdc25-peptide | PKA buffer | 0.6 | 4 | 0.1 | 5 | 60 | 1.8 ng/well Anti-P-14-3-3 binding motif-Eu; 0.11 μg/well CR130-100 | Develop at RT 10 min |

-continued

| Enzyme | Construct/Mw | Substrate | Assay Buffer | Enzyme Conc. (ng/well) | Substrate Conc. (μM) | ATP Conc. (mM) | DMSO Conc. (%) | Reaction Time (min) | Detection condition | Comments |
|---|---|---|---|---|---|---|---|---|---|---|
| COT | Flag-COT30-397/45 kD | Biotin-MEK-peptide | COT Buffer | 25 | 0.5 | 0.1 | 5 | 60 | 8.6 ng/well Anti-P-MEK-Eu; 0.34 ng/well SAXL | Develop at 4° C. overnight |
| Erk2 (UBI) | GST-Erk2/ 68 kD | Biotin-MBP protein (UBI) | COT Buffer | 1 | 0.05 | 0.1 | 5 | 60 | 15 ng/well Anti-P-MBP-Eu; 0.34 μg/well SAXL | Develop at 4° C. overnight |
| IKK1 | His-IKK1/ 80 kD | Biotin-IκBα-peptide | COT Buffer | 60 | 0.5 | 0.1 | 5 | 50 | 13.6 ng/well Anti-P-IκBα-Eu; 0.34 μg/well SAXL | Develop at 4° C. overnight |
| IKK2 | His-IKK2/ 80 kD | Biotin-IκBα-peptide | COT Buffer | 60 | 0.5 | 0.1 | 5 | 50 | 13.6 ng/well Anti-P-IκBα-Eu; 0.34 μg/well SAXL | Develop at 4° C. overnight |
| JNK1 (UBI) | His-JNK1/ 45 kD | Biotin-MBP protein (UBI) | MK2 buffer | 40 | 2 | 0.1 | 5 | 60 | 15 ng/well Anti-P-MBP-Eu; 0.34 μg/well SAXL | Develop at 4° C. overnight |
| MAPKAP K2 | GST-MK2 (36-400)/68 kD | Biotin-cdc25-peptide | MK2 buffer | 1.5 | 1 | 0.01 | 5 | 60 | 1.8 ng/well Anti-P-14-3-3 binding motif-Eu; 0.11 μg/well CR130-100 | Develop at RT 10 min |
| MAPKAP K3 | GST-MK3 (35-382)/ 66.9 KD | Biotin-cdc25-peptide | MK2 buffer | 3 | 1 | 0.1 | 5 | 60 | 1.8 ng/well Anti-P-14-3-3 binding motif-Eu; 0.11 μg/well CR130-100 | Develop at RT 10 min |
| MEK1 (UBI) | GST-MEK1-His6/71 kDa | unactive Erk2 (UBI) | COT Buffer | 3 | 0.1 | 0.1 | 5 | 60 | 15 ng/well Anti-P-Erk-Eu; 0.39 μg/well Anti-GST-XL | Develop at 4° C. overnight |
| MEKK3 | Flag-MEKK3 (2-627)/ 73 kDa | Unactive MEK1 Unactive Erk2 Biotin-MBP protein (all from UBI) | COT Buffer | 85 | 40 ng/well MEK1 250 ng/well Erk2 0.06 uM Biotin-MBP | 0.1 | 5 | 50 | 15 ng/well Anti-P-MBP-Eu; 0.34 μg/well SAXL | Develop at 4° C. overnight |
| NIK/ p100 | Flag-NIK; HA-p100/ 203.3 kD | Biotin-IκBα-peptide | COT Buffer | 8.5 | 0.5 | 0.1 | 5 | 60 | 13.6 ng/well Anti-P-IκBα-Eu; 0.34 μg/well SAXL | Develop at 4° C. overnight |
| p38-alpha (UBI) | GST-p38α/ 64 kD | Biotin-MBP protein (UBI) | COT Buffer | 1.5 | 0.1 | 0.1 | 5 | 60 | 15 ng/well Anti-P-MBP-Eu; 0.34 μg/well SAXL | Develop at 4° C. overnight |
| PKA (Invitrogen) | Catalytic subunit, human recombinant/ 43 kDa | Biotin-Bad-peptide | PKA buffer | 1.6 | 1 | 0.1 | 5 | 60 | 13.6 ng/well Anti-P-BAD-Eu; 0.17 μg/well SAXL | Develop at 4° C. overnight |
| PKC-alpha (UBI) | His-PKCα/ 78 kD | Biotin-cdc25-peptide | PKC buffer | 0.4 | 2 | 0.1 | 5 | 60 | 1.8 ng/well Anti-P-14-3-3 binding motif-Eu; 0.11 μg/well CR130-100 | Develop at RT 10 min |
| PKC-delta (UBI) | His-PKCδ/ 77.5 kD | Biotin-cdc25-peptide | PKC buffer | 1.5 | 1 | 0.1 | 5 | 60 | 1.8 ng/well Anti-P-14-3-3 binding motif-Eu; 0.11 μg/well CR130-100 | Develop at RT 10 min |
| PRAK (UBI) | His-PRAK/ 54 kD | Biotin-MBP protein (UBI) | MK2 buffer | 40 | 1 | 0.1 | 5 | 60 | 29.2 ng/well Anti-P-MBP-Eu; 0.67 μg/well SAXL | Develop at 4° C. overnight |

-continued

| Enzyme | Construct/Mw | Substrate | Assay Buffer | Enzyme Conc. (ng/well) | Substrate Conc. (μM) | ATP Conc. (mM) | DMSO Conc. (%) | Reaction Time (min) | Detection condition | Comments |
|---|---|---|---|---|---|---|---|---|---|---|
| Raf-1 (UBI) | Full length human recombinant Raf-1/74 kD | Unactive MEK1 Unactive Erk2 Biotin-MBP protein (all from UBI) | COT Buffer | 0.1 U/well | 7.5 ng/well MEK1 60 ng/well Erk2 0.12 μM Biotin-MBP | 0.1 | 5 | 60 | 15 ng/well Anti-P-MBP-Eu; 0.34 μg/well SAXL | Develop at 4° C. overnight |
| SGK1 (UBI) | His-SGK1 (1-60a.a. deleted, S422D) | Biotin-Bad-peptide | MK2 buffer | 0.3 | 4 | 0.1 | 5 | 60 | 13.6 ng/well Anti-P-BAD-Eu; 0.17 μg/well SAXL | Develop at 4° C. overnight |
| cTAK1 (UBI) | Full length/ 90 kDa | Biotin-cdc25-peptide | COT Buffer | 30.5 | 4 | 0.1 | 5 | 60 | 1.8 ng/well Anti-P-14-3-3 binding motif-Eu; 0.11 μg/well CR130-100 | Develop at RT 10 min |

Reaction Buffers:
COT Buffer:
50 mM Tris-HCl, pH7.5; 10 mM MgCl$_2$; 1 mM EGTA; 2 mM DTT; 0.01% Brij; 5 mM Beta-phosphoglycerol
MK2 Buffer:
20 mM MOPS, pH7.2; 10 mM MgCl$_2$; 5 mM EGTA; 5 mM Beta-phosphoglycerol; 1 mM Na$_3$VO$_4$; 0.01% Triton-X-100; 1 mM DTT
Akt Buffer:
20 mM HEPES, pH7.5; 10 mM MgCl$_2$; 0.01% Triton X-100; 1 mM DTT
CKII Buffer:
20 mM Tris, pH7.5; 10 mM MgCl$_2$; 10 mM KCl; 0.01% Triton-X-100; 1 mM DTT; 0.5 mM Na$_3$VO$_4$
PKA Buffer:
25 mM HEPES, pH7.4; 10 mM MgCl$_2$; 0.01% Triton-X-100; 0.5 mM DTT; 0.1 mM Na$_3$VO$_4$
PKC Buffer:
20 mM MOPS, pH7.2; 10 mM MgCl$_2$; 5 mM EGTA; 1.2 mM DTT; 0.01% Triton-X-100; 10 mM Beta-phosphoglycerol; 1.2 mM N$_a$3VO$_4$; 0.1 mg/mL phosphatidylserine; 0.01 mg/mL diacylglycerol; 0.5 mM CaCl$_2$
Substrates:
Biotin-IκBα-peptide: Biotin-Ahx-LDDRHDS-GLDSMKDC-amide
Biotin-Bad-peptide: Biotin-EELSPFRGRSRSAPPNL-WAAQR-amide
Biotin-CKII-substrate-peptide: Biotin-Ahx-RRADDSD-DDDD-amide
Biotin-cdc25-peptide: Biotin-Ahx-AKVSRSGLYR-SPSMPENLNRPR
Biotin-MEK-peptide: biotin-AGAGSGQLIDSMANS-FVGTR
Biotin-MBP protein, GST-unactive MEK1, unactive Erk2 were all purchased from UBI
Detection Reagents:
Anti-P-MBP was purchased from UBI, labeled by Cis-Bio International
Anti-P-MEK, Anti-P-BAD, Anti-P-IκBα, Anti-P-Erk were all purchased from Cell-Signaling, and labeled by Cis-Bio International
Anti-P-14-3-3 Binding Motif was purchased from Cell-Signaling, labeled by Perkin Elmer
SAXL was purchased from Prozyme
CR130-100 was purchased from Perkin Elmer
Anti-GST-XL was purchased from Cis-Bio International
Cellular Assays
HSP27 Cellular Assay in THP-1 Cells
THP-1 cells were serum starved (0.5% FBS) for about 24 hours and seeded to 96 well plates at a density of 2×10$^5$ cells/well in 100 ul of low serum media. Test compounds were solubilized in DMSO and added to cells over the range of 25 uM-8 nM (final DMSO conc 0.5%). Compounds were pre-incubated for about 30 mins. before the addition of 1 ug/ml LPS. Cells were stimulated for about 45 mins., washed and lysed in 100 ul of Biorad cell lysis buffer. Level of HSP27 phosphorylation was measured via Bio-Plex phosphoprotein assay utilizing pHSP27 Beadmates from Upstate.
LPS Induced TNF in THP-1 Cells
Thp-1 cells were serum starved (0.5% FBS) for about 24 hours and seeded to 96 well plates at a density of 2×10$^5$ cells/well in 100 ul of low serum media. Test compounds were solubilized in DMSO and added to cells over the range of 25 uM-8 nM (final DMSO conc 0.5%). Compounds were pre-incubated for 30 mins before the addition of 1 ug/ml LPS. Cells were stimulated for about 3 hrs. Supernatant media was removed and TNF release was quantified by ELISA. Cellular toxicity was determined by the addition of MTT to the remaining cells.
L PS Induced TNF in Peripheral Blood Mononuclear Cell (PBMC) Assay Protocol:
Prepare PBMC's from leukopak's by Ficoll separation. Adjust the cell density to 1×10$^7$ cells/ml in media.
Media used is RPMI Medium 1640 (Gibco BRL, Grand Island, N.Y., Catalog Number 31800)+2% human AB sera (Sigma Chemical Company, St. Louis, Mo., Catalog Number S7148, heat inactivated) with 100 U/ml penicillin (Gibco BRL, Catalog Number 15140), 2 mM L-glutamine (Gibco BRL, Catalog Number 25030), 1×MEM Non-Essential Amino Acids (Gibco BRL, Catalog Number 11140), and 10 mM pH 7.3 Hepes. Media is filtered through a 0.2-micron filter unit.
To the wells of 96 well plate(s) apply: 100 uL/well inhibitors (at 2× concentrations) in 1% Dimethyl Sulphoxide, 99% media+100 uL/well PBMC's (1E6 cells/well.)
Pre-incubate cells and inhibitors (test compounds) in 37° C. CO$_2$ incubator for about 30 minutes.
Apply 10 ng/ml Lipopolysaccharide *Escherichia coli* (Calbiochem, La Jolla, Calif., Catalog Number 437625) and incubate plate(s) overnight (about 16 hours) in a 37° C. $CO_2$ incubator to stimulate cytokine production.

Harvest supernates for cytokine analysis: Spin plate(s) in a centrifuge at 180 g for about 10 minutes with no brake to pellet cells (we used a Beckman GPKR centrifuge and spin at 1,000 rpm.) Remove 100 uL/well supernate for cytokine analysis.

For hTNF ELISA, use R&D Systems Catalog Number DTA50 kits and dilute samples about ½0.

After supernates are harvested, cells are used for MTT Assay to assess compound toxicity.

PBMC MTT Assay to Assess Cellular Toxicity:

MTT is converted into a colored product when it is cleaved by the mitochondrial reductase system, which is present in metabolically active cells. The MTT Assay can be used as a measure of cellular viability.

Follow the LPS induced TNF Peripheral Blood Mononuclear Cell (PBMC) Assay Protocol and harvest supernates for cytokine analysis. Use the remaining PBMC's in 96-well plates for the MTT Assay.

To cells (in about $1 \times 10^6$ cells/100 uL/well) apply 50 µL/well MTT (2.5 mg/ml in D-PBS, 3-[4,5-dimethylthiazol-2-yl]-2,5-diphenyl-tetrazolium bromide, Sigma Chemical Company, Catalog Number M-2128) and incubate for 4 hours in a 37° C. $CO_2$ incubator.

Apply 50 µL/well of 20% Sodium Dodecyl Sulfate (Natriumlauryl-sulfat, BioRad, Hercules, Calif., Catalog Number 161-0301) and incubate in a 37° C. $CO_2$ incubator overnight. Read the absorbance at 570 nM-630 nM in an ELISA plate reader. The percent viability of cells is then calculated. Toxicity from putative inhibitor(s) is determined by comparison to a control without inhibitor. This is the 100% viable control (1% DMSO/media+cells+MTT+SDS.) OD570/630 of sample/OD570/630 of 100% viable control X 100=% viability of sample.

LPS Induced TNF in PECs

Collect PEC's (peritoneal exudated cells) by washing the peritoneal cavity of B6 mice injected 4 days prior with 2 ml of 3% thioglycollate IP.

Wash cells with D-PBS and plate $2.5 \times 10^5/0.25$ ml/well in 96 well plates in 10% FBS RPMI media supplemented with Penicillin-Streptomycin and 2 mM L-Glutamine. Grow cells overnight in 37° C. $CO_2$ incubator. Pre-incubate cells and inhibitors in 1% DMSO/media 0.5% FBS for about 30 minutes. Apply Lipopolysaccharide *Escherichia coli* (1 µg/ml, Calbiochem, La Jolla, Calif., Catalog Number 437625) and stimulate cells 2 hours in 37° C. $CO_2$ incubator.

Harvest supernates for cytokine analysis:

Spin plate(s) in a centrifuge at 180 g for about 10 minutes with no brake to pellet cells.

Remove 50 µL/well supernate for cytokine analysis.

To measure mTNFcytokine levels, use R & D Systems Catalog Number MTA00 ELISA kits. Calculate $TNFIC_{50}$.

LPS Induced TNF and IL-1β in Differentiated Human Peripheral Blood Mononuclear Cells (PBMC)

PBMCs are prepared from leukopaks and stored frozen in vials in liquid nitrogen freezer.

Thaw PBMCs and plate in 48 well plates at $2 \times 10^6$ cells per well in 400 µl media (RPMI+2% Hu ab serum+Penicillin/Streptomycin+L-glutamine+non-essential amino acids+Hepes+50 ng/ml Recombinant Human MCSF). Incubate 24 h at 37° C. 5% $CO_2$. Wash cells 3× with media (no MCSF). In separate 48 well plate, dilute compounds in Media+2% Hu ab serum. For compounds at 10 mM add 10 µl of the compound to 990 µl media then do 1:5 serial dilutions in Media+1% DMSO 200 µl+800 µl media.

Remove media from cells and add 250 µl of compound dilutions in duplicate wells of 48 well plates of cells. To negative and positive control wells, add 250 µl media+1% DMSO. Incubate for about 30 minutes 37° C. 5% $CO_2$. Stimulate cells with 10 ng/ml LPS for 3 h 30' at 37° C. 5% $CO_2$. LPS stock 500 µg/ml: dilute stock 1:5000 in media then add 25 µl to each well except negative controls which get media alone. Incubate for about 3 hours 30 minutes at 37° C. 5% $CO_2$.

Add Nigericin (Sigma Cat. # N-7143 FW=747):

(Nigericin Final concentration=20 µM: dissolve 2.7 mg in 805 µl ethanol. Dilute this 1:8 in media 250 µl to 1.75 ml. Add 10 µl/well of 48 well plates.) Incubate 30 minutes 37° C. 5% $CO_2$. After 30 minutes, remove supernatant to 96 well plates and assay human IL-1β and human TNFα using R & D Systems ELISA Kits.

Compounds of formula I may have therapeutic utility in the treatment of diseases involving both identified, including those not mentioned herein, and as yet unidentified protein tyrosine kinases which are inhibited by compounds of formula I. All compounds exemplified herein significantly inhibit either COT or MK2 at concentrations of 50 micromolar or below.

In Vivo Models

In Vivo Inhibition of LPS-Induced Cytokines

Mice are injected i.v. with LPS (from *Escherichia coli* Serotype 0111:B4, Sigma #L-4130), dissolved in saline. In order to monitor TNF-α production, 0.1 mpk LPS is given and to measure IFN-γ, IL-1β, IL-18, IL-6, and L-12, 5mpk LPS is given. The mice are then cardiac bled for serum at the appropriate time points listed below. The animals are bled at 90 minutes for TNF-α or at 4 hours for IFN-γ, IL-1β, IL-18, IL-6, IL-12, then the serum cytokine levels are measured by ELISA. In compound efficacy studies, the compound is dosed either p.o. or i.p. one hour prior to the LPS injection and the levels of target cytokines are measured and compared with those obtained for the control group in order to calculate $ED_{50}$ levels.

Compounds can also be tested in animal models of human disease. These are exemplified by experimental auto-immune encephalomyelitis (EAE) and collagen-induced arthritis (CIA). EAE models which mimic aspects of human multiple sclerosis have been described in both rats and mice (reviewed FASEB J. 5:2560-2566, 1991; murine model: Lab. Invest. 4(3):278, 1981; rodent model: J. Immunol 146(4):1163-8, 1991). Briefly, mice or rats are immunized with an emulsion of myelin basic protein (MBP), or neurogenic peptide derivatives thereof, and CFA. Acute disease can be induced with the addition of bacterial toxins such as *bordetella pertussis*. Relapsing/remitting disease is induced by adoptive transfer of T-cells from MBP/peptide immunized animals.

CIA may be induced in DBA/1 mice by immunization with type II collagen (J. Immunol: 142(7):2237-2243). Mice will develop signs of arthritis as early as ten days following antigen challenge and may be scored for as long as ninety days after immunization. In both the EAE and CIA models, a compound may be administered either prophylactically or at the time of disease onset. Efficacious drugs should reduce severity and/or incidence.

Certain compounds of this invention which inhibit one or more angiogenic receptor PTK, and/or a protein kinase such as lck involved in mediating inflammatory responses can reduce the severity and incidence of arthritis in these models.

The teachings of all references, including journal articles, patents and published patent applications, are incorporated herein by reference in their entirety.

The following examples are for illustrative purposes and are not to be construed as limiting the scope of the present invention.

Abbreviations

ACN Acetonitrile
Racemic-BINAP (±)-2,2'-Bis(diphenylphosphino)-1,1'-binaphthalene
(R)-BINAP (R)-(+)-2,2'-Bis(diphenylphosphino)-1,1'-binaphthalene
(S)-BINAP (S)-(−)-2,2'-Bis(diphenylphosphino)-1,1'-binaphthalene
Boc tert-Butoxycarbonyl
t-BuOH tert-Butyl alcohol
t-BuOK Potassium tert-butoxide
Cbz Benzyloxycarbonyl
DCC N,N'-Dicyclohexylcarbodiimide
DCM Dichloromethane
DIC N,N'-Diisopropylcarbodiimide
DIEA N,N-Diisopropylethylamine
DMA N,N-Dimethylacetamide
DME 1,2-Dimethoxyethane
DMF N,N-Dimethylformamide
DMFDMA N,N-Dimethylformamide dimethyl acetal
DMSO Dimethyl sulfoxide
DPPF 1,1'-Bis(diphenylphosphino)ferrocene
EDC 1-(3-Dimethylaminopropyl)-3-ethylcarbodiimide
$Et_2O$ Diethyl ether
$Et_3N$ Triethylamine
EtOAc Ethyl acetate
HATU O-(7-Azabenzotriazol-1-yl)-N,N,N',N'-tetramethyluronium hexafluorophosaphate
HBTU O-Benzotriazol-1-yl-N,N,N',N'-tetramethyluronium hexafluorophosaphate
HOAc Acetic acid
HOAT 1-Hydroxy-7-azabenzotriazole
HOBT 1-Hydroxybenzotriazole
HPLC High Performance Liquid Chromatography
KOAc Potassium acetate
LDA Lithium diisopropylamide
MP-carbonate Polymer bound tetraalkylammonium carbonate
PMB p-Methoxybenzyl
$PPh_3$ Triphenylphosphine
PPTS Pyridinium p-toluenesulfonate
i-PrOH 2-Propanol
RP Reverse Phase
$R_t$ Retention time
SEM 2-(Trimethylsilyl)ethoxymethyl
SEM-Cl 2-(Trimethylsilyl)ethoxymethyl chloride
Si-DCT Silica bound dichlorotriazine
TBAF tetra-n-Butylammonium fluoride
TBDMS tert-Butyldimethylsilane
TFA Trifluoroacetic acid
TFFH Fluoro-N,N,N',N'-tetramethylformamidinium hexafluorophosphate
THF Tetrahydrofuran
TMS Trimethylsilyl
XANTPHOS 9,9-Dimethyl-4,5-bis(diphenylphosphino) xanthene Synthetic Details Analytical data is defined either within the general procedures or in the tables of examples. Unless otherwise stated, all $^1H$ or $^{13}C$ NMR data were collected on a Varian Mercury Plus 400 MHz; chemical shifts are quoted in parts per million (ppm). High performance liquid chromatography (HPLC) analytical data are either detailed within the experimental or referenced to the table of HPLC conditions, using the lower case method letter, in Table 1.

TABLE 1

List of HPLC methods

| Method | HPLC Conditions |
|---|---|
| a | LC/MS (30% to 95% acetonitrile/0.01M aqueous ammonium acetate over 4.5 min at 0.8 mL/min; UV λ = 190-400 nm; Genesis C18, 3 μm, 30 × 4.6 mm column; ESI +ve/−ve) |
| b | RP-HPLC (5% to 85% acetonitrile/0.05M aqueous ammonium acetate, buffered to pH 4.5, over 20 min at 1 mL/min; UV λ = 254 nm; Hypersil C18, 100 Å, 5 μm, 250 × 4.6 mm column) |
| c | LC/MS (5% to 100% acetonitrile/5 mM ammonium acetate over 5 min at 2.0 ml/min; UV λ = 250-380 nm; Genesis C18,4 μm, 33 × 4.6 mm column; ESI +ve/−ve) |
| d | LC/MS (5% to 100% acetonitrile/5 mM ammonium acetate over 5 min at 2.0 ml/min; UV λ = 250-380 nm; Pecosphere C18, 3 μm, 33 × 4.6 mm column; ESI +ve/−ve) |
| e | LC/MS (30% to 95% acetonitrile/0.01M aqueous ammonium acetate over 2.0 min; 95% acetonitrile/0.01M aqueous ammonium acetate for 1.5 min at 1.0 mL/min; UV λ = 210-360 nm; Genesis C8, 4 μm, 30 × 4.6 mm column; ESI +ve/−ve) |
| f | LC/MS (10% to 40% acetonitrile/0.01M aqueous ammonium acetate over 4.0 min; 40% to 95% acetonitrile/0.01M aqueous ammonium acetate over 2.0 min; 95% acetonitrile/0.01M aqueous ammonium acetate for 1.0 min at 1.0 mL/min; UV λ = 210-360 nm; Genesis C8, 4 μm, 30 × 4.6 mm column; ESI +ve/−ve) |
| g | LC/MS (5% to 95% acetonitrile/0.01M aqueous ammonium acetate over 2.0 min; 95% acetonitrile/0.01M aqueous ammonium acetate for 1.5 min at 1.4 mL/min; UV λ = 210-360 nm; Genesis C8, 4 μm, 30 × 4.6 mm column; ESI +ve/−ve) |
| h | LC/MS (30% to 95% acetonitrile/0.01M aqueous ammonium acetate over 2.0 min; 95% acetonitrile/0.01M aqueous ammonium acetate for 3.5 min at 1.0 mL/min; UV λ = 190-400 nm; Genesis C8, 4 μm, 30 × 4.6 mm column; ESI +ve/−ve) |
| i | LC/MS (5% to 35% acetonitrile/0.01M aqueous ammonium acetate over 4.0 min; 35%-95% acetonitrile/0.01M aqueous ammonium acetate over 2 min; 95% acetonitrile/0.01 M aqueous ammonium acetate for 1.0 min at 1.0 mL/min; UV λ = 190-400 nm; Genesis C8, 4 μm, 30 × 4.6 mm column; ESI +ve/-ve) |
| J | RP-HPLC (5% to 100% acetonitrile/0.05M aqueous ammonium acetate, buffered to pH 4.5, over 10 min at 1 mL/min; UV λ = 254 nm; Hypersil C18, 100 Å, 5 μm, 250 × 4.6 mm column) |
| k | LC/MS (5% to 95% acetonitrile/5 mM aqueous ammonium acetate over 3.0 min; 95% to 100% acetonitrile/5 mM aqueous ammonium acetate over 0.7 min; 100% to 5% acetonitrile/5 mM aqueous ammonium acetate over 0.1 min; 5% acetonitrile/5 mM aqueous ammonium acetate for 0.2 min at 2.0 ml/min; λ = 250-380 nm; Pecosphere C18, 3 μm, 33 × 4.6 mm column; ESI +ve/-ve) |
| l | LC/MS (5% acetonitrile/0.01M aqueous ammonium acetate for 0.25 min; 5-95% acetonitrile/0.01M aqueous ammonium acetate over 2.5 min; 95% acetonitrile/0.01M aqueous ammonium acetate for 0.85 min; 95-5% acetonitrile/0.01M aqueous ammonium acetate over 0.15 min; 5% acetonitrile/0.01M aqueous ammonium acetate for 0.25 min at 1.0 mL/min; UV λ = 210-360 nm; Genesis C8, 4 μm, 30 × 4.6 mm column ESI +ve/-ve) |
| m | LC/MS (10% to 100% acetonitrile/0.1% aqueous trifluoroacetic acid over 3 min; hold at 100% acetonitrile for 1 min at 1.5 mL/min; ELSD; UV λ = 254 nm; Phenomenex Luna C8(2), 5 μm, 100 Å, 30 × 2.0 mm column; APCI +ve) $^1$MS data from flow injection ESI + experiment not the LC-MS method (ion not detected in LC-MS run) |

GENERAL PROCEDURES AND EXAMPLES

The general synthetic schemes that were utilized to construct the majority of compounds disclosed in this application are described below in (Schemes 1-25).

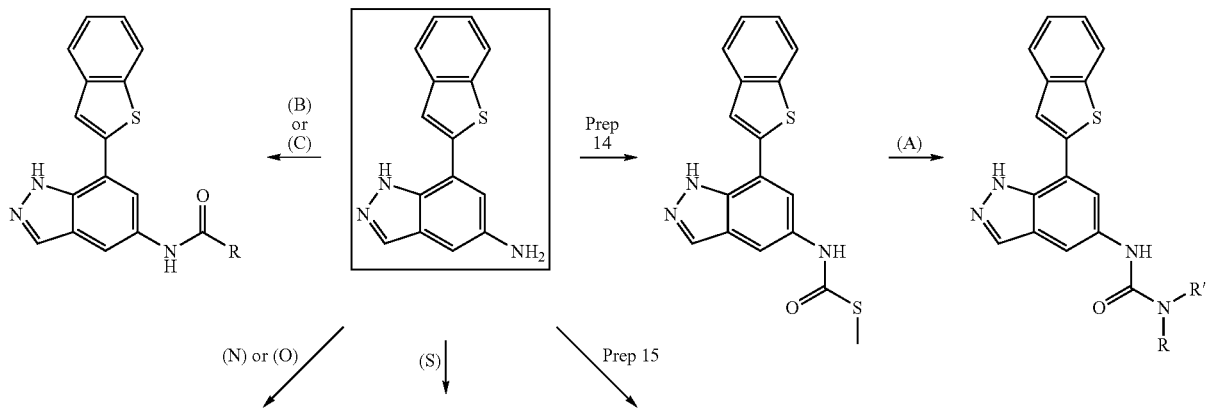

Scheme 1. General synthetic transformations of 7-benzo[b]thiophen-2-yl-1H-indazole (general procedures A, B, C, N, O, S, and W)

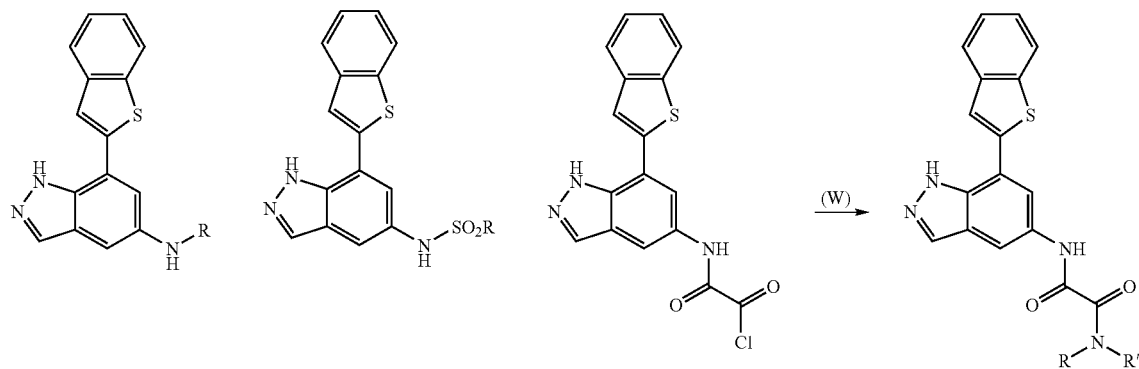

Scheme 2. Additional formations of an amide from a carboxylic acid and an amine (general procedure B)

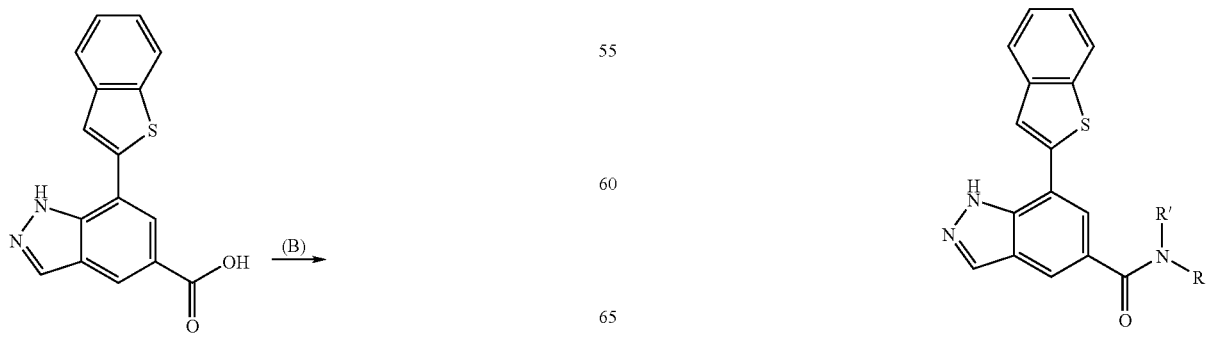

45
-continued
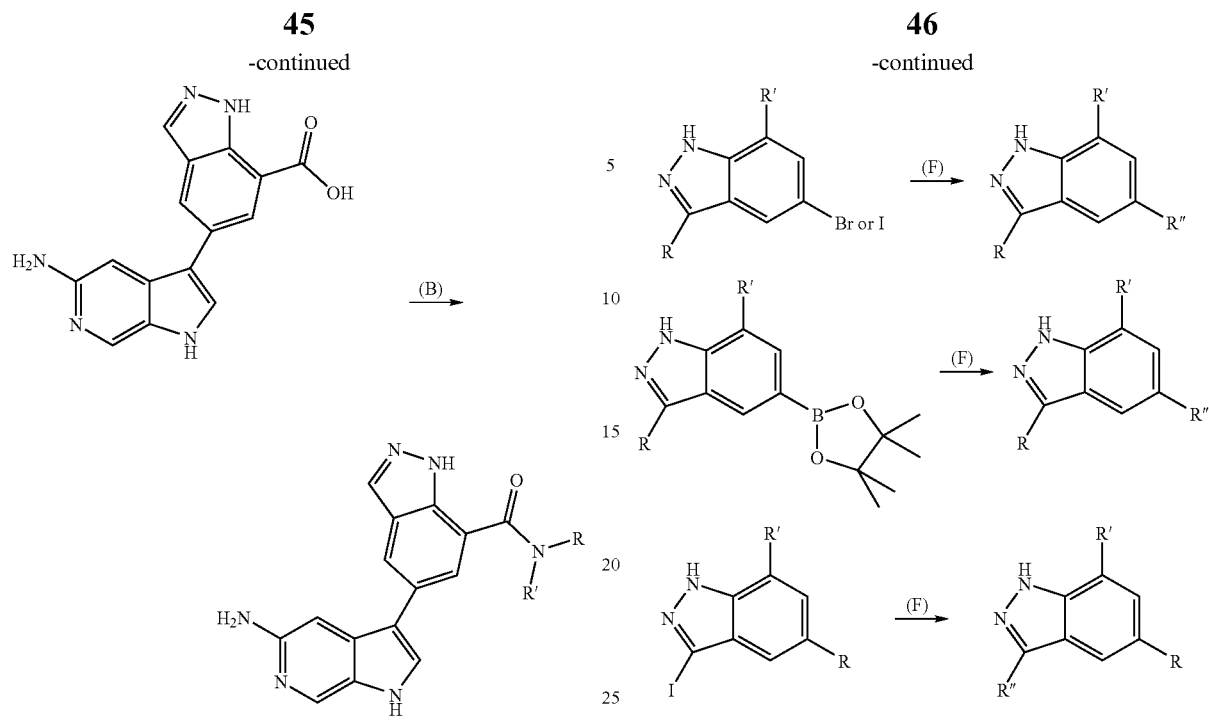
46
-continued
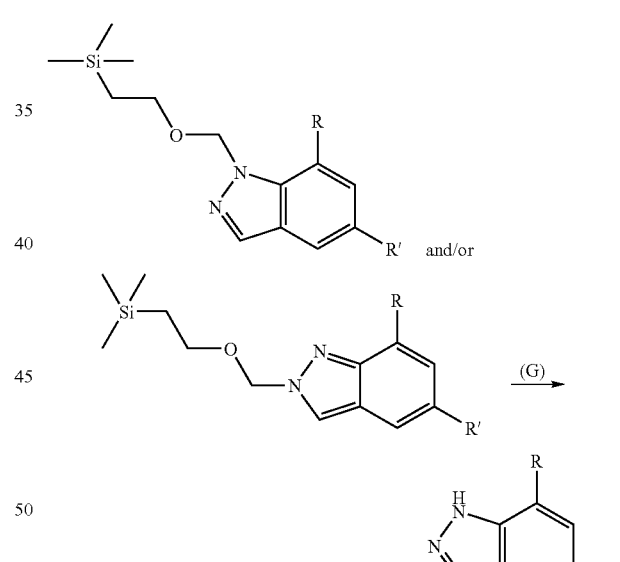
Scheme 3. Protection of an indazole with a trimethyl-silanylethoxymethyl group (general procedure D)
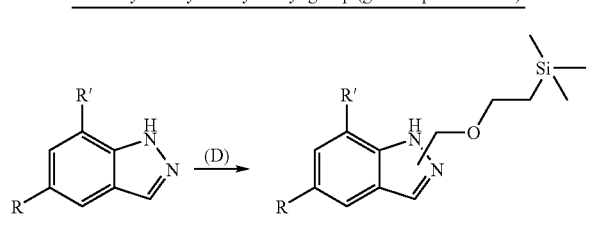
Scheme 4. Conversion of Conversion of a bromide to a boronic acid (general procedure E)
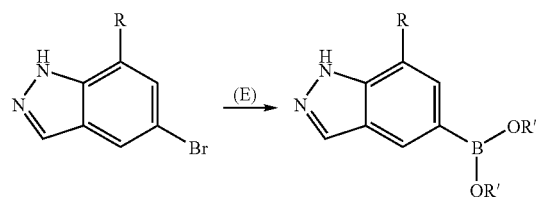
Scheme 5. General examples of Suzuki coupling of a boronate or boronic acid with an aryl halide substrate (general procedure F)
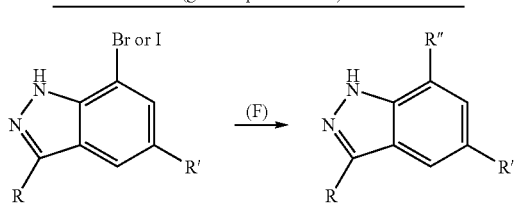

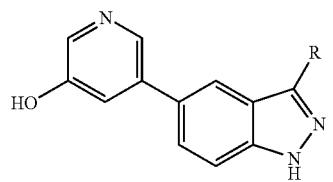

Scheme 8. Reduction of an aldehyde to an alcohol (general procedure J)

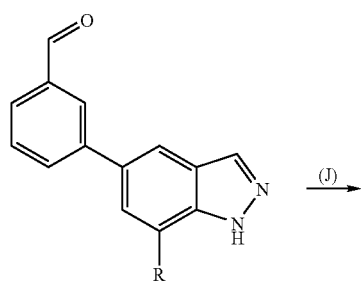

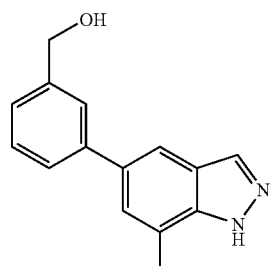

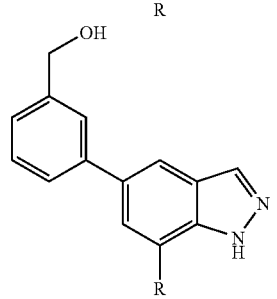

Scheme 9. Nucleophilic substitution of an aryl sulfone (general procedure K)

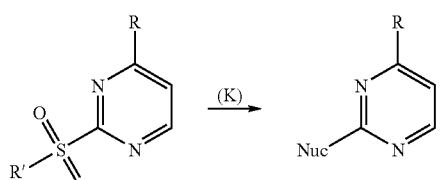

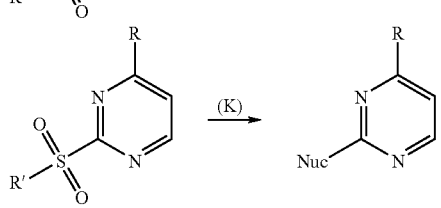

Scheme 10. Reduction of a nitroaromatic compound to an aniline (general procedure L)

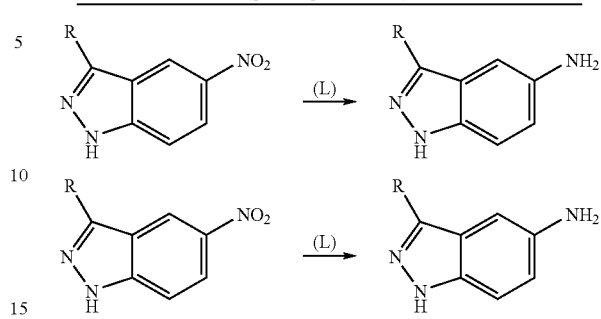

Scheme 11. Amide formation from an ester (general procedure M)

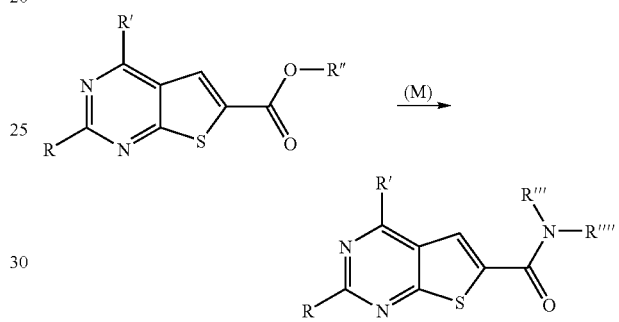

Scheme 12. Additional nucleophilic substitution of aromatic halide with amine (general procedure N)

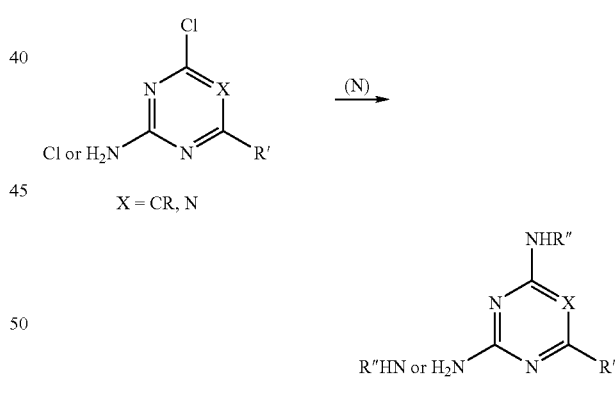

Scheme 13. General examples of reductive alkylations of an amine with an aldehyde or a ketone (general procedure O)

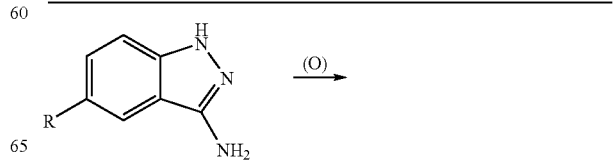

49
-continued
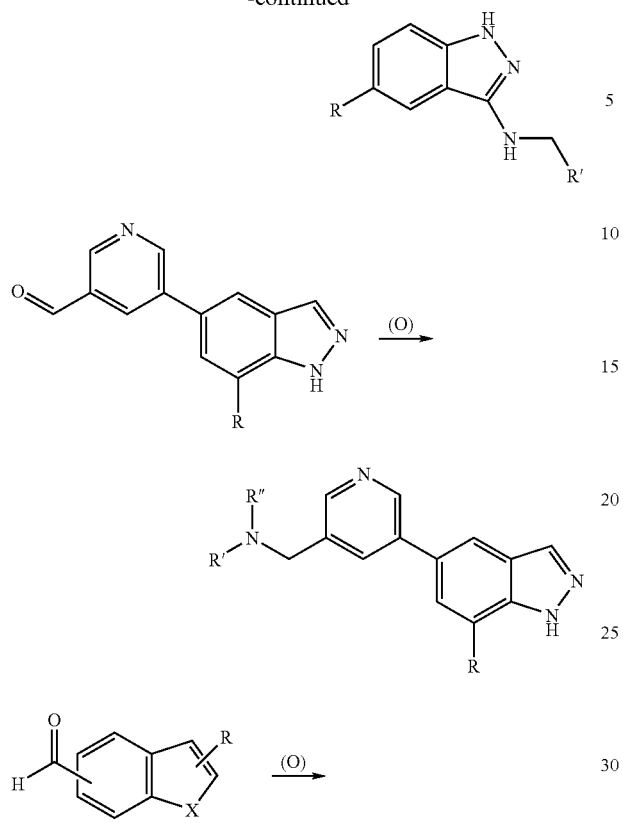
Scheme 14. Deprotection of a methyl-protected alcohol using boron tribromide (general procedure P)
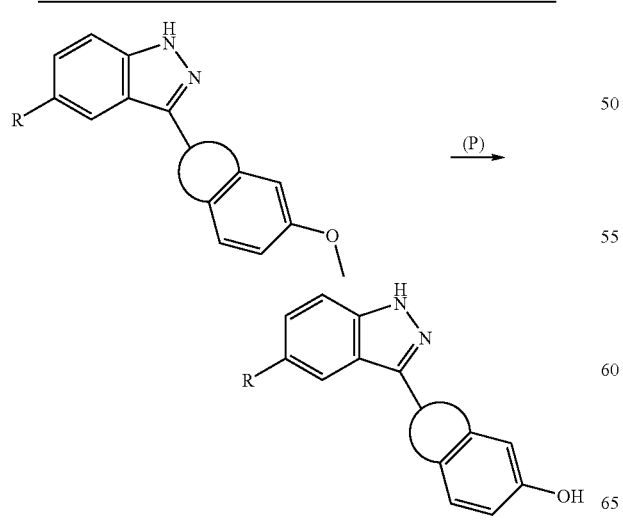
50
Scheme 15. General examples of acid catalyzed cleavage of carbamates (general procedure Q)
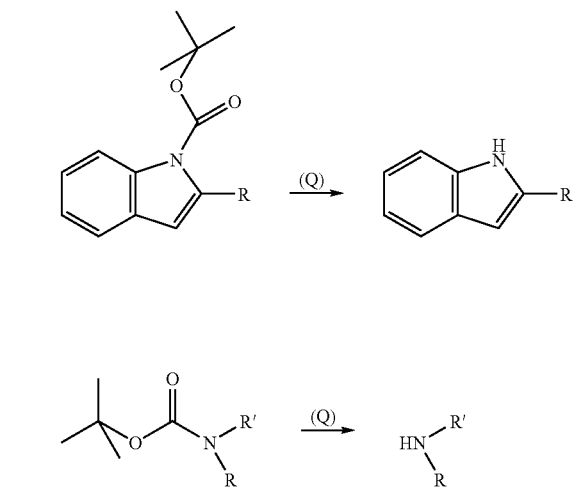
Scheme 16. Base-promoted amine alkylation (general procedure R)
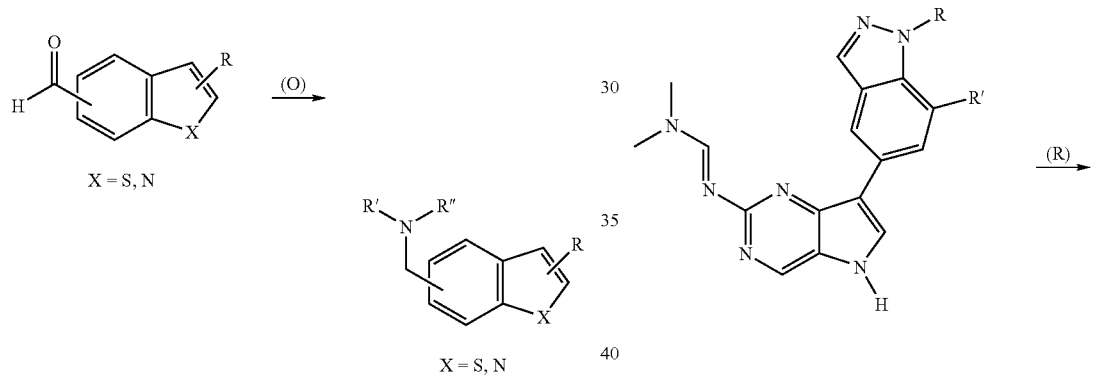
Scheme 17. Mitsunobu coupling of an alcohol (general procedure T)
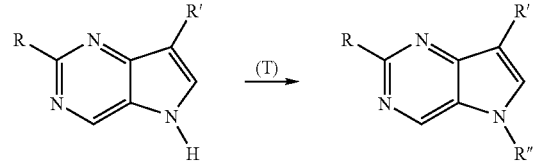

Scheme 18. General examples of Sonogashira couplings of a halide with acetylene compounds (general procedure U)

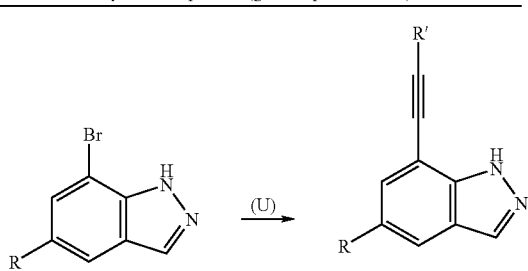

Scheme 19. General examples of hydrolysis of an ester to a carboxylic acid (general procedure V)

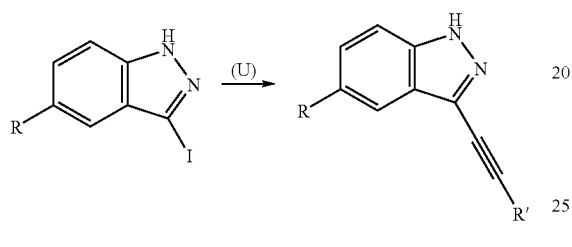

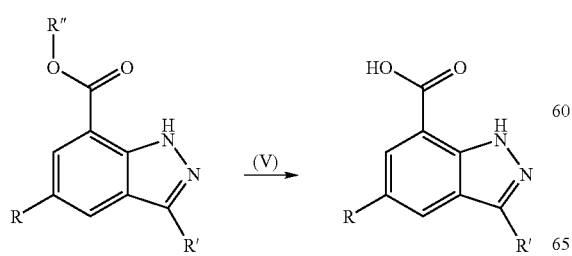

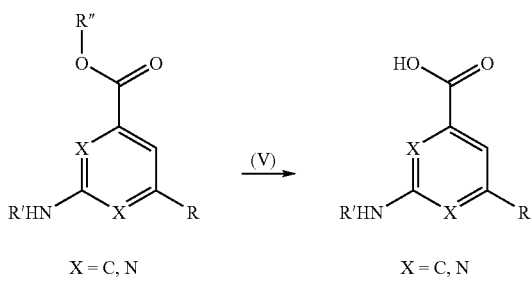

X = C, N

Scheme 20. General examples of amide coupling between an acid chloride and an amine (general procedure W)

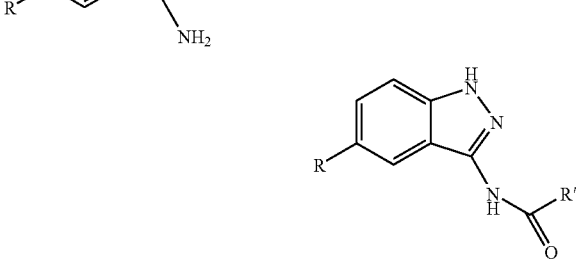

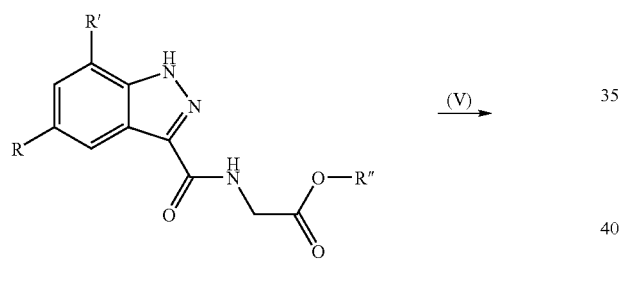

Scheme 21. Indazole formation with hydrazine (general procedure X)

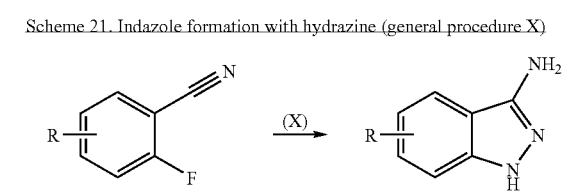

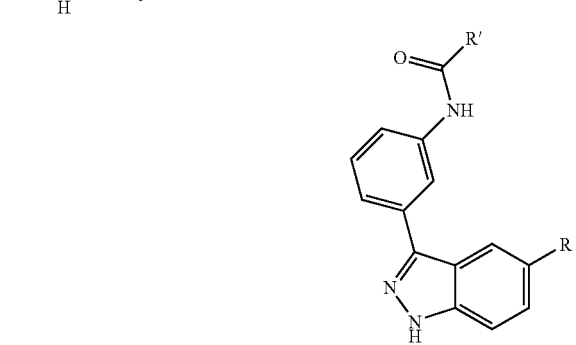

Scheme 22. General examples of Pd mediated couplings of an aryl halide with an amine followed by acid deprotection (general procedure Y)
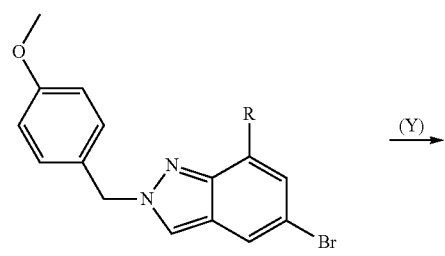
Scheme 24. Deprotection of a Cbz-protected amino group (general procedure AA)
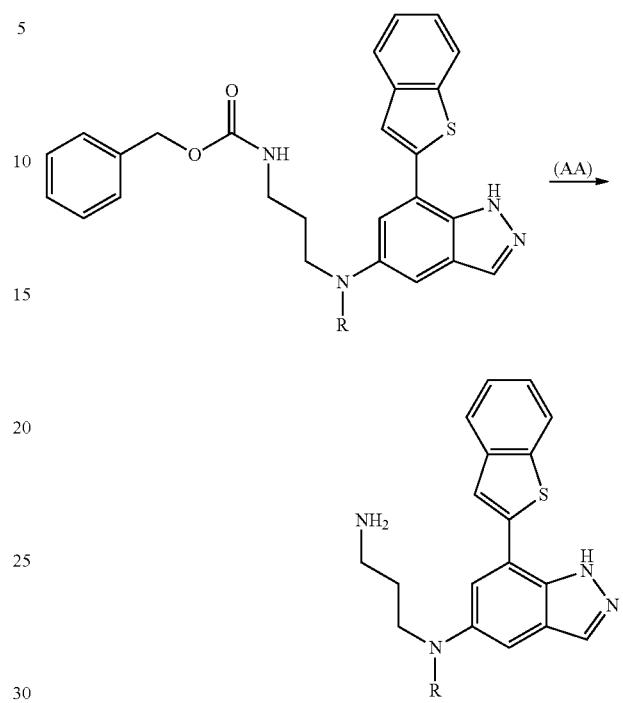
Scheme 23. Acid cleavage of a THP-protecting group (general procedure Z)
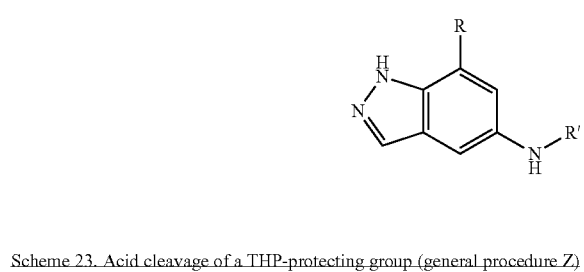
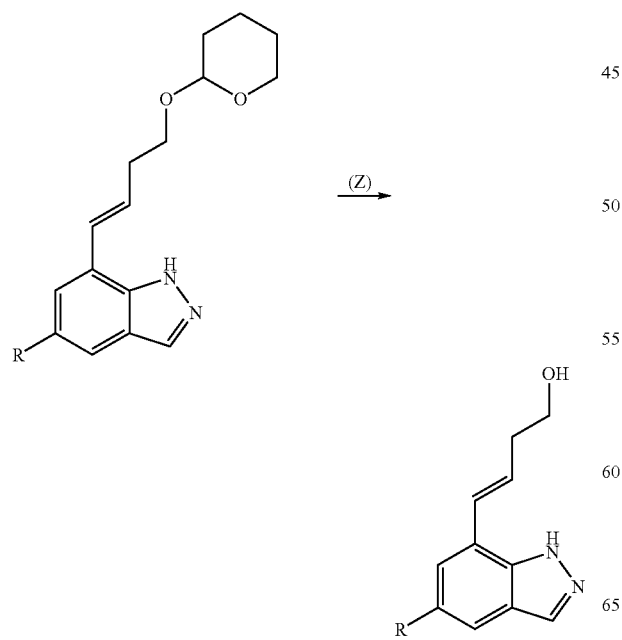
Scheme 25. Acid cleavage of a TBDMS-protected amino group (general procedure H)
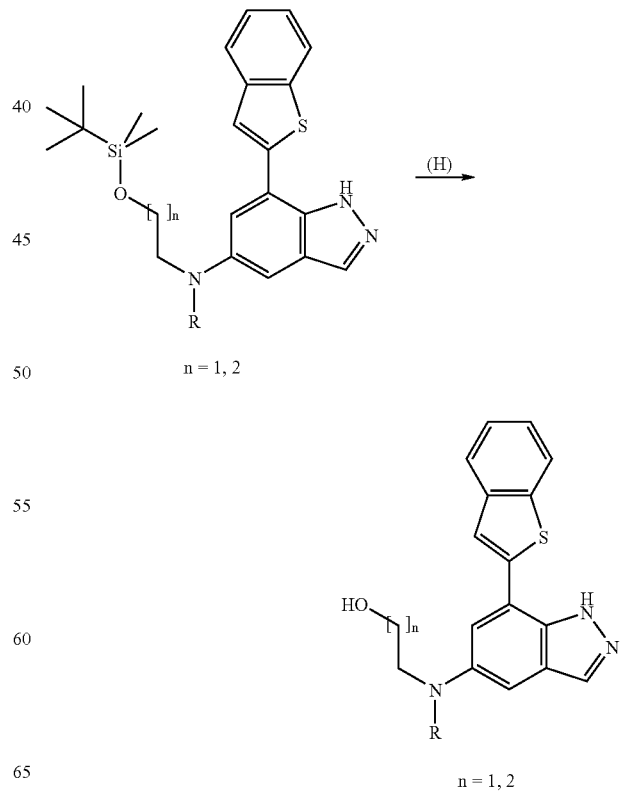

List of General Procedures
General Procedure A: Formation of a urea from an amine
General Procedure B: Formation of an amide from a carboxylic acid and amine
General Procedure C: Formation of an amide from a carboxylic acid and amine using Si-DCT
General Procedure D: Protection of an indazole with a trimethyl-silanylethoxymethyl group
General Procedure E: Conversion of a bromide to a boronic acid or boronate
General Procedure F: Suzuki coupling of a boronate or boronic acid with an aryl halide substrate
General Procedure G: Deprotection of a trimethylsilanylethoxymethyl (SEM) protected indazole
General Procedure H: Acid cleavage of a TBDMS-protecting group
General Procedure I: Deprotection of a benzyl ether
General Procedure J: Reduction of an aldehyde to an alcohol
General Procedure K: Nucleophilic substitution of an aryl sulfone
General Procedure L: Reduction of a nitroaromatic compound to an aniline
General Procedure M: Amide formation from an ester
General Procedure N: Nucleophilic substitution of an aromatic halide with amine
General Procedure O: Reductive Alkylation of an Amine with an Aldehyde or a Ketone
General Procedure P: Deprotection of a methyl-protected alcohol using boron tribromide
General Procedure Q: Acid catalyzed cleavage of esters, amidines, and carbamates
General Procedure R: Base-promoted amine alkylation
General Procedure S: Formation of a sulfonamide from an amine
General Procedure T: Mitsunobu coupling
General Procedure U: Sonogashira coupling of an aryl halide with an acetylene
General Procedure V: Hydrolysis of ester to a carboxylic acid
General Procedure W: Amide formation from an acid chloride and an amine
General Procedure X: Indazole formation using hydrazine
General Procedure Y: Pd mediated coupling of an aryl halide with an amine followed by acid deprotection
General Procedure Z: Acid cleavage of a THP-protecting group
General Procedure AA: Deprotection of a Cbz-protected amino group The general procedure letter codes constitute a synthetic route to the final product. A worked example of how the route is determined is given below using the synthesis of Example #G.19 as a non-limiting illustration. Example #G.19 was prepared from 2-(3-{2-(dimethylamino-methyleneamino)-7-[7-benzo[b]thiophen-2-yl-1-(2-trimethylsilanyl-ethoxymethyl)-1H-indazol-5-5-yl]-pyrrolo[3,2-d]pyrimidin-5-yl}-propan-1-oxy)tetrahydropyran using general procedure G, as represented in the following synthetic scheme:

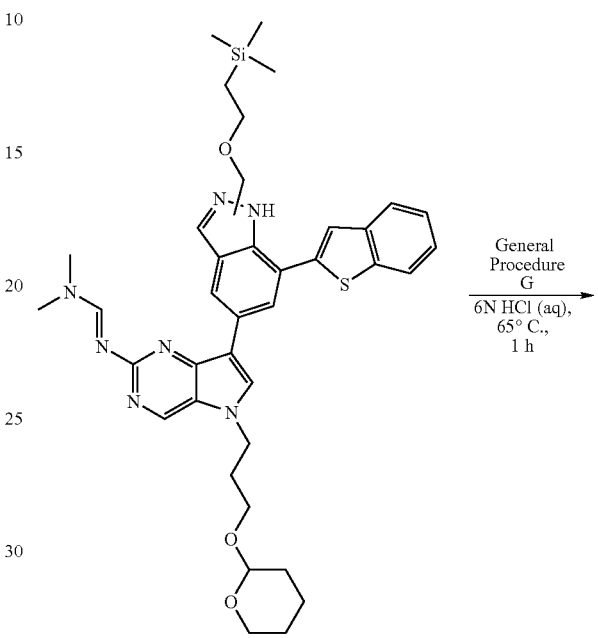

Precursor to Example #G. 19

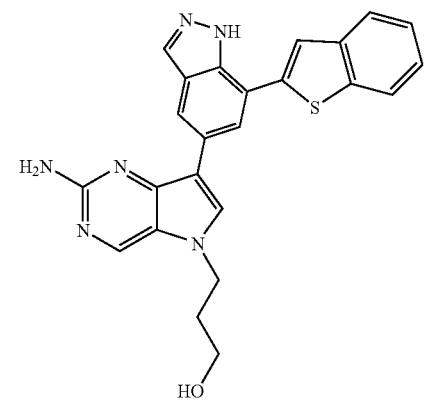

Example #G. 19

The precursor to Example #G.19, 2-(3-{2-(dimethylamino-methyleneamino)-7-[7-benzo[b]thiophen-2-yl-1-(2-trimethylsilanyl-ethoxymethyl)-1H-indazol-5-yl]-pyrrolo[3,2-d]pyrimidin-5-yl}-propan-1-oxy)tetrahydropyran was prepared via the noted reaction sequence: Preparation #23, E, F (using Preparation #4), R (using 2-(3-bromo-propan-1-oxy)tetrahydropyran, which translates into the following synthetic scheme:

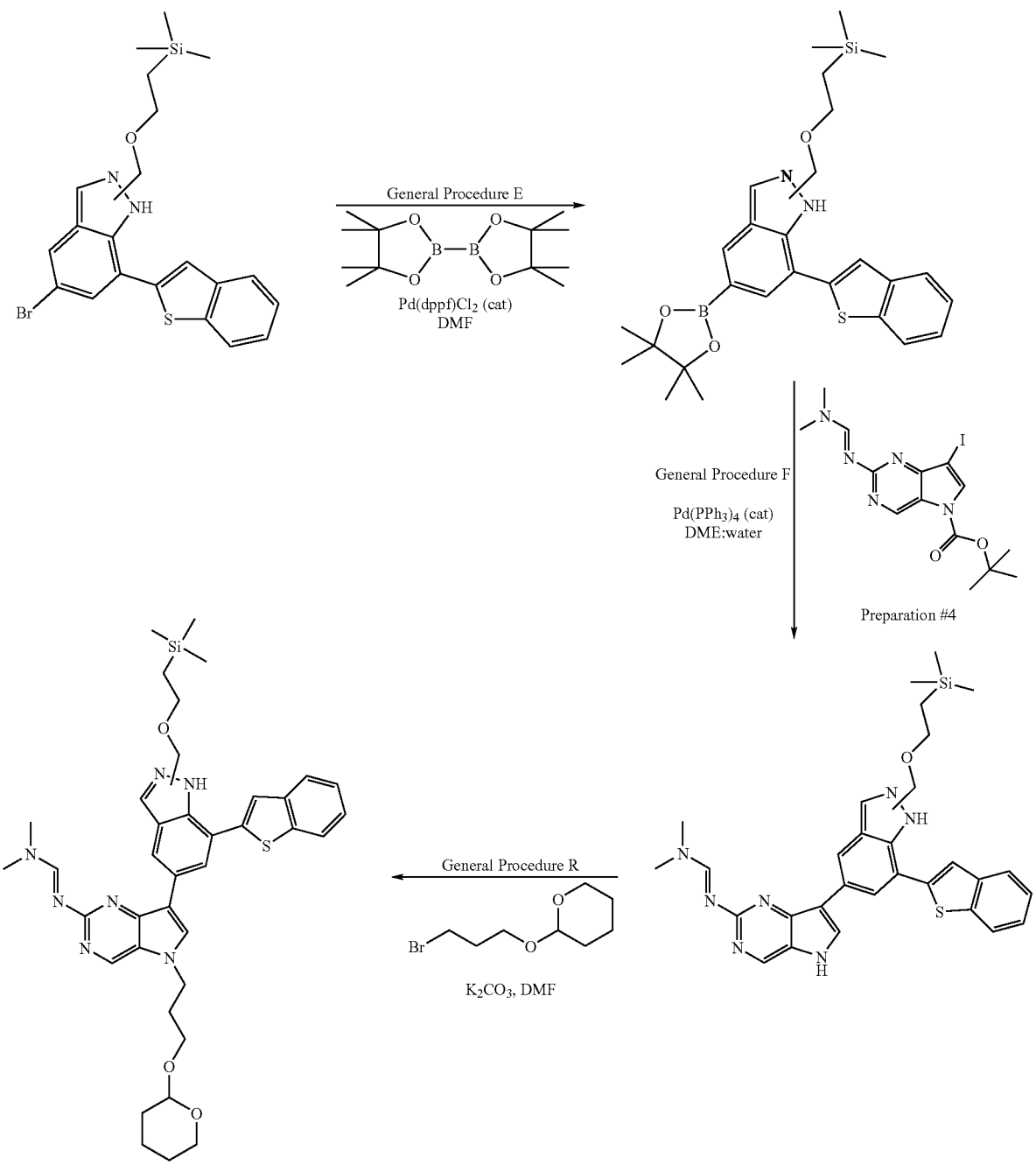

The general synthetic methods used in each General Procedure follow, and include an illustration of a compound that was synthesized using the designated General Procedure. None of the specific conditions and reagents noted in the following are to be construed as limiting the scope of the instant invention and are provided for illustrative purposes only.

General Procedure A: Formation of a Urea from an Amine

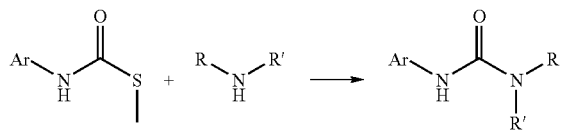

To a mixture of thiocarbamic acid methyl ester in an organic solvent (for example, methylene chloride or ethanol, preferably ethanol) is added an amine (2 to 4 equivalents, preferably 3 equivalents). The reaction mixture is stirred at about 40-70° C. (preferably about 50° C.) for about 3-24 hours (preferably, about 5-10 hours). The solvent is removed under reduced pressure to afford the crude product. The crude product can be further purified by crystallization or chromatography.

Illustration of General Procedure A

Example #11

1-(7-Benzo[b]thiophen-2-yl-1H-indazol-5-yl)-3-(2-pyridin-2-yl-ethyl)-urea

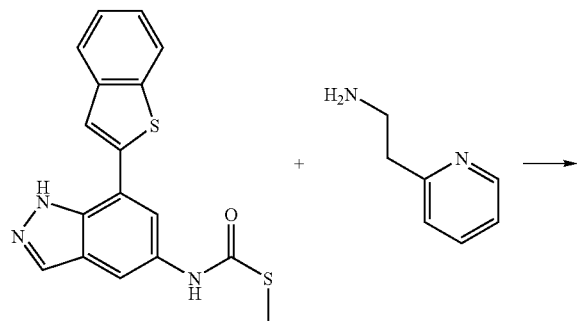

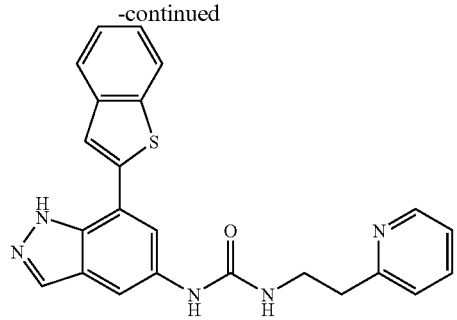

A mixture of 7-benzo[b]thiophen-2-yl-1H-indazole-5-yl-thiocarbamic acid methyl ester (Preparation #14, 25.0 mg, 0.074 mmol) and 2-pyridin-2-yl-ethylamine (23 mg, 0.185 mmol) in ethanol (2 mL) was stirred at about 50° C. for about 8 hours. The solvent was removed under reduced pressure and the product was purified by crystallization in ethanol to give 1-(7-benzo[b]thiophen-2-yl-1H-indazol-5-yl)-3-(2-pyridin-2-yl-ethyl)-urea (12 mg, 39% yield); RP HPLC (Table 1, Method e) $R_t$=1.82 min; MS m/z: (M–H)⁻ 412.

TABLE A

Examples synthesized using general procedure A from Preparation #14

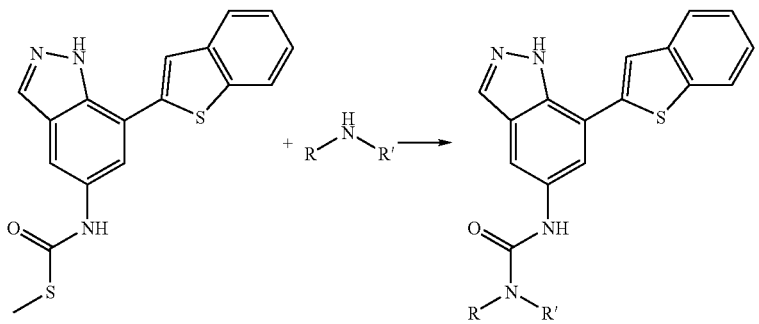

| Amine | Product | Example # | HPLC $R_t$(min)(Method) | m/z |
|---|---|---|---|---|
| 4-Nitroaniline | 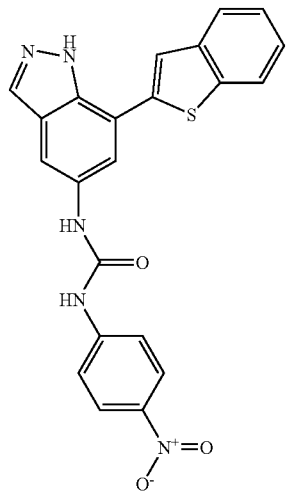 | A.1 | 2.21(a) | 558 (M – H)⁻ |

TABLE A-continued
Examples synthesized using general procedure A from Preparation #14
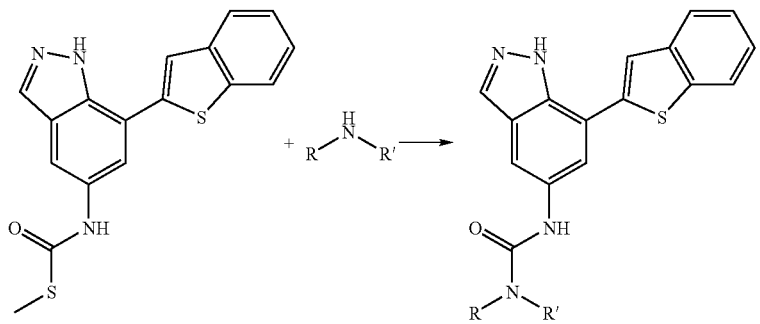
| Amine | Product | Example # | HPLC R$_t$(min)(Method) | m/z |
|---|---|---|---|---|
| 2-Piperidin-1-yl-ethylamine | | A.2 | 1.96(a) | 4.20 (M + H)$^+$ |
| 2-(1H-Imidazol-4-yl)-ethylamine | | A.3 | 1.63(a) | 403 (M + H)$^+$ |

TABLE A-continued

Examples synthesized using general procedure A from Preparation #14

| Amine | Product | Example # | HPLC R$_t$(min)(Method) | m/z |
|---|---|---|---|---|
| 2-Methoxy-ethylamine | | A.4 | 1.75(a) | 367 (M + H)$^+$ |
| N,N-Dimethyl-ethane-1,2-diamine | | A.5 | 1.75(a) | 380 (M + H)$^+$ |
| Tetrahydro-pyran-4-ylamine | | A.6 | 1.70(a) | 391 (M − H)$^−$ |

TABLE A-continued
Examples synthesized using general procedure A from Preparation #14
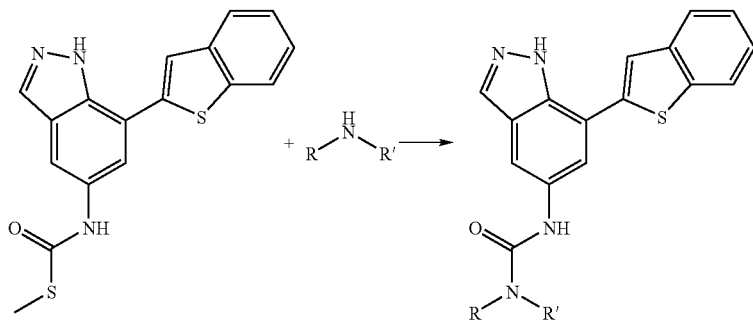
| Amine | Product | Example # | HPLC $R_t$(min)(Method) | m/z |
|---|---|---|---|---|
| 2-Pyridin-3-yl-ethylamine | | A.7 | 1.60(a) | 414 $(M + H)^+$ |
| 3-Amino-propan-1-ol | | A.8 | 1.50(a) | 367 $(M + H)^+$ |

TABLE A-continued
Examples synthesized using general procedure A from Preparation #14
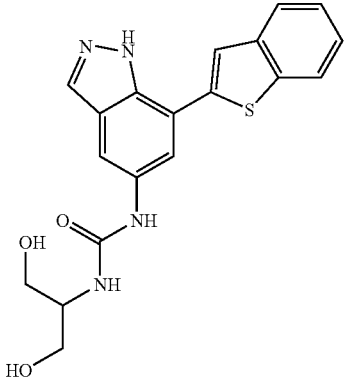
| Amine | Product | Example # | HPLC R$_t$(min)(Method) | m/z |
|---|---|---|---|---|
| 2-Amino-propane-1,3-diol | | A.9 | 1.32(a) | 383 (M + H)$^+$ |
| Pyridin-2-yl-methylamine | | A.10 | 1.75(a) | 400 (M + H)$^+$ |
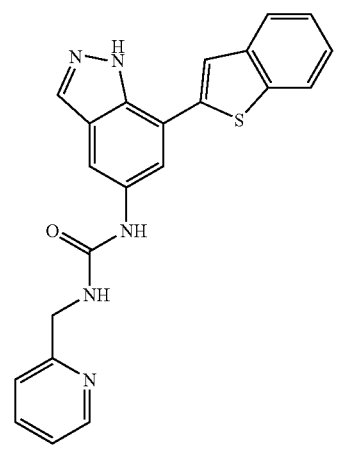

TABLE A-continued
Examples synthesized using general procedure A from Preparation #14
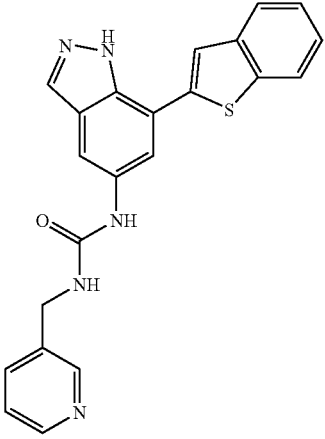
| Amine | Product | Example # | HPLC R$_t$(min)(Method) | m/z |
|---|---|---|---|---|
| Pyridin-3-yl-methylamine | 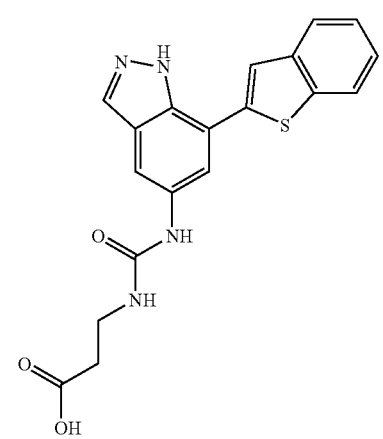 | A.11 | 1.71(a) | 400 (M + H)$^+$ |
| 3-Amino-propionic acid | | A.12 | 0.65(a) | 381 (M + H)$^+$ |

TABLE A-continued
Examples synthesized using general procedure A from Preparation #14
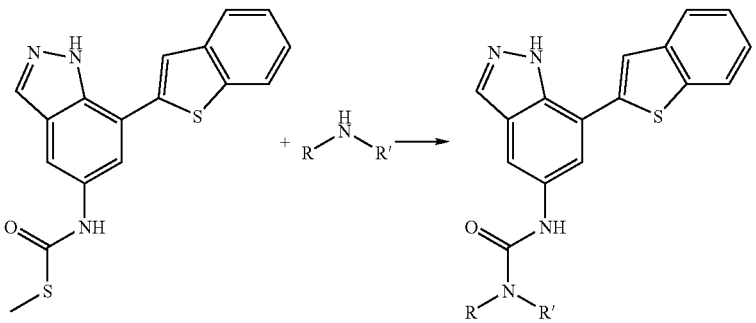
| Amine | Product | Example # | HPLC R$_t$(min)(Method) | m/z |
|---|---|---|---|---|
| 2-Amino-ethanol | 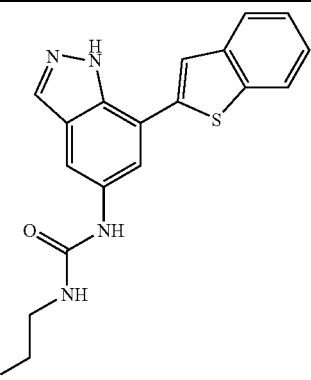 | A.13 | 1.42(a) | 383 (M + H)$^+$ |
| 1-Methoxy-but-2-ylamine | 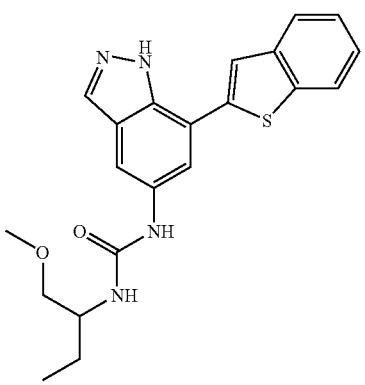 | A.14 | 1.93(a) | 393 (M − H)$^−$ |
| (5-Methyl-pyrazin-2-yl)-methylamine | 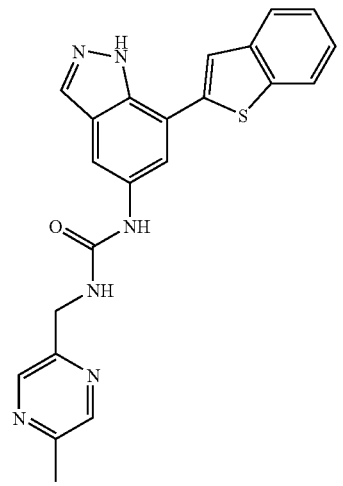 | A.15 | 1.71(a) | 415 (M + H)$^+$ |

TABLE A-continued
Examples synthesized using general procedure A from Preparation #14
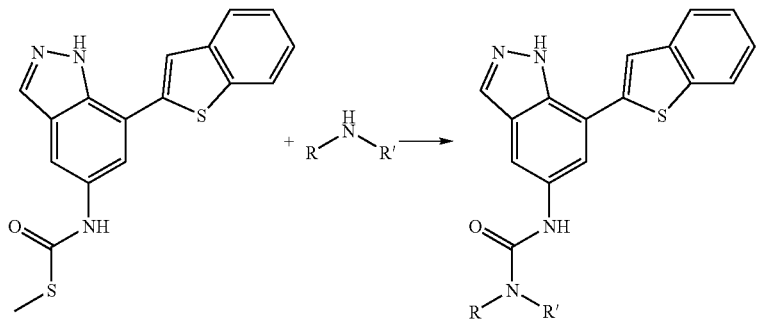
| Amine | Product | Example # | HPLC $R_t$(min)(Method) | m/z |
|---|---|---|---|---|
| 2-(1-Methyl-1H-pyrrol-2-yl)-ethylamine | 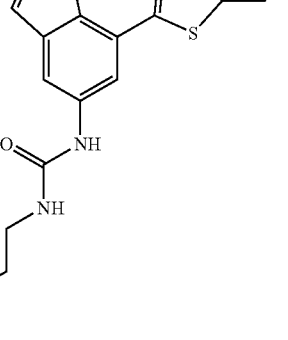 | A.16 | 2.05(a) | 416 (M + H)$^+$ |
| 2-Pyridin-4-yl-ethylamine | 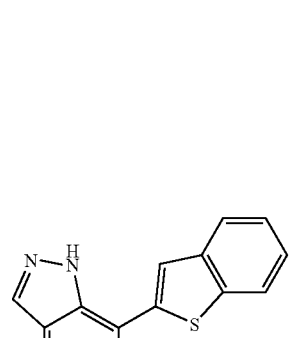 | 1.17 | 1.62(a) | 412 (M − H)$^-$ |

TABLE A-continued

Examples synthesized using general procedure A from Preparation #14

| Amine | Product | Example # | HPLC R$_t$(min)(Method) | m/z |
|---|---|---|---|---|
| (1,3,5-Trimethyl-1H-pyrazol-4-yl)-methylamine | | A.18 | 1.61(a) | 429 (M − H)$^-$ |
| 3-Amino-propionamide | | A.19 | 1.36(a) | 380 (M + H)$^+$ |

TABLE A-continued

Examples synthesized using general procedure A from Preparation #14

| Amine | Product | Example # | HPLC R$_t$(min)(Method) | m/z |
|---|---|---|---|---|
| (6-Chloro-pyridin-3-yl)-methylamine | | A.20 | 1.92(a) | 434 (M + H)$^+$ |
| 1-Pyridin-3-yl-ethylamine | | A.21 | 1.70(a) | 412 (M − H)$^-$ |

TABLE A-continued
Examples synthesized using general procedure A from Preparation #14
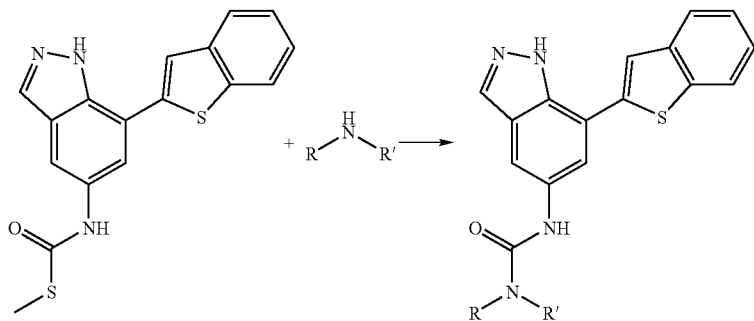
| Amine | Product | Example # | HPLC R$_t$(min)(Method) | m/z |
| --- | --- | --- | --- | --- |
| 1-Methyl-piperidin-4-ylamine | | A.22 | 1.78(a) | 404 (M − H)$^-$ |
| 2-Piperazin-1-yl-ethanol | | A.23 | 1.42(a) | 422 (M + H)$^+$ |

TABLE A-continued

Examples synthesized using general procedure A from Preparation #14

| Amine | Product | Example # | HPLC R$_t$(min)(Method) | m/z |
|---|---|---|---|---|
| Bis-(2-methoxy-ethyl)-amine | | A.24 | 2.09(a) | 425 (M + H)$^+$ |
| 1-Methyl piperazine | | A.25 | 1.62(a) | 392 (M + H)$^+$ |

TABLE A-continued

Examples synthesized using general procedure A from Preparation #14

| Amine | Product | Example # | HPLC R$_t$(min)(Method) | m/z |
|---|---|---|---|---|
| [2-(Thiophen-2-yl)-thiazol-4-yl]-methylamine | | A.26 | 2.09(a) | 488 (M + H)$^+$ |
| Benzothiazol-2-yl-methylamine | | A.27 | 2.00(a) | 456 (M + H)$^+$ |

TABLE A-continued

Examples synthesized using general procedure A from Preparation #14

| Amine | Product | Example # | HPLC R_t(min)(Method) | m/z |
|---|---|---|---|---|
| Oxazol-2-yl-methylamine | | A.28 | 1.65(a) | 388 (M − H)⁻ |
| Imidazo[1,2-α]pyridin-2-yl-methylamine | | A.29 | 1.69(a) | 437 (M − H)⁻ |

TABLE A-continued

Examples synthesized using general procedure A from Preparation #14

| Amine | Product | Example # | HPLC R$_t$(min)(Method) | m/z |
|---|---|---|---|---|
| Benzo[2,1,3]thiadiazol-5-yl-methylamine | | A.30 | 1.98(a) | 455 (M − H)$^-$ |
| 5-Aminomethyl-2H-[1,2,4]triazol-3-ylamine | | A.31 | 1.19(a) | 403 (M − H)$^-$ |

TABLE A-continued

Examples synthesized using general procedure A from Preparation #14

| Amine | Product | Example # | HPLC R$_t$(min)(Method) | m/z |
|---|---|---|---|---|
| 5-(2-Amino-ethyl)-2H-[1,2,4]triazol-3-ylamine | | A.32 | 1.22(a) | 419 (M + H)$^+$ |
| Morpholine | | A.33 | 1.79(a) | 379 (M + H)$^+$ |
| 2-Methylamino-ethanol | | A.34 | 1.50(a) | 367 (M + H)$^+$ |

TABLE A-continued
Examples synthesized using general procedure A from Preparation #14
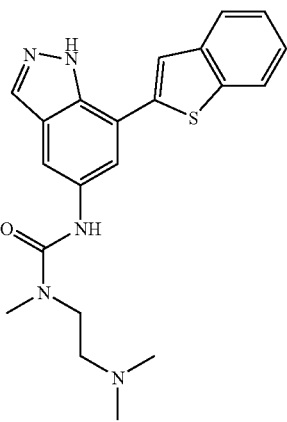
| Amine | Product | Example # | HPLC R$_t$(min)(Method) | m/z |
|---|---|---|---|---|
| N,N,N'-Trimethyl-ethane-1,2-diamine | | A.35 | 1.32(a) | 394 (M + H)$^+$ |
| N,N,N'-Trimethyl-propane-1,3-diamine | | A.36 | 1.37(a) | 408 (M + H)$^+$ |
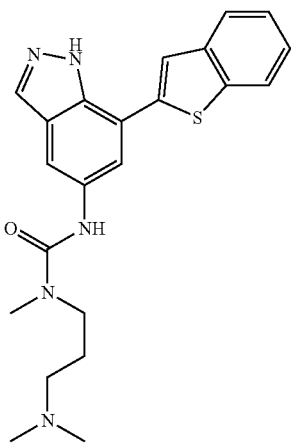

TABLE A-continued
Examples synthesized using general procedure A from Preparation #14
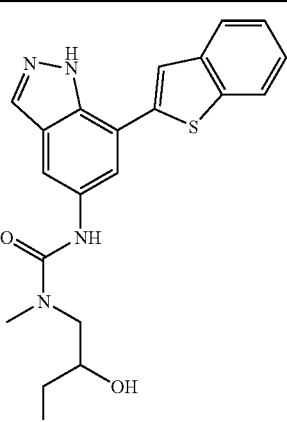
| Amine | Product | Example # | HPLC R$_t$(min)(Method) | m/z |
|---|---|---|---|---|
| 3-Methylamino-propane-1,2-diol | | A.37 | 1.38(a) | 397 (M + H)$^+$ |
| Piperidin-4-yl-methanol | | A.38 | 1.57(a) | 407 (M + H)$^+$ |

TABLE A-continued
Examples synthesized using general procedure A from Preparation #14
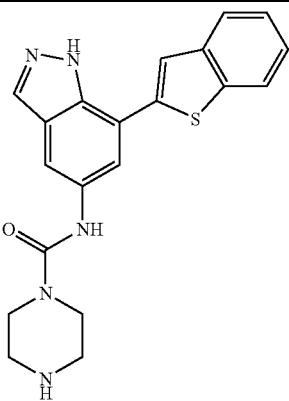
| Amine | Product | Example # | HPLC R$_t$(min)(Method) | m/z |
|---|---|---|---|---|
| Piperazine | 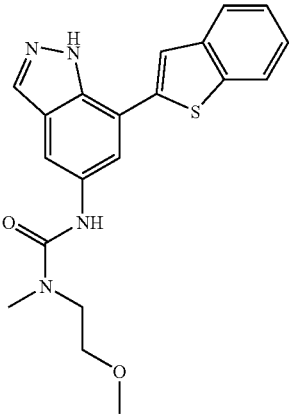 | A.39 | 1.14(a) | 378 (M + H)$^+$ |
| (2-Methoxy-ethyl)-methyl-amine | 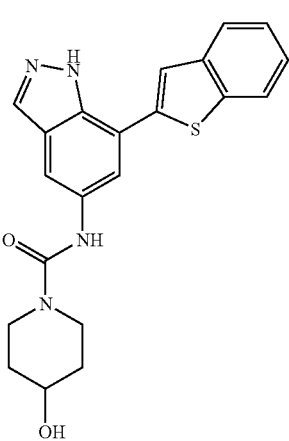 | A.40 | 1.92(a) | 381 (M + H)$^+$ |
| Piperidin-4-ol | | A.41 | 1.51(a) | 393 (M + H)$^+$ |

TABLE A-continued
Examples synthesized using general procedure A from Preparation #14
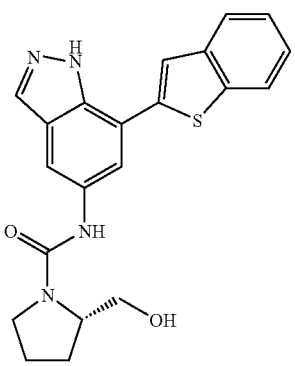
| Amine | Product | Example # | HPLC R$_t$(min)(Method) | m/z |
|---|---|---|---|---|
| (S)-1-Pyrrolidin-2-yl-methanol | 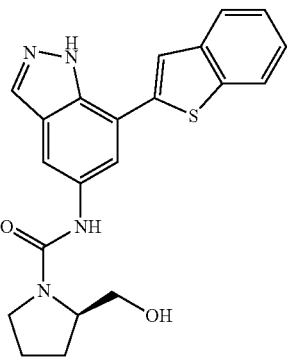 | A.42 | 1.71(a) | 393 (M + H)$^+$ |
| (R)-1-Pyrrolidin-2-yl-methanol | 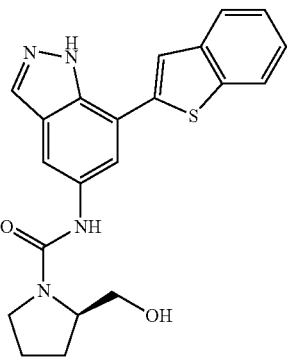 | A.43 | 1.71(a) | 393 (M + H)$^+$ |
| Bis-(2-ethanol)amine | 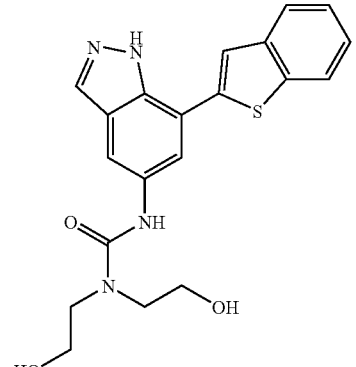 | A.44 | 1.46(a) | 397 (M + H)$^+$ |

TABLE A-continued
Examples synthesized using general procedure A from Preparation #14
| Amine | Product | Example # | HPLC R$_t$(min)(Method) | m/z |
|---|---|---|---|---|
| Ammonia | 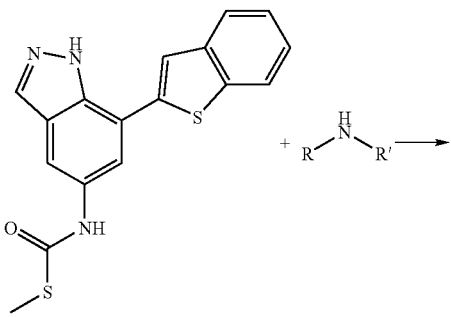 | A.45 | 1.42(a) | 309 (M + H)$^+$ |
| Methylamine | 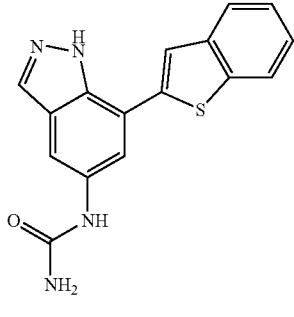 | A.46 | 1.67(a) | 323 (M + H)$^+$ |
| Dimethylamine | 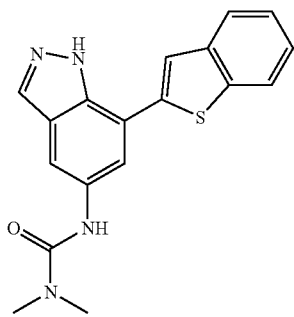 | A.47 | 1.78(a) | 335 (M − H)$^−$ |

TABLE A-continued

Examples synthesized using general procedure A from Preparation #14

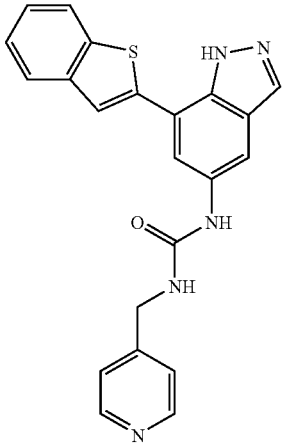

| Amine | Product | Example # | HPLC R$_t$(min)(Method) | m/z |
|---|---|---|---|---|
| Pyrid-4-yl methylamine | 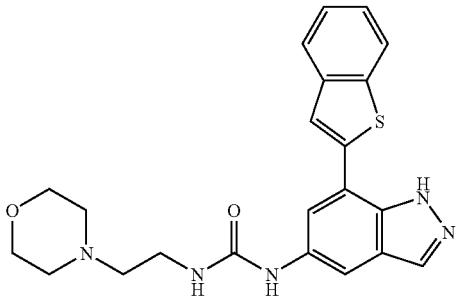 | A.48 | 1.67(a) | 400.0(M + H)$^+$ <br> 398.0(M − H)$^-$ |
| 4-(2-Aminoethyl) morpholine | 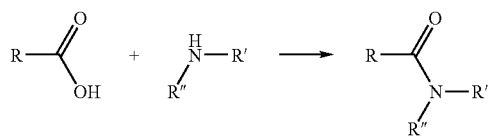 | A.49 | 1.57(a) | 422.0(M + H)$^+$ <br> 419.5(M − H)$^-$ |

General Procedure B: Formation of an Amide from Carboxylic Acid and Amine

To a mixture of a carboxylic acid (1-2.5 equivalents, preferably 1-1.5 equivalents) and an amine (1-2.5 equivalents, preferably 1-1.5 equivalents) in an organic solvent (for example, THF, EtOAc, Et$_2$O, or DMF, preferably DMF) is added the coupling reagent (for example, DCC, DIC, EDC, HBTU, HATU or TFFH, preferably HBTU) (1-5 equivalents, preferably 1.2 equivalents), with or without a coupling additive (for example, HOBT or HOAT, preferably HOBT) (0.1-5 equivalents, preferably 0.2 equivalents) and, optionally, DIEA (0.1-25 equivalents, preferably 3 equivalents). The reaction mixture is stirred at about 20-70° C. (preferably about 50° C.) for about 5-40 hours (preferably about 35 hours) and then cooled to ambient temperature. The reaction mixture can be purified in three different ways: 1). The reaction mixture is treated with MP-carbonate (3-10 equivalents, preferably 5 equivalents) with or without methanol. After about 4-48 hours (preferably about 14 hours), the reaction solution is separated from the resin by filtration and concentrated under reduced pressure to afford the crude product that can be further purified by crystallization or chromatography. If the product precipitates prior to filtration of the resin, the suspension containing the product is separated from the resin via pipette and filtered to afford the crude product that can be further purified by crystallization or chromatography. 2). The reaction mixture is partitioned between water and an organic solvent (for example, CH$_2$Cl$_2$, EtOAc or Et$_2$O, preferably $CH_2Cl_2$). The organic layer is separated and the aqueous layer is further extracted with organic solvent. The combined organic extracts are dried over a desiccant and evaporated under reduced pressure to afford the product that can be further purified by crystallization or chromatography. 3). The reaction mixture is directly concentrated under reduced pressure and the residue is purified by crystallization or chromatography.

Illustration of General Procedure B

Example #12

N-Benzyl 5-(5-Amino-1H-pyrrolo[2,3-c]pyridin-3-yl)-1H-indazole-7-carboxamide acetate

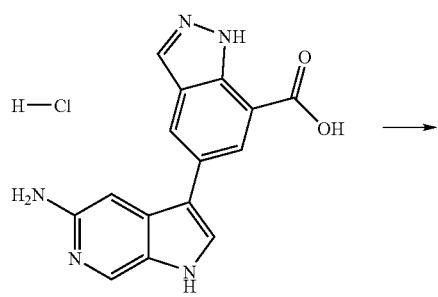

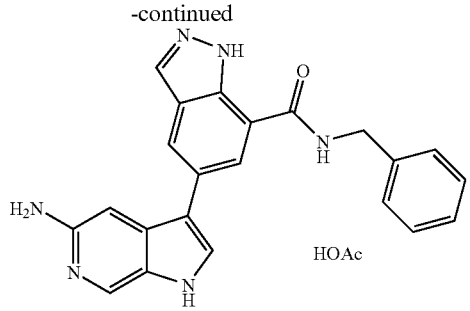

A solution of 5-(5-amino-1H-pyrrolo[2,3-c]pyridin-3-yl)-1H-indazole-7-carboxylic acid hydrochloride (Preparation #13, 32.9 mg, 0.10 mmol) and benzylamine (24.0 µL, 0.22 mmol) in DMF (1.0 mL) were treated with o-(7-azabenzotriazol-1-yl)-N,N,N',N'-tetramethyluronium hexafluorophosphate (38.0 mg, 0.10 mmol) at ambient temperature and the reaction was stirred for about 1 hour. The reaction was concentrated under reduced pressure and the residue was purified by preparative HPLC (Waters Symmetry C8 column (25×100 mm, 7 µm particle size) using a gradient of 10%-100% $CH_3CN/0.1\%$ aqueous TFA over 8 min (10 min run time) at a flow rate of 40 mL/min). Product fractions were combined and concentrated to remove organic solvents and then lyophilized to yield N-benzyl 5-(5-amino-1H-pyrrolo[2,3-c]pyridin-3-yl)-1H-indazole-7-carboxamide acetate (10 mg, 23%) as an off-white powder; RP-HPLC (Table 1, Method e) $R_t$ 1.94 min; m/z: $(M-H)^-$ 381.

TABLE B.1

Examples were prepared using general procedure B

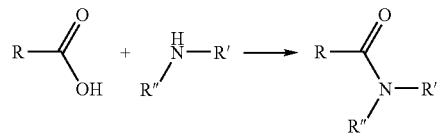

| Acid | Amine | Product | Ex # | HPLC $R_t$(min)(Method) | m/z |
|---|---|---|---|---|---|
| Preparation #13 | Aniline | | B.1.1 | 1.97(e) | 367 $(M - H)^-$ |
| Preparation #11c, V | Aniline | | B.1.2 | 1.63(e) | 314 and 316 $(M + H^+)$ |

TABLE B.2

Examples prepared using general procedure B from Example #F.8.1

| Acid | Product | Example # | HPLC Rt(min)(Method) | m/z |
|---|---|---|---|---|
| 1H-Benzimidazole-5-carboxylic acid | | B.2.1 | 1.69(e) | 409.9 (M + H)⁺ |
| Imidazo[2,1-b]thiazole-6-carboxylic acid | | B.2.2 | 2.02(e) | 415.9 (M + H)⁺ |
| 1H-Pyrazole-4-carboxylic acid | | B.2.3 | 1.60(e) | 359.9 (M + H)⁺ |

TABLE B.2-continued

Examples prepared using general procedure B from Example #F.8.1

| Acid | Product | Example # | HPLC Rt(min)(Method) | m/z |
|---|---|---|---|---|
| 1H-Indazole-3-carboxylic acid | | B.2.4 | 2.14(e) | 409.9 (M + H)⁺ |
| [(2R)-3,6-Dioxopiperazin-2-yl]acetic acid | | B.2.5 | 1.26(e) | 419.9 (M + H)⁺ |
| 3-Methyl-5-(4-methyl-1,2,3-thiadiazol-5-yl)isoxazole-4-carboxylic acid | | B.2.6 | 2.21(e) | 470.5 (M − H)⁻ |

TABLE B.2-continued

Examples prepared using general procedure B from Example #F.8.1

| Acid | Product | Example # | HPLC Rt(min)(Method) | m/z |
|---|---|---|---|---|
| N-(Aminocarbonyl)glycine | | B.2.7 | 1.33(e) | 365.9 (M + H)$^+$ |
| 3-Amino-1-carboxymethyl-pyridin-2-one trifluoroacetate | | B.2.8 | 1.61(e) | 415.9 (M + H)$^+$ |
| 3-Aminopyrazine-2-carboxylic acid | | B.2.9 | 2.24(e) | 384.5 (M − H)$^-$ |

TABLE B.2-continued
Examples prepared using general procedure B from Example #F.8.1
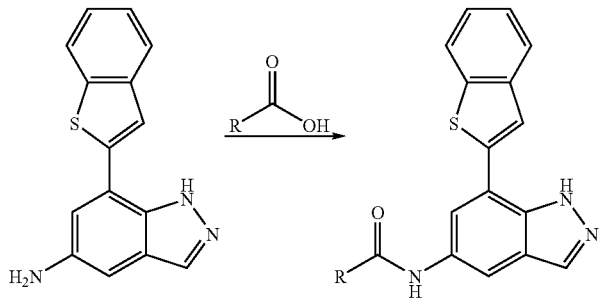
| Acid | Product | Example # | HPLC Rt(min)(Method) | m/z |
|---|---|---|---|---|
| 6-Aminonicotinic acid | | B.2.10 | 1.70(e) | 385.9 (M + H)+ |
| 2-Hydroxy cinchoninic acid | | B.2.11 | 1.84(e) | 437.1 (M + H)+ |
| 1H-Benzimidazol-2-ylacetic acid | | B.2.12 | 1.87(e) | 388.0 (M + H)+ |

TABLE B.2-continued
Examples prepared using general procedure B from Example #F.8.1
| Acid | Product | Example # | HPLC Rt(min)(Method) | m/z |
|---|---|---|---|---|
| 2-(Acetylamino)-1,3-thiazole-4-carboxylic acid | 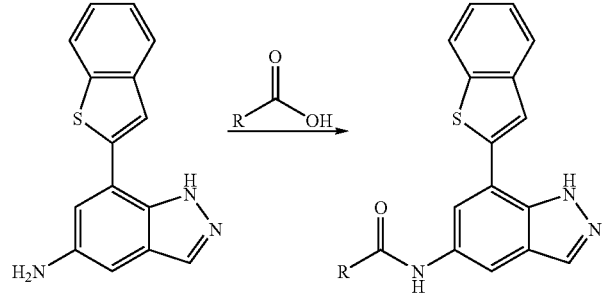 | B.2.13 | 1.84(e) | 433.8 (M + H)+ |
| 2-Aminonicotinic acid | 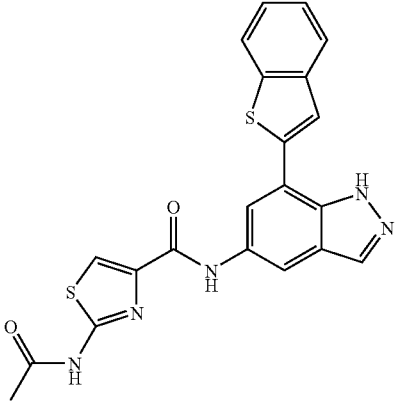 | B.2.14 | 1.99(e) | 385.9 (M + H)+ |
| 3-Aminoisonicotinic acid | 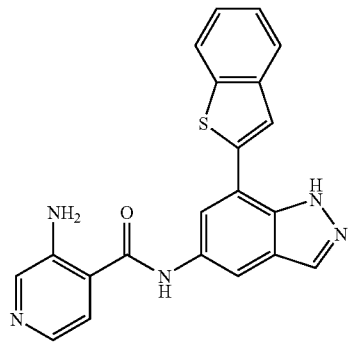 | B.2.15 | 1.85(e) | 386.0 (M + H)+ |

TABLE B.2-continued

Examples prepared using general procedure B from Example #F.8.1

| Acid | Product | Example # | HPLC Rt(min)(Method) | m/z |
|---|---|---|---|---|
| 4-(Methylamino)-6-morpholin-4-yl-1,3,5-triazine-2-carboxylic acid | | B.2.16 | 2.00(e) | 486.9 (M + H)+ |
| 3-[(4R)-2,5-Dioxoimidazolidin-4-yl]propanoic acid | | B.2.17 | 1.45(e) | 417.9 (M − H)− |
| 2,6-Dihydroxypyrimidine-4-carboxylic acid-lithium monohydrate | | B.2.18 | 1.34(e) | 401.6 (M − H)− |

TABLE B.2-continued

Examples prepared using general procedure B from Example #F.8.1

| Acid | Product | Example # | HPLC Rt(min)(Method) | m/z |
|---|---|---|---|---|
| 3-(1H-Imidazol-2-yl)propanoic acid | | B.2.19 | 1.34(e) | 388.0 (M + H)+ |
| 3-(5,6,7,8-Tetrahydro-1,8-naphthyridin-2-yl)propanoic acid | | B.2.20 | 1.73(e) | 454.0 (M + H)+ |
| 4-Aminopyrimidine-5-carboxylic acid | | B.2.21 | 1.76(e) | 387.3 (M + H)+ |

TABLE B.2-continued

Examples prepared using general procedure B from Example #F.8.1

| Acid | Product | Example # | HPLC Rt(min)(Method) | m/z |
|---|---|---|---|---|
| 5-Methyl-4-oxo-3,4-dihydro-thieno[2,3-d]pyrimidine-6-carboxylic acid | | B.2.22 | 1.78(e) | 458.3 (M + H)+ |
| 7-Amino-2-methylpyrazolo[1,5-a]pyrimidine-6-carboxylic acid | | B.2.23 | 2.00(e) | 440.3 (M + H)+ |
| 2,1,3-Benzoxadiazole-5-carboxylic acid | | B.2.24 | 2.27(e) | 406.3 (M + H)+ |

TABLE B.2-continued

Examples prepared using general procedure B from Example #F.8.1

| Acid | Product | Example # | HPLC Rt(min)(Method) | m/z |
|---|---|---|---|---|
| 1H-Imidazole-2-carboxylic acid | | B.2.25 | 1.82(e) | 360.2 (M + H)+ |
| 1H-Benzimidazole-2-carboxylic acid | | B.2.26 | 2.19(e) | 410.2 (M + H)+ |
| 2,7-Dimethylpyrazolo[1,5-α]pyrimidine-6-carboxylic acid | | B.2.27 | 1.95(e) | 439.4 (M + H)+ |

TABLE B.2-continued

Examples prepared using general procedure B from Example #F.8.1

| Acid | Product | Example # | HPLC Rt(min)(Method) | m/z |
|---|---|---|---|---|
| 5-Oxo-2,3-dihydro-5H-[1,3]thia-zolo[3,2-α]py-rimidine-6-carboxylic acid | | B.2.28 | 1.97(e) | 446.2 (M + H)+ |
| 3-Hydroxy quinoxaline-2-carboxylic acid | | B.2.29 | 1.85(e) | 438.3 (M + H)+ |
| 5-Aminonicotinic acid | | B.2.30 | 1.60(g) | 386.2 (M + H)+ |

TABLE B.2-continued

Examples prepared using general procedure B from Example #F.8.1

| Acid | Product | Example # | HPLC Rt(min)(Method) | m/z |
|---|---|---|---|---|
| 6-Oxo-1,4,5,6-tetrahydro-pyridazine-3-carboxylic acid | | B.2.31 | 1.63(g) | 390.2 (M + H)+ |
| 2-(Acetylamino)isonicotinic acid | | B.2.32 | 1.68(g) | 428.3 (M + H)+ |
| (3R)-5-Oxopyrrolidine-3-carboxylic acid | | B.2.33 | 1.49(g) | 377.2 (M + H)+ |

TABLE B.2-continued

Examples prepared using general procedure B from Example #F.8.1

| Acid | Product | Example # | HPLC Rt(min)(Method) | m/z |
|---|---|---|---|---|
| (4R)-2,6-Dioxohexahydropyrimidine-4-carboxylic acid | | B.2.34 | 1.48(g) | 406.3 (M + H)+ |
| 1H-Imidazole-4-carboxylic acid | | B.2.35 | 1.58(g) | 360.2 (M + H)+ |
| 1H-1,2,3-Benzotriazole-5-carboxylic acid | | B.2.36 | 1.66(g) | 411.2 (M + H)+ |

TABLE B.2-continued
Examples prepared using general procedure B from Example #F.8.1
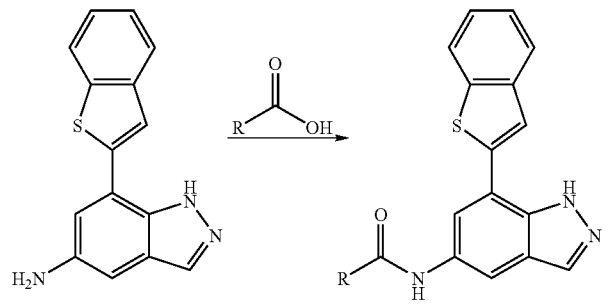
| Acid | Product | Example # | HPLC Rt(min)(Method) | m/z |
|---|---|---|---|---|
| 1H-Pyrazole-3-carboxylic acid | | B.2.37 | 1.68(g) | 360.2 (M + H)+ |
| 1-Methyl-1H-benzimidazole-2-carboxylic acid | | B.2.38 | 2.24(g) | 424.3 (M + H)+ |
| Sodium benzothiazole-2-carboxylate | | B.2.39 | 2.35(g) | 427.2 (M + H)+ |

TABLE B.3
Examples prepared using general procedure C from Preparation #7.
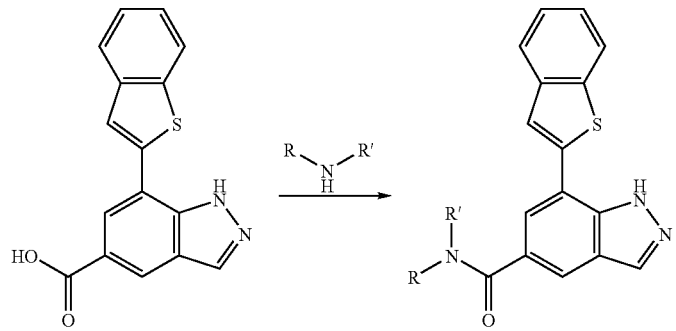
| Amine Precursor | Product | Example # | R$_t$/min(Method) | m/z(ESI+) |
|---|---|---|---|---|
| N-(2-amino-phenyl)-acetamide | | B.3.1 | 1.44(e) | 426.9 (M + H)⁺ |
| 3-methoxymethyl-pyrrolidine | | B.3.2 | 1.52(e) | 391.9 (M + H)⁺ |

TABLE B.3-continued
Examples prepared using general procedure C from Preparation #7.
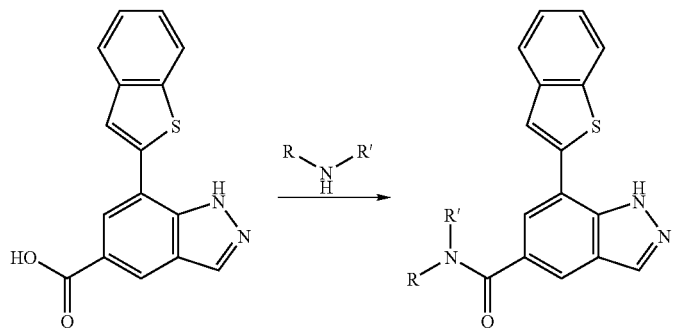
| Amine Precursor | Product | Example # | R$_t$/min(Method) | m/z(ESI+) |
|---|---|---|---|---|
| 5-amino-piperidin-2-one | 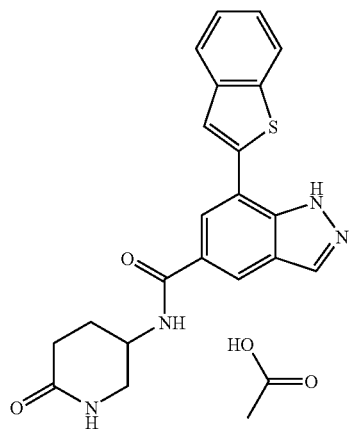 | B.3.3 | 1.43(e) | 391 (M + H)$^+$ |
| Piperidin-4-ylmethyl-pyrimidin-2-yl-amine | 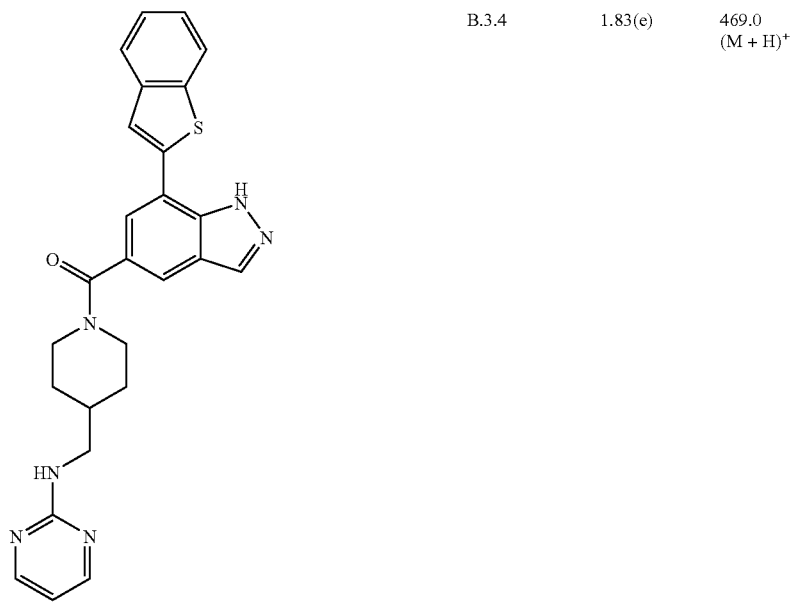 | B.3.4 | 1.83(e) | 469.0 (M + H)$^+$ |

TABLE B.3-continued
Examples prepared using general procedure C from Preparation #7.
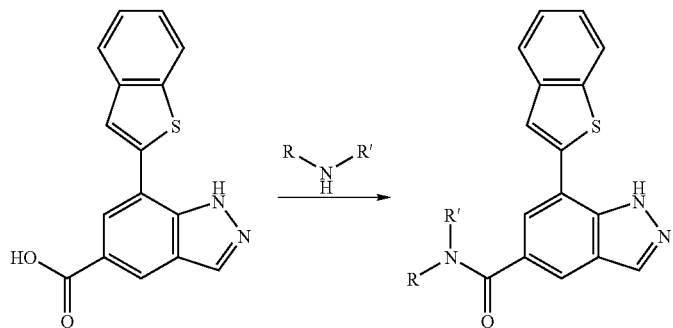
| Amine Precursor | Product | Example # | R$_t$/min(Method) | m/z(ESI+) |
|---|---|---|---|---|
| 3-Imidazol-1-yl-propylamine | | B.3.5 | 1.71(e) | 401 (M + H)$^+$ |
| Piperidin-4-yl-methanol | | B.3.6 | 1.13(e) | 391.9 (M + H)$^+$ |

TABLE B.3-continued
Examples prepared using general procedure C from Preparation #7.
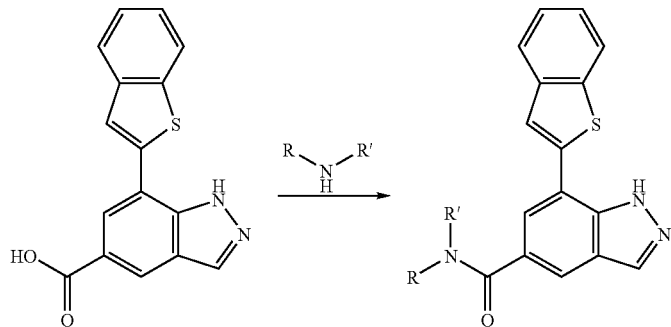
| Amine Precursor | Product | Example # | R$_t$/min(Method) | m/z(ESI+) |
|---|---|---|---|---|
| 1-Methyl-1H-benzoimidazol-4-ylamine | | B.3.7 | 2.13(e) | 423.9 (M + H)+ |
| 2-Pyrrolidin-3-yl-pyridine | | B.3.8 | 1.88(e) | 424.9 (M + H)+ |

TABLE B.3-continued
Examples prepared using general procedure C from Preparation #7.
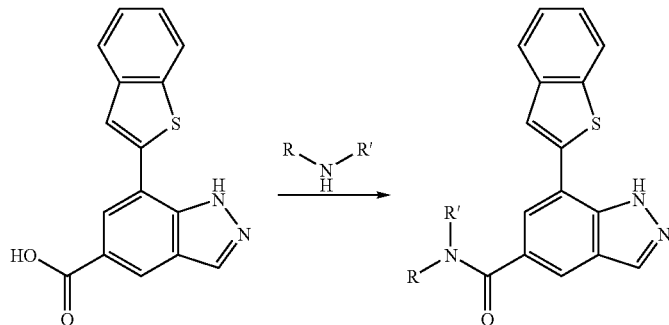
| Amine Precursor | Product | Example # | R$_t$/min(Method) | m/z(ESI+) |
|---|---|---|---|---|
| 5-Methylsulfanyl-1H-[1,2,4]triazol-3-ylamine | | B.3.9 | 1.72(e) | 404.6 (M + H)$^+$ |
| 5-Benzooxazol-2-yl-2-methoxy-phenyl amine | | B.3.10 | 2.13(e) | 517.0 (M + H)$^+$ |

TABLE B.3-continued
Examples prepared using general procedure C from Preparation #7.
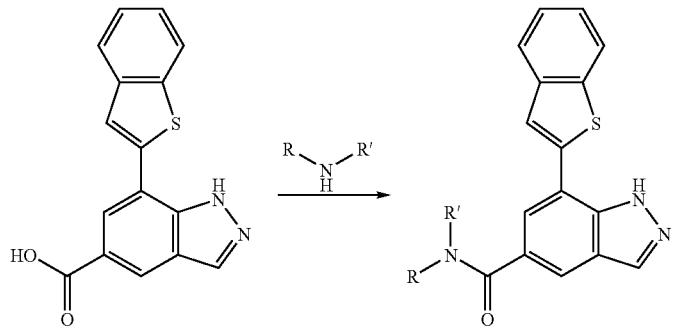
| Amine Precursor | Product | Example # | R$_t$/min(Method) | m/z(ESI+) |
|---|---|---|---|---|
| N-(6-Amino-benzothiazol-2-yl)-acetamide | | B.3.11 | 1.45(e) | 483.9 (M + H)$^+$ |
| 1H-Indazol-6-ylamine | | B.3.12 | 1.47(e) | 408.0 (M − H)$^−$ |

TABLE B.3-continued
Examples prepared using general procedure C from Preparation #7.
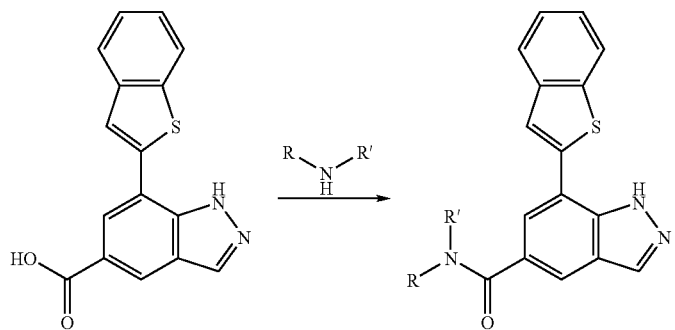
| Amine Precursor | Product | Example # | R$_t$/min(Method) | m/z(ESI+) |
|---|---|---|---|---|
| 1H-Indazol-5-ylamine | | B.3.13 | 1.37(e) | 407.6 (M − H)$^-$ |
| 1H-Benzoimidazol-5-ylamine | | B.3.14 | 1.23(e) | 409.9 (M + H)$^+$ |

TABLE B.3-continued
Examples prepared using general procedure C from Preparation #7.
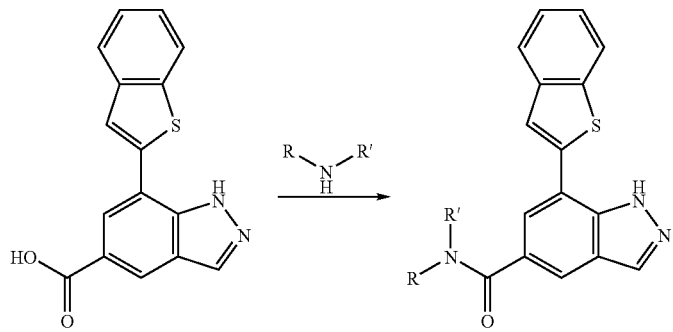
| Amine Precursor | Product | Example # | R$_t$/min(Method) | m/z(ESI+) |
| --- | --- | --- | --- | --- |
| Quinazolin-4-ylamine | 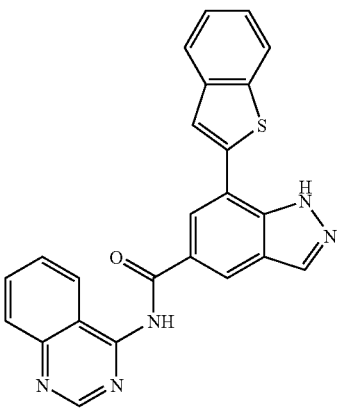 | B.3.15 | 2.35(e) | 420.2 (M − H)$^-$ |
| 4-(4-Fluoro-phenyl)-5-methyl-2H-pyrazol-3-ylamine | 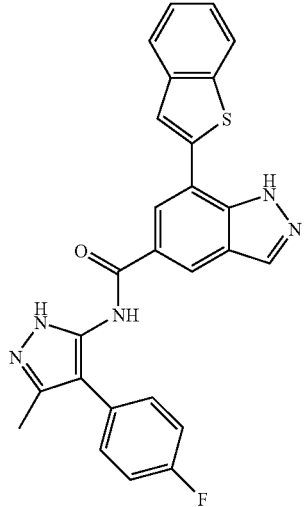 | B.3.16 | 2.48(e) | 466.3 (M − H)$^-$ |

TABLE B.3-continued
Examples prepared using general procedure C from Preparation #7.
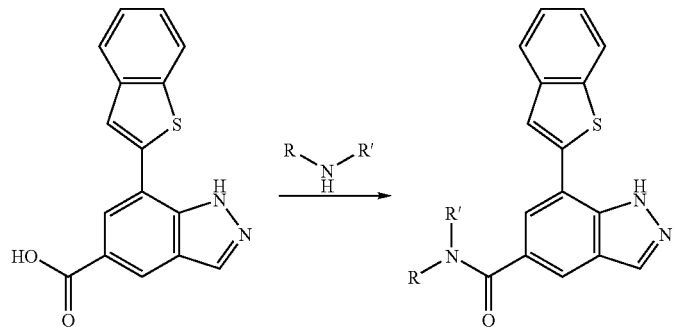
| Amine Precursor | Product | Example # | R$_t$/min(Method) | m/z(ESI+) |
|---|---|---|---|---|
| 5-Methyl-1H-[1,2,4]triazol-3-ylamine | | B.3.17 | 2.02(e) | 375.1 (M + H)+ |
| 4-Cyclohexyl-phenylamine | | B.3.18 | 2.71(e) | 450.4 (M − H)− |

TABLE B.3-continued
Examples prepared using general procedure C from Preparation #7.
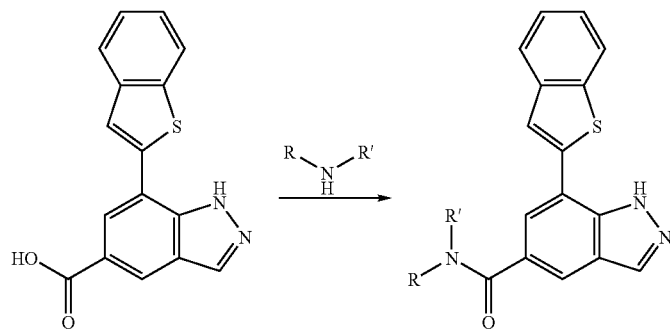
| Amine Precursor | Product | Example # | R$_t$/min(Method) | m/z(ESI+) |
| --- | --- | --- | --- | --- |
| 2-Amino-4-hydroxy-benzamide | 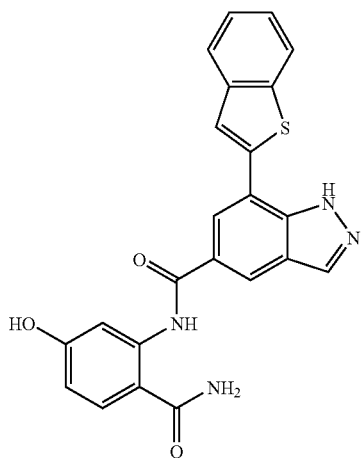 | B.3.19 | 1.85(e) | 427.2 (M − H)$^-$ |
| C-Oxazol-2-yl-methylamine | 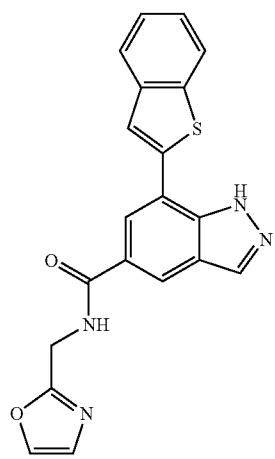 | B.3.20 | 1.62(e) | 373.2 (M − H)$^-$ |

TABLE B.3-continued
Examples prepared using general procedure C from Preparation #7.
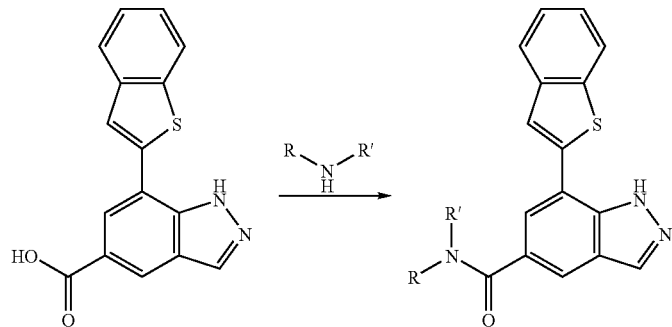
| Amine Precursor | Product | Example # | R$_t$/min(Method) | m/z(ESI+) |
|---|---|---|---|---|
| [1,3,4]Thiadiazol-2-ylamine | | B.3.21 | 1.79(e) | 376.1 (M − H)$^-$ |
| 4-Methyl-thiazol-2-ylamine | | B.3.22 | 2.11(e) | 391.1 (M + H)$^+$ |
| 5-Furan-2-yl-1H-pyrazol-3-ylamine | | B.3.23 | 2.21(e) | 424.2 (M − H)$^-$ |

TABLE B.3-continued
Examples prepared using general procedure C from Preparation #7.
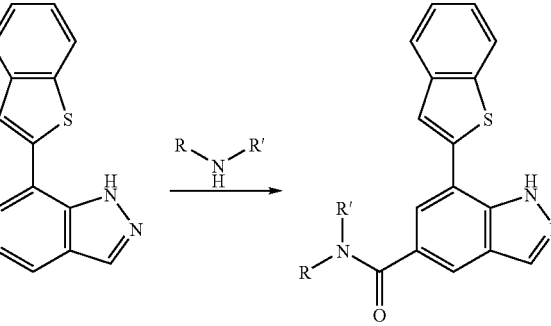
| Amine Precursor | Product | Example # | R$_t$/min(Method) | m/z(ESI+) |
|---|---|---|---|---|
| 2-(1H-Indol-2-yl)-phenylamine | | B.3.24 | 2.35(e) | 483.2 (M − H)⁻ |
| Biphenyl-2-ylamine | | B.3.25 | 2.35(e) | 444.3 (M − H)⁻ |
| 4-(1H-Imidazo[1,2-a]pyridin-2-yl)-phenylamine | | B.3.26 | 1.97(e) | 486.3 (M + H)⁺ |

TABLE B.3-continued
Examples prepared using general procedure C from Preparation #7.
| Amine Precursor | Product | Example # | R$_t$/min(Method) | m/z(ESI+) |
|---|---|---|---|---|
| 5-Amino-1,3-dihydro-benzoimidazol-2-one | 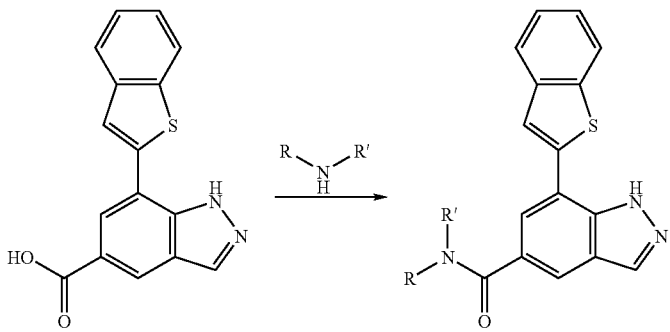 | B.3.27 | 1.49(e) | 424.2 (M − H)⁻ |
| 2-Methyl-benzothiazol-5-ylamine | 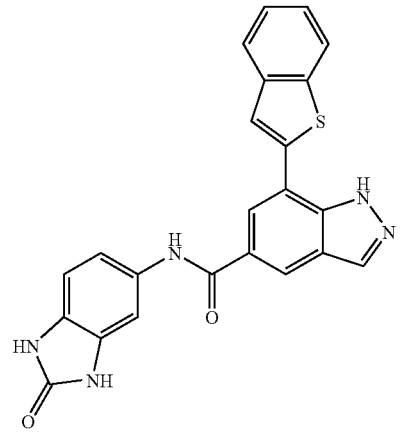 | B.3.28 | 2.09(e) | 439.3 (M − H)⁻ |
| 5-Aminomethyl-2H-[1,2,4]triazol-3-ylamine | 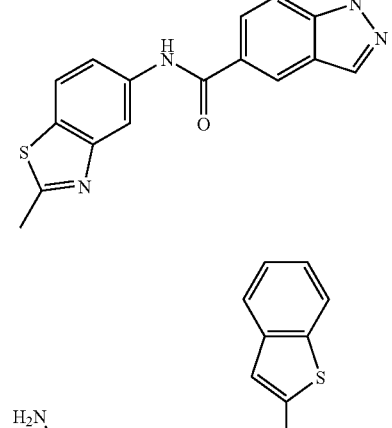 | B.3.29 | 1.20(e) | 388.2 (M − H)⁻ |

TABLE B.3-continued
Examples prepared using general procedure C from Preparation #7.
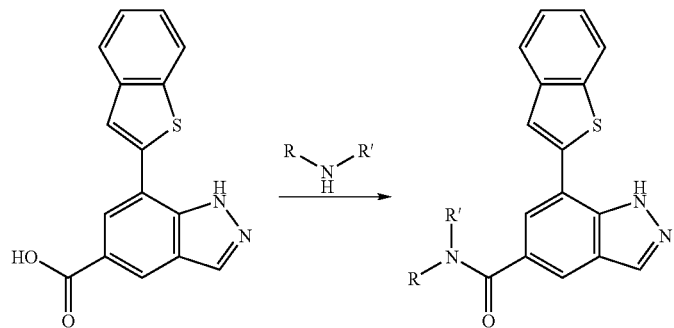
| Amine Precursor | Product | Example # | R$_t$/min(Method) | m/z(ESI+) |
|---|---|---|---|---|
| 2-Amino-fluoren-9-one | | B.3.30 | 2.36(e) | 470.3 (M − H)$^-$ |
| N-(3-Amino-phenyl)-benzamide | | B.3.31 | 2.10(e) | 487.3 (M − H)$^-$ |
| C-(5-Methyl-3-phenyl-isoxazol-4-yl)-methylamine | | B.3.32 | 2.08(e) | 2.08 (M − H)$^-$ |

TABLE B.3-continued
Examples prepared using general procedure C from Preparation #7.
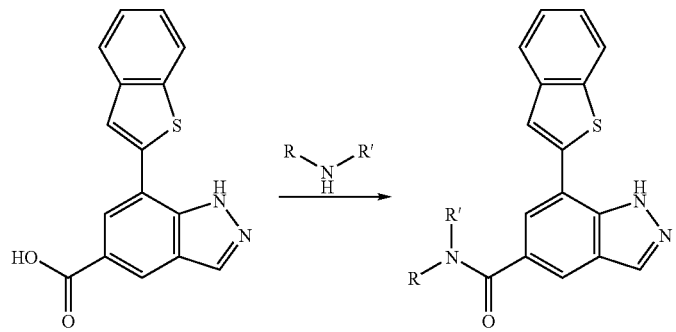
| Amine Precursor | Product | Example # | R$_t$/min(Method) | m/z(ESI+) |
|---|---|---|---|---|
| Indan-5-ylamine | | B.3.33 | 2.37(e) | 408.3 (M − H)$^-$ |
| 2-(4-Phenoxy-phenyl)-ethylamine | | B.3.34 | 2.38(e) | 488.3 (M − H)$^-$ |
| 4-Amino-4-methyl-pentan-2-one | | B.3.35 | 1.94(e) | 390.2 (M − H)$^-$ |

TABLE B.3-continued

Examples prepared using general procedure C from Preparation #7.

| Amine Precursor | Product | Example # | R$_t$/min(Method) | m/z(ESI+) |
|---|---|---|---|---|
| 5-(2-Amino-ethyl)-2H-[1,2,4]triazol-3-ylamine | | B.3.36 | 1.21(e) | 403.2 (M − H)$^-$ |
| Benzo[b]thiophen-5-ylamine | | B.3.37 | 2.26(e) | 424.3 (M − H)$^-$ |
| 3-Amino-4-methoxy-benzamide | | B.3.38 | 1.69(e) | 443.3 (M + H)$^+$ |

TABLE B.3-continued
Examples prepared using general procedure C from Preparation #7.
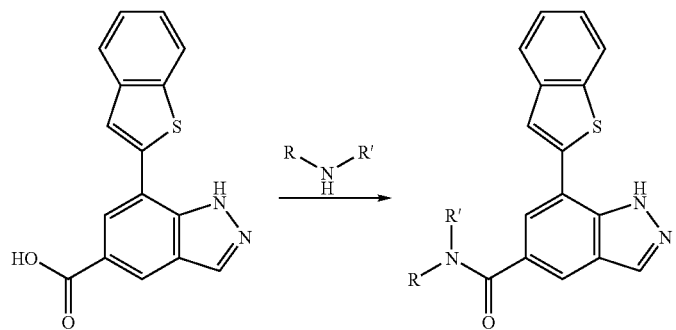
| Amine Precursor | Product | Example # | R$_t$/min(Method) | m/z(ESI+) |
|---|---|---|---|---|
| 2-Methoxy-phenylamine | 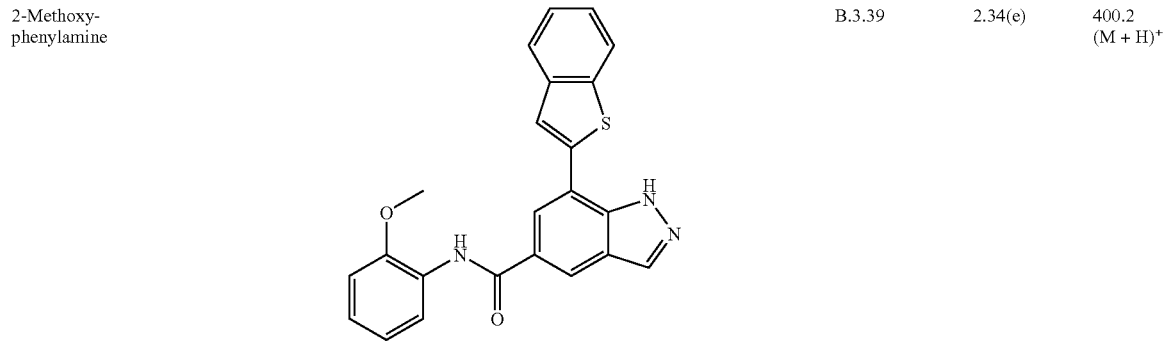 | B.3.39 | 2.34(e) | 400.2 (M + H)$^+$ |
| 4-Methoxy-biphenyl-3-ylamine | 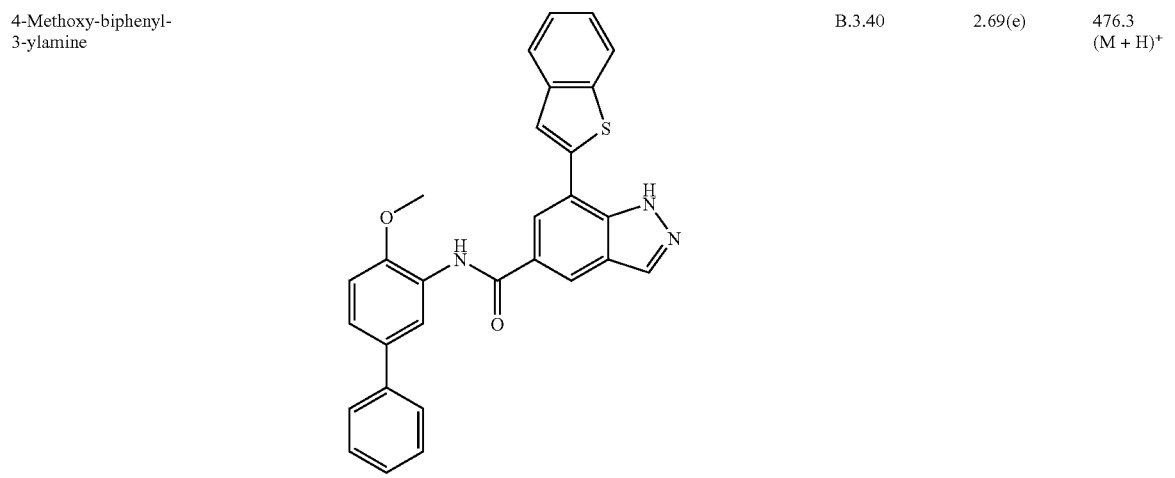 | B.3.40 | 2.69(e) | 476.3 (M + H)$^+$ |

TABLE B.3-continued

Examples prepared using general procedure C from Preparation #7.

| Amine Precursor | Product | Example # | R$_t$/min(Method) | m/z(ESI+) |
| --- | --- | --- | --- | --- |
| N-(3-Amino-4-methoxy-phenyl)-acetamide | | B.3.41 | 1.86(e) | 457.3 (M + H)$^+$ |
| 2,5-Dimethoxy-phenylamine | | B.3.42 | 2.39(e) | 430.3 (M + H)$^+$ |
| 3-Methoxy-phenylamine | | B.3.43 | 2.24(e) | 400.3 (M + H)$^+$ |

168
TABLE B.3-continued
Examples prepared using general procedure C from Preparation #7.
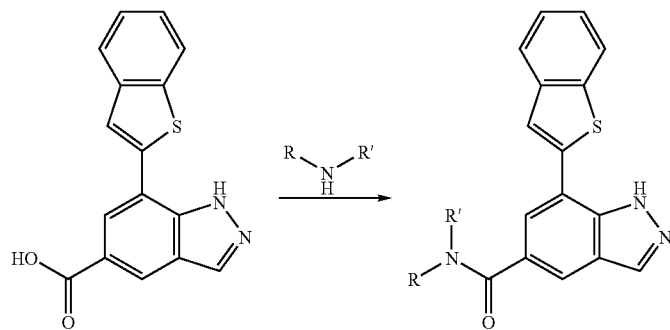
| Amine Precursor | Product | Example # | R$_t$/min(Method) | m/z(ESI+) |
|---|---|---|---|---|
| 4-Methoxy-phenylamine | 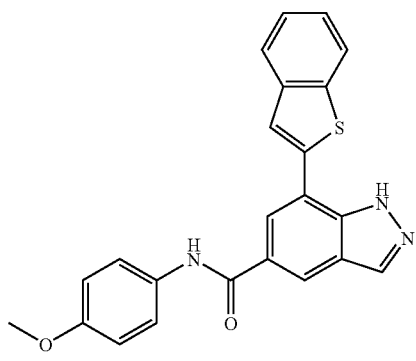 | B.3.44 | 2.17(e) | 400.3 (M + H)$^+$ |
| 3-(1H-Benzoimidazol-2-yl)-phenylamine | 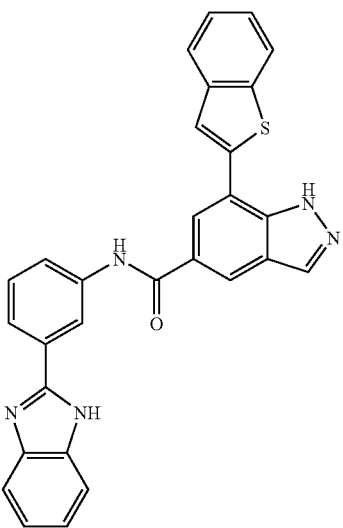 | B.3.45 | 2.11(e) | 486.3 (M + H)$^+$ |

TABLE B.3-continued
Examples prepared using general procedure C from Preparation #7.
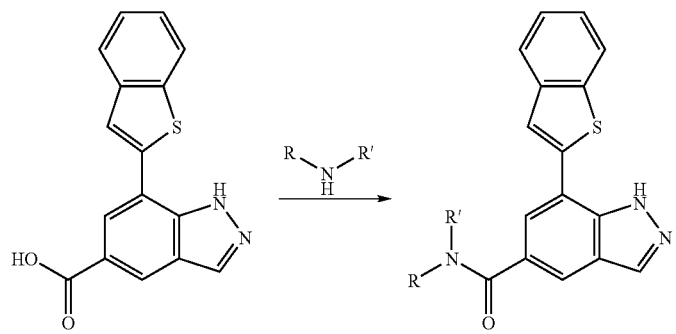
| Amine Precursor | Product | Example # | R$_t$/min(Method) | m/z(ESI+) |
|---|---|---|---|---|
| 3-Amino-benzamidine | | B.3.46 | 1.95(e) | 412.3 (M + H)$^+$ |
| 3-Amino-benzoic acid methyl ester | | B.3.47 | 2.29(e) | 458.3 (M + H)$^+$ |

TABLE B.3-continued
Examples prepared using general procedure C from Preparation #7.
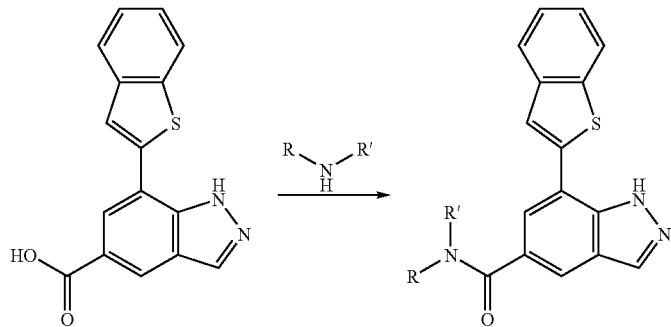
| Amine Precursor | Product | Example # | R$_t$/min(Method) | m/z(ESI+) |
|---|---|---|---|---|
| 3-(1H-Tetrazol-5-yl)-phenylamine | | B.3.48 | 1.56(e) | 438.3 (M + H)$^+$ |
| 2-Amino-phenol | | B.3.49 | 2.16(e) | 386.2 (M + H)$^+$ |

TABLE B.3-continued
Examples prepared using general procedure C from Preparation #7.
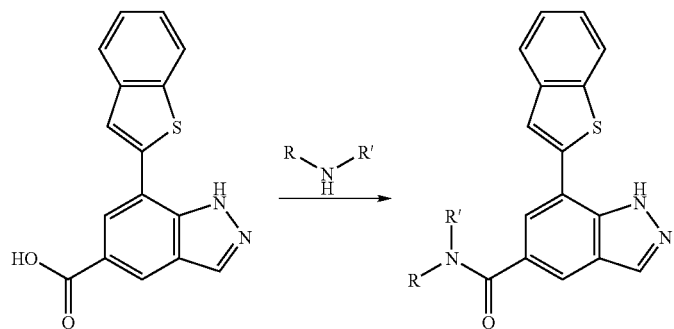
| Amine Precursor | Product | Example # | R$_t$/min(Method) | m/z(ESI+) |
|---|---|---|---|---|
| 3-Amino-4-hydroxy-benzoic acid methyl ester | | B.3.50 | 2.13(e) | 444.2 (M + H)$^+$ |
| 3-Benzooxazol-2-yl-phenylamine | | B.3.51 | 2.54(e) | 484.7 (M − H)$^-$ |

TABLE B.3-continued

Examples prepared using general procedure C from Preparation #7.

| Amine Precursor | Product | Example # | R$_t$/min(Method) | m/z(ESI+) |
|---|---|---|---|---|
| Phenylamine | | B.3.52 | 2.27(e) | 370.2 (M + H)$^+$ |
| 5-Amino-2-phenyl-2,4-dihydro-pyrazol-3-one | | B.3.53 | 1.77(e) | 450.5 (M − H)$^−$ |
| 4-Amino-N-[5-methyl-3H-[1,3,4]oxadiazol-(2E)-ylidene]-benzenesulfonamide | | B.3.54 | 1.51(e) | 529.0 (M − H)$^−$ |

TABLE B.3-continued
Examples prepared using general procedure C from Preparation #7.
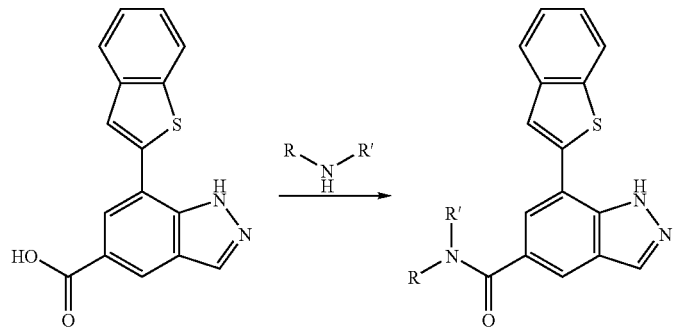
| Amine Precursor | Product | Example # | $R_t$/min(Method) | m/z(ESI+) |
|---|---|---|---|---|
| 5-Trifluoromethyl-[1,3,4]thiadiazol-2-ylamine | | B.3.55 | 2.42(e) | 443.8 (M − H)⁻ |
| N-(3-Amino-phenyl)-acetamide | | B.3.56 | 1.86(e) | 427.3 (M + H)⁺ |
| 6-Morpholin-4-yl-pyridin-3-ylamine | | B.3.57 | 1.92(e) | 456.3 (M + H)⁺ |

TABLE B.3-continued

Examples prepared using general procedure C from Preparation #7.

| Amine Precursor | Product | Example # | R$_t$/min(Method) | m/z(ESI+) |
|---|---|---|---|---|
| 2-Amino-5,6-dihydro-4H-benzothiazol-7-one | | B.3.58 | 2.12(e) | 445.3 (M + H)$^+$ |
| N-(4-Amino-2,5-dimethoxy-phenyl)-benzamide | | B.3.59 | 2.46(e) | 547.0 (M + H)$^+$ |
| 4-Morpholin-4-yl-phenylamine | | B.3.60 | 2.06(e) | 455.4 (M + H)$^+$ |

TABLE B.3-continued
Examples prepared using general procedure C from Preparation #7.
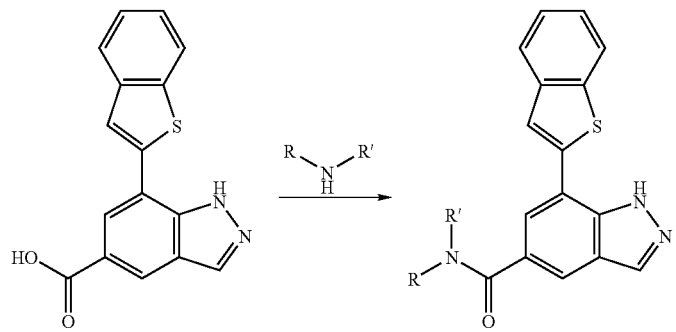
| Amine Precursor | Product | Example # | R_t/min(Method) | m/z(ESI+) |
|---|---|---|---|---|
| 4-(6-Methyl-benzothiazol-2-yl)-phenylamine | | B.3.61 | 2.77(e) | 515.5 (M − H)⁻ |
| 4-Benzooxazol-2-yl-phenylamine | | B.3.62 | 2.56(e) | 487.2 (M + H)⁺ |

TABLE B.3-continued
Examples prepared using general procedure C from Preparation #7.
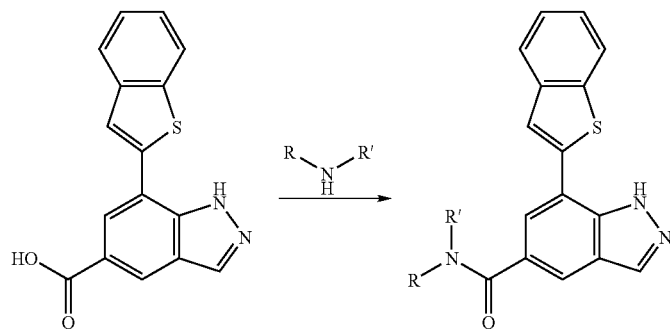
| Amine Precursor | Product | Example # | R$_t$/min(Method) | m/z(ESI+) |
|---|---|---|---|---|
| 4-(1H-Benzoimidazol-2-yl)-phenylamine | 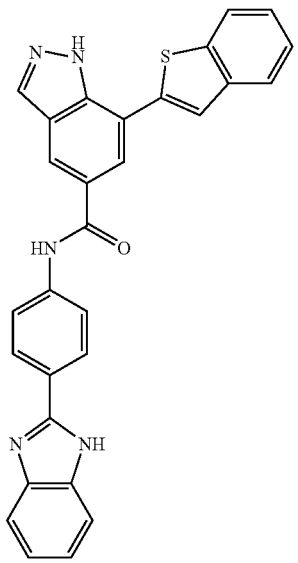 | B.3.63 | 2.0(e) | 483.8 (M − H)− |
| 5-(1H-Benzoimidazol-2-yl)-2-methoxy-phenylamine (Labotest) | 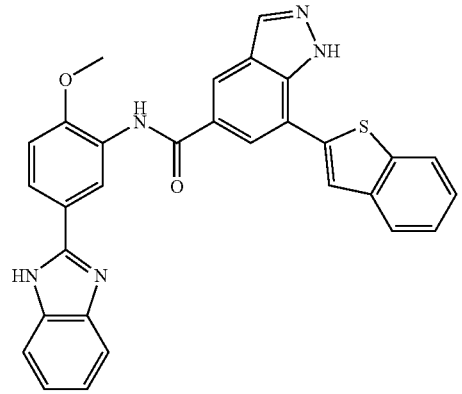 | B.3.64 | 2.1(e) | 516.2 (M + H)+ |

TABLE B.3-continued
Examples prepared using general procedure C from Preparation #7.
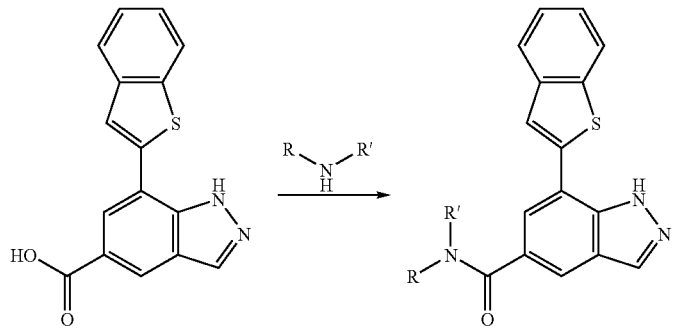
| Amine Precursor | Product | Example # | R$_t$/min(Method) | m/z(ESI+) |
| --- | --- | --- | --- | --- |
| Glycinamide | | B.3.65 | 1.37(e) | 351.2 (M + H)$^+$ |
| 4-Amino-N-(3,4-dimethyl-isoxazol-5-yl)-benzenesulfonamide | | B.3.66 | 2.04(e) | 542.3 (M − H)$^-$ |
| 4-Amino-N-thiazol-2-yl-benzenesulfonamide | | B.3.67 | 1.85(e) | 530.4 (M − H)$^-$ |

TABLE B.3-continued

Examples prepared using general procedure C from Preparation #7.

| Amine Precursor | Product | Example # | R$_t$/min(Method) | m/z(ESI+) |
|---|---|---|---|---|
| 6-(4-Methyl-piperazine-1-yl)-pyridin-3-ylamine | | B.3.68 | 1.35(e) | 467.5 (M − H)⁻ |
| 4-Amino-N-(5-methyl-isoxazol-3-yl)-benzenesulfonamide | | B.3.69 | 2.08(e) | 527.9 (M + H)⁺ |
| 5-Amino-pyridine-2-sulfonic acid isopropylamide | | B.3.70 | 2.62(e) | 489.1 (M + H)⁺ |

TABLE B.3-continued
Examples prepared using general procedure C from Preparation #7.
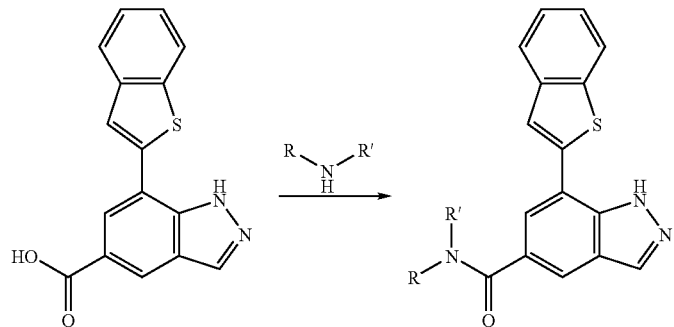
| Amine Precursor | Product | Example # | R$_t$/min(Method) | m/z(ESI+) |
|---|---|---|---|---|
| 6-(Propane-1-sulfonyl)-1H-benzoimidazol-2-ylamine | | B.3.71 | 2.07(e) | 514.6 (M − H)$^-$ |
| 4-Amino-N-(4,6-dimethyl-pyrimidin-2-yl)-benzenesulfonamide | | B.3.72 | 1.94(e) | 553.5 (M − H)$^-$ |
| 4-Amino-N-(2,6-dimethyl-pyrimidin-4-yl)-benzenesulfonamide | | B.3.73 | 1.59(e) | 553.5 (M − H)$^-$ |

TABLE B.3-continued
Examples prepared using general procedure C from Preparation #7.
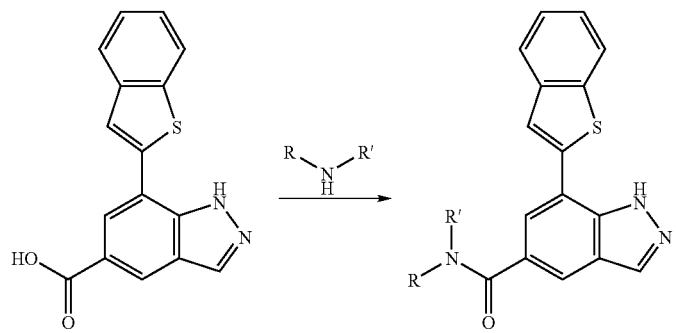
| Amine Precursor | Product | Example # | R$_t$/min(Method) | m/z(ESI+) |
|---|---|---|---|---|
| N-(4-Amino-2-methoxy-phenyl)-2-methoxy-benzamide | | B.3.74 | 2.38(e) | 547.2 (M − H)$^-$ |
| 5-tert-Butyl-[1,3,4]thiadiazol-2-yl amine | | B.3.75 | 2.34(e) | 432.2 (M − H)$^-$ |
| 3-Amino-benzamide | | B.3.76 | 1.75(e) | 411.2 (M − H)$^-$ |

TABLE B.3-continued
Examples prepared using general procedure C from Preparation #7.
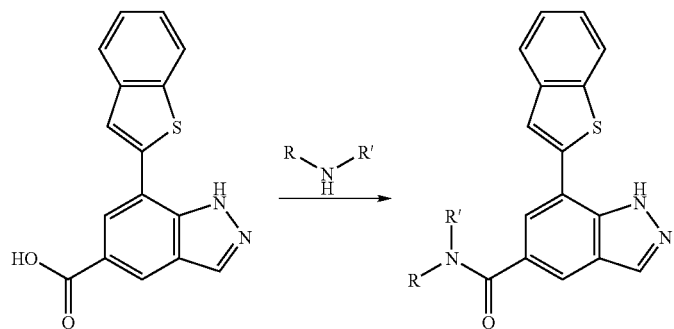
| Amine Precursor | Product | Example # | R$_t$/min(Method) | m/z(ESI+) |
|---|---|---|---|---|
| 2-(1H-Imidazol-4-yl)-ethylamine | | B.3.77 | 1.54(e) | 388.0 (M + H)$^+$ |
| Pyridin-2-yl-methylamine | | B.3.78 | 1.80(e) | 384.0 (M + H)$^+$ |
| Dimethyl-(R)-pyrrolidin-3-yl-amine | | B.3.79 | 1.89(e) | 389.0 (M − H)$^−$ |

TABLE B.3-continued
Examples prepared using general procedure C from Preparation #7.
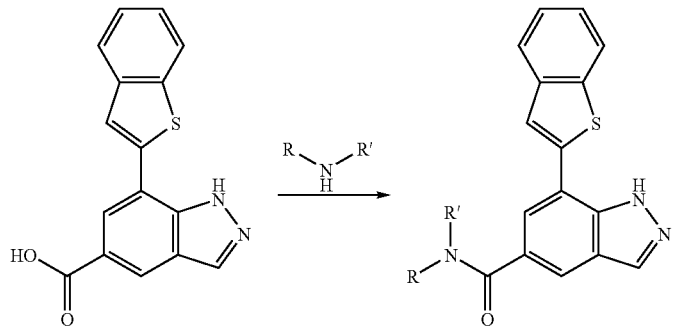
| Amine Precursor | Product | Example # | R$_t$/min(Method) | m/z(ESI+) |
|---|---|---|---|---|
| Piperidine-3-carboxamide | | B.3.80 | 1.44(e) | 404.9 (M + H)$^+$ |
TABLE B.4
Examples prepared using general procedure C from Example #N.2.8
| Amine Precursor | Product | Example # | R$_t$/min(Method) | m/z(ESI+) |
|---|---|---|---|---|
| Phenylamine | | B.4.1 | 192(e) | 346 (M + H)$^+$ |

TABLE B.4-continued

Examples prepared using general procedure C from Example #N.2.8

| Amine Precursor | Product | Example # | R$_t$/min(Method) | m/z(ESI+) |
|---|---|---|---|---|
| Amino-acetic acid methyl ester | | B.4.2 | 2.63(e) | 341 (M + H)$^+$ |
| Benzylamine | | B.4.3 | 1.48(e) | 360 (M + H)$^+$ |
| Tetrahydro-pyran-4-ylamine | | B.4.4 | 0.72(e) | 354 (M + H)$^+$ |
| N,N,N'-Trimethyl-propane-1,3-diamine | | B.4.5 | 0.63(e) | 369.7 (M + H)$^+$ |

TABLE B.4-continued
Examples prepared using general procedure C from Example #N.2.8
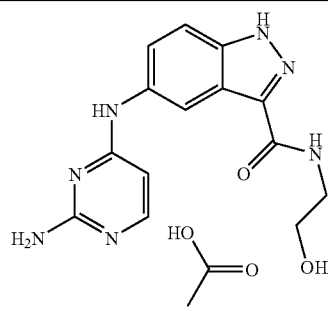
| Amine Precursor | Product | Example # | R$_t$/min(Method) | m/z(ESI+) |
|---|---|---|---|---|
| 2-Amino-ethanol | | B.4.6 | 0.53(e) | 314 (M + H)$^+$ |
| 4-Fluoro-benzylamine | | B.4.7 | 1.57(e) | 378 (M + H)$^+$ |
| N,N-Dimethyl-benzene-1,4-diamine | | B.4.8 | 1.58(e) | 389 (M + H)$^+$ |
| 4-Methoxy-benzylamine | | B.4.9 | 1.52(e) | 390 (M + H)$^+$ |

TABLE B.4-continued

Examples prepared using general procedure C from Example #N.2.8

| Amine Precursor | Product | Example # | R$_t$/min(Method) | m/z(ESI+) |
|---|---|---|---|---|
| C-Benzo[b]thiophen-3-yl-methylamine | | B.4.10 | 1.78(e) | 416 (M + H)$^+$ |
| 4-Fluoro-phenylamine | | B.4.11 | 1.65(e) | 364 (M + H)$^+$ |
| 3-Amino-propan-1-ol | | B.4.12 | 0.57(e) | 328 (M + H)$^+$ |
| 4-Amino-phenol | | B.4.13 | 0.95(e) | 362 (M + H)$^+$ |

TABLE B.4-continued
Examples prepared using general procedure C from Example #N.2.8
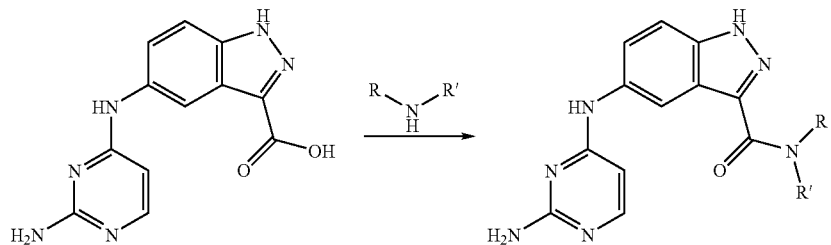
| Amine Precursor | Product | Example # | R$_t$/min(Method) | m/z(ESI+) |
|---|---|---|---|---|
| 4-Chloro-phenylamine | | B.4.14 | 1.82(e) | 380 (M + H)$^+$ |
| p-Tolylamine | | B.4.15 | 1.72(e) | 360 (M + H)$^+$ |
| (4-Amino-phenyl)-methanol | | B.4.16 | 0.80(e) | 375 (M + H)$^+$ |

TABLE B.4-continued
Examples prepared using general procedure C from Example #N.2.8
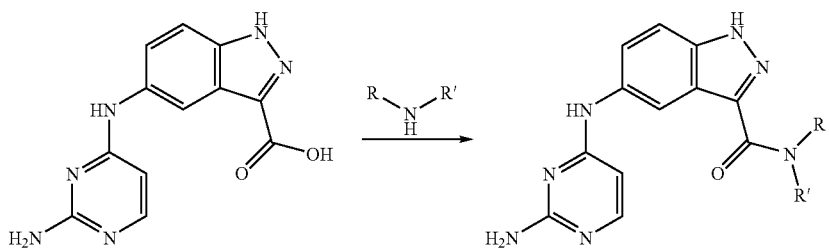
| Amine Precursor | Product | Example # | R$_t$/min(Method) | m/z(ESI+) |
|---|---|---|---|---|
| 1H-Benzoimidazol-5-ylamine | 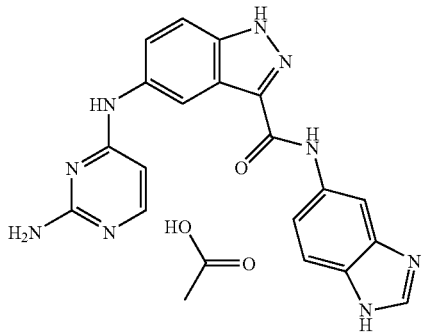 | B.4.17 | 0.72(e) | 385.7 (M + H)$^+$ |
| Biphenyl-4-ylamine | 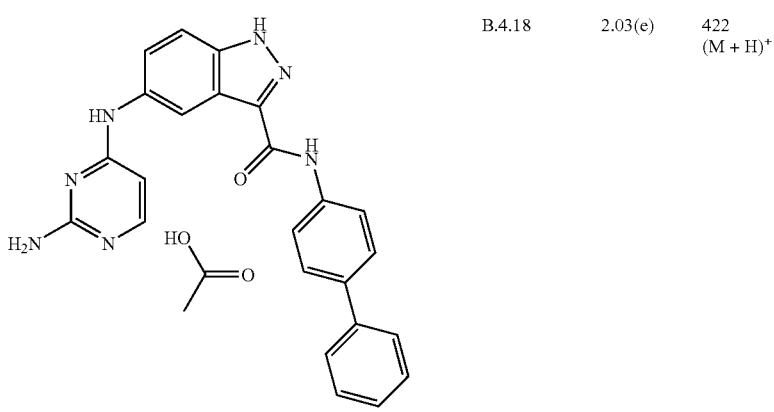 | B.4.18 | 2.03(e) | 422 (M + H)$^+$ |
| Naphthalen-2-ylamine | 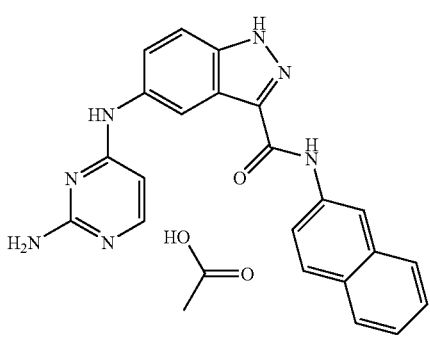 | B.4.19 | 1.87(e) | 396 (M + H)$^+$ |

TABLE B.4-continued

Examples prepared using general procedure C from Example #N.2.8

| Amine Precursor | Product | Example # | R$_t$/min(Method) | m/z(ESI+) |
|---|---|---|---|---|
| 4-Methoxy-naphthalen-2-ylamine | | B.4.20 | 1.98(e) | 426 (M + H)+ |
| m-Tolylamine | | B.4.21 | 1.70(e) | 360.4 (M + H)+ |
| 1H-Benzotriazol-5-ylamine | | B.4.22 | 0.75(e) | 387 (M + H)+ |

TABLE B.4-continued
Examples prepared using general procedure C from Example #N.2.8
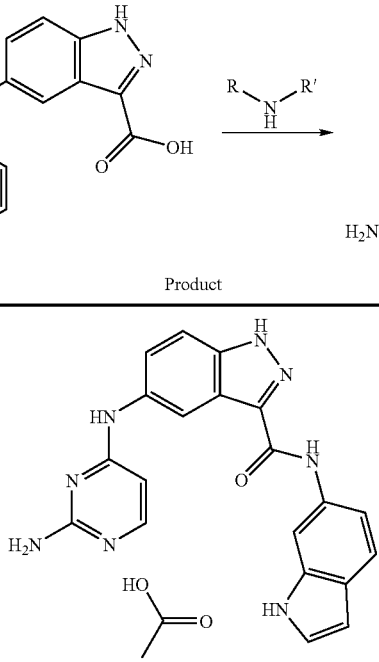
| Amine Precursor | Product | Example # | R$_t$/min(Method) | m/z(ESI+) |
|---|---|---|---|---|
| 1H-Indol-6-ylamine | | B.4.23 | 1.42(e) | 385 (M + H)$^+$ |
| 3-Amino-phenol | | B.4.24 | 1.23(e) | 362 (M + H)$^+$ |
| 5-Amino-1,3-dihydro-benzoimidazol-2-one | | B.4.25 | 0.67(e) | 402 (M + H)$^+$ |

TABLE B.4-continued

Examples prepared using general procedure C from Example #N.2.8

| Amine Precursor | Product | Example # | R$_t$/min(Method) | m/z(ESI+) |
|---|---|---|---|---|
| 2-(4-Amino-phenyl)-ethanol | | B.4.26 | 1.15(e) | 389.9 (M + H)$^+$ |
| 4-Amino-2-fluoro-phenol | | B.4.27 | 1.22(e) | 380 (M + H)$^+$ |
| 2-Amino-phenol | | B.4.28 | 1.52(e) | 362 (M + H)$^+$ |

General Procedure C: Formation of an Amide from Carboxylic Acid and Amine Using Si-DCT

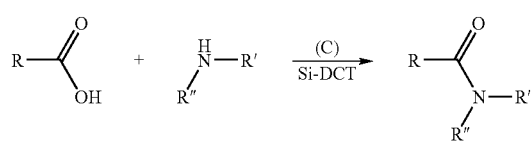

In a 20 mL vial, a solution of N-methylmorpholine (2-5 equivalents, preferably 4 equivalents) in an organic solvent (for example, THF, $CH_2Cl_2$, $CH_3CN$, or $CH_3CN/CH_2Cl_2$ 1:1) is added to Si-dichlorotriazine (Si-DCT) (2-4 equivalents, preferably 3 equivalents). A solution of the carboxylic acid (1.1-2.5 equivalents, preferably 1.25 equivalents) in an organic solvent (for example, THF, $CH_2Cl_2$, $CH_3CN$, or 1:1 $CH_3CN/CH_2Cl_2$, preferably 1:1 $CH_3CN/CH_2Cl_2$) is added and mixed for about 1 min. A solution of the amine (1 equiva-

213 lent) in an organic solvent (for example, THF, CH$_2$Cl$_2$, CH$_3$CN, or 1:1 CH$_3$CN/CH$_2$Cl$_2$, preferably 1:1 CH$_3$CN/CH$_2$Cl$_2$) is then added. The reaction is shaken at about 10-60° C., preferably about ambient temperature, for about 10-24 hours, preferably about 16 hours. The crude reaction solution is mixed with DMF, eluted through a Si-carbonate (1 g, 6 mL) cartridge with additional organic solvent (for example, MeOH), and concentrated in vacuo. The crude product can then be further purified by crystallization or chromatography.

Illustration of General Procedure C.

Example #13

Furan-2-carboxylic acid (7-benzo[b]thiophen-2-yl-1H-indazol-5-yl)-amide

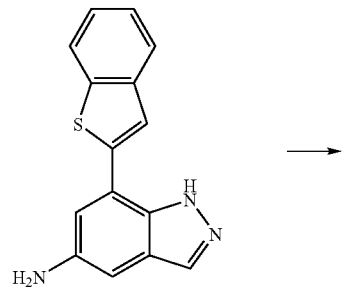

214

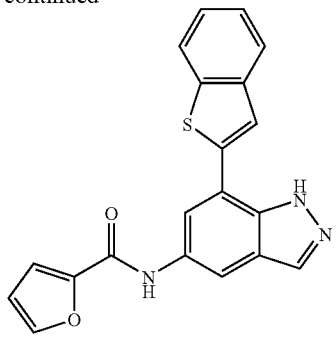

In a 20 mL vial, a solution of N-methylmorpholine (0.060 g, 0.60 mmol) in MeCN/CH$_2$Cl$_2$ (1:1, 0.688 mL) was added to Si-dichlorotriazine (SiliCycle, Inc; 0.60 mmol/g, 0.74 g, 0.44 mmol). Then, a solution of 2-furoic acid (0.021 g, 0.19 mmol) in MeCN (0.925 mL) was added and mixed for about 1 min., prior to the addition of a solution of 7-benzo[b]thiophen-2-yl-1H-indazol-5-ylamine (Example #F.8.1, 0.039 g, 0.15 mmol) in MeCN/CH$_2$Cl$_2$ (1:1, 0.688 mL). The reaction mixture was shaken at ambient temperature for about 16 hours. The crude reaction solution was mixed with DMF (5 mL) to aid in solubility, eluted through a Si-carbonate (SiliCycle, Inc; 1 g, 6 mL) cartridge using MeOH (approx 3 mL), and concentrated in vacuo. The crude product was then purified by preparative HPLC (Waters Symmetry C8 column (25×100 mm, 7 μm particle size) using a gradient of 10%-100% CH$_3$CN/0.1% aqueous TFA over 8 min (10 min run time) at a flow rate of 40 mL/min) to afford furan-2-carboxylic acid (7-benzo[b]thiophen-2-yl-1H-indazol-5-yl)-amide (0.0025 g, 4.7%); RP-HPLC (Table 1, Method 1) R$_t$ 2.51 min; m/z: (M+H)$^+$ 360.

TABLE C.1

Examples prepared using general procedure C using Example #F.8.1

| Acid | Product | Example # | HPLC R$_t$ min(Method) | m/z |
|---|---|---|---|---|
| Tetrahydro-3-furoic acid | | C.1.1 | 2.31(l) | 364 (M + H)$^+$ |

TABLE C.1-continued
Examples prepared using general procedure C using Example #F.8.1
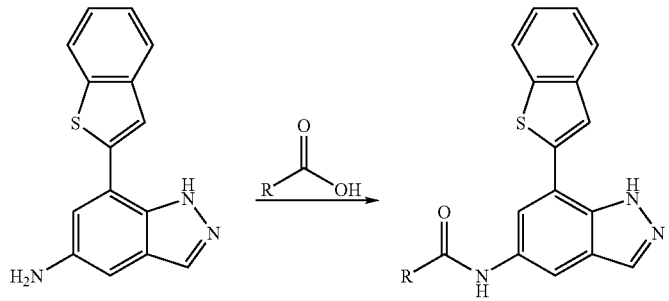
| Acid | Product | Example # | HPLC R$_t$ min(Method) | m/z |
|---|---|---|---|---|
| 2-Methoxy phenylacetic acid | 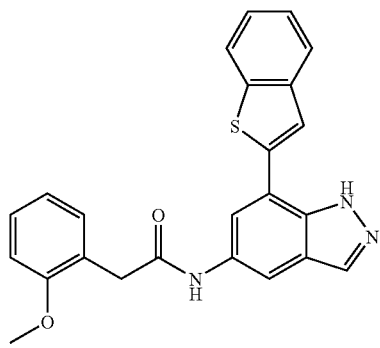 | C.1.2 | 2.65(l) | 414 (M + H)$^+$ |
| 3-Methoxy phenylacetic acid | 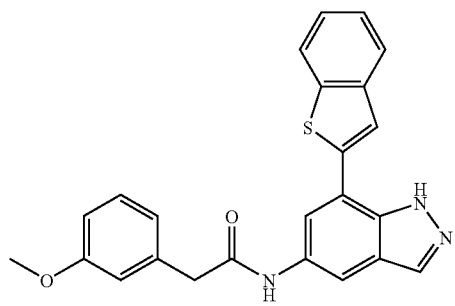 | C.1.3 | 2.62(l) | 414 (M + H)$^+$ |
| 4-Methoxy phenylacetic acid | 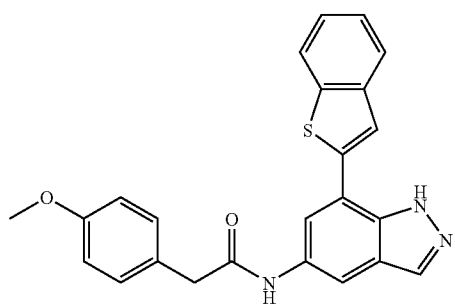 | C.1.4 | 2.61(l) | 414 (M + H)$^+$ |

TABLE C.1-continued
Examples prepared using general procedure C using Example #F.8.1
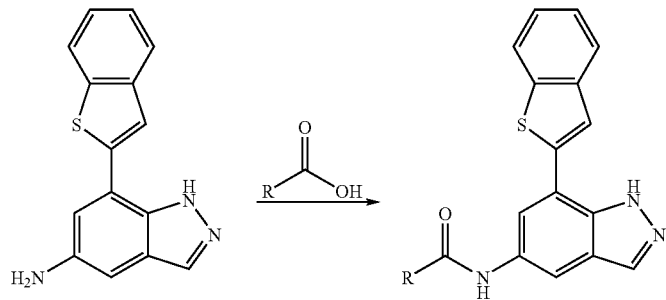
| Acid | Product | Example # | HPLC R$_t$ min(Method) | m/z |
|---|---|---|---|---|
| 3-(Trifluoromethoxy)phenylacetic acid | | C.1.5 | 2.85(1) | 468 (M + H)$^+$ |
| 3,4-(Methylenedioxy)phenylacetic acid | | C.1.6 | 2.59(1) | 428 (M + H)$^+$ |
| 3-Ethoxypropionic acid | | C.1.7 | 2.43(1) | 366 (M + H)$^+$ |

TABLE C.1-continued
Examples prepared using general procedure C using Example #F.8.1
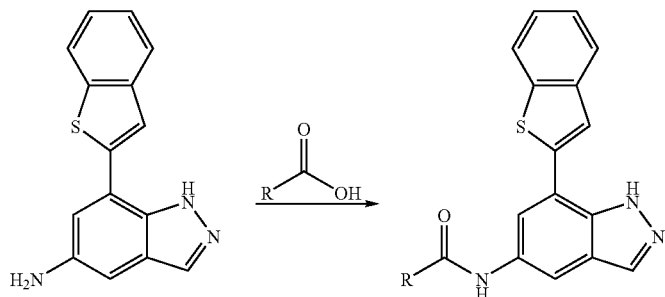
| Acid | Product | Example # | HPLC R$_t$ min(Method) | m/z |
|---|---|---|---|---|
| L-Pyroglutamic acid | | C.1.8 | 2.07(l) | 377 (M + H)$^+$ |
| D-Pyroglutamic acid | | C.1.9 | 2.07(l) | 377 (M + H)$^+$ |
| 1-(Aminocarbonyl)-1-cyclopropane carboxylic acid | | C.1.10 | 2.24(l) | 377 (M + H)$^+$ |

TABLE C.1-continued
Examples prepared using general procedure C using Example #F.8.1
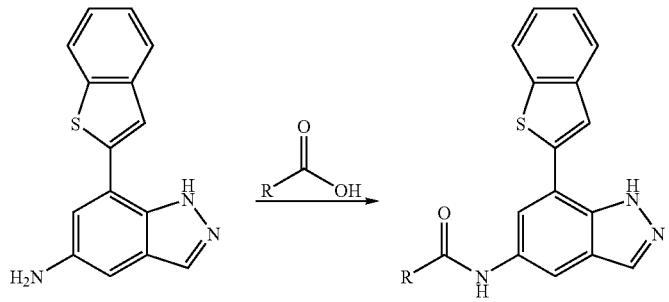
| Acid | Product | Example # | HPLC R$_t$ min(Method) | m/z |
|---|---|---|---|---|
| Benzyloxyacetic acid | | C.1.11 | 2.72(l) | 414 (M + H)$^+$ |
| 4-Methoxycyclohexane carboxylic acid | | C.1.12 | 2.53(l) | 406 (M + H)$^+$ |
| 1-Phenyl-1-cyclopropane carboxylic acid | | C.1.13 | 2.85(l) | 410 (M + H)$^+$ |

TABLE C.1-continued
Examples prepared using general procedure C using Example #F.8.1
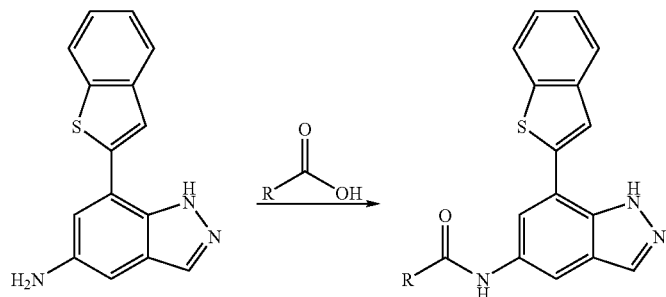
| Acid | Product | Example # | HPLC R$_t$ min(Method) | m/z |
|---|---|---|---|---|
| (S)-(+)-2-Phenylbutyric acid | | C.1.14 | 2.83(l) | 412 (M + H)$^+$ |
| 4-Phenylbutyric acid | | C.1.15 | 2.78(l) | 412 (M + H)$^+$ |
| N-(2-Furoyl)glycine | | C.1.16 | 2.63(l) | 376 (M + H)$^+$ |

TABLE C.1-continued
Examples prepared using general procedure C using Example #F.8.1
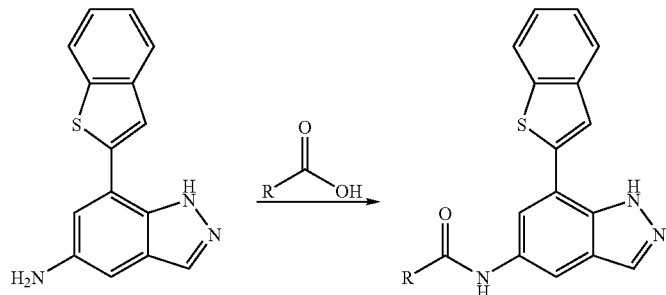
| Acid | Product | Example # | HPLC R$_t$ min(Method) | m/z |
|---|---|---|---|---|
| 4-(2-Thienyl)butyric acid | | C.1.17 | 2.75(l) | 418 (M + H)$^+$ |
| 1-Acetylpiperidine-4-carboxylic acid | | C.1.18 | 2.21(l) | 419 (M + H)$^+$ |
| N-(N,N-Di-propyl)-L-alanine | | C.1.19 | 2.92(l) | 421 (M + H)$^+$ |

TABLE C.1-continued
Examples prepared using general procedure C using Example #F.8.1
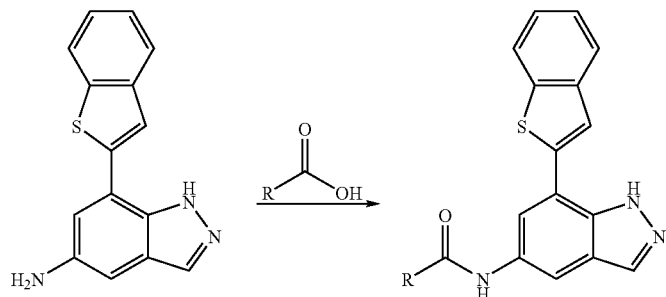
| Acid | Product | Example # | HPLC R$_t$ min(Method) | m/z |
|---|---|---|---|---|
| 3-Benzoylpropionic acid | 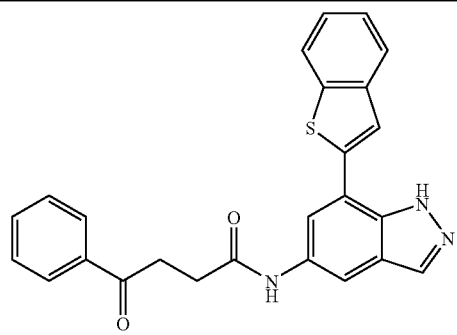 | C.1.20 | 2.62(l) | 426 (M + H)$^+$ |
| Hippuric acid | 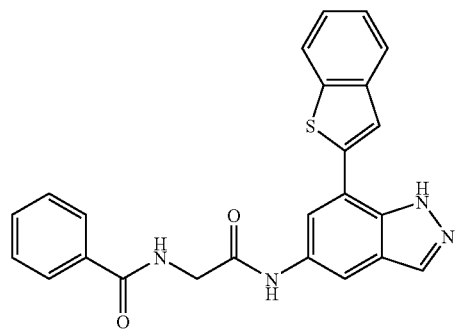 | C.1.21 | 1.86(m) | 427.1$^1$ (M + H)$^+$ |
| 3-(3-Methoxyphenyl) propionic acid | 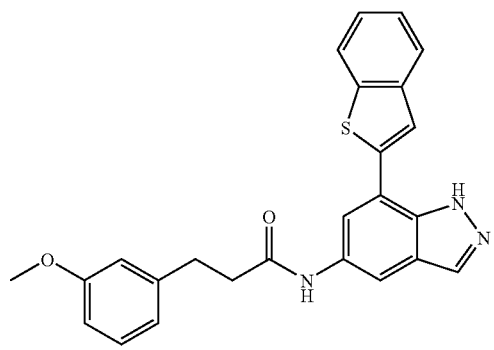 | C.1.22 | 2.30(l) | 360 (M + H)$^+$ |

TABLE C.1-continued
Examples prepared using general procedure C using Example #F.8.1
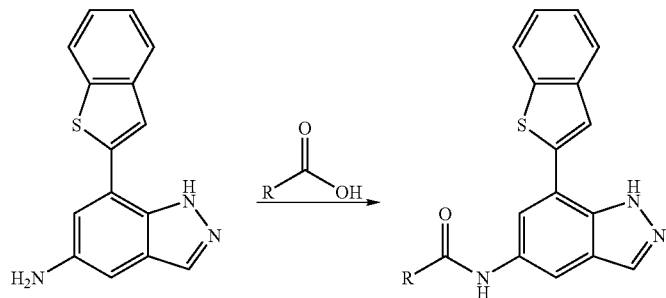
| Acid | Product | Example # | HPLC R$_t$ min(Method) | m/z |
|---|---|---|---|---|
| 3-Methoxyphenoxyacetic acid | | C.1.23 | 2.69(l) | 430 (M + H)$^+$ |
| 4-Oxo-4-(2-thienyl)butyric acid | | C.1.24 | 2.56(l) | 432 (M + H)$^+$ |
| 2-(4-Methylpyrimidin-2-ylthio)acetic acid | | C.1.25 | 2.48(l) | 432 (M + H)$^+$ |

TABLE C.1-continued
Examples prepared using general procedure C using Example #F.8.1
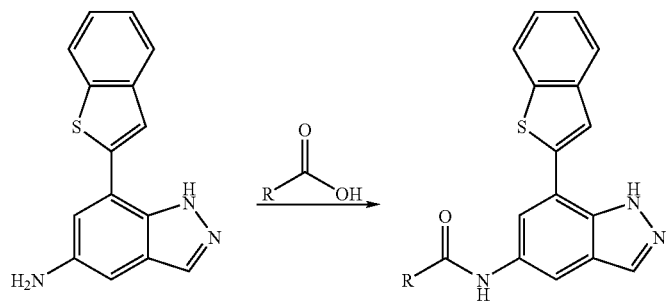
| Acid | Product | Example # | HPLC R$_t$ min(Method) | m/z |
|---|---|---|---|---|
| Glutaranilic acid | | C.1.26 | 2.48(l) | 455 (M + H)$^+$ |
| 4-Methylsulfonyl phenylacetic acid | | C.1.27 | 2.40(l) | 462 (M + H)$^+$ |
| N-p-Tosylglycine | | C.1.28 | 2.52(l) | 477 (M + H)$^+$ |

TABLE C.1-continued
Examples prepared using general procedure C using Example #F.8.1
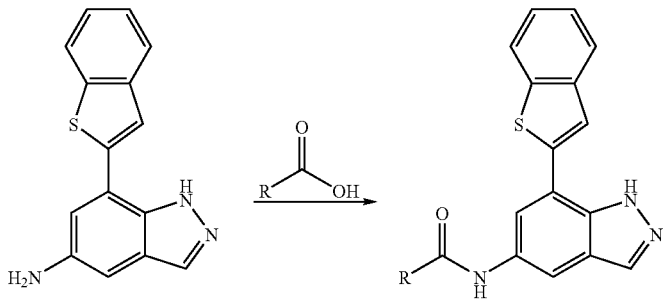
| Acid | Product | Example # | HPLC R$_t$ min(Method) | m/z |
|---|---|---|---|---|
| 4-Acetyl benzoic acid | | C.1.29 | 2.56(l) | 412 (M + H)$^+$ |
| 4-(Methylthio) benzoic acid | | C.1.30 | 2.74(l) | 416 (M + H)$^+$ |
| 3-Fluoro-4-methoxy benzoic acid | | C.1.31 | 2.67(l) | 418 (M + H)$^+$ |

TABLE C.1-continued
Examples prepared using general procedure C using Example #F.8.1
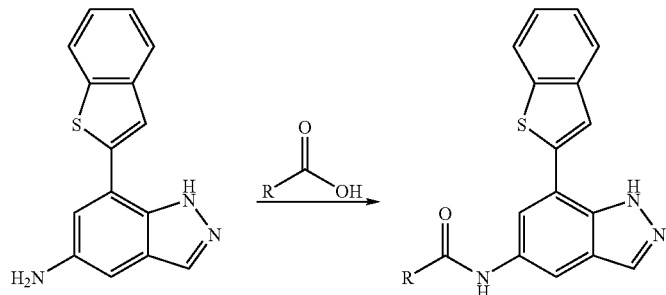
| Acid | Product | Example # | HPLC R$_t$ min(Method) | m/z |
|---|---|---|---|---|
| 2-Acetamido benzoic acid | | C.1.32 | 2.55(l) | 425 (M − H)⁻ |
| 3-Acetamido benzoic acid | | C.1.33 | 2.35(l) | 427 (M + H)⁺ |
| 4-Diethylamino benzoic acid | | C.1.34 | 2.85(l) | 441 (M + H)⁺ |

TABLE C.1-continued
Examples prepared using general procedure C using Example #F.8.1
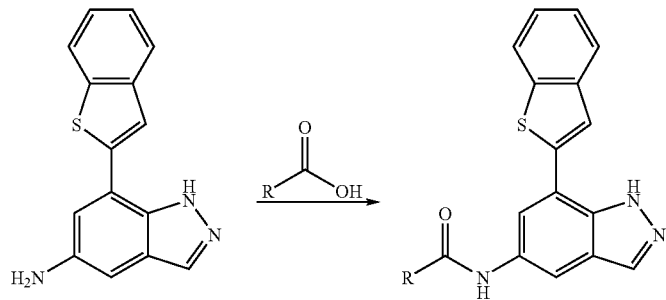
| Acid | Product | Example # | HPLC R$_t$ min(Method) | m/z |
|---|---|---|---|---|
| N-Phenylanthranilic acid | | C.1.35 | 3.02(l) | 461 (M + H)$^+$ |
| 3-Furoic acid | | C.1.36 | 2.52(l) | 360 (M + H)$^+$ |
| Thiophene-2-carboxylic acid | | C.1.37 | 2.63(l) | 374 (M + H)$^+$ |

TABLE C.1-continued
Examples prepared using general procedure C using Example #F.8.1
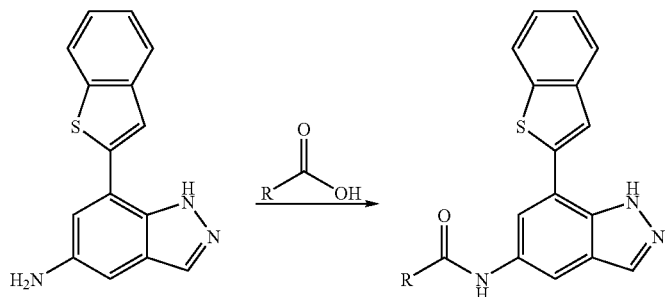
| Acid | Product | Example # | HPLC R<sub>t</sub> min(Method) | m/z |
|---|---|---|---|---|
| 3-Methyl-2-thiophene carboxylic acid | | C.1.38 | 2.70(l) | 390 (M + H)+ |
| Pyrrole-2-carboxylic acid | | C.1.39 | 2.49(l) | 359 (M + H)+ |
| Thiazole-4-carboxylic acid | | C.1.40 | 2.53(l) | 377 (M + H)+ |

TABLE C.1-continued
Examples prepared using general procedure C using Example #F.8.1
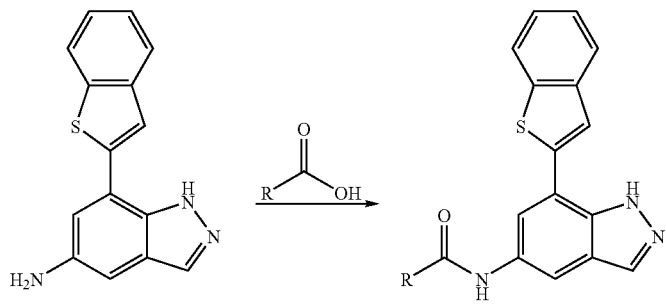
| Acid | Product | Example # | HPLC R$_t$ min(Method) | m/z |
|---|---|---|---|---|
| Thiazole-5-carboxylic acid | 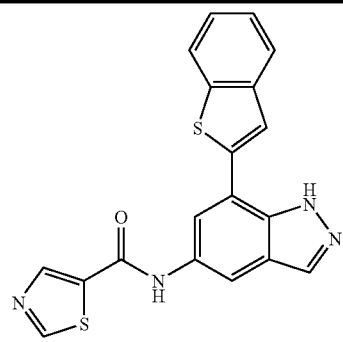 | C.1.41 | 2.43(l) | 375 (M − H)$^-$ |
| 1H-Pyrazole-5-carboxylic acid | 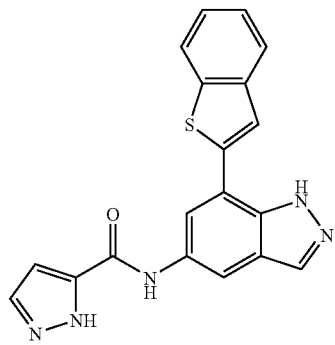 | C.1.42 | 2.30(l) | 360 (M + H)$^+$ |
| Isoxazole-5-carboxylic acid | 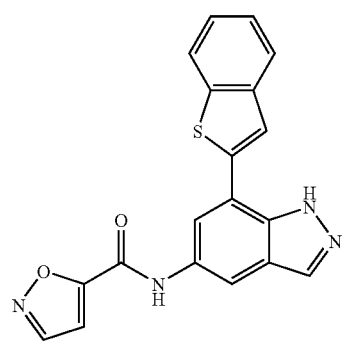 | C.1.43 | 2.46(l) | 361 (M + H)$^+$ |

TABLE C.1-continued
Examples prepared using general procedure C using Example #F.8.1
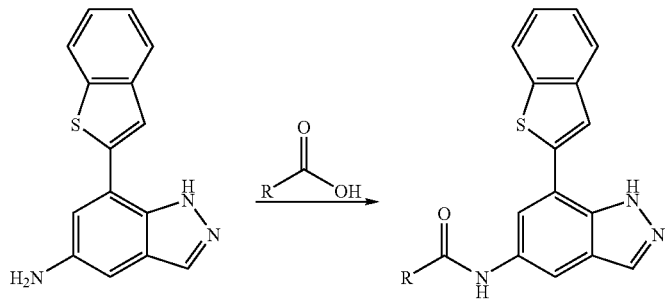
| Acid | Product | Example # | HPLC R$_t$ min(Method) | m/z |
|---|---|---|---|---|
| 3,5-Dimethyl isoxazole-4-carboxylic acid | | C.1.44 | 2.51(l) | 389 (M + H)$^+$ |
| 5-Methyl-3-phenylisoxazole-4-carboxylic acid | | C.1.45 | 2.72(l) | 451 (M + H)$^+$ |
| Picolinic acid | | C.1.46 | 2.68(l) | 371 (M + H)$^+$ |

TABLE C.1-continued
Examples prepared using general procedure C using Example #F.8.1
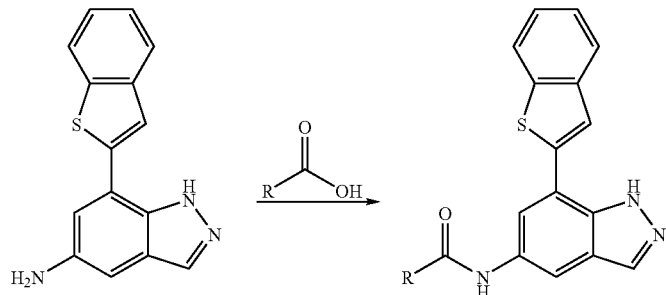
| Acid | Product | Example # | HPLC R_t min(Method) | m/z |
|---|---|---|---|---|
| 2-Hydroxynicotinic acid | | C.1.47 | 1.73(m) | 387.5[1] (M + H)+ |
| 6-Hydroxynicotinic acid | | C.1.48 | 2.12(l) | 387 (M + H)+ |
| 2-Pyridylacetic acid | | C.1.49 | 2.37(l) | 385 (M + H)+ |

TABLE C.1-continued
Examples prepared using general procedure C using Example #F.8.1
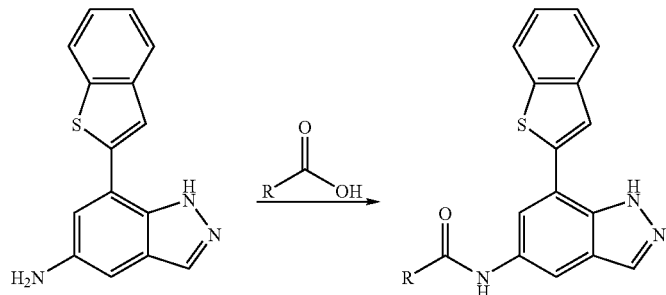
| Acid | Product | Example # | HPLC R$_t$ min(Method) | m/z |
|---|---|---|---|---|
| 3-Pyridylacetic acid | | C.1.50 | 2.32(l) | 385 (M + H)$^+$ |
| Pyrimidine-4-carboxylic acid | | C.1.51 | 1.88(m) | 372.0 (M + H)$^+$ |
| 2-Methylpyrazine-5-carboxylic acid | | C.1.52 | 2.58(l) | 386 (M + H)$^+$ |

TABLE C.1-continued
Examples prepared using general procedure C using Example #F.8.1
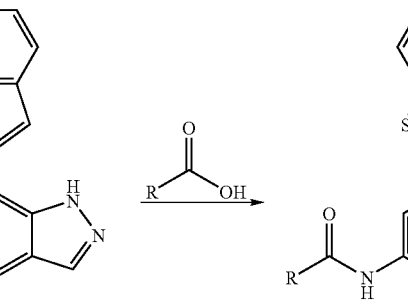
| Acid | Product | Example # | HPLC R$_t$ min(Method) | m/z |
|---|---|---|---|---|
| Indole-3-carboxylic acid | 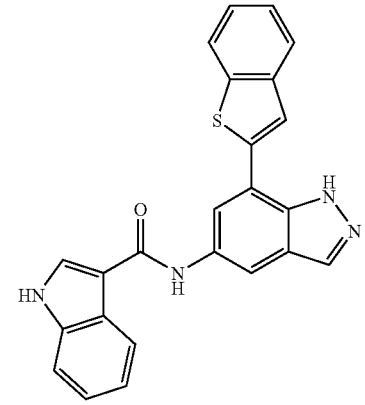 | C.1.53 | 2.05(m) | 409.1 (M + H)$^+$ |
| 5-Methyl-1-phenylpyrazole-4-carboxylic acid | 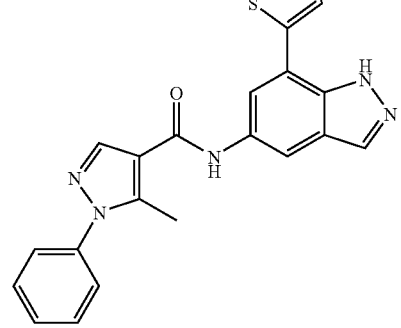 | C.1.54 | 2.68(l) | 450 (M + H)$^+$ |
| 4-Oxo-4,5,6,7-tetrahydrobenzo[b]furan-3-carboxylic acid | | C.1.55 | 2.76(l) | 428 (M + H)$^+$ |

TABLE C.1-continued
Examples prepared using general procedure C using Example #F.8.1
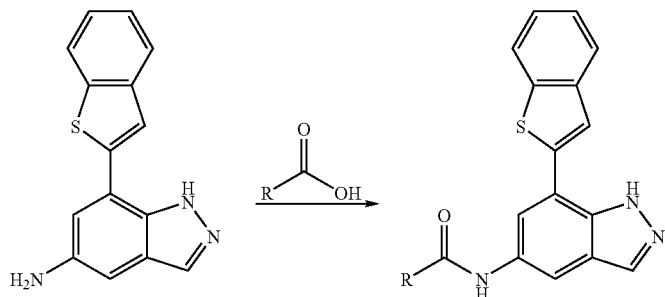
| Acid | Product | Example # | HPLC R$_t$ min(Method) | m/z |
|---|---|---|---|---|
| 6-Chloro-2H-1-benzopyran-3-carboxylic acid | 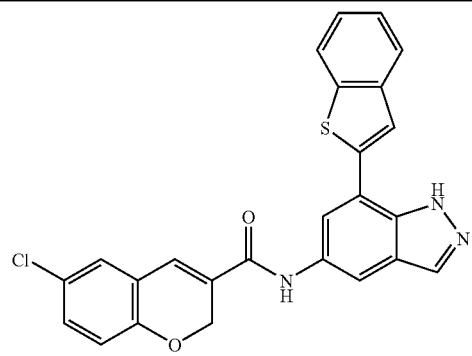 | C.1.56 | 2.93(l) | 458 (M + H)$^+$ |
| 3-(Dimethylamino) propanoic acid | 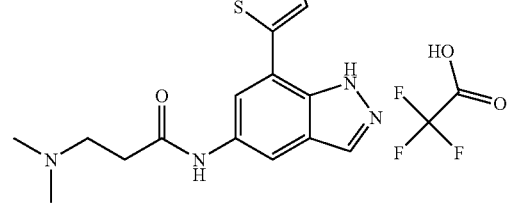 | C.1.57 | 2.05(l) | 365 (M + H)$^+$ |
| 1-Pyrrolidine propanoic acid | 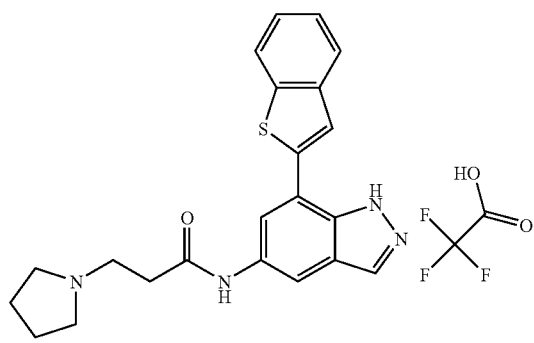 | C.1.58 | 2.12(l) | 391 (M + H)$^+$ |

TABLE C.1-continued
Examples prepared using general procedure C using Example #F.8.1
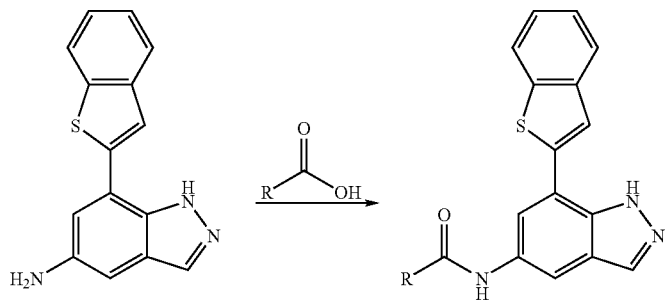
| Acid | Product | Example # | HPLC R$_t$ min(Method) | m/z |
|---|---|---|---|---|
| 1-Piperidine propionic acid | | C.1.59 | 2.18(l) | 405 (M + H)$^+$ |
| 4-Morpholinoacetic acid | | C.1.60 | 2.34(l) | 393 (M + H)$^+$ |
| 5-(5-Amino-1H-pyrrolo[2,3-c]pyridin-3-yl)-1H-indazole-7-carboxylic acid | | C.1.61 | 1.894(k) | 373 (M + H)$^+$ |
| 5-(5-Amino-1H-pyrrolo[2,3-c]pyridin-3-yl)-1H-indazole-7-carboxylic acid | | C.1.62 | 1.628(k) | 384 (M + H)$^+$ |

TABLE C.1-continued

Examples prepared using general procedure C using Example #F.8.1

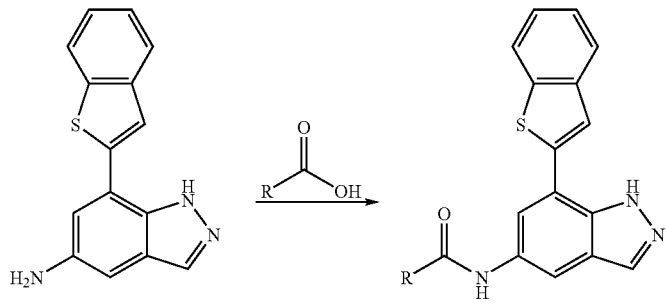

| Acid | Product | Example # | HPLC R$_t$ min(Method) | m/z |
|---|---|---|---|---|
| 5-(5-Amino-1H-pyrrolo[2,3-c]pyridin-3-yl)-1H-indazole-7-carboxylic acid | | C.1.63 | 1.536(k) | 384 (M + H)$^+$ |
| 5-(5-Amino-1H-pyrrolo[2,3-c]pyridin-3-yl)-1H-indazole-7-carboxylic acid | | C.1.64 | 1.487(k) | 384 (M + H)$^+$ |
| 5-(5-Amino-1H-pyrrolo[2,3-c]pyridin-3-yl)-1H-indazole-7-carboxylic acid | | C.1.65 | 1.301(k) | 364 (M + H)$^+$ |
| 5-(5-Amino-1H-pyrrolo[2,3-c]pyridin-3-yl)-1H-indazole-7-carboxylic acid | | C.1.66 | 1.442(k) | 390 (M + H)$^+$ |

TABLE C.1-continued

Examples prepared using general procedure C using Example #F.8.1

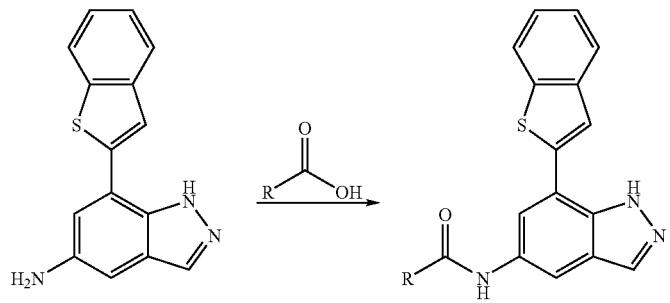

| Acid | Product | Example # | HPLC R$_t$ min(Method) | m/z |
|---|---|---|---|---|
| 5-(5-Amino-1H-pyrrolo[2,3-c]pyridin-3-yl)-1H-indazole-7-carboxylic acid | | C.1.67 | 1.461(k) | 404 (M + H)$^+$ |
| 5-(5-Amino-1H-pyrrolo[2,3-c]pyridin-3-yl)-1H-indazole-7-carboxylic acid | | C.1.68 | 2.093(k) | 387 (M + H)$^+$ |
| 5-(5-Amino-1H-pyrrolo[2,3-c]pyridin-3-yl)-1H-indazole-7-carboxylic acid | | C.1.69 | 2.201(k) | 436 (M + H)$^+$ |
| 5-(5-Amino-1H-pyrrolo[2,3-c]pyridin-3-yl)-1H-indazole-7-carboxylic acid | Chiral | C.1.70 | 1.624(k) | 377 (M + H)$^+$ |

TABLE C.1-continued

Examples prepared using general procedure C using Example #F.8.1

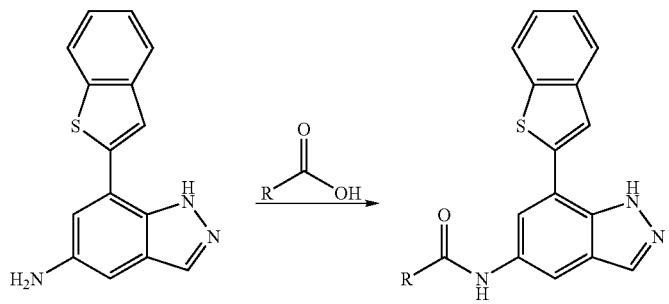

| Acid | Product | Example # | HPLC R$_t$ min(Method) | m/z |
|---|---|---|---|---|
| 5-(5-Amino-1H-pyrrolo[2,3-c]pyridin-3-yl)-1H-indazole-7-carboxylic acid | Chiral | C.1.71 | 1.628(k) | 377 (M + H)$^+$ |
| 5-(5-Amino-1H-pyrrolo[2,3-c]pyridin-3-yl)-1H-indazole-7-carboxylic acid | | C.1.72 | 1.819(k) | 347 (M + H)$^+$ |
| 5-(5-Amino-1H-pyrrolo[2,3-c]pyridin-3-yl)-1H-indazole-7-carboxylic acid | | C.1.73 | 2.007(k) | 361 (M + H)$^+$ |
| 5-(5-Amino-1H-pyrrolo[2,3-c]pyridin-3-yl)-1H-indazole-7-carboxylic acid | | C.1.74 | 2.436(k) | 389 (M + H)$^+$ |

TABLE C.1-continued

Examples prepared using general procedure C using Example #F.8.1

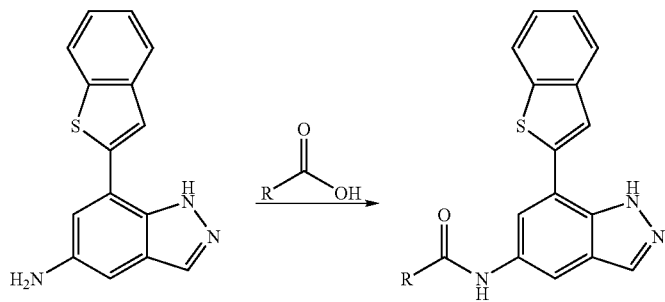

| Acid | Product | Example # | HPLC R$_t$ min(Method) | m/z |
|---|---|---|---|---|
| 5-(5-Amino-1H-pyrrolo[2,3-c]pyridin-3-yl)-1H-indazole-7-carboxylic acid | | C.1.75 | 1.652(k) | 361 (M + H)$^+$ |
| 5-(5-Amino-1H-pyrrolo[2,3-c]pyridin-3-yl)-1H-indazole-7-carboxylic acid | | C.1.76 | 1.391(k) | 363 (M + H)$^+$ |
| 5-(5-Amino-1H-pyrrolo[2,3-c]pyridin-3-yl)-1H-indazole-7-carboxylic acid | | C.1.77 | 2.101(k) | 383 (M + H)$^+$ |
| 5-(5-Amino-1H-pyrrolo[2,3-c]pyridin-3-yl)-1H-indazole-7-carboxylic acid | | C.1.78 | 2.021(k) | 383 (M + H)$^+$ |

TABLE C.1-continued

Examples prepared using general procedure C using Example #F.8.1

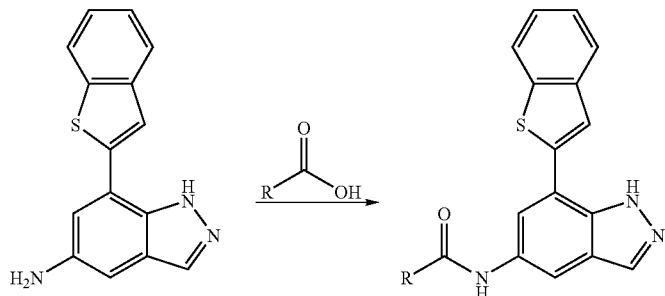

| Acid | Product | Example # | HPLC R$_t$ min(Method) | m/z |
|---|---|---|---|---|
| 5-(5-Amino-1H-pyrrolo[2,3-c]pyridin-3-yl)-1H-indazole-7-carboxylic acid | | C.1.79 | 2.328(k) | 399 (M + H)$^+$ |
| 5-(5-Amino-1H-pyrrolo[2,3-c]pyridin-3-yl)-1H-indazole-7-carboxylic acid | | C.1.80 | 2.129(k) | 399 (M + H)$^+$ |
| 5-(5-Amino-1H-pyrrolo[2,3-c]pyridin-3-yl)-1H-indazole-7-carboxylic acid | | C.1.81 | 2.555(k) | 403 (M + H)$^+$ |
| 5-(5-Amino-1H-pyrrolo[2,3-c]pyridin-3-yl)-1H-indazole-7-carboxylic acid | | C.1.82 | 2.563(k) | 403 (M + H)$^+$ |

TABLE C.1-continued
Examples prepared using general procedure C using Example #F.8.1
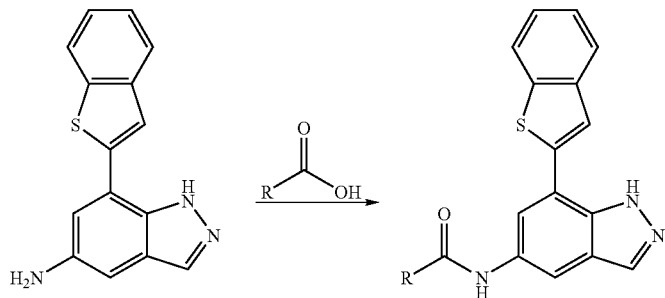
| Acid | Product | Example # | HPLC R_t min(Method) | m/z |
|---|---|---|---|---|
| 5-(5-Amino-1H-pyrrolo[2,3-c]pyridin-3-yl)-1H-indazole-7-carboxylic acid | | C.1.83 | 2.845(k) | 461 $(M + H)^+$ |
| 5-(5-Amino-1H-pyrrolo[2,3-c]pyridin-3-yl)-1H-indazole-7-carboxylic acid | | C.1.84 | 2.179(k) | 412 $(M + H)^+$ |
| 5-(5-Amino-1H-pyrrolo[2,3-c]pyridin-3-yl)-1H-indazole-7-carboxylic acid | | C.1.85 | 2.142(k) | 413 $(M + H)^+$ |

TABLE C.1-continued

Examples prepared using general procedure C using Example #F.8.1

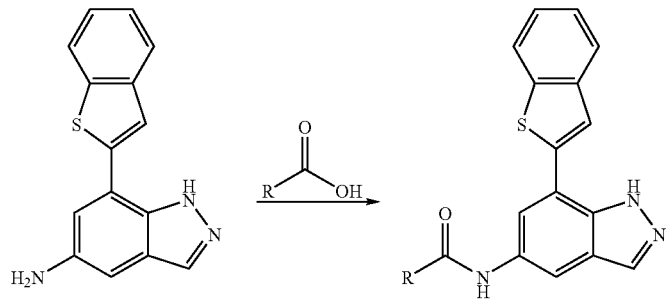

| Acid | Product | Example # | HPLC R$_t$ min(Method) | m/z |
|---|---|---|---|---|
| 5-(5-Amino-1H-pyrrolo[2,3-c]pyridin-3-yl)-1H-indazole-7-carboxylic acid | | C.1.86 | 2.096(k) | 413 (M + H)$^+$ |
| 5-(5-Amino-1H-pyrrolo[2,3-c]pyridin-3-yl)-1H-indazole-7-carboxylic acid | | C.1.87 | 2.107(k) | 413 (M + H)$^+$ |
| 5-(5-Amino-1H-pyrrolo[2,3-c]pyridin-3-yl)-1H-indazole-7-carboxylic acid | | C.1.88 | 2.338(k) | 417 (M + H)$^+$ |
| 5-(5-Amino-1H-pyrrolo[2,3-c]pyridin-3-yl)-1H-indazole-7-carboxylic acid | | C.1.89 | 2.37(k) | 417 (M + H)$^+$ |

TABLE C.1-continued
Examples prepared using general procedure C using Example #F.8.1
| Acid | Product | Example # | HPLC R$_t$ min(Method) | m/z |
|---|---|---|---|---|
| 5-(5-Amino-1H-pyrrolo[2,3-c]pyridin-3-yl)-1H-indazole-7-carboxylic acid | 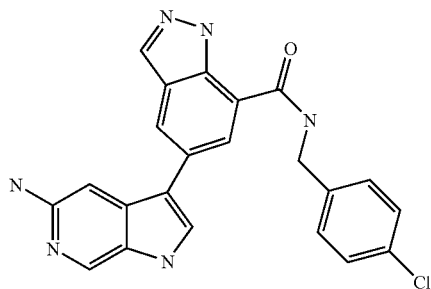 | C.1.90 | 2.31(k) | 417 (M + H)$^+$ |
| 5-(5-Amino-1H-pyrrolo[2,3-c]pyridin-3-yl)-1H-indazole-7-carboxylic acid | 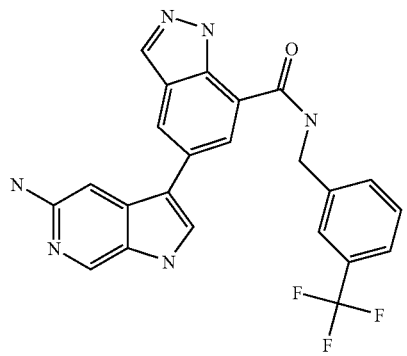 | C.1.91 | 2.446(k) | 451 (M + H)$^+$ |
| 5-(5-Amino-1H-pyrrolo[2,3-c]pyridin-3-yl)-1H-indazole-7-carboxylic acid | 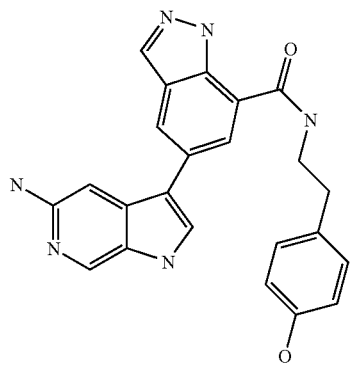 | C.1.92 | 1.74(k) | 413 (M + H)$^+$ |

TABLE C.1-continued
Examples prepared using general procedure C using Example #F.8.1
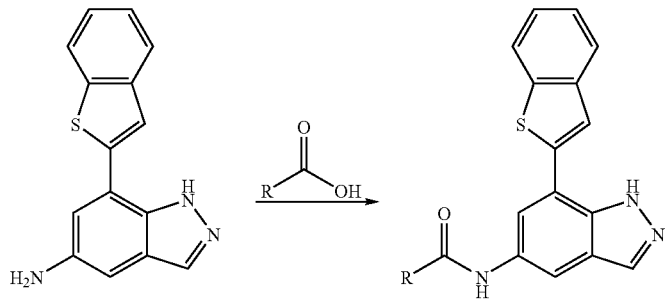
| Acid | Product | Example # | HPLC R_t min(Method) | m/z |
|---|---|---|---|---|
| 5-(5-Amino-1H-pyrrolo[2,3-c]pyridin-3-yl)-1H-indazole-7-carboxylic acid | 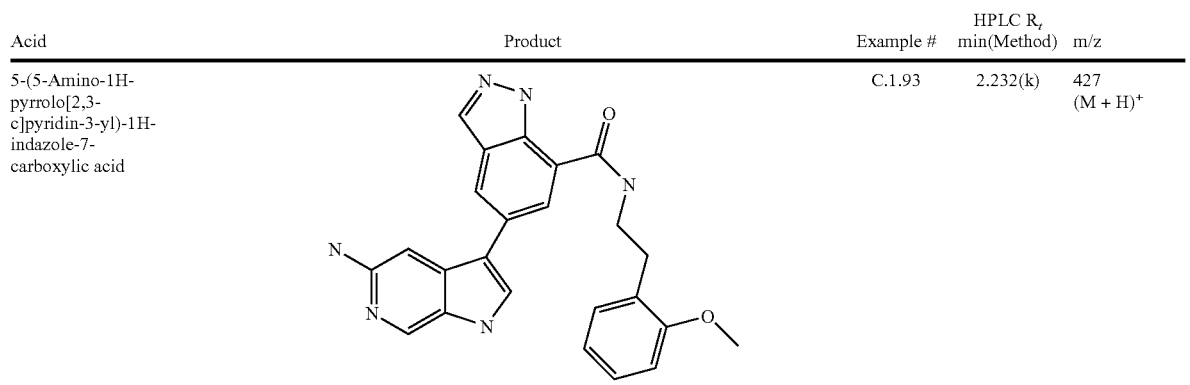 | C.1.93 | 2.232(k) | 427 (M + H)+ |
| 5-(5-Amino-1H-pyrrolo[2,3-c]pyridin-3-yl)-1H-indazole-7-carboxylic acid | 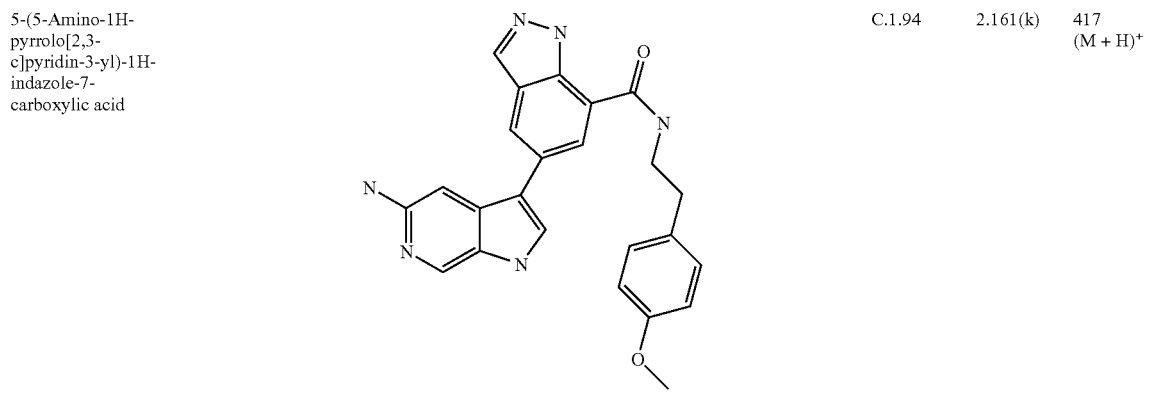 | C.1.94 | 2.161(k) | 417 (M + H)+ |
| 5-(5-Amino-1H-pyrrolo[2,3-c]pyridin-3-yl)-1H-indazole-7-carboxylic acid | 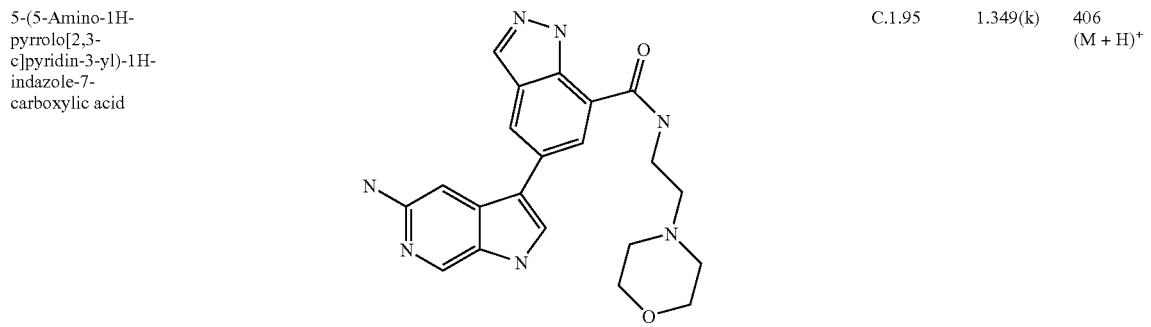 | C.1.95 | 1.349(k) | 406 (M + H)+ |

TABLE C.1-continued

Examples prepared using general procedure C using Example #F.8.1

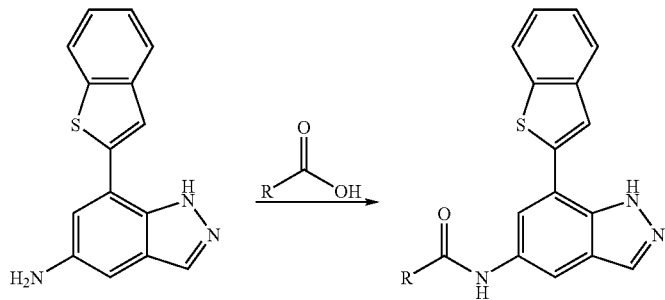

| Acid | Product | Example # | HPLC R_t min(Method) | m/z |
|---|---|---|---|---|
| 5-(5-Amino-1H-pyrrolo[2,3-c]pyridin-3-yl)-1H-indazole-7-carboxylic acid | | C.1.96 | 2.26(k) | 399 (M + H)+ |
| 5-(5-Amino-1H-pyrrolo[2,3-c]pyridin-3-yl)-1H-indazole-7-carboxylic acid | | C.1.97 | 1.994(k) | 389 (M + H)+ |
| 5-(5-Amino-1H-pyrrolo[2,3-c]pyridin-3-yl)-1H-indazole-7-carboxylic acid | | C.1.98 | 2.074 | 389 (M + H)+ |
| 5-(5-Amino-1H-pyrrolo[2,3-c]pyridin-3-yl)-1H-indazole-7-carboxylic acid | | C.1.99 | 2.99(e) | 426 (M + H)+ |

TABLE C.1-continued

Examples prepared using general procedure C using Example #F.8.1

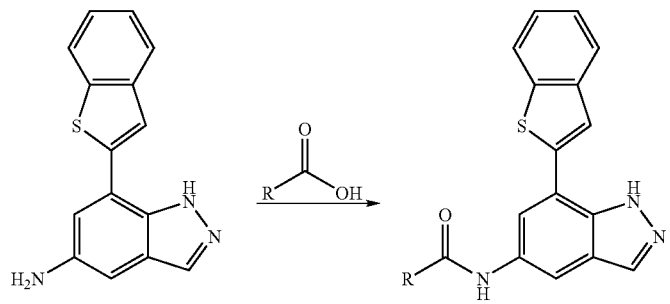

| Acid | Product | Example # | HPLC R$_t$ min(Method) | m/z |
|---|---|---|---|---|
| 5-(5-Amino-1H-pyrrolo[2,3-c]pyridin-3-yl)-1H-indazole-7-carboxylic acid | | C.1.100 | 3.09(e) | 468 (M + H)$^+$ |
| 5-(5-Amino-1H-pyrrolo[2,3-c]pyridin-3-yl)-1H-indazole-7-carboxylic acid | | C.1.101 | 3.28(e) | 452 (M + H)$^+$ |
| 5-(5-Amino-1H-pyrrolo[2,3-c]pyridin-3-yl)-1H-indazole-7-carboxylic acid | | C.1.102 | 3.22(e) | 481 (M + H)$^+$ |
| 5-(5-Amino-1H-pyrrolo[2,3-c]pyridin-3-yl)-1H-indazole-7-carboxylic acid | | C.1.103 | 0.96(e) | 381 |

TABLE C.1-continued
Examples prepared using general procedure C using Example #F.8.1
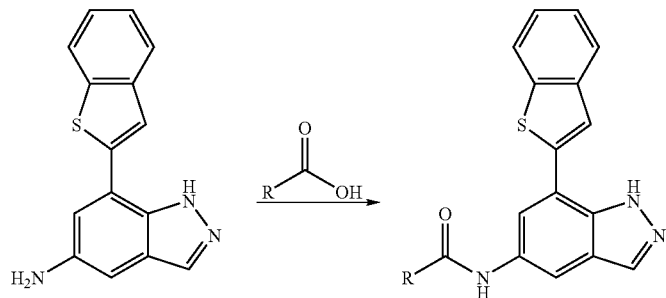
| Acid | Product | Example # | HPLC R$_t$ min(Method) | m/z |
|---|---|---|---|---|
| 5-(5-Amino-1H-pyrrolo[2,3-c]pyridin-3-yl)-1H-indazole-7-carboxylic acid | | C.1.104 | 1.09(e) | 395.2 |
| 5-(5-Amino-1H-pyrrolo[2,3-c]pyridin-3-yl)-1H-indazole-7-carboxylic acid | | C.1.105 | 0.77(e) | 396.2 |
| 5-(5-Amino-1H-pyrrolo[2,3-c]pyridin-3-yl)-1H-indazole-7-carboxylic acid | | C.1.106 | 0.85(e) | 399.2 |
| 5-(5-Amino-1H-pyrrolo[2,3-c]pyridin-3-yl)-1H-indazole-7-carboxylic acid | | C.1.107 | 1.17(e) | 408.2 |

TABLE C.1-continued

Examples prepared using general procedure C using Example #F.8.1

| Acid | Product | Example # | HPLC R$_t$ min(Method) | m/z |
|---|---|---|---|---|
| 5-(5-Amino-1H-pyrrolo[2,3-c]pyridin-3-yl)-1H-indazole-7-carboxylic acid | | C.1.108 | 1.29(e) | 466 |
| 5-(5-Amino-1H-pyrrolo[2,3-c]pyridin-3-yl)-1H-indazole-7-carboxylic acid | | C.1.109 | 0.78(e) | 462.1 |
| 5-(5-Amino-1H-pyrrolo[2,3-c]pyridin-3-yl)-1H-indazole-7-carboxylic acid | | C.1.110 | 1.30(e) | 467.1 |

TABLE C.1-continued
Examples prepared using general procedure C using Example #F.8.1
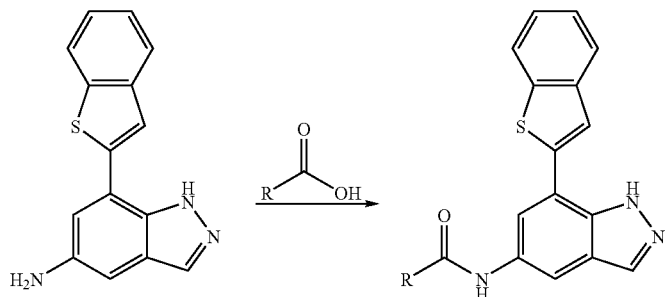
| Acid | Product | Example # | HPLC R$_t$ min(Method) | m/z |
|---|---|---|---|---|
| 5-(5-Amino-1H-pyrrolo[2,3-c]pyridin-3-yl)-1H-indazole-7-carboxylic acid | | C.1.111 | 1.29(e) | 426 |
| 5-(5-Amino-1H-pyrrolo[2,3-c]pyridin-3-yl)-1H-indazole-7-carboxylic acid | | C.1.112 | 0.45(e) | 398.1 |
| 5-(5-Amino-1H-pyrrolo[2,3-c]pyridin-3-yl)-1H-indazole-7-carboxylic acid | | C.1.113 | 0.61(e) | 467.2 |

TABLE C.1-continued

Examples prepared using general procedure C using Example #F.8.1

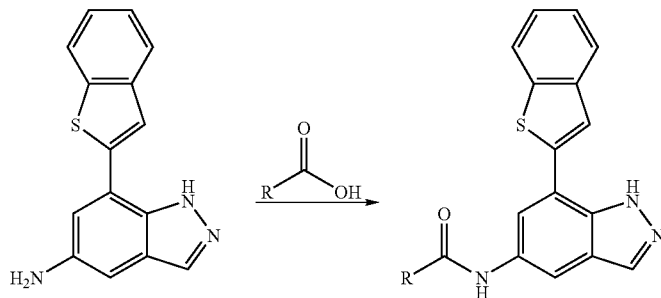

| Acid | Product | Example # | HPLC R$_t$ min(Method) | m/z |
|---|---|---|---|---|
| 5-(5-Amino-1H-pyrrolo[2,3-c]pyridin-3-yl)-1H-indazole-7-carboxylic acid | | C.1.114 | 1.19(e) | 397.3 |
| 5-(2-Amino-5H-pyrrolo[3,2-d]pyrimidin-7-yl)-1H-indazole-7-carboxylic acid | | C.1.115 | 1.33(e) | 382 |
| 5-(2-Amino-5H-pyrrolo[3,2-d]pyrimidin-7-yl)-1H-indazole-7-carboxylic acid | | C.1.116 | 1.30(e) | 370.1 |
| 5-(5-Amino-1H-pyrrolo[2,3-c]pyridin-3-yl)-1H-indazole-7-carboxylic acid | | C.1.117 | 1.15(e) | 408.2 |

General Procedure D: Protection of an Indazole with a trimethyl-silanylethoxymethyl Group

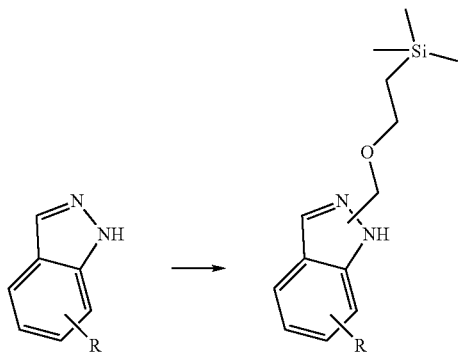

A mixture of an indazole (1 equivalent) and a base (for example, Na$_2$CO$_3$, NaOH, Cs$_2$CO$_3$ or t-BuOK, preferably Na$_2$CO$_3$) (1-10 equivalents, preferably 1-2 equivalents) and SEMCl (1-2 equivalents, preferably 1.2 equivalents) in a solvent (for example, DME or CH$_2$Cl$_2$, preferably CH$_2$Cl$_2$) mixed with either water or in an anhydrous solvent, (for example, DMF or DMA, preferably DMF) is stirred at about 10-40° C. (preferably about 20-25° C.) for about 0.5-24 hours (preferably about 1-2 hours) under an inert atmosphere. Saturated aqueous NH$_4$Cl is added and the solvents are removed under reduced pressure. The residue is dissolved in an organic solvent (CH$_2$Cl$_2$ or EtOAc, preferably EtOAc) and washed with water. The organic layer is dried over a desiccant (for example, magnesium sulfate or sodium sulfate, preferably magnesium sulfate) and further purified by crystallization or chromatography.

Illustration of General Procedure D:
Preparation #23. 7-Benzo[b]thiophen-2-yl-5-bromo-1-(2-trimethylsilanyl-ethoxymethyl)-1H-indazole, and,
Preparation #24. 7-Benzo[b]thiophen-2-yl-5-bromo-2-(2-trimethylsilanyl-ethoxymethyl)-2H-indazole

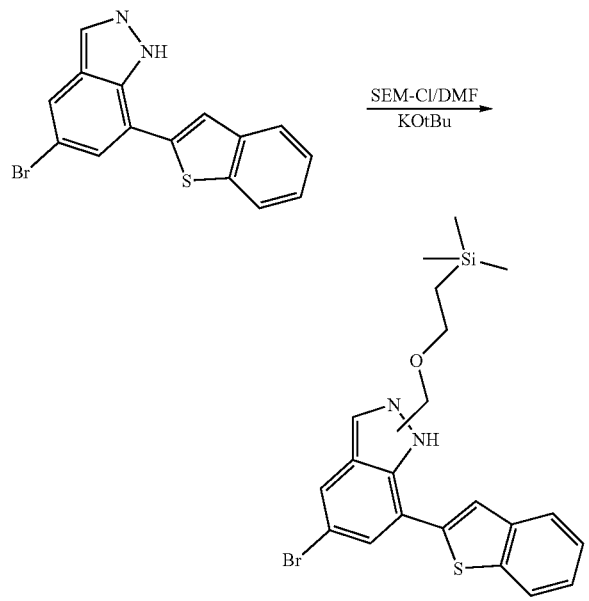

To a mixture of 7-benzo[b]thiophen-2-yl-5-bromo-1H-indazole (Preparation #26, 38.0 g, 0.116 mol) in DMF (570 mL) at about 5° C. was added t-BuOK (15.5 g, 0.139 mmol). The mixture was stirred for about 30 minutes then SEM-Cl (23.2 g, 0.139 mmol) was added over the course of about 5 minutes while maintaining the temperature between about 0-5° C. After warming to ambient temperature and stirring the solution for about 30 minutes the solution was treated with saturated aqueous NH$_4$Cl (approximately 5 mL). The solvents were removed under reduced pressure and the residue was partitioned between EtOAc:water (1:1, 700 mL). The organic layer was further washed with water (150 mL) and brine (150 mL), dried over anhydrous MgSO$_4$, filtered and concentrated to give an oil that solidified upon standing. Heptane (500 mL) was added and the mixture was heated to about 100° C. to dissolve all of the solids. The mixture was cooled to ambient temperature and the resulting solids were collected by filtration to afford 7-benzo[b]thiophen-2-yl-5-bromo-2-(2-trimethylsilanyl-ethoxymethyl)-2H-indazole (33 g, 62%); (DMSO-d$_6$, 400 MHz) δ 8.73 (s, 1H), 8.61 (s, 1H), 8.11 (d, 1H), 8.04 (m, 1H), 7.95 (m, 1H), 7.79 (d, 1H), 7.45 (m, 2H), 5.89 (s, 2H), 3.79 (m, 2H), 0.96 (m, 2H), 0.00 (s, 9H); RP-HPLC (Table 1, Method e) R$_t$ 3.63 min; m/z: (M+H)$^+$. 461.
The filtrate was concentrated and purified by flash chromatography over silica gel using heptane/EtOAc (9:1) as an eluent to give 7-benzo[b]thiophen-2-yl-5-bromo-1-(2-trimethylsilanyl-ethoxymethyl)-1H-indazole 7.8 g (15%) as an oil which solidified upon standing; (DMSO-d$_6$, 400 MHz) δ 8.50 (s, 1H), 8.40 (s, 1H), 8.26 (m, 1H), 8.12 (m, 1H), 7.89 (s, 1H), 7.80 (d, 1H), 7.67 (m, 2H), 5.64 (s, 2H), 3.34 (m, 2H), 0.81 (m, 2H), 0.00 (s, 9H); RP-HPLC (Table 1, Method e) R$_t$ 3.63 min; m/z: (M+H)$^+$. 461.

General Procedure E: Conversion of an Aryl Halide to a Boronic Acid or Boronate

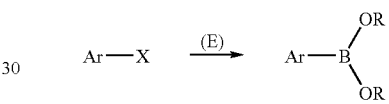

To a mixture of a boronating reagent (bis(pinacolato)diboron or pinacolatoborane, preferably bis(pinacolato)diboron) (1-1.5 equivalents, preferably 1.3 equivalents), an aryl halide (for example, an aryl bromide or an aryl iodide, preferably an aryl iodide) (0.5-3 equivalents, preferably 1 equivalent), a palladium catalyst (for example tris(benzylideneacetone)dipalladium (0), tetrakis(triphenylphosphine)palladium(0), bis(acetato)triphenylphosphinepalladium(II) (~5% Pd) polymer-bound FibreCat™ or [1,1'-bis(diphenylphosphino)ferrocene]dichloropalladium(II), complex with dichloromethane) (preferably dichloro[1,1'-bis(diphenylphosphino)ferrocene]-palladium (II) dichloromethane adduct) (0.03-0.15 equivalent, preferably 0.10 equivalents) and a base (for example, NaOAc or KOAc, preferably KOAc) (1.5-3.0 equivalents, preferably 2.5 equivalents) is added an organic solvent (for example, DMF, dioxane, or THF, preferably DMF). The mixture is heated at about 50-100° C. (preferably about 80° C.) for about 1-24 hours (preferably about 15 hours) under an inert atmosphere. The mixture is allowed to cool to ambient temperature, and the solvent is removed under reduced pressure. The residue can then be further purified by chromatography or crystallization.

Illustration of General Procedure E.
Preparation #25: 7-Benzo[b]thiophen-2-yl-5-(4,4,5,5-tetramethyl-[1,3,2]dioxa borolan-2-yl)-1H-indazole

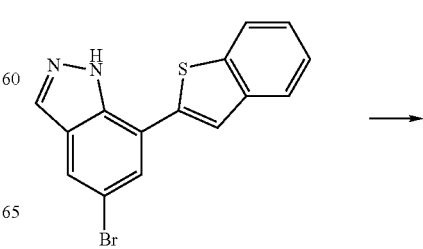

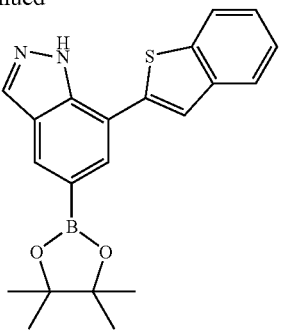

A mixture of 7-benzo[b]thiophen-2-yl-5-bromo-1H-indazole (Preparation #26, 5.0 g, 15.2 mmol), bis(pinacolato)diboron (5.78, 22.8 mmol), KOAc (3.72 g, 38 mmol) and [1,1'-bis(diphenylphosphino)ferrocene]dichloropalladium (II), complex with dichloromethane (1:1) (0.99 g, 1.22 mmol) in DMF (125 mL) was heated at about 100° C. under an atmosphere of nitrogen for about 18 hours. The dark reaction solution was cooled to ambient temperature, diluted with CH$_2$Cl$_2$ (25 mL) then washed with water (2×20 mL). The reaction mixture was cooled, concentrated under reduced pressure, triturated with CH$_2$Cl$_2$ (175 mL), filtered and the filtrate concentrated under reduced pressure. The resulting material was purified by flash chromatography over silica gel using CH$_2$Cl$_2$/EtOAc (97:3) as the eluent and the material was triturated with heptane (25 mL) to give 7-benzo[b]thiophen-2-yl-5-(4,4,5,5-tetramethyl-[1,3,2]dioxaborolan-2-yl)-1H-indazole as a white solid (2.23 g, 39%); (DMSO-d$_6$, 400 MHz) δ 13.5 (s, 1H), 8.31 (s, 1H), 8.22 (s, 1H), 8.06 (s, 1H), 8.02 (d, 1H), 7.89 (d, 1H), 7.83 (s, 1H), 7.43 (m, 2H), 1.35 (s, 12H); RP-HPLC (Table 1, Method e) R$_t$ 2.77 min; m/z (M−H)⁻ 374.5.

General Procedure F: Suzuki Coupling of a Boronate or Boronic acid with an Aryl Halide Substrate

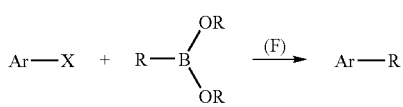

To a mixture of a boronate ester or a boronic acid (1-5 equivalents, preferably 2 equivalents), an aryl halide (for example, an aryl bromide, aryl chloride or an aryl iodide, preferably an aryl iodide) (0.7-3 equivalents, preferably 1 equivalent) and an inorganic base (for example, KF, Na$_2$CO$_3$ or Cs$_2$CO$_3$, preferably Cs$_2$CO$_3$) (2-16 equivalents, preferably 2.5 equivalents) in a degassed organic solvent (for example THF, DME, DMF, 1,4-dioxane, DME/water or toluene, preferably DMF or DME/water) is added a palladium catalyst (for example tris(benzylideneacetone)dipalladium (0), tetrakis(triphenylphosphine)palladium(0), bis(acetato)triphenylphosphinepalladium(II) (~5% Pd) polymer-bound FibreCat™ or [1,1'-bis(diphenylphosphino)ferrocene]dichloropalladium(II), complex with dichloromethane, preferably tetrakis(triphenylphosphine)palladium(0)) (0.01-0.10 equivalents, preferably 0.05 equivalents). If necessary, tributylphosphinetetraflouroborate (0.01 to 0.20 equivalents, preferably 0.05 equivalents) is also added. The reaction mixture is heated at about 40-150° C. (preferably about 80° C.) for about 2-24 hours (preferably about 18 hours) or at about 100-200° C. (preferably 150° C.) for about 5-60 minutes (preferably about 15 minutes) in a microwave under an inert atmosphere. The reaction mixture is allowed to cool to ambient temperature. Subsequently, the solvents are removed under reduced pressure and the residue is suspended in a mixture of EtOAc and water; the mixture is stirred for 30 minutes and the resulting solid is collected by filtration; the product can be further purified by chromatography or crystallization. Alternatively, the cooled reaction mixture is diluted with water or an aqueous basic solution (such as saturated aqueous NaHCO$_3$) and extracted (1-5 times, preferably 3 times) with a suitable solvent (such as EtOAc or CH$_2$Cl$_2$) then the combined organic extracts are dried (for example, over Na$_2$SO$_4$ or MgSO$_4$), decanted or filtered, and concentrated under reduced pressure to afford the product that can be further purified by chromatography or crystallization. If a tert-butoxycarbonyl (Boc) protected amine is used, then the material is subsequently suspended in a mixture of methanol/6 N HCl and heated to about 65° C. for about one hour then cooled, concentrated and purified by chromatography or crystallization.

Illustrations of General Procedure F.

Example #13a

7-Benzo[b]thiophen-2-yl-5-bromo-1H-indazole

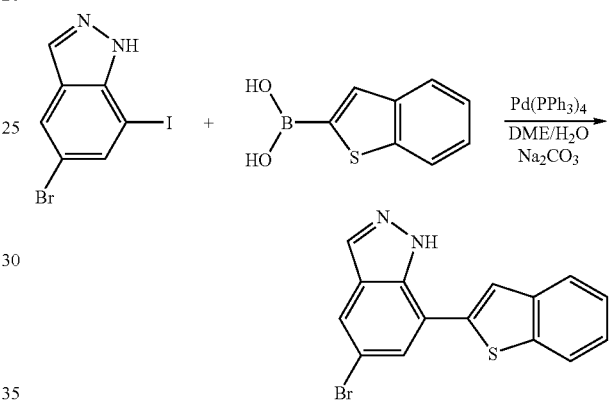

A mixture of 5-bromo-7-iodo-1H-indazole (Preparation #22a, 30.0 g, 92.9 mmol) and thianapthene-2-boronic acid (21.5 g, 120.7 mmol), DME (480 mL), water (48 mL), Na$_2$CO$_3$ (29.5 g, 279 mmol) and tetrakis triphenylphosphine palladium (0) (8.6 g, 7.43 mmol) was heated at about 90° C. in an oil bath under an atmosphere of nitrogen for about 15 hours. The solvent was removed under reduced pressure and the residue was suspended in a mixture of ethyl acetate (600 mL) and water (300 mL). The mixture was stirred for about 30 minutes and the resulting solid was collected by filtration and dried to yield 7-Benzo[b]thiophen-2-yl-5-bromo-1H-indazole (21.4 g, 70%); (DMSO-d$_6$, 400 MHz) δ 13.63 (s, 1H), 8.24 (s, 1H), 8.05-8.09 (m, 3H), 7.92 (d, 1H), 7.65 (s, 1H), 7.16 (m, 2H); RP-HPLC (Table 1, Method e) R$_t$=2.69 min; m/z: (M−H)⁻ 328.4.

Example #13c

N-Phenyl-5-pyridin-3-yl-1H-indazole-7-carboxamide

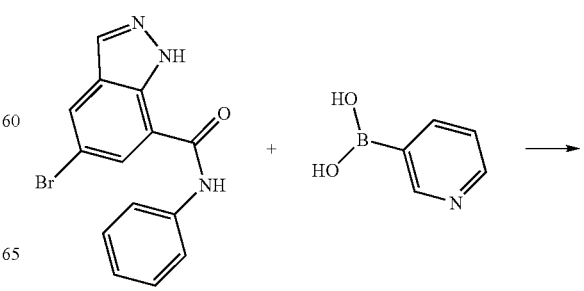

289
-continued

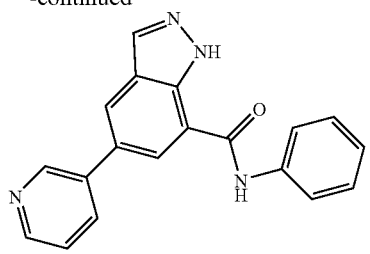

A mixture of N-phenyl-5-bromo-1H-indazole-7-carboxamide (Example #B.1.2, 0.05 g, 0.16 mmol) and pyridine-3-yl-boronic acid (0.11 g, 0.8 mmol), 1,2-dimethoxyethane (1.3 mL), water (0.7 mL), Cs$_2$CO$_3$ (0.16 g, 0.48 mmol) and [1,1'-bis(diphenylphosphino)ferrocene]dichloropalladium(II), complex with dichloromethane (0.013 g, 0.016 mmol) was heated at about 150° C. in the microwave under an atmosphere of nitrogen for about 15 minutes. The crude product was filtered and the solvent was removed under reduced pressure. The residue was dissolved in DMSO then purified by reverse phase HPLC (Waters Symmetry C8 column (25×100 mm, 7 μm particle size) using a gradient of 10%-100% CH$_3$CN/0.1% aqueous TFA over 8 min (10 min run time) at a flow rate of 40 mL/min) to yield N-phenyl-5-pyridin-3-yl-1H-indazole-7-carboxamide (0.014 g, 6%); (DMSO-d$_6$, 400 MHz) δ 13.4 (bs, 1H), 10.5 (bs, 1H), 9.12 (d, 1H), 8.62 (d, 1H), 8.48 (s, 1H), 8.34 (s, 1H), 8.28 (m, 2H), 7.84 (d, 2H), 7.56 (m, 1H), 7.42 (m, 2H), 7.16 (m, 2H); RP-HPLC (Table 1, Method e) R$_t$=1.81 min; m/z: (M+H)$^+$ 315.3.

TABLE F.1

Examples prepared using general procedure F from Preparation #25

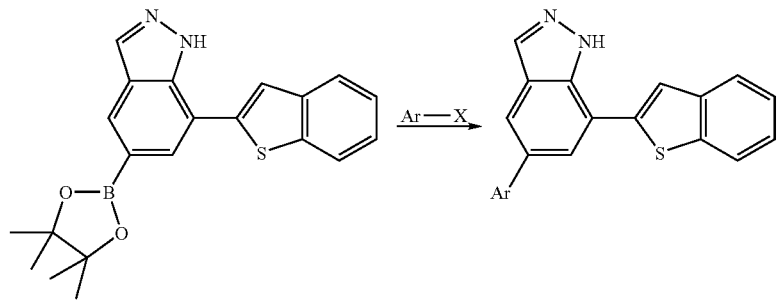

| Aryl Halide | Product | Example # | HPLC R$_t$(min)(method) | m/z |
|---|---|---|---|---|
| 2-Chloro-4-iodo-pyridine | | F.1.1 | 2.63(e) | 359.5 (M − H)$^-$ |
| 5-Bromo-nicotinonitrile | | F.1.2 | 2.28(e) | 350.8 (M − H)$^-$ |

TABLE F.1-continued
Examples prepared using general procedure F from Preparation #25
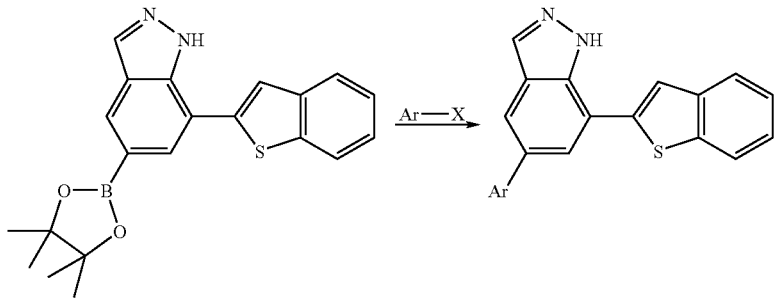
| Aryl Halide | Product | Example # | HPLC $R_t$(min)(method) | m/z |
|---|---|---|---|---|
| 5-Bromo-nicotinamide | | F.1.3 | 1.70(e) | 368.7 (M − H)⁻ |
| (5-Bromo-pyridin-2-yl)-methanol | | F.1.4 | 1.93(e) | 355.8 (M − H)⁻ |
| 1-(5-Bromo-pyridin-2-yl)-ethanone | | F.1.5 | 2.44(e) | 368.1 (M − H)⁻ |

TABLE F.1-continued
Examples prepared using general procedure F from Preparation #25
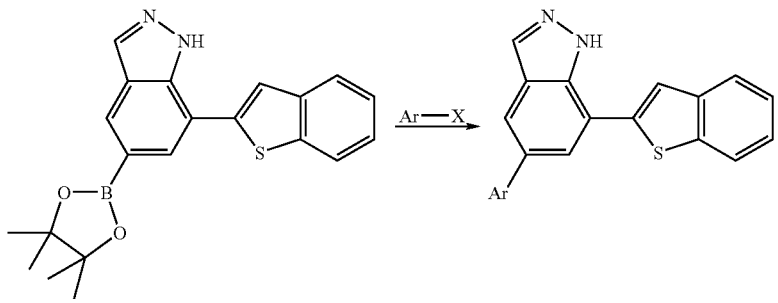
| Aryl Halide | Product | Example # | HPLC $R_t$(min)(method) | m/z |
|---|---|---|---|---|
| 5-Bromo-nicotinic acid hydrazide | | F.1.6 | 1.55(e) | 384.0 (M − H)⁻ |
| 5-Bromo-pyridine-2-carbonitrile | | F.1.7 | 2.39(e) | 351.1 (M − H)⁻ |
| 5-Bromo-pyridine-2-carboxylic acid | | F.1.8 | 1.55(e) | 369.9 (M − H)⁻ |

TABLE F.1-continued
Examples prepared using general procedure F from Preparation #25
| Aryl Halide | Product | Example # | HPLC R$_t$(min)(method) | m/z |
|---|---|---|---|---|
| 5-Bromo-pyridine-3-carboxaldehyde | 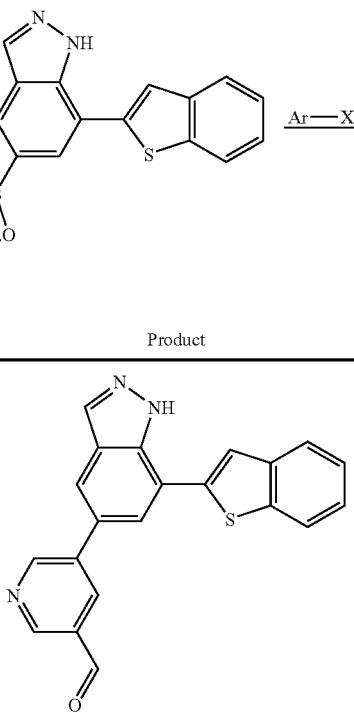 | F.1.9 | 2.26(e) | 354.2 (M − H)$^-$ |
| (3-Bromo-phenyl)-urea | 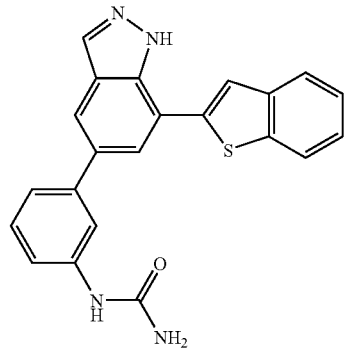 | F.1.10 | 1.94(e) | 382.7 (M − H)$^-$ |
| 3-Bromo-thieno[3,2-c]pyridin-4-yl amine | 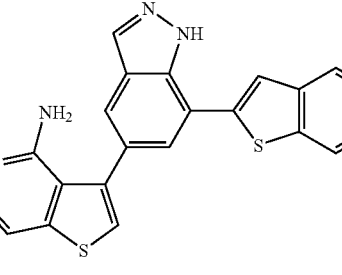 | F.1.11 | 2.49(e) | 399.0 (M − H)$^-$ |
| 3-Bromo-furo[3,2-c]pyridin-4-ylamine | 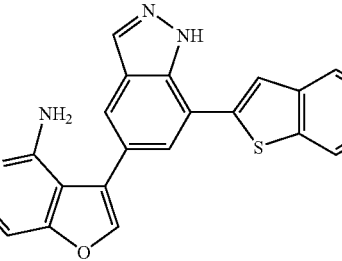 | F.1.12 | 2.39(e) | 383.0 (M − H)$^-$ |

TABLE F.1-continued

Examples prepared using general procedure F from Preparation #25

| Aryl Halide | Product | Example # | HPLC R$_t$(min)(method) | m/z |
|---|---|---|---|---|
| Cis-{3-iodo-1-[4-(4-methyl-piperazin-1-yl)-cyclohexyl]-1H-pyrazolo[3,4-d]pyrimidin-4-ylamine} | | F.1.13 | 1.79(e) | 564.1 (M + H)$^+$ |
| 3-Iodo-pyridin-4-ylamine | | F.1.14 | 1.88(e) | 343.0 (M + H)$^+$ |
| 3-Iodo-pyridin-2-ylamine | | F.1.15 | 2.30(e) | 343.0 (M + H)$^+$ |

TABLE F.1-continued
Examples prepared using general procedure F from Preparation #25
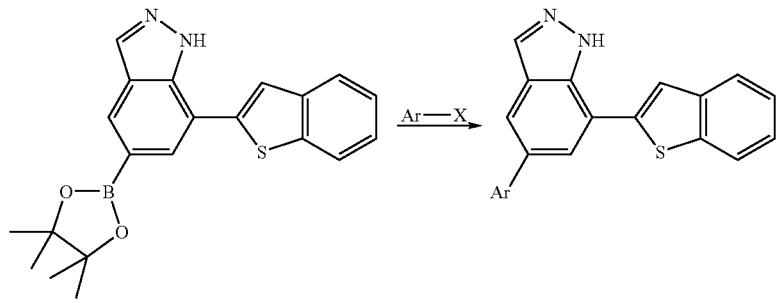
| Aryl Halide | Product | Example # | HPLC R$_t$(min)(method) | m/z |
|---|---|---|---|---|
| 4-(3-Iodo-pyridin-2-yl)-morpholine | | F.1.16 | 2.41(e) | 412.9 (M + H)⁺ |
| 3-Iodo-1-methyl-1H-pyrazolo[3,4-d]pyrimidin-4-ylamine | | F.1.17 | 1.96(e) | 398.0 (M + H)⁺ |
| 3-Iodo-2-isopropoxy-pyridine | | F.1.18 | 2.79(e) | 383.7 (M + H)⁺ |
| 3-Iodo-2-methoxy-pyridine | | F.1.19 | 2.56(e) | 357.9 (M + H)⁺ |

TABLE F.1-continued
Examples prepared using general procedure F from Preparation #25
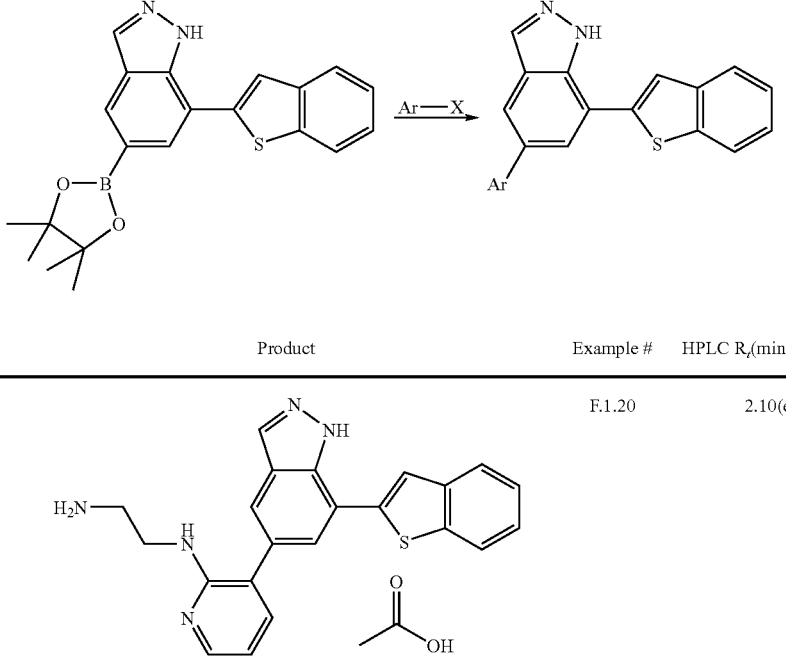
| Aryl Halide | Product | Example # | HPLC R$_t$(min)(method) | m/z |
|---|---|---|---|---|
| [2-(6-Iodo-pyridin-2-ylamino)-ethyl]-carbamic acid tert-butyl ester | | F.1.20 | 2.10(e) | 386.0 (M + H)$^+$ |
| [2-(6-Iodo-pyridin-2-yloxy)-ethyl]-carbamic acid tert-butyl ester | | F.1.21 | 2.02(e) | 387.0 (M + H)$^+$ |
| Thiophene-2-carboxylic acid(5-bromo-4,6-dimethyl-pyrimidin-2-yl)-amide | | F.1.22 | 2.02(e) | 481.9 (M + H)$^+$ |

TABLE F.1-continued

Examples prepared using general procedure F from Preparation #25

| Aryl Halide | Product | Example # | HPLC R$_t$(min)(method) | m/z |
|---|---|---|---|---|
| N-(5-Bromo-3-methyl-pyridin-2-yl)-acetamide | | F.1.23 | 1.83(e) | 399.0 (M + H)$^+$ |
| N-(2-Bromo-pyridin-3-yl)-acetamide | | F.1.24 | 1.70(e) | 385.0 (M + H)$^+$ |
| 5-Iodo-6-methyl-pyrimidin-4-ylamine | | F.1.25 | 2.16(e) | 358.0 (M + H)$^+$ |

TABLE F.1-continued
Examples prepared using general procedure F from Preparation #25
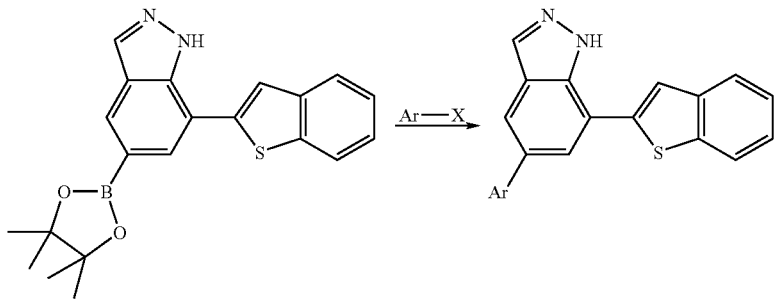
| Aryl Halide | Product | Example # | HPLC R$_t$(min)(method) | m/z |
|---|---|---|---|---|
| N-(5-Iodo-6-methyl-pyridin-2-yl)-2,2-dimethyl-propionamide | | F.1.26 | 2.42(e) | 441.0 (M + H)$^+$ |
| 5-Bromo-4-methyl-pyridin-2-ylamine | | F.1.27 | 2.14(e) | 354.6 (M − H)$^−$ |
| 3-Bromo-5-(1H-tetrazol-5-yl)-pyridine | | F.1.28 | 1.30(e) | 441.0 (M + H)$^+$ |

TABLE F.1-continued
Examples prepared using general procedure F from Preparation #25
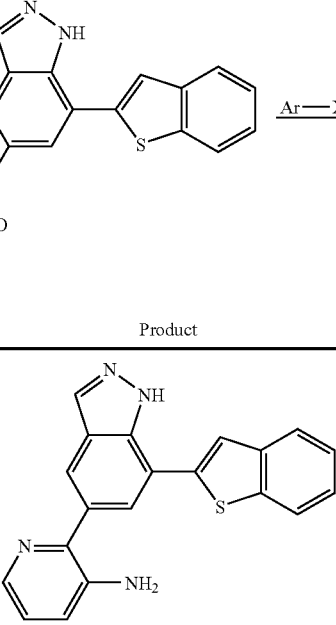
| Aryl Halide | Product | Example # | HPLC R$_t$(min)(method) | m/z |
|---|---|---|---|---|
| 2-Bromo-pyridin-3-ylamine | | F.1.29 | 1.92(e) | 342.9 (M + H)$^+$ |
| 4-Bromo-6-trifluoromethyl-1H-benzoimidazole | | F.1.30 | 2.39(e) | 432.4 (M − H)$^-$ |
| 1-(5-Bromo-2-chloro-pyridin-3-yl)-3-phenyl-urea | | F.131 | 2.56(e) | 493.9 (M − H)$^-$ |
| 3-Iodo-indazole-1-carboxylic acid tert-butyl ester | | F.1.32 | 2.27(e) | 364.6 (M − H)$^-$ |

TABLE F.1-continued
Examples prepared using general procedure F from Preparation #25
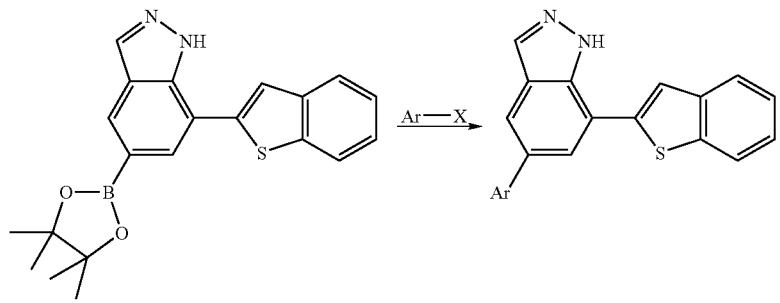
| Aryl Halide | Product | Example # | HPLC R$_t$(min)(method) | m/z |
|---|---|---|---|---|
| 2-Cyclopropyl methoxy-3-iodo-pyridine | | F.1.33 | 2.81(e) | 396.0 (M − H)⁻ |
| 6'-Bromo-3,4,5,6-tetrahydro-2H-[1,2']bipyriidnyl-3'-ylamine | | F.1.34 | 2.84(e) | 426 (M + H)⁺ |
| 4-Bromo-quinolin-3-ylamine | | F.1.35 | 2.44(e) | 393 (M + H)⁺ |

//TABLE F.1-continued

Examples prepared using general procedure F from Preparation #25

| Aryl Halide | Product | Example # | HPLC R$_t$(min)(method) | m/z |
|---|---|---|---|---|
| 4-(3-Iodo-pyridin-2-yl)-piperazine-1-carboxylic acid tert-butyl ester | | F.1.36 | 2.29(e) | 412 (M + H)$^+$ |
| 6-Bromo-pyridin-2-ylamine | | F.1.37 | 2.19(e) | 341 (M + H)$^+$ |
| 3-(5-Bromo-thiophen-2-yl)-1H-pyrazole | | F.1.38 | 2.42(e) | 399 (M + H)$^+$ |

TABLE F.1-continued
Examples prepared using general procedure F from Preparation #25
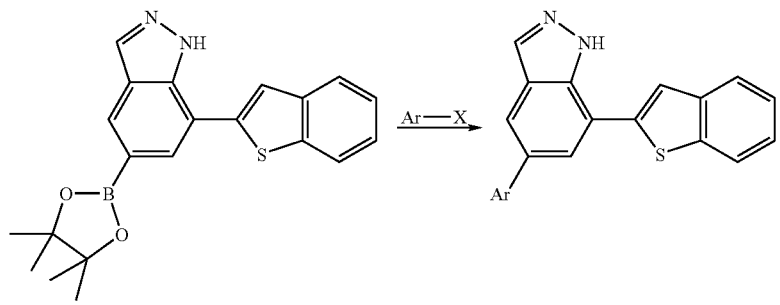
| Aryl Halide | Product | Example # | HPLC R$_t$(min)(method) | m/z |
|---|---|---|---|---|
| 3-Bromo-5-methyl-pyridin-2-ylamine | | F.1.39 | 2.50(e) | 357 (M + H)$^+$ |
| 7-Bromo-4H-benzo[1,4]thiazin-3-one | | F.1.40 | 2.30(e) | 412 (M − H)$^-$ |
| [2-(3-Iodo-pyridin-2-ylsulfanyl)-ethyl]-carbamic acid tert-butyl ester | | F.1.41 | 2.30(e) | 401 (M − H)$^-$ |

TABLE F.1-continued

Examples prepared using general procedure F from Preparation #25

| Aryl Halide | Product | Example # | HPLC R$_t$(min)(method) | m/z |
|---|---|---|---|---|
| 5-Bromo-pyrazin-2-yl amine | | F.1.42 | 1.98(e) | 342 (M − H)$^-$ |
| 5-Bromo-2-methoxy-nicotinic acid methyl ester | | F.1.43 | 1.21(e) | 400 (M − H)$^-$ |
| 3-Fluoro-4-iodo-pyridine | | F.1.44 | 2.78(e) | 344 (M − H)$^-$ |

TABLE F.1-continued

Examples prepared using general procedure F from Preparation #25

| Aryl Halide | Product | Example # | HPLC R$_t$(min)(method) | m/z |
|---|---|---|---|---|
| 3-Fluoro-2-iodo-pyridine | | F.1.45 | 2.48(e) | 344 (M − H)$^-$ |
| 2-Chloro-5-iodo-pyridine | | F.1.46 | 2.53(e) | 360 (M − H)$^-$ |
| N-(5-iodo-3-methyl-pyridin-2-yl)thiophene-2-carboxamide | | F.1.47 | 2.2(e) | 466.8 (M + H)$^+$ |
| N-(5-Iodo-6-methyl-pyridin-2-yl)-isobutyramide | | F.1.48 | 2.3(e) | 427.0 (M + H)$^+$ |

TABLE F.1-continued

Examples prepared using general procedure F from Preparation #25

| Aryl Halide | Product | Example # | HPLC R$_t$(min)(method) | m/z |
|---|---|---|---|---|
| 4-Bromo-1H-indazole | | F.1.49 | 2.4(e) | 364.5 (M − H)$^-$ |
| 1-Bromo-4-(4-fluorophenyl)-isoquinolin-3-yl amine | | F.1.50 | 2.9(e) | 486.9 (M + H)$^+$ |
| N-(5-Iodo-3-methyl-pyridin-2-yl)-furan-2-carboxamide | | F.1.51 | 2.1(e) | 450.9 (M + H)$^+$ |
| N-(5-Iodo-pyridin-2-yl)-acetamide | | F.1.52 | 2.1(e) | 383.2 (M − H)$^-$ |

TABLE F.1-continued

Examples prepared using general procedure F from Preparation #25

| Aryl Halide | Product | Example # | HPLC R$_t$(min)(method) | m/z |
|---|---|---|---|---|
| 4-Bromo-quinoline-2-carboxamide | | F.1.53 | 2.5(e) | 420.9 (M + H)$^+$ |
| 5-Bromo-1H-pyrrolo[2,3-b]pyridine | | F.1.54 | 2.5(e) | 365.0 (M − H)$^-$ |
| 5-Iodo-3-methyl-pyridin-2-ylamine | | F.1.55 | 2.4(e) | 354.6 (M − H)$^-$ |
| 5-Bromo-1H-indazole | | F.1.56 | 2.3(e) | 364.6 (M − H)$^-$ |

TABLE F.1-continued
Examples prepared using general procedure F from Preparation #25
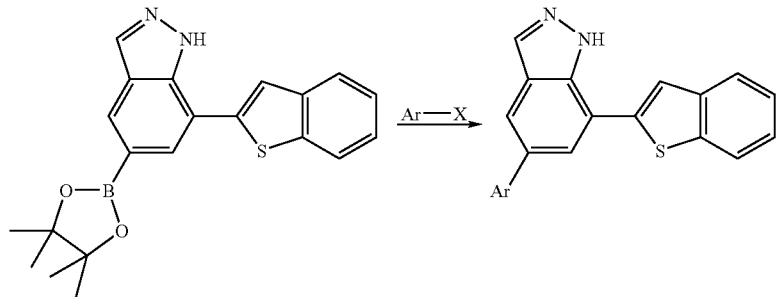
| Aryl Halide | Product | Example # | HPLC R$_t$(min)(method) | m/z |
|---|---|---|---|---|
| 6-Iodo-1H-quinazolin-4-one | 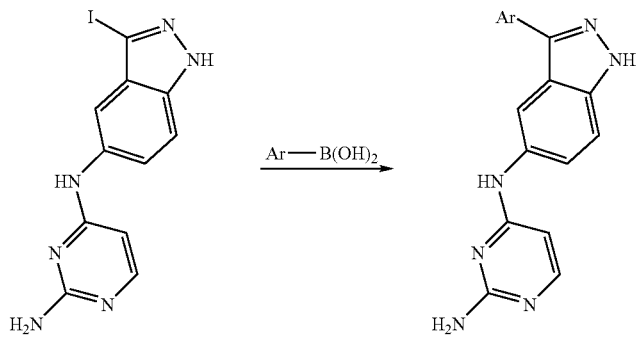 | F.1.57 | 2.1(e) | 392.6 (M − H)$^-$ |
TABLE F.2
Examples prepared using general procedure F from Example #N.2.2
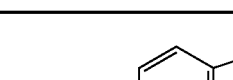
| Boronates/ Boronic Acids | Product | Example # | HPLC R$_t$ (min) (method) | m/z (ESI+) |
|---|---|---|---|---|
| 4-Hydroxyphenyl boronic acid | | F.2.1 | 1.1 (e) | 317.6 (M − H)$^-$ |

TABLE F.2-continued

| Reagent | Structure | ID | RT | MS |
|---|---|---|---|---|
| 2-Hydroxyphenyl boronic acid | 5-[(2-aminopyrimidin-4-yl)amino]-3-(2-hydroxyphenyl)-1H-indazole · AcOH | F.2.2 | 1.7 (e) | 317.6 (M − H)⁻ |
| 3-Hydroxyphenyl boronic acid | 5-[(2-aminopyrimidin-4-yl)amino]-3-(3-hydroxyphenyl)-1H-indazole · AcOH | F.2.3 | 1.1 (e) | 317.4 (M − H)⁻ |
| 4-Hydroxymethyl phenyl boronic acid | 5-[(2-aminopyrimidin-4-yl)amino]-3-(4-hydroxymethylphenyl)-1H-indazole · AcOH | F.2.4 | 0.98 (e) | 333.2 (M + H)⁺ |
| 6-Methoxy-2-naphthalene boronic acid | 5-[(2-aminopyrimidin-4-yl)amino]-3-(6-methoxynaphthalen-2-yl)-1H-indazole | F.2.5 | 1.87 (e) | 383.8 (M + H)⁺ |
| Benzamide-3-boronic acid | 5-[(2-aminopyrimidin-4-yl)amino]-3-(3-carbamoylphenyl)-1H-indazole · 2 AcOH | F.2.6 | 0.93 (e) | 346.1 (M + H)⁺ |

TABLE F.2-continued
| | | | | |
|---|---|---|---|---|
| Benzamide 4-boronic acid | 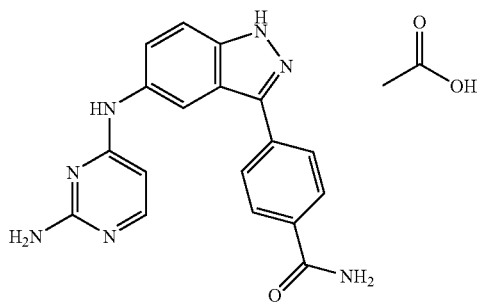 | F.2.7 | 0.67 (e) | 346.8 (M + H)+ |
| 3-(Trifluoromethyl) phenylboronic acid | 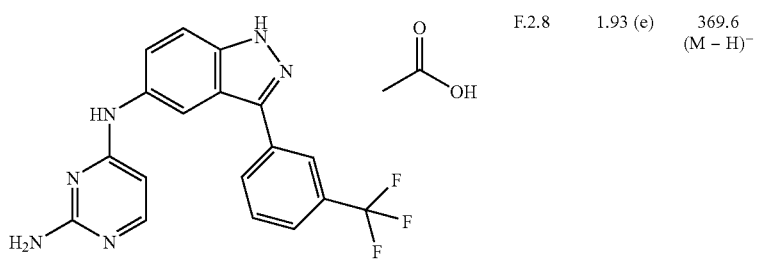 | F.2.8 | 1.93 (e) | 369.6 (M − H)− |
| 3-(Isopropyl) phenylboronic acid | 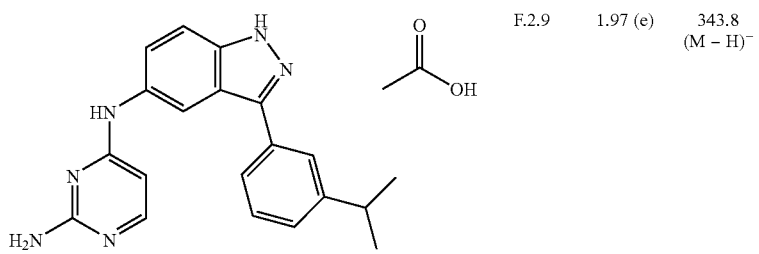 | F.2.9 | 1.97 (e) | 343.8 (M − H)− |
| 3-(Trifluoro methoxy) phenylboronic acid | 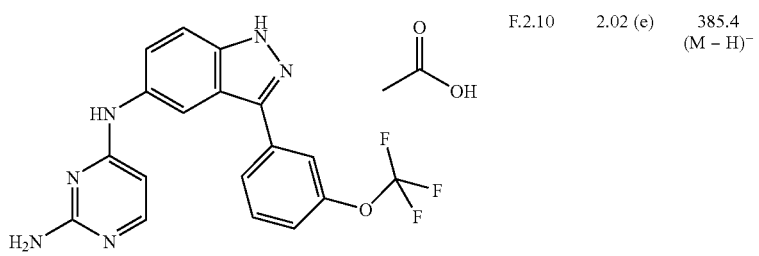 | F.2.10 | 2.02 (e) | 385.4 (M − H)− |
| 3-(Methoxy) phenylboronic acid | 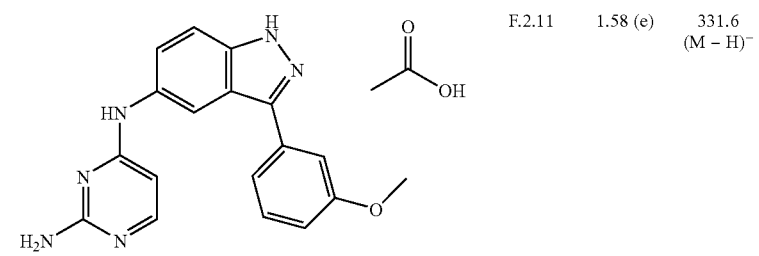 | F.2.11 | 1.58 (e) | 331.6 (M − H)− |

TABLE F.2-continued
| | | | | | |
|---|---|---|---|---|---|
| 3-(Benzyloxy)phenylboronic acid | 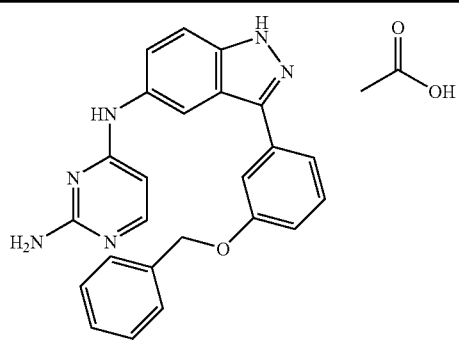 | 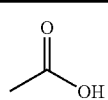 | F.2.12 | 2.05 (e) | 409.2 (M + H)+ |
| 3-Biphenyl boronic acid | 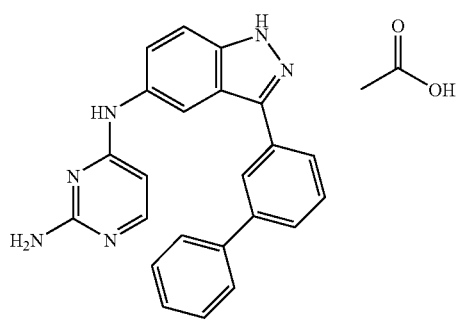 | 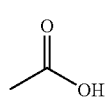 | F.2.13 | 2.02 (e) | 377.6 (M − H)− |
| 3-Cyanophenyl boronic acid | 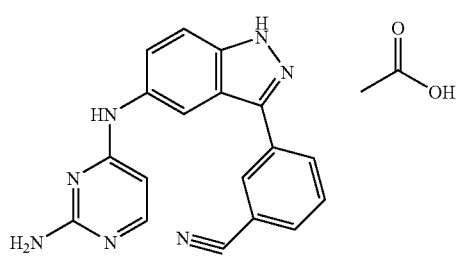 | 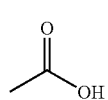 | F.2.14 | 1.52 (e) | 328.1 (M + H)+ |
| 3-Ethoxyphenyl boronic acid | 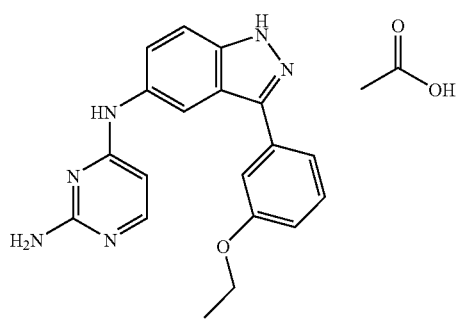 | 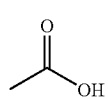 | F.2.15 | 1.82 (e) | 347.3 (M + H)+ |
| 3-Aminophenyl boronic acid | 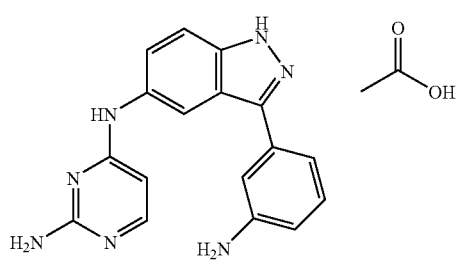 | 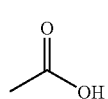 | F.2.16 | 0.93 (e) | 318.7 (M + H)+ |

TABLE F.2-continued
| | | | | |
|---|---|---|---|---|
| 3,5-Dimethylphenyl boronic acid | 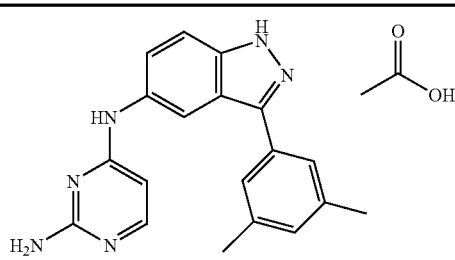 | F.2.17 | 1.75 (e) | 331.0 (M + H)+ |
| 3-Methyl-4-methoxyphenyl boronic acid | 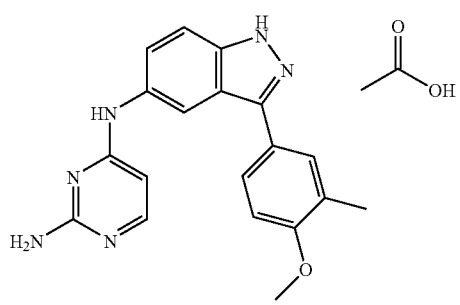 | F.2.18 | 1.55 (e) | 347.0 (M + H)+ |
| 3-(Hydroxymethyl) phenyl boronic acid | 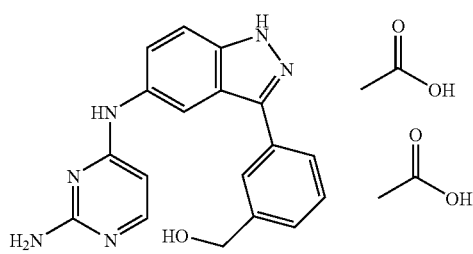 | F.2.19 | 0.93 (e) | 333.3 (M + H)+ |
| 3,4-Dimethylphenyl boronic acid | 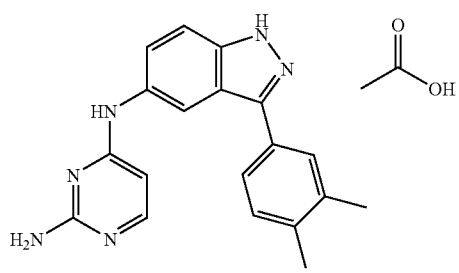 | F.2.20 | 1.65 (e) | 331.0 (M + H)+ |
| 3,4-Dimethoxyphenyl boronic acid | 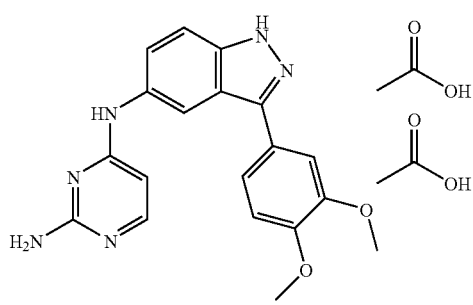 | F.2.21 | 1.30 (e) | 362.0 (M + H)+ |

TABLE F.2-continued
| | | | | |
|---|---|---|---|---|
| 3-Methyl-4-fluoro phenyl boronic acid |  | F.2.22 | 1.24 (e) | 335.3 (M + H)+ |
| Thianaphthene-2-boronic acid | 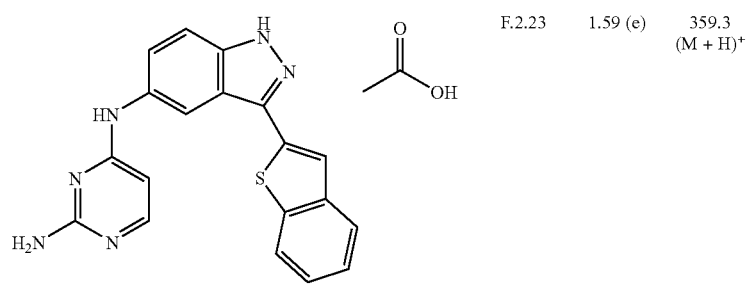 | F.2.23 | 1.59 (e) | 359.3 (M + H)+ |
| 5-(Dimethylamino)-1-benzothiophen-2-yl boronic acid | 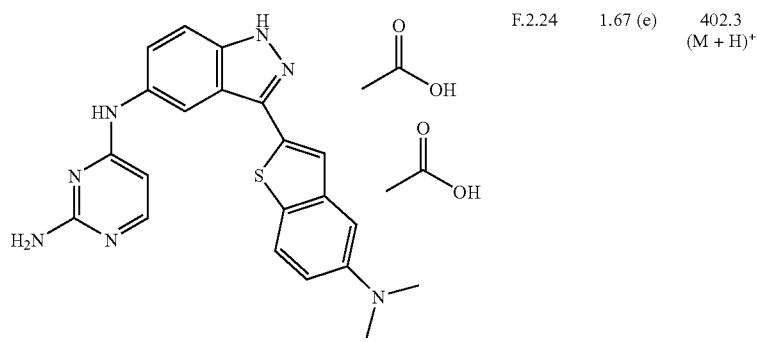 | F.2.24 | 1.67 (e) | 402.3 (M + H)+ |
| 5-Methoxy-1-benzothiophen-2-yl boronic acid | 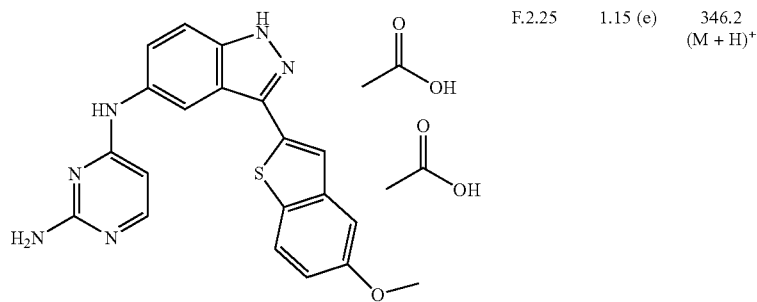 | F.2.25 | 1.15 (e) | 346.2 (M + H)+ |

TABLE F.2-continued
| | | Example # | R*t* (min) (method) | m/z (ESI+) |
|---|---|---|---|---|
| 4-Carboxyphenyl boronic acid | 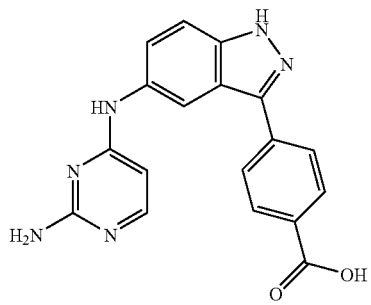 | F.2.26 | 0.5 (e) | 345.5 (M − H)⁻ |
TABLE F.3
Examples prepared using general procedure F using 6-bromo-1H-indazole
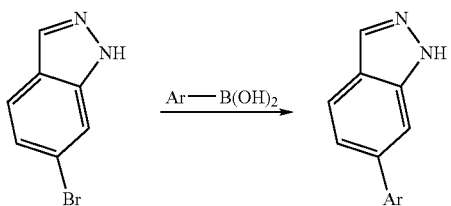
| Boronic Acid | Product | Example # | R*t* (min) (method) | m/z (ESI+) |
|---|---|---|---|---|
| Benzothiophene-2-boronic acid | | F.3.1 | 2.34 (e) | 248.8 (M − H)⁻ |
| 2-Methoxy-5-pyridineboronic acid | | F.3.2 | 1.70 (e) | 224.1 (M − H)⁻ |

TABLE F.4

Examples prepared using general procedure F using 5-(2-aminopyrimidin-4-yl)amino-3-chloro-7-iodo-1H-indazole

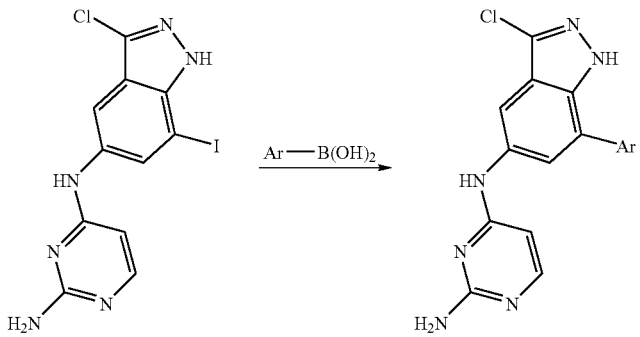

5-(2-Aminopyrimidin-4-yl)amino-3-chloro-7-iodo-1H-indazole was prepared from 3-Chloro-5-nitro-1H-indazole (J. Med. Chem., 46(26); 2003; 5663-5673, via halogenation conditions used in the synthesis of Preparation #22a, and general procedure N (using 2-amino-4-chloro-pyrimidine)).

| Boronic Acid | Product | Example # | $R_t$ (min) (method) | m/z (ESI+) |
|---|---|---|---|---|
| Benzothiophene-2-boronic acid | | F.4.1 | 1.89 (e) | 393.2 (M + H)+ |
| 3-Quinoline boronic acid | | F.4.2 | 1.42 (e) | 388.3 (M + H)+ |

TABLE F.5
Examples prepared using general procedure F from Example #N.2.7
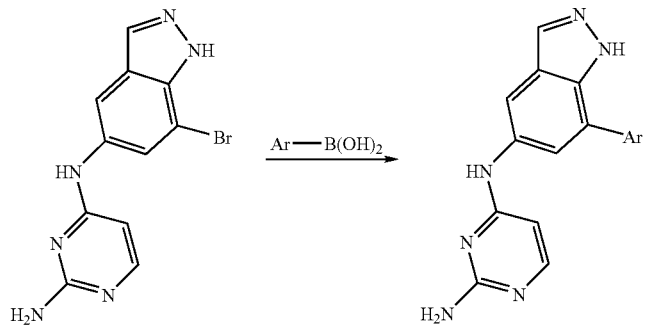
| Boronate | Product | Example # | HPLC R$_t$ (min) (method) | m/z (ESI+) |
|---|---|---|---|---|
| 4,4,5,5-Tetramethyl-2-vinyl-[1,3,2]dioxaborolane | | F.5.1 | 0.93 (e) | 250.9 (M − H)⁻ |
| Indole-6-boronic acid | | F.5.2 | 1.38 (e) | 342.3 (M + H)⁺ |
| 2-[5-(4,4,5,5-Tetramethyl-[1,3,2]dioxaborolan-2-yl)-indol-1-yl]-acetamide (5-(4,4,5,5-Tetramethyl-[1,3,2]dioxaborolan-2-yl)-indole, R) | | F.5.3 | 1.18 (e) | 399.3 (M + H)⁺ |

TABLE F.5-continued
| | | | | |
|---|---|---|---|---|
| 5-Formylbenzo[b]thiophene-2-boronic acid pinacol | 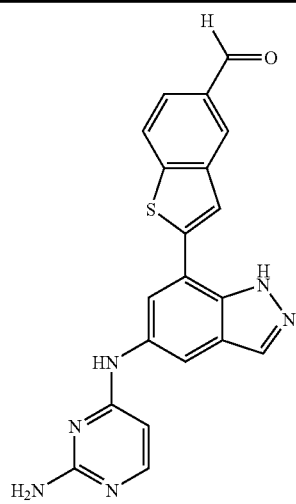 | F.5.4 | 1.41 (e) | 387.3 (M + H)+ |
| 3-Pyridylboronic acid | 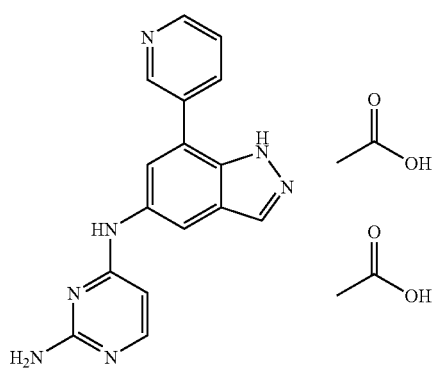 | F.5.5 | 1.10 (e) | 304.3 (M + H)+ |
| N,N-dimethyl-1-[5-(4,4,5,5-tetramethyl-1,3,2-dioxaborolan-2-yl)-1H-indol-3-yl]methanamine (Preparation #22b) | 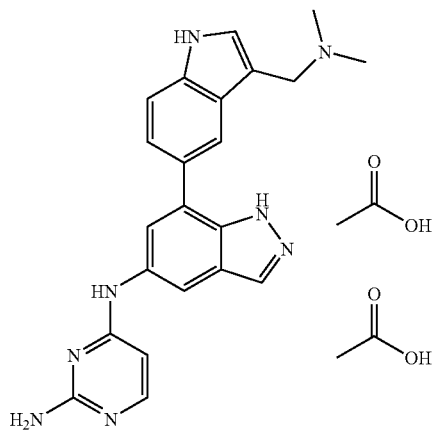 | F.5.6 | 1.43 (e) | 399.0 (M + H)+ |

TABLE F.5-continued
| | | | | |
|---|---|---|---|---|
| Thieno[2,3-b]pyridin-2-ylboronic acid (Preparation #22c) | 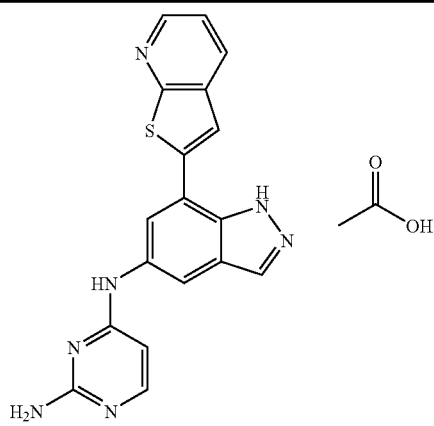 | F.5.7 | 1.25 (e) | 360.3 (M + H)+ |
| 2-[6-(4,4,5,5-Tetramethyl-1,3,2-dioxaborolan-2-yl)-1H-indol-1-yl]acetamide (6-(4,4,5,5-Tetramethyl-1,3,2-dioxaborolan-2-yl)-1H-indole, R) | 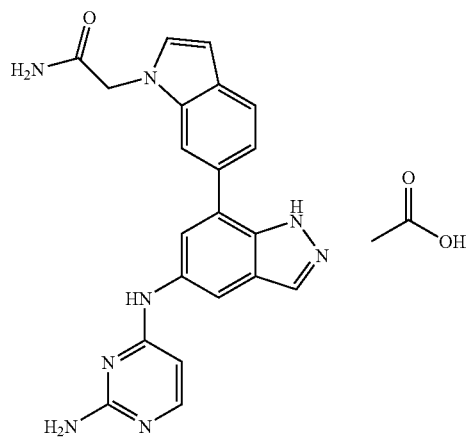 | F.5.8 | 1.19 (e) | 399.4 (M + H)+ |
| Indole-2-boronic-1,4-dicarboxylic acid 1-tert-butyl ester 4-methyl ester (Preparation #21) | 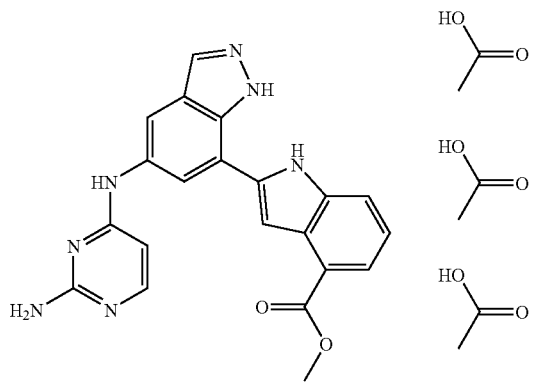 | F.5.9 | 1.2 (e) | 400.3 (M + H)+ |
| 4-Diisopropyl carbamoyl-indole-2-boronic-1-carboxylic acid 1-tert-butyl ester (Preparation #22) | 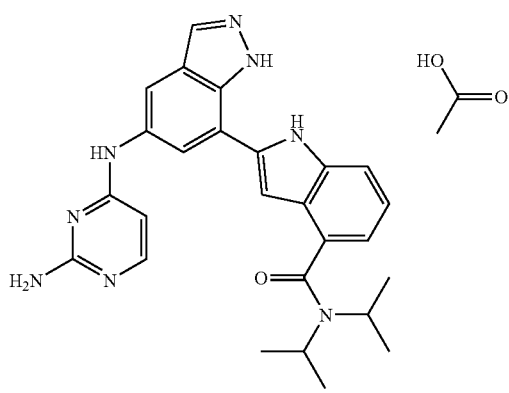 | F.5.10 | 1.5 (e) | 467 (M − H)− |

TABLE F.5-continued
| | | | | |
|---|---|---|---|---|
| Indole-2-boronic-1,7-dicarboxylic acid 1-tert-butyl ester 7-methyl ester (Preparation #20) | 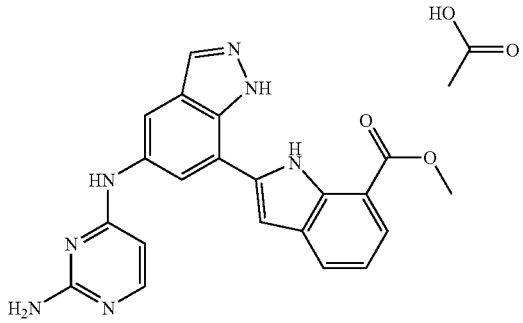 | F.5.11 | 1.4 (e) | 400.3 (M + H)+ |
| 5-Cyano-indole-2-boronic-1-carboxylic acid 1-tert-butyl ester | 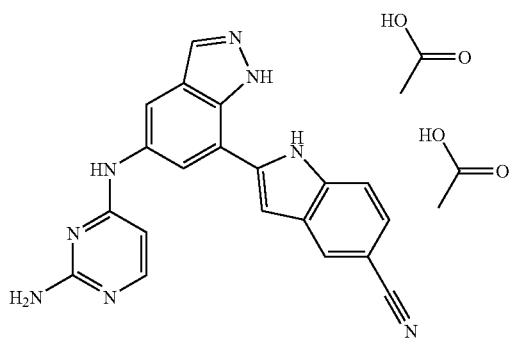 | F.5.12 | 1.0 (e) | 367.4 (M + H)+ |
| 2-[(E)-4-(4,4,5,5-Tetramethyl-[1,3,2]dioxaborolan-2-yl)-but-3-enyloxy]-tetrahydro-pyran | 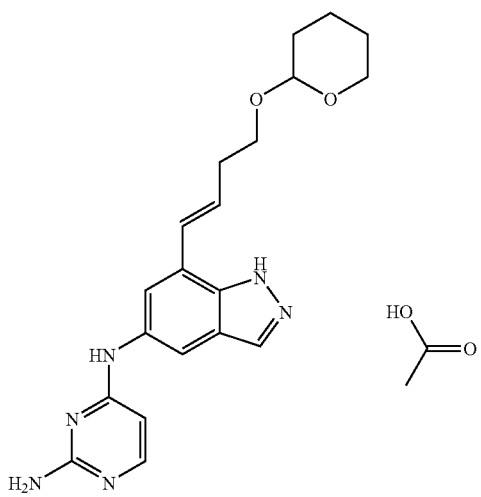 | F.5.13 | 1.47 (e) | 381.2 (M + H)+ |
| 2-((E)-2-Trimethylsilanyl-vinyl)-[1,3,2]dioxaborolane | 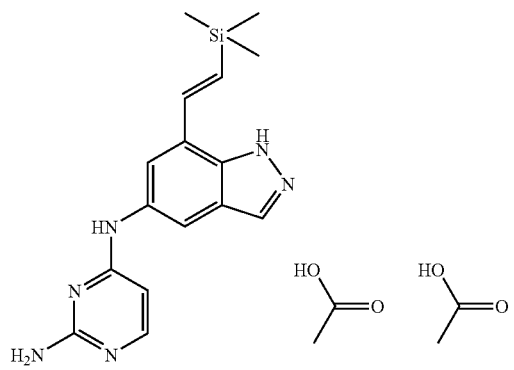 | F.5.14 | 1.95 (e) | 325.1 (M + H)+ |

TABLE F.5-continued
| | | | | |
|---|---|---|---|---|
| 5-Boronic acid-quinoline | 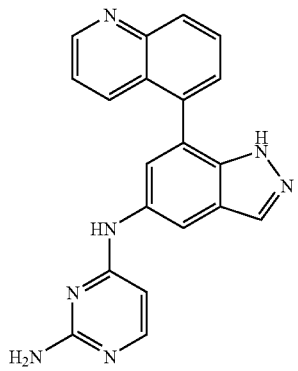 | F.5.15 | 0.95 (e) | 354.1 (M + H)+ |
| Thiophen-2-yl-boronic acid | 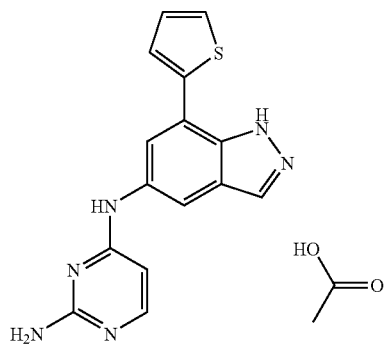 | F.5.16 | 1.15 (e) | 309.0 (M + H)+ |
| 5-Boronic acid-pyrimidine | 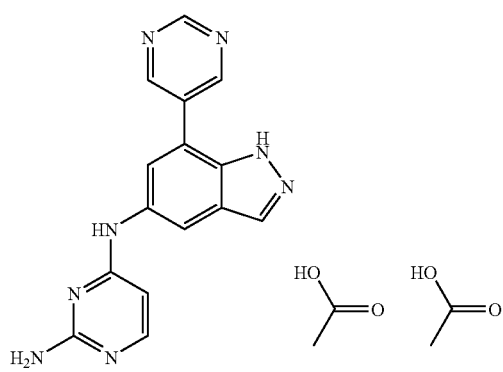 | F.5.17 | 0.98 (e) | 304.9 (M + H)+ |
| 8-Boronic acid-quinoline | 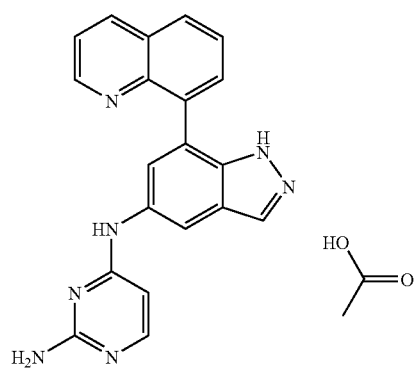 | F.5.18 | 1.17 (e) | 354.1 (M + H)+ |

TABLE F.5-continued
| | | | | |
|---|---|---|---|---|
| 6-Boronic acid-naphthalen-2-ol | 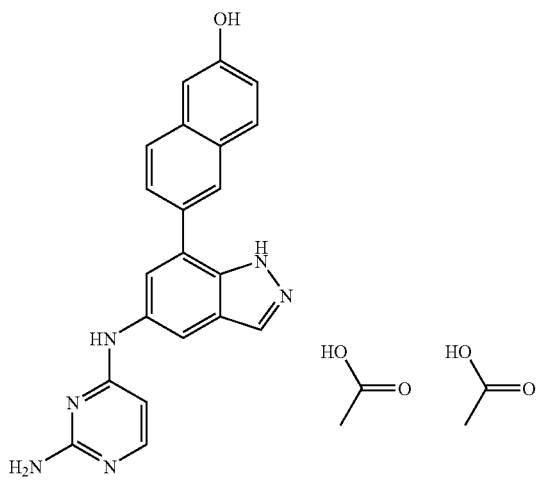 | F.5.19 | 1.43 (e) | 369.1 (M + H)+ |
| 6-Methoxy-naphthalen-2-yl-boronic acid | 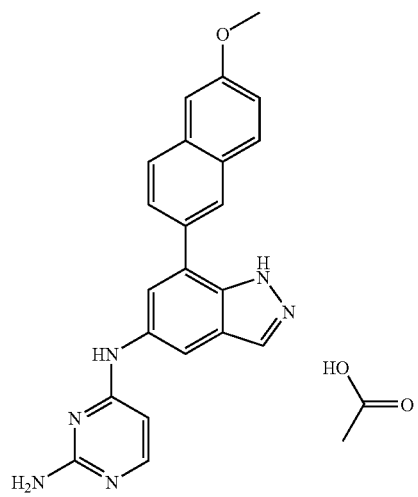 | F.5.20 | 1.80 (e) | 383.1 (M + H)+ |
| 5-Boronic acid-isoquinoline | 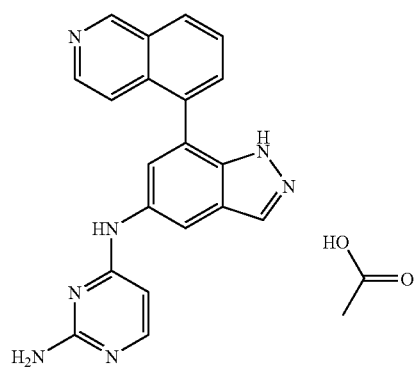 | F.5.21 | 1.25 (e) | 354.1 (M + H)+ |

TABLE F.5-continued
| | | | | |
|---|---|---|---|---|
| Furan-2-yl-boronic acid | 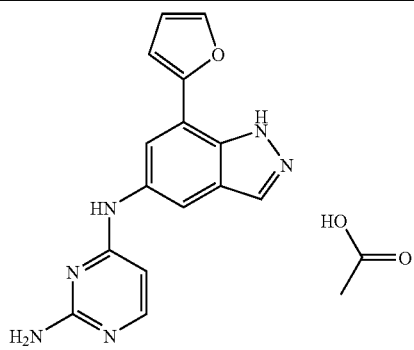 | F.5.22 | 0.75 (e) | 302.9 (M + H)+ |
| (5-Boronic acid-thiophen-2-yl)-methanol | 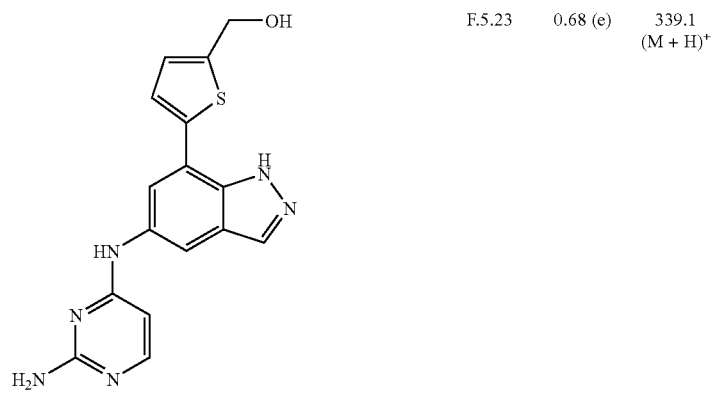 | F.5.23 | 0.68 (e) | 339.1 (M + H)+ |
| 5-Phenyl-thiophen-2-yl-boronic acid | 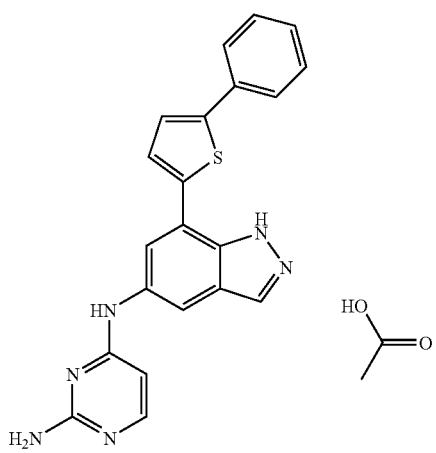 | F.5.24 | 1.92 (e) | 385.1 (M + H)+ |
| 6-Boronic acid-quinoxaline | 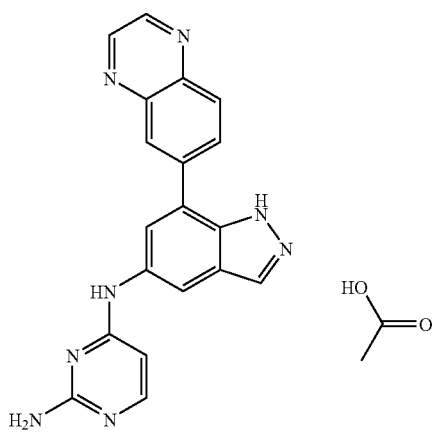 | F.5.25 | 0.97 (e) | 355.1 (M + H)+ |

TABLE F.5-continued
| | | | | |
|---|---|---|---|---|
| 6-Boronic acid-quinoline | 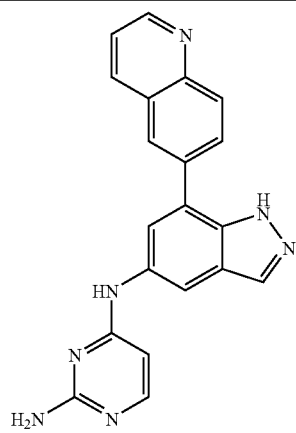 | F.5.26 | 1.23 (e) | 354.1 (M + H)+ |
| 2-[2,2']Bithiophenyl-5-yl-4,4,5,5-tetramethyl-[1,3,2]dioxaborolane | 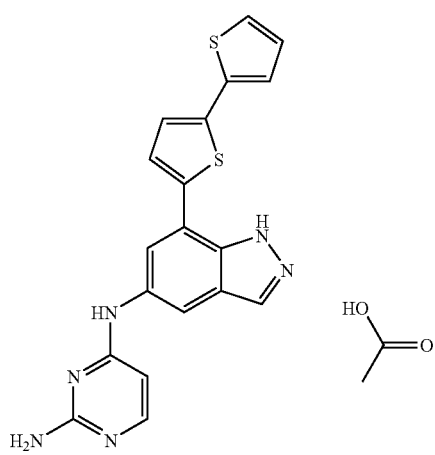 | F.5.27 | 2.00 (e) | 391.1 (M + H)+ |
| 5-Methyl-benzo[b]thiophen-2-yl-boronic acid | 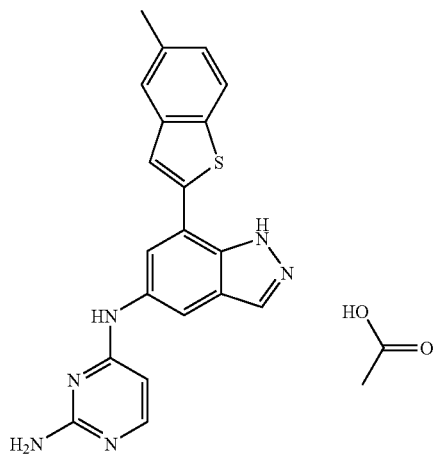 | F.5.28 | 1.94 (e) | 373.1 (M + H)+ |

TABLE F.5-continued
| | | | | |
|---|---|---|---|---|
| (E)-2-(3-Methoxy-phenyl)-vinyl-boronic acid | 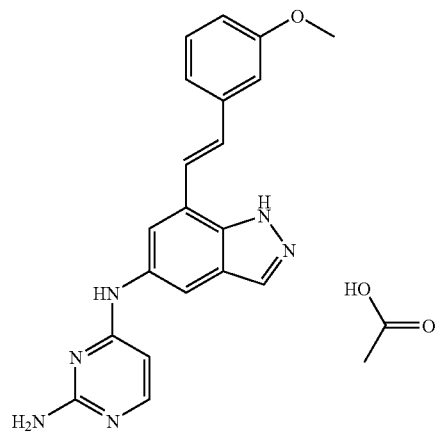 | F.5.29 | 1.77 (e) | 359.1 (M + H)+ |
| (E)-2-(4-Methoxy-phenyl)-vinyl-boronic acid | 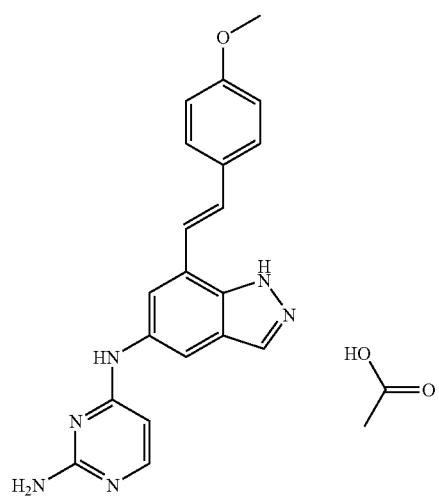 | F.5.30 | 1.76 (e) | 359.1 (M + H)+ |
| 4-Boronic acid-pyridine | 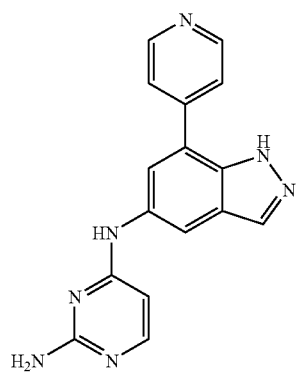 | F.5.31 | 0.79 (e) | 304.0 (M + H)+ |

TABLE F.5-continued
| | | | | |
|---|---|---|---|---|
| 2-Boronic acid-1H-indole | 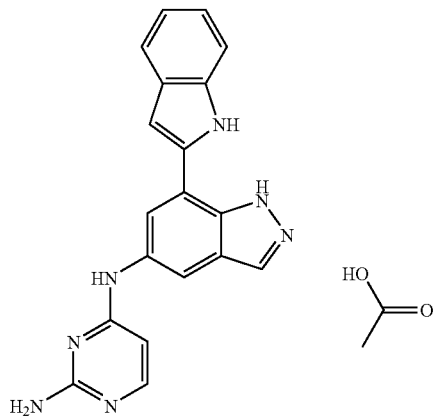 | F.5.32 | 1.21 (e) | 342.0 (M + H)+ |
| (3-Boronic acid-phenyl)-methanol | 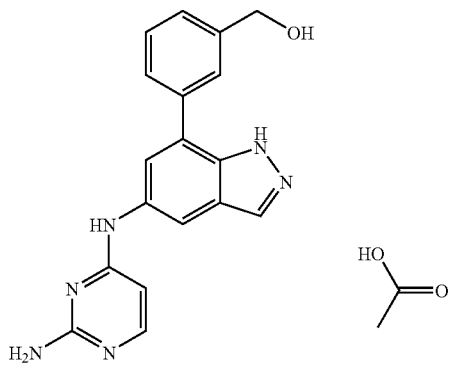 | F.5.33 | 0.56 (e) | 333.3 (M + H)+ |
| N-(3-Boronic acid-phenyl)-methanesulfonamide | 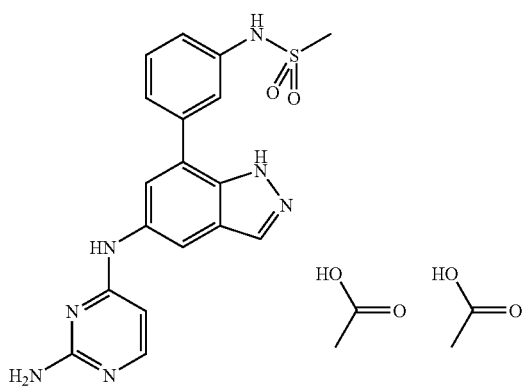 | F.5.34 | 0.63 (e) | 396.3 (M + H)+ |

TABLE F.5-continued
| | | | | |
|---|---|---|---|---|
| [3-(4,4,5,5-Tetramethyl-[1,3,2]dioxaborolan-2-yl)-phenyl]-acetonitrile | 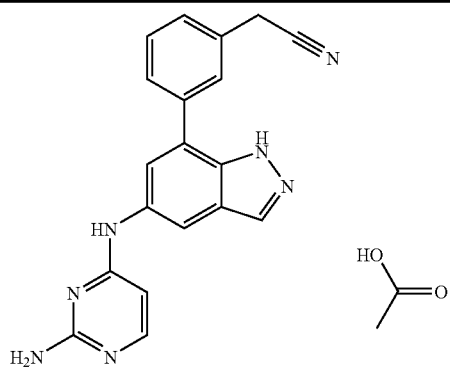 | F.5.35 | 0.84 (e) | 342.3 (M + H)+ |
| 3-Boronic acid-benzylamine | 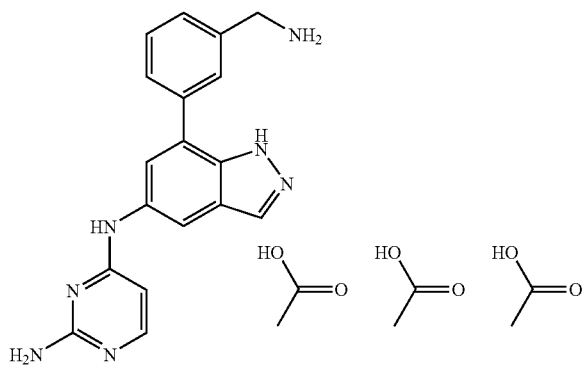 | F.5.36 | 0.38 (e) | 332.3 (M + H)+ |
| 3-Boronic acid-benzylamine | 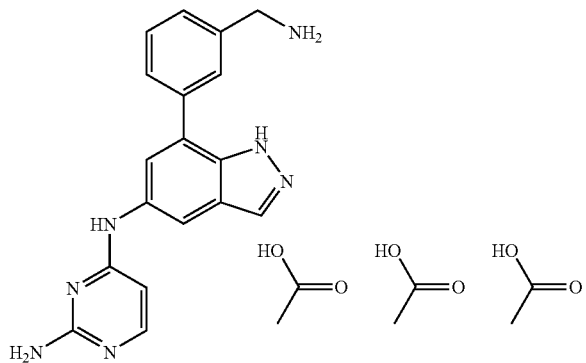 | F.5.37 | 0.63 (e) | 381.3 (M + H)+ |
| 3-(4,4,5,5-Tetramethyl-[1,3,2]dioxaborolan-2-yl)-benzonitrile | 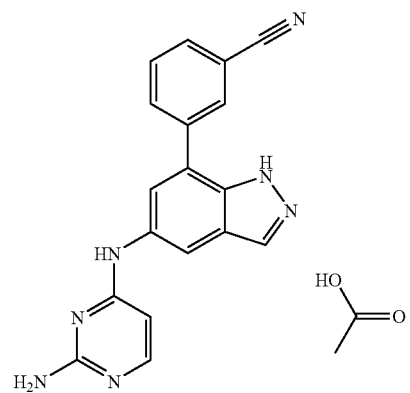 | F.5.38 | 0.87 (e) | 328.3 (M + H)+ |

TABLE F.5-continued
| | | | | |
|---|---|---|---|---|
| 2-Boronic acid-6-methyl-1H-indole | 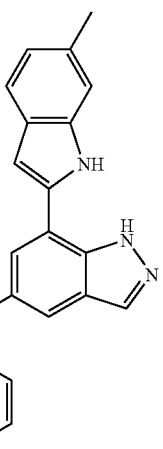 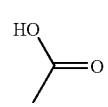 | F.5.39 | 1.46 (e) | 356.6 (M + H)+ |
| 2-Boronic acid-5-methoxy-1H-indole | 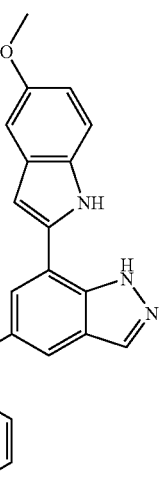 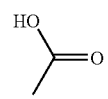 | F.5.40 | 1.18 (e) | 372.3 (M + H)+ |
| 2-Boronic acid-5-methyl-1H-indole | 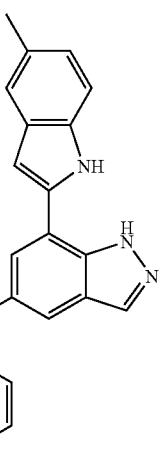 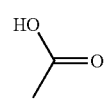 | F.5.41 | 1.45 (e) | 356.3 (M + H)+ |

TABLE F.6

Examples prepared using general procedure F using 3-iodo-5-(2-aminopyrimidin-4-yl)amino-1H-indazole

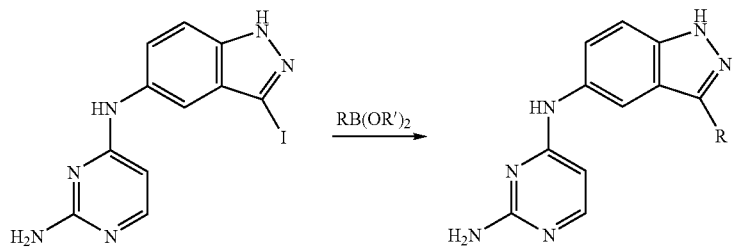

3-Iodo-5-(2-aminopyrimidin-4-yl)amino-1H-indazole was prepared from Preparation #28 via general procedure N using 2-amino-4-chloropyrimdine.

| Boronate | Product | Example # | HPLC $R_t$ (min) (method) | m/z |
|---|---|---|---|---|
| 4-Methylphenyl boronic acid | | F.6.1 | 5.80 (a) | 317 (M + H)+ |
| 4-[5-(4,4,5,5-Tetramethyl-[1,3,2]dioxaborolan-2-yl)-pyridin-2-yl]-morpholine | | F.6.2 | 4.40 (a) | 389 (M + H)+ |
| 4-(4,4,5,5-Tetramethyl-1,3,2-dioxaborolan-2-yl)-1H-pyrazole | | F.6.3 | 0.60 (a) | 293 (M + H)+ |
| 4-(4,4,5,5-Tetramethyl-1,3,2-dioxaborolan-2-yl)aniline | | F.6.4 | 0.80 (a) | 318 (M + H)+ |

TABLE F.6-continued
| | | | | |
|---|---|---|---|---|
| 2-Methylphenyl boronic acid | 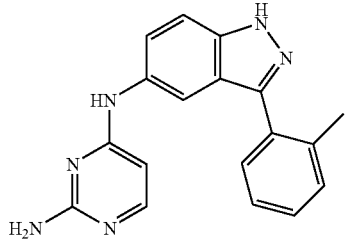 | F.6.5 | 1.70 (a) | 317 (M + H)+ |
| Phenylboronic acid | 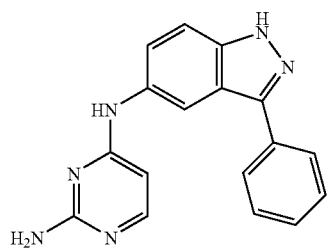 | F.6.6 | 1.70 (a) | 303 (M + H)+ |
| 3-Fluorophenyl boronic acid | 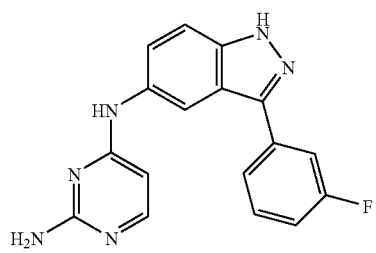 | F.6.7 | 1.90 (a) | 321 (M + H)+ |
| 2-Fluorophenyl boronic acid | 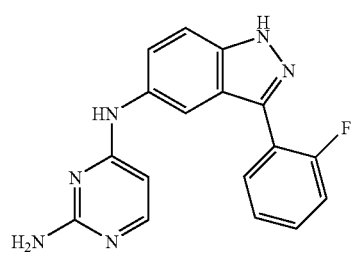 | F.6.8 | 1.60 (a) | 321 (M + H)+ |
| 4-Fluorophenyl boronic acid | 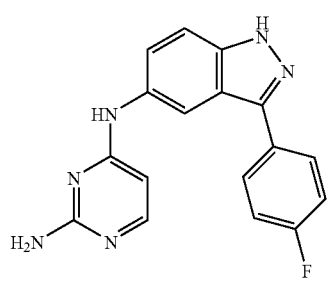 | F.6.9 | 1.80 (a) | 321 (M + H)+ |
| Pyridin-3-yl boronic acid | 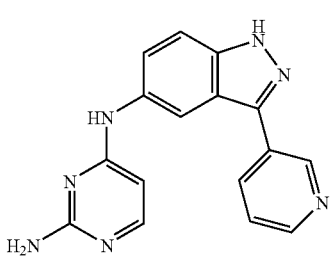 | F.6.10 | 0.80 (a) | 304 (M + H)+ |

TABLE F.6-continued
| | | | | |
|---|---|---|---|---|
| Thiophen-3-yl boronic acid | 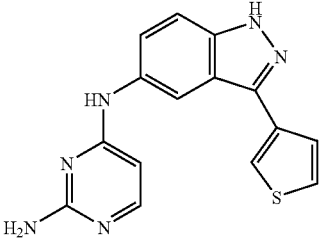 | F.6.11 | 1.50 (a) | 309 (M + H)+ |
| Indol-5-yl boronic acid | 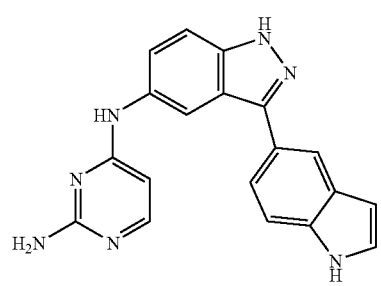 | F.6.12 | 1.40 (a) | 342 (M + H)+ |
| 1-(Tert-butoxycarbonyl)-1H-pyrrol-2-yl boronic acid | 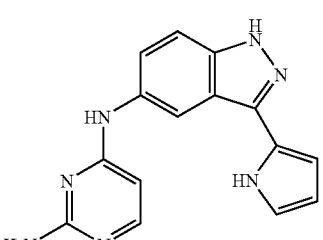 | F.6.13 | 1.10 (a) | 292 (M + H)+ |
| 4-(Methane sulfonyl)phenyl boronic acid | 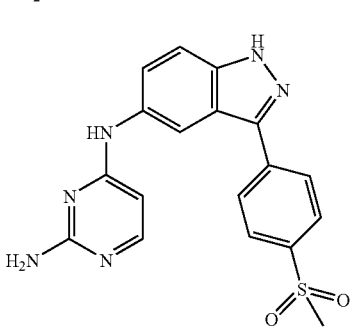 | F.6.14 | 1.20 (a) | 381 (M + H)+ |
| Pyrimidin-5-yl boronic acid | 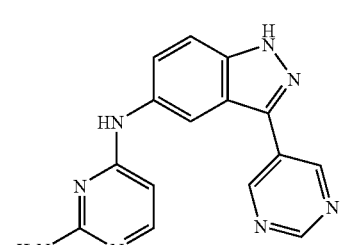 | F.6.15 | 1.80 (a) | 347 (M + H)+ |
| 3-Methylphenyl boronic acid | 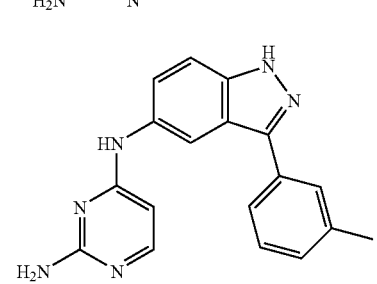 | F.6.16 | 2.00 (a) | 317 (M + H)+ |

TABLE F.6-continued

| | | | | |
|---|---|---|---|---|
| 3-(N,N-Dimethylamino)phenylboronic acid | (structure) | F.6.17 | 1.90 (a) | 346 (M + H)+ |
| 4-Fluoro-3-methylphenyl boronic acid | (structure) | F.6.18 | 2.00 (a) | 335 (M + H)+ |
| 3,4-Difluorophenyl boronic acid | (structure) | F.6.19 | 2.10 (a) | 339 (M + H)+ |
| 2-Methoxy-5-methylphenyl boronic acid | (structure) | F.6.20 | 1.80 (a) | 347 (M + H)+ |
| 1-Naphthalene boronic acid | (structure) | F.6.21 | 2.10 (a) | 353 (M + H)+ |
| 3-Quinoline boronic acid | (structure) | F.6.22 | 1.40 (a) | 354 (M + H)+ |

TABLE F.6-continued

| | | | | |
|---|---|---|---|---|
| 2,3-Dihydro-1-benzofuran-5-yl boronic acid | | F.6.23 | 1.70 (a) | 345 (M + H)+ |
| 4-Isoquinoline boronic acid | | F.6.24 | 1.40 (a) | 354 (M + H)+ |
| Benzo[b]thiophene-2-boronic acid | | F.6.25 | 2.40 (a) | 359 (M + H)+ |
| 2-Naphthalene boronic acid | | F.6.26 | 2.30 (a) | 353 (M + H)+ |
| 2,2'-Bithiophene-5-boronic acid | | F.6.27 | 2.60 (a) | 390 (M + H)+ |

TABLE F.7

Examples prepared using general procedure F from 3-iodo-5-(6-aminopyrrolo[2,3-d]pyrimidin-4-yl)amino-1H-indazole (prepared from Preparation #28 using general procedure N starting with 6-amino-4-chloropyrrolo[2,3-d]pyrimidine.)

| Boronate | Product | Ex # | $R_t$ (min) (method) | m/z |
|---|---|---|---|---|
| Benzo[b]thiophene-2-boronic acid | | F.7.1 | 2.40 (a) | 398 (M + H)+ |

TABLE F.8

Examples prepared using general procedure F from Preparation #6

| Boronic Acid | Product | Example # | $R_t$ (min) (method) | m/z (ESI+) |
|---|---|---|---|---|
| Benzothiophene-2-boronic acid | | F.8.1 | 1.82 (e) | 266.0 (M + H)+ |

TABLE F.9

Examples prepared using general procedure F from Example #2

| Boronic Acid | Product | Example # | R$_t$ (min) (method) | m/z (ESI+) |
|---|---|---|---|---|
| Phenylboronic acid | | F.9.1 | 1.85 (e) | 343.1 (M + H)$^+$ |

TABLE F.10

Examples prepared using general procedure F from 7-(1H-inden-2-yl)-5-(4,4,5,5-tetramethyl-[1,3,2]dioxaborolan-2-yl)-1-(2-trimethylsilanyl-ethoxymethyl)-1H-indazole (Preparation #23 then E)

| Aryl Halide | Product | Example # | R$_t$ (min) (method) | m/z |
|---|---|---|---|---|
| 7-Benzo[b]thiophen-2-yl-5-bromo-1-(2-trimethylsilanyl-ethoxymethyl)-1H-indazole (Preparation #23) | | F.10.1 | 4.9 (h) | 759 (M + H)$^+$ |

TABLE F.11

Examples prepared using general procedure F from Example #N.2.2

| Boronate/boronic acid Precursor | Product | Example # | $R_t$/min (method) | m/z or $^1$H NMR ($d_6$ DMSO, 400 MHz) |
|---|---|---|---|---|
| Thiophen-3-yl-boronic acid | | F.11.1 | 1.13 (e) | 309.3 (M + H)$^+$ |
| Naphthalen-2-yl-boronic acid | | F.11.2 | 1.59 (e) | 351.3 (M + H)$^+$ |
| p-Tolyl-boronic acid | | F.11.3 | 1.36 (e) | 317 (M + H)$^+$ |

TABLE F.11-continued
| | | | | |
|---|---|---|---|---|
| Phenyl-boronic acid | 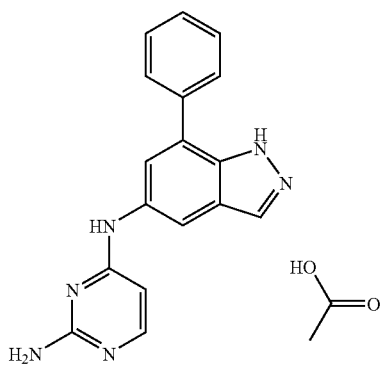 | F.11.4 | 1.18 (e) | 303 (M + H)+ |
| 5-Boronic acid-1H-indole | 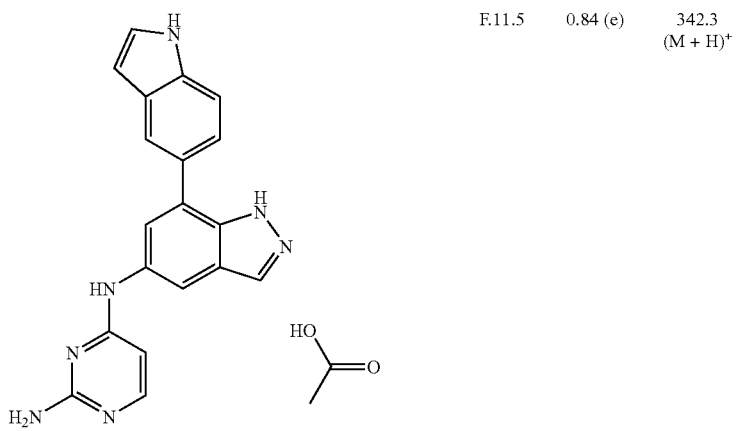 | F.11.5 | 0.84 (e) | 342.3 (M + H)+ |
| Benzofuran-2-yl-boronic acid | 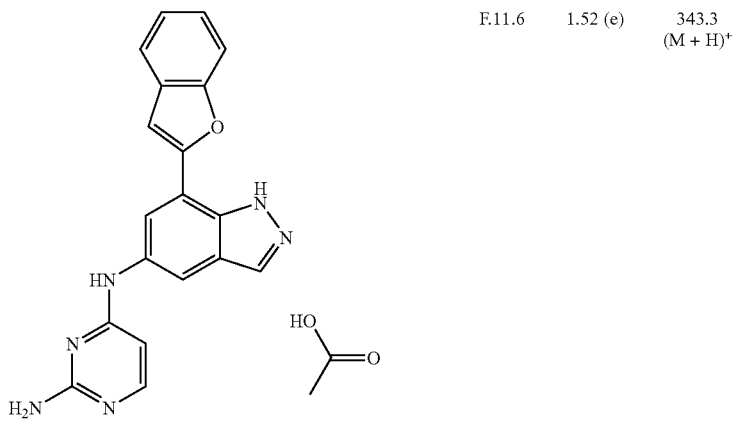 | F.11.6 | 1.52 (e) | 343.3 (M + H)+ |
| 4-Chloro-phenyl-boronic acid | 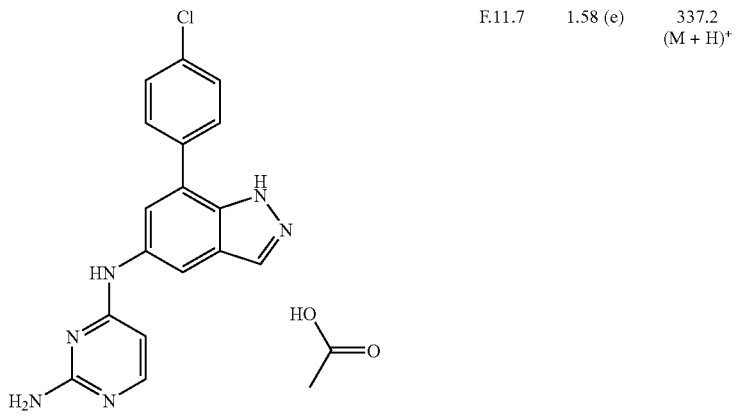 | F.11.7 | 1.58 (e) | 337.2 (M + H)+ |

TABLE F.11-continued
| | | | | |
|---|---|---|---|---|
| 3-Boronic acid-quinoline | 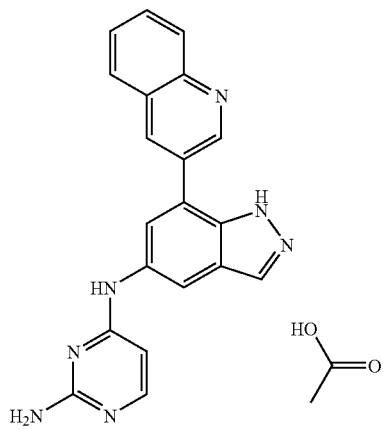 | F.11.8 | 1.09 (e) | 354 (M + H)+ |
| 4-Phenol-boronic acid | 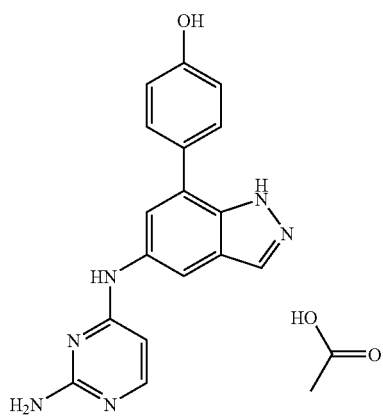 | F.11.9 | 0.73 (e) | 319.3 (M + H)+ |
| N-(4-boronic acid-phenyl)-acetamide | 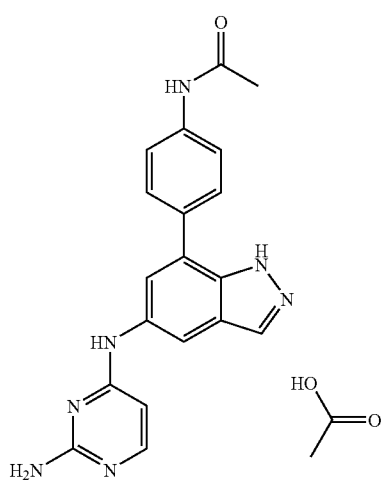 | F.11.10 | 0.67 (e) | 360 (M + H)+ |

TABLE F.11-continued
| | | | | |
|---|---|---|---|---|
| Furan-3-yl-boronic acid | 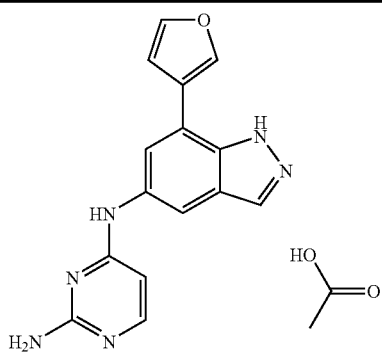 | F.11.11 | 1.12 (e) | 293.2 (M + H)+ |
| 2-Boronic acid-1H-pyrrole | 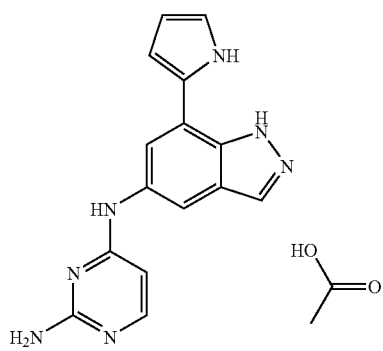 | F.11.12 | 0.85 (e) | 292 (M + H)+ |
| 3-Methoxy-phenyl-boronic acid | 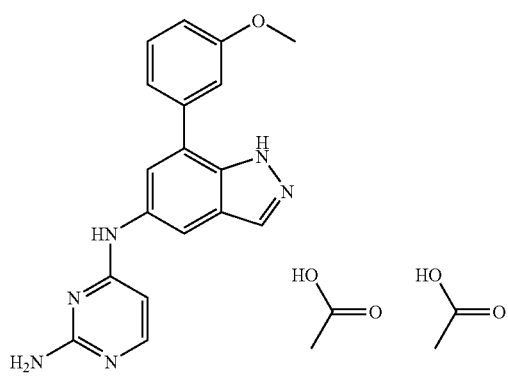 | F.11.13 | 1.47 (e) | 333.2 (M + H)+ |
| (4-Boronic acid-phenyl)-dimethyl-amine | 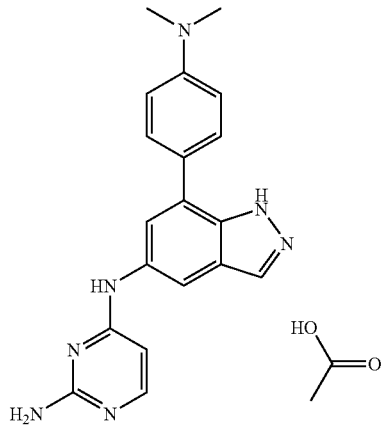 | F.11.14 | 1.53 (e) | 346 (M + H)+ |

TABLE F.11-continued
| | | | | |
|---|---|---|---|---|
| (3-Boronic acid-phenyl)-dimethyl-amine | 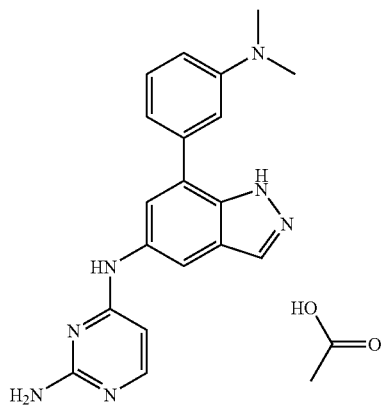 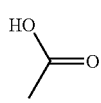 | F.11.15 | 1.57 (e) | 346 (M + H)+ |
| 3-Boronic acid-benzamide | 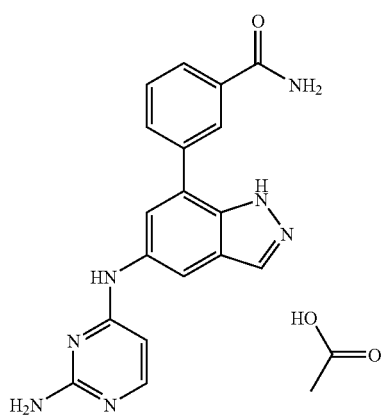 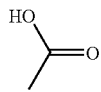 | F.11.16 | 0.65 (e) | 346 (M + H)+ |
| (E)-Styryl-boronic acid | 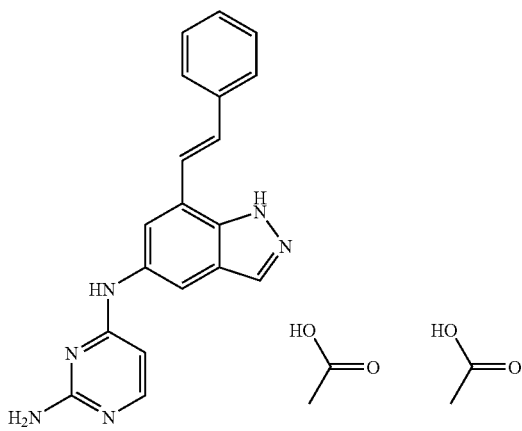 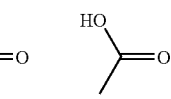 | F.11.17 | 1.50 (e) | 329.2 (M + H)+ |

TABLE F.11-continued

| 4-Fluoro-3-methyl-phenyl-boronic acid | [structure] | F.11.18 | 1.67 (e) | 335.2 (M + H)+ |

TABLE F.12

Examples prepared using general procedure F from Example X.1.2

| Halide Precursor | Product | Example # | R_t/min(method) | m/z(ESI+) |
|---|---|---|---|---|
| 3-Hydroxybenzeneboronic acid | [structure] | F.12.1 | 1.07(e) | 226.3 (M + H)+ |
| Biphenyl-2-ol-5-(4,4,5,5-tetramethyl-1,3,2-dioxaborolan-2-yl) (E) | [structure] | F.12.2 | 1.59(e) | 302.3 (M + H)+ |
| 1H-indazole-5-(4,4,5,5-tetramethyl-1,3,2-dioxaborolan-2-yl) (E) | [structure] | F.12.3 | 1.03(e) | 250.3 (M + H)+ |
| 5-indolylboronic acid | [structure] | F.12.4 | 1.38(e) | 249.3 (M + H)+ |

TABLE F.12-continued

Examples prepared using general procedure F from Example X.1.2

| Halide Precursor | Product | Example # | R₁/min(method) | m/z(ESI+) |
|---|---|---|---|---|
| 2-chloro-phenylamine-4-(4,4,5,5-tetramethyl-1,3,2-dioxaborolan-2-yl) (E) | | F.12.5 | 1.40(e) | 259.2 (M + H)⁺ |
| 2-Benzo[b]thiophen-2-yl-4-(4,4,5,5-tetramethyl-1,3,2-dioxaborolan-2-yl) phenol (E) | | F.12.6 | 1.84(e) | 358.3 (M + H)⁺ |
| 1H-indazol-3-ylamine-5-(4,4,5,5-tetramethyl-1,3,2-dioxaborolan-2-yl) (E) | | F.12.7 | 0.64(e) | 265.3 (M + H)⁺ |
| 4-hydroxybenzeneboronic acid | | F.12.8 | 0.97(e) | 226.2 (M + H)⁺ |
| 2-chloro-4-(4,4,5,5-tetramethyl-1,3,2-dioxaborolan-2-yl) phenol (E) | | F.12.9 | 1.30(e) | 260.2 (M + H)⁺ |
| 4-Benzyloxy-3-chloro-phenyl-boronic acid | | F.12.10 | 2.08(e) | 350.2 (M + H)⁺ |

TABLE F.12-continued

Examples prepared using general procedure F from Example X.1.2

| Halide Precursor | Product | Example # | R$_t$/min(method) | m/z(ESI+) |
|---|---|---|---|---|
| 2-Benzo[b]thiophen-2-yl-boronic acid* | | F.12.11 | 1.93(e) | 266.3 (M + H)$^+$ |
| 5-(4,4,5,5-Tetramethyl-[1,3,2]dioxaborolan-2-yl)-indazole-1-carboxylic acid tert-butyl ester* | | F.12.12 | 1.01(e) | 250.3 (M + H)$^+$ |
| Pyridine-4-yl-boronic acid* | | F.12.13 | 0.82(e) | 211 (M + H)$^+$ |
| Pyridine-3-yl-boronic acid | | F.12.14 | 1.03(e) | 211 (M + H)$^+$ |
| Pyridine-3-yl-boronic acid** | | F.12.15 | 0.90(e) | 211 (M + H)$^+$ |

*Reacted with 3-Amino-4-bromo-indazole
**Reacted with 3-Amino-6-bromo-indazole

TABLE F.13
Examples prepared using general procedure F from Example #B.1.2
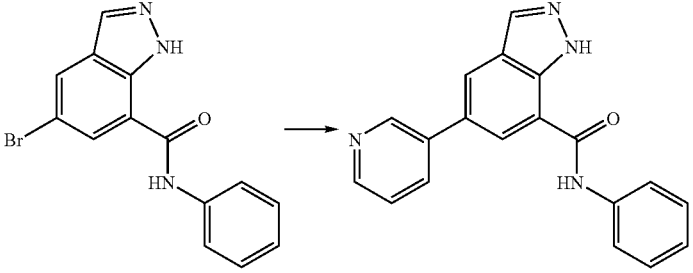
| Boronic acid | Product | Example # | R$_t$/min(method) | m/z or $^1$H NMR(d$_6$ DMSO, 400 MHz) |
|---|---|---|---|---|
| Pyridine-3-yl-boronic acid | 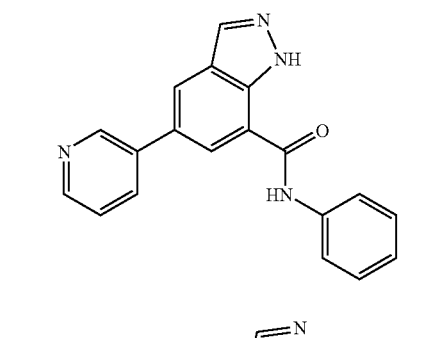 | F.13.1 | 1.81(e) | 313.2 (M + H)$^+$ |
| Benzonitrile-3-yl-boronic acid | | F.13.2 | 2.08(e) | 337.3 (M − H)$^-$ |
| Benzonitrile-2-yl-boronic acid | 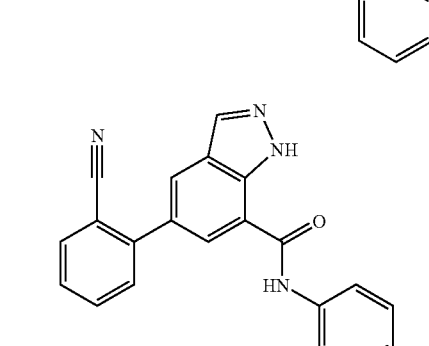 | F.13.3 | 1.98(e) | 337.2 (M − H)$^-$ |
| Benzamide-2-yl-boronic acid | 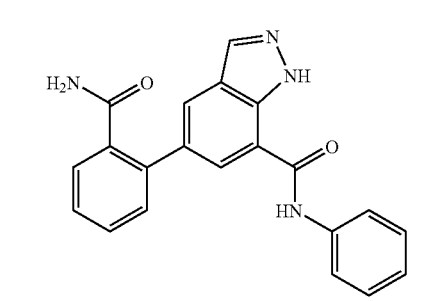 | F.13.4 | 1.49(e) | 357.1 (M + H)$^+$ |

TABLE F.13-continued

Examples prepared using general procedure F from Example #B.1.2

| Boronic acid | Product | Example # | R$_t$/min(method) | m/z or $^1$H NMR(d$_6$ DMSO, 400 MHz) |
|---|---|---|---|---|
| Benzamide-3-yl-boronic acid | | F.13.5 | 1.51(e) | 355 (M + H)$^+$ |
| 5-(boronic acid-2-yl)-isoquinoline | | F.13.6 | 1.86(e) | 363.2 (M + H)$^+$ |
| 4-(boronic acid-2-yl)-benzoic acid methyl ester | | F.13.7 | 2.31(e) | 370 (M + H)$^+$ |

TABLE F.14
Examples prepared using General Procedure F from Preparation #56
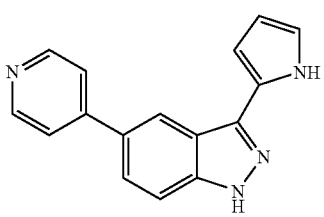
| Halide | Product | Example # | R$_t$/min(method) | m/z or $^1$H NMR(d$_6$ DMSO, 400 MHz) |
|---|---|---|---|---|
| 4-Iodo-pyridine | 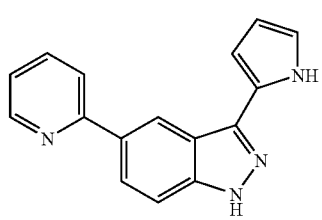 | F.14.1 | 2.18(e) | 261 (M + H)$^+$ |
| 2-Bromo-pyridine | | F.14.2 | 2.53(e) | 261 (M + H)$^+$ |
| 3-Benzyloxy-5-bromo-pyridine | 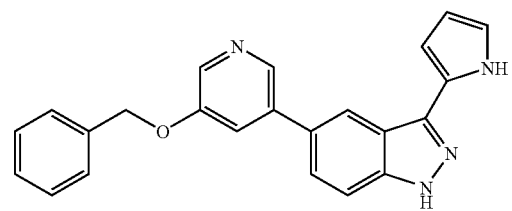 | F.14.3 | 2.98(e) | 367 (M + H)$^+$ |

TABLE F.15

Examples prepared using general procedure F using 5-(Dimethylamino-methyleneamino)-3-iodo-pyrrolo[2,3-c]pyridine-1-carboxylic acid tert-butyl ester followed by deprotection (outlined in Procedure #5, step 1)

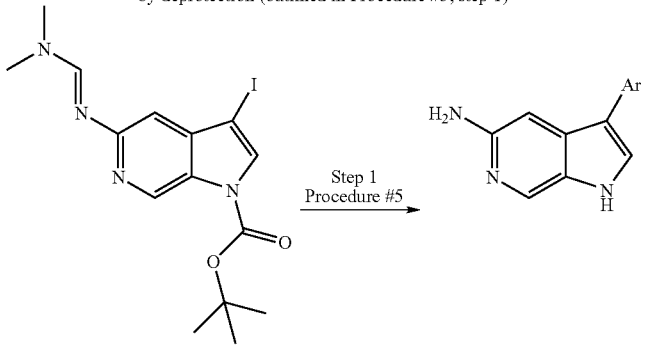

Step 1
Procedure #5

5-(Dimethylamino-methyleneamino)-3-iodo-pyrrolo[2,3-c]pyridine-1-carboxylic acid tert-butyl ester was prepared according to Preparation #4 via Preparation 10a and 10b using 4-Methyl-5-nitro-pyridin-2-ylamine.

| Boronate | Product | Example # | $R_t$/min(method) | m/z |
|---|---|---|---|---|
| 2-Chloro-4-(4,4,5,5-tetramethyl-[1,3,2]dioxaboro-lan-2-yl)-phenol | | F.15.1 | 1.16(e) | 260.2 (M + H)$^+$ |
| 2-(3-Benzo[b]thiophen-2-yl-4-methoxy-phenyl)-4,4,5,5-tetramethyl-[1,3,2]dioxaboro-lane | | F.15.2 | 1.89(e) | 358.3 (M + H)$^+$ |
| 4-Boronic acid-N-cyclopropyl-benzamide | | F.15.3 | 0.61(e) | 293.2 (M + H)$^+$ |
| 3-boronic acid-benzamide | | F.15.4 | 0.46(e) | 253 (M + H)$^+$ |

TABLE F.15-continued

Examples prepared using general procedure F using 5-(Dimethylamino-methyleneamino)-3-iodo-pyrrolo[2,3-c]pyridine-1-carboxylic acid tert-butyl ester followed by deprotection (outlined in Procedure #5, step 1)

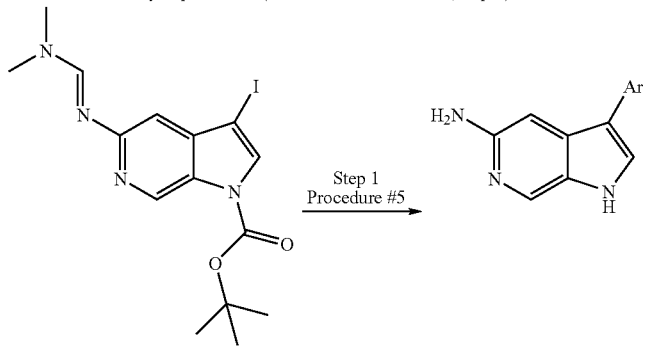

5-(Dimethylamino-methyleneamino)-3-iodo-pyrrolo[2,3-c]pyridine-1-carboxylic acid tert-butyl ester was prepared according to Preparation #4 via Preparation 10a and 10b using 4-Methyl-5-nitro-pyridin-2-ylamine.

| Boronate | Product | Example # | $R_t$/min(method) | m/z |
|---|---|---|---|---|
| Indole-6-boronic acid | | F.15.5 | 1.14(e) | 249.2 $(M + H)^+$ |
| 4-boronic acid-benzoic acid | | F.15.6 | 0.44(e) | 254.2 $(M + H)^+$ |
| 4-Boronic acid-N-methyl-benzenesulfonamide | | F.15.7 | 0.69(e) | 303.2 $(M + H)^+$ |

TABLE F.15-continued

Examples prepared using general procedure F using 5-(Dimethylamino-methyleneamino)-3-iodo-pyrrolo[2,3-c]pyridine-1-carboxylic acid tert-butyl ester followed by deprotection (outlined in Procedure #5, step 1)

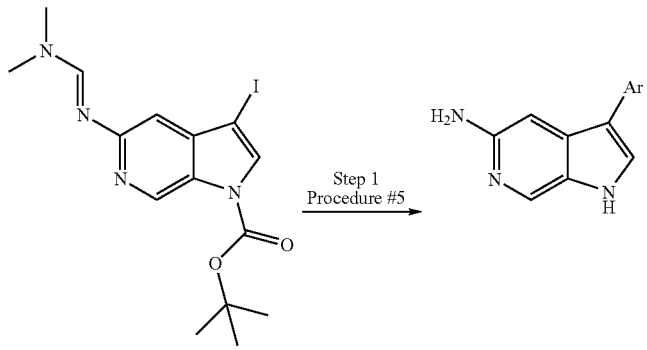

5-(Dimethylamino-methyleneamino)-3-iodo-pyrrolo[2,3-c]pyridine-1-carboxylic acid tert-butyl ester was prepared according to Preparation #4 via Preparation 10a and 10b using 4-Methyl-5-nitro-pyridin-2-ylamine.

| Boronate | Product | Example # | $R_t$/min(method) | m/z |
|---|---|---|---|---|
| 4-Boronic acid-benzenesulfona-mide | | F.15.8 | 0.56(e) | 289.2 (M + H)+ |
| 4-Boronic acid-benzylamine | | F.15.9 | 1.44(e) | 239.2 (M + H)+ |
| 3-boronic acid-N,N-dimethyl-benzamide | | F.15.10 | 0.60(e) | 281.2 (M + H)+ |

TABLE F.15-continued

Examples prepared using general procedure F using 5-(Dimethylamino-methyleneamino)-3-iodo-pyrrolo[2,3-c]pyridine-1-carboxylic acid tert-butyl ester followed by deprotection (outlined in Procedure #5, step 1)

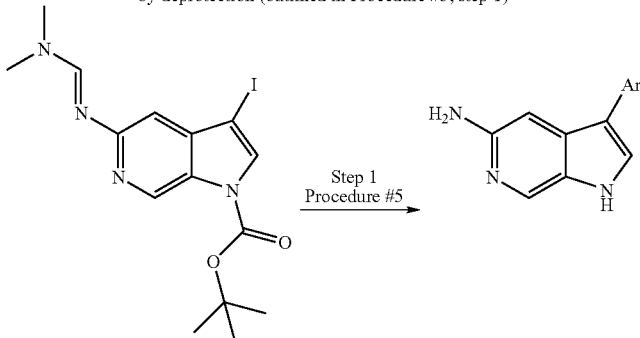

5-(Dimethylamino-methyleneamino)-3-iodo-pyrrolo[2,3-c]pyridine-1-carboxylic acid tert-butyl ester was prepared according to Preparation #4 via Preparation 10a and 10b using 4-Methyl-5-nitro-pyridin-2-ylamine.

| Boronate | Product | Example # | $R_t$/min(method) | m/z |
|---|---|---|---|---|
| 4-boronic acid-N,N-dimethyl-benzamide | | F.15.11 | 0.56(e) | 281.2 $(M + H)^+$ |
| 3-boronic acid-benzamide | | F.15.12 | 0.48(e) | 253.2 $(M + H)^+$ |

General Procedure G: Deprotection of a SEM-Protected Indazole

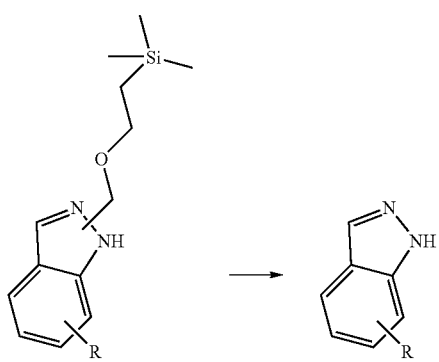

A mixture of a SEM protected indazole in a solvent (for example MeOH, EtOH, i-PrOH, $CH_2Cl_2$ or dioxane, preferably MeOH) is treated with an excess amount of a mineral acid (for example HCl, HF or TFA, preferably HCl) and then stirred at about 25-85° C. (preferably about 65° C.) for about 1-24 hours (preferably about 1 hour). The solvent is evaporated and the product isolated and further purified by crystallization or chromatography.

Illustration of General Procedure G:

Example #14

5-(7-Benzo[b]thiophen-2-yl-1H-indazol-5-yl)-pyrimidin-2-ylamine

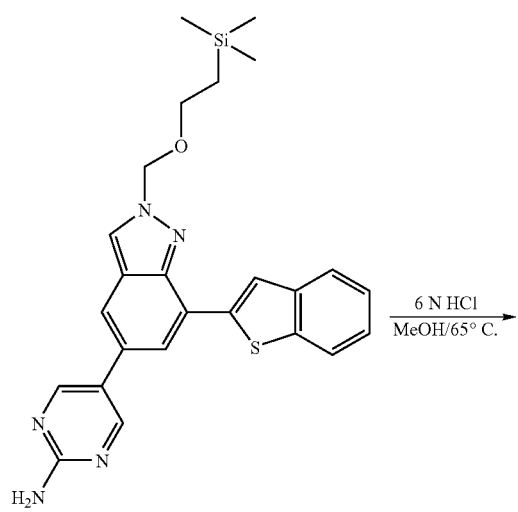

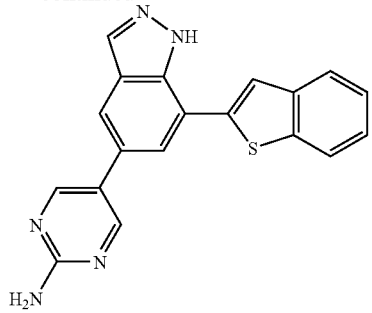

A mixture of 6N HCl (1 mL) and 5-[7-benzo[b]thiophen-2-yl-2-(2-trimethylsilanyl-ethoxymethyl)-2H-indazol-5-yl]-pyrimidin-2-ylamine (0.063 g, 0.133 mmol) (prepared from 7-Benzo[b]thiophen-2-yl-5-(4,4,5,5-tetramethyl-[1,3,2]dioxaborolan-2-yl)-2-(2-trimethylsilanyl-ethoxymethyl)-2H-indazole (Preparation #23, E) and 5-iodo-pyrimidin-2-ylamine according to general procedure F) in MeOH (2 mL) was heated to about 65° C. for about 1 hour. The solvents were removed under reduced pressure and the residue treated with NaHCO$_3$ (4 mL) and EtOAc (2 mL). The insoluble product was collected by filtration then dried to give 5-(7-benzo[b]thiophen-2-yl-1H-indazol-5-yl)-pyrimidin-2-ylamine (27 mg, 60%) as an off white solid; (DMSO-d$_6$, 400 MHz) δ 13.56 (bs, 1H), 8.66 (s, 2H), 8.29 (s, 1H), 8.15 (s, 1H), 8.04 (m, 2H), 7.93 (m, 1H), 7.79 (d, 1H), 7.43 (m, 2H), 7.76 (bs, 2H); RP-HPLC (Table 1, Method e) R$_t$=2.03 MS m/z: (M−H)$^-$ 341.7.

TABLE G

Examples prepared using general procedure G

| Precursor | Product | Example # | HPLC R$_t$(min)(method) | m/z |
|---|---|---|---|---|
| Preparation #5 | 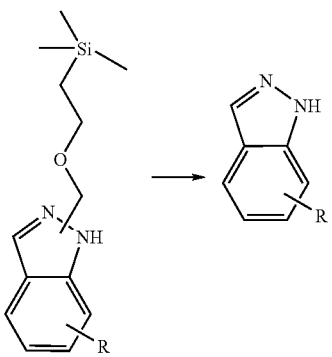 | G.1 | 1.68(e) | 383.0 (M + H)$^+$ |

TABLE G-continued

Examples prepared using general procedure G

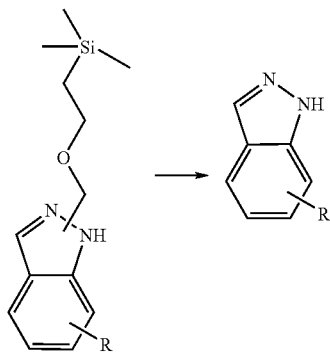

| Precursor | Product | Example # | HPLC R$_t$(min)(method) | m/z |
|---|---|---|---|---|
| {3-[7-(7-Benzo[b]thiophen-2-yl-1-(2-trimethylsilanyl-ethoxymethyl)-1H-indazol-5-yl)-2-(dimethylamino-methyleneamino)-pyrrolo[3,2-d]pyrimidin-5-yl]-propyl}-carbamic acid tert-butyl ester (Preparation #5, R (using tert-butyl 3-bromopropyl carbamate) | | G.2 | 1.29(e) | 440.3 (M + H)$^+$ |
| {2-[7-(7-Benzo[b]thiophen-2-yl-1-(2-trimethylsilanyl-ethoxymethyl)-1H-indazol-5-yl)-2-(dimethylamino-methyleneamino)-pyrrolo[3,2-d]pyrimidin-5-yl]-ethyl}-carbamic acid tert-butyl ester (Preparation #5, R (using tert-butyl 2-bromoethyl carbamate)) | | G.3 | 1.30(e) | 426.3 (M + H)$^+$ |

TABLE G-continued

Examples prepared using general procedure G

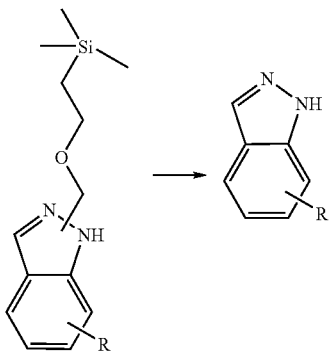

| Precursor | Product | Example # | HPLC R$_t$(min)(method) | m/z |
|---|---|---|---|---|
| {2-Amino-7-[7-benzo[b]thiophen-2-yl-1-(2-trimethylsilanylethoxymethyl)-1H-indazol-5-yl]-pyrrolo[3,2-d]pyrimidin-5-yl}-acetic acid (Preparation #5, R (using methyl 2-bromoacetate), V) | | G.4 | 0.97(e) | 441.3 (M + H)$^+$ |
| 2-{2-Amino-7-[7-benzo[b]thiophen-2-yl-1-(2-trimethylsilanylethoxymethyl)-1H-indazol-5-yl]-pyrrolo[3,2-d]pyrimidin-5-yl}propionic acid (Preparation #5, R (using tert-butyl 2-bromopropionoate),Q, V) | | G.5 | 1.02(e) | 455.2 (M + H)$^+$ |

TABLE G-continued

Examples prepared using general procedure G

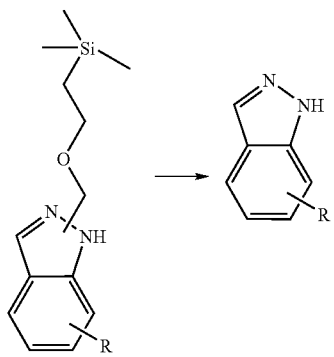

| Precursor | Product | Example # | HPLC R$_t$(min)(method) | m/z |
|---|---|---|---|---|
| 7-[7-Benzo[b]thiophen-2-yl-1-(2-trimethylsilanyl-ethoxymethyl)-1H-indazol-5-yl]-5-cyclopentyl-5H-pyrrolo[3,2-d]pyrimidin-2-ylamine (Preparation #5a, T (using cyclopentanol)) | | G.6 | 2.15(e) | 451.3 (M + H)$^+$ |
| 7-[7-Benzo[b]thiophen-2-yl-1-(2-trimethylsilanyl-ethoxymethyl)-1H-indazol-5-yl]-5-isopropyl-5H-pyrrolo[3,2-d]pyrimidin-2-ylamine (Preparation #5a, T (isopropanol)) | | G.7 | 1.96(e) | 425.3 (M + H)$^+$ |

TABLE G-continued

Examples prepared using general procedure G

| Precursor | Product | Example # | HPLC R$_t$(min)(method) | m/z |
|---|---|---|---|---|
| 3-{2-Amino-7-[7-benzo[b]thiophen-2-yl-1-(2-trimethylsilanyl-ethoxymethyl)-1H-indazol-5-yl]-pyrrolo[3,2-d]pyrimidin-5-yl}-propionic acid (Preparation #5, R (3-bromo ethyl propionate),V) | | G.8 | 1.16(e) | 453.1 (M + H)$^+$ |
| 7-[7-Benzo[b]thiophen-2-yl-1-(2-trimethylsilanyl-ethoxymethyl)-1H-indazol-5-yl]-5-(2-morpholin-4-yl-ethyl)-5H-pyrrolo[3,2-d]pyrimidin-2-ylamine N,N-dimethylformamidine (Preparation #5, R (using1-(2-bromoethyl)morpholine) | | G.9 | 1.85(e) | 494.2 (M − H)$^+$ |

TABLE G-continued

Examples prepared using general procedure G

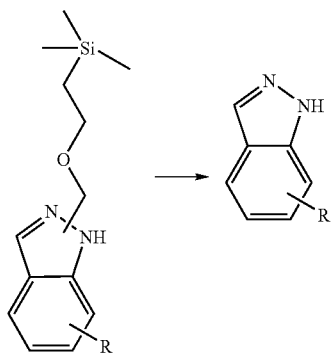

| Precursor | Product | Example # | HPLC R$_t$(min)(method) | m/z |
|---|---|---|---|---|
| 3-{2-Amino-7-[7-benzo[b]thiophen-2-yl-1-(2-trimethylsilanylethoxymethyl)-1H-indazol-5-yl]-pyrrolo[3,2-d]pyrimidin-5-yl}propionamide (Preparation #5, R (using methyl 3-bromopropionate, M) | | G.10 | 1.46(e) | 454.3 (M + H)$^+$ |
| 4-{2-[7-[7-Benzo[b]thiophen-2-yl-1-(2-trimethylsilanyl-ethoxymethyl)-1H-indazol-5-yl]-2-(dimethylamino-methyleneamino)-pyrrolo[3,2-d]pyrimidin-5-yl]-ethyl}-piperidine-1-carboxylic acid tert-butyl ester (Preparation #5, R (using 4-(2-bromo-ethyl)-piperidine-1-carboxylic acid tert-butyl ester) | | G.11 | 1.58(e) | 494.3 (M + H)$^+$ |

TABLE G-continued

Examples prepared using general procedure G

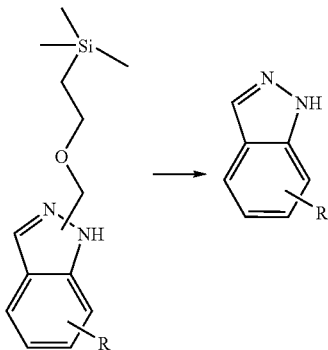

| Precursor | Product | Example # | HPLC R$_t$(min)(method) | m/z |
|---|---|---|---|---|
| N-Methyl-3-{5-amino-3-[7-benzo[b]thiophen-2-yl-1-(2-trimethylsilanylethoxymethyl)-1H-indazol-5-yl]-pyrrolo[3,2-d]pyrimidin-1-yl}-propionamide (Preparation #5, R (3-bromoethyl propionate), M) | | G.12 | 1.56(e) | 468.4 (M + H)$^+$ |
| 3-{2-(Dimethylamino-methyleneamino)-7-[7-benzo[b]thiophen-2-yl-1-(2-trimethylsilanyl-ethoxymethyl)-1H-indazol-5-yl]-pyrrolo[3,2-d]pyrimidin-5-yl}-propionic acid methyl ester (Preparation #5, R (using 3-bromomethyl propionate)) | | G.13 | 1.87(e) | 469.0 (M + H)$^+$ |

TABLE G-continued

Examples prepared using general procedure G

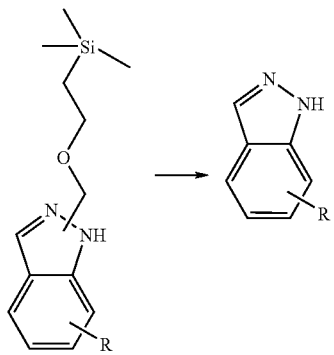

| Precursor | Product | Example # | HPLC R$_t$(min)(method) | m/z |
|---|---|---|---|---|
| 3-{2-Amino-7-[7-benzo[b]thiophen-2-yl-1-(2-trimethylsilanyl-ethoxymeth-yl)-1H-indazol-5-yl]-pyrrolo[3,2-d]pyrimidin-5-yl}-N,N-dimethyl propionamide (Preparation #5, R (3-bromo methyl propionate), M) | | G.14 | 1.73(e) | 482.3 (M + H)$^+$ |
| 7-[7-Benzo[b]thiophen-2-yl-1-(2-trimethylsilanyl-ethoxymethyl)-1H-indazol-5-yl]-5-(2-piperidin-3-yl-ethyl)-5H-pyrrolo[3,2-d]pyrimidin-2-yl-N,N-dimethylamino-methyleneamine (Preparation #5, R (using 3-(2-bromo-ethyl)-piperidine-1-carboxylic acidtert-butyl ester) | | G.15 | 1.58(e) | 494.0 (M + H)$^+$ |

TABLE G-continued

Examples prepared using general procedure G

| Precursor | Product | Example # | HPLC R$_t$(min)(method) | m/z |
|---|---|---|---|---|
| 3-{2-Amino-7-[7-benzo[b]thiophen-2-yl-1-(2-trimethylsilanyl-ethoxymeth-yl)-1H-indaozl-5-yl]-pyrrolo[3,2-d]pyrimidin-5-yl}-N-(2-amino-ethyl)-propionamide (Preparation #5, R (3-bromo methyl propionate), M) | | G.16 | 1.31(e) | 497.0 (M + H)$^+$ |
| {3-[7-(7-Benzo[b]thiophen-2-yl-1-(2-trimethylsilanyl-ethoxymethyl)-1H-indazol-5-yl)-2-(dimethylamino-methyleneamino)-pyrrolo[3,2-d]pyrimidin-5-yl]-butyl}-carbamic acid tert-butyl ester (Preparation #5, R (using tert-butyl 4-bromo-butyl carbamate) | | G.17 | 1.40(e) | 454.1 (M + H)$^+$ |

TABLE G-continued

Examples prepared using general procedure G

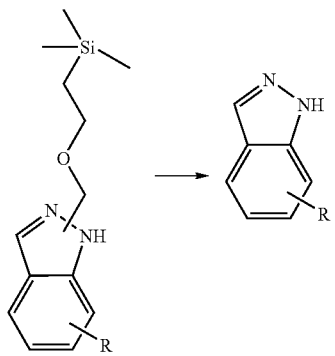

| Precursor | Product | Example # | HPLC R$_t$(min)(method) | m/z |
|---|---|---|---|---|
| 7-[7-Benzo[b]thiophen-2-yl-1-(2-trimethylsilanyl-ethoxymethyl)-1H-indazol-5-yl]-5-(3-methoxy-propyl)-5H-pyrrolo[3,2-d]pyrimidin-2-yl-N,N-dimethylamino-methyleneamine (Preparation #5, R (using 1-bromo-3-methoxypropane)) | | G.18 | 2.24(e) | 455.0 (M + H)$^+$ |
| 2-(3-{2-(Dimethylamino-methyleneamino)-7-[7-benzo[b]thiophen-2-yl-1-(2-trimethylsilanyl-ethoxymethyl)-1H-indazol-5-yl]-pyrrolo[3,2-d]pyrimidin-5-yl}-propan-1-oxy)tetrahydropyran (Preparation #5, R (using 2-(3-bromo-propan-1-oxy)tetrahydropyran)) | | G.19 | 1.64(e) | 441.3 (M + H)$^+$ |

TABLE G-continued

Examples prepared using general procedure G

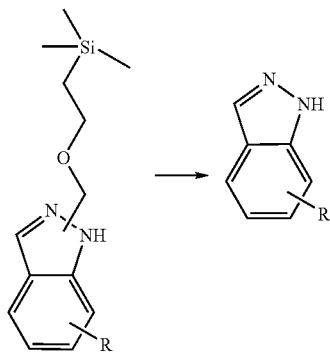

| Precursor | Product | Example # | HPLC R$_t$(min)(method) | m/z |
|---|---|---|---|---|
| 2-{2-Amino-7-[7-benzo[b]thiophen-2-yl-1-(2-trimethylsilanyl-ethoxymeth-yl)-1H-indazol-5-yl]-pyrrolo[3,2-d]pyrimidin-5-yl}-acetamide (Preparation #5, R (using 2-bromo methyl acetate), M) | | G.20 | 1.49(e) | 440.0 (M + H)⁺ |
| 4-{2-Amino-7-[7-benzo[b]thiophen-2-yl-1-(2-trimethylsilanyl-ethoxymeth-yl)-1H-indazol-5-yl]-pyrrolo[3,2-d]pyrimidin-5-yl}-butyric acid (Preparation #5, R (using methyl 4-bromo-butanoate), V) | | G.21 | 1.61(e) | 467.0 (M − H)⁺ |

TABLE G-continued

Examples prepared using general procedure G

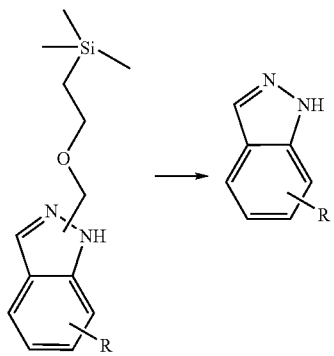

| Precursor | Product | Example # | HPLC R$_t$(min)(method) | m/z |
|---|---|---|---|---|
| 4-{2-Amino-7-[7-benzo[b]thiophen-2-yl-1-(2-trimethylsilanyl-ethoxymeth-yl)-1H-indaozl-5-yl]-pyrrolo[3,2-d]pyrimidin-5-yl}-butyramide (Preparation #5, R (using methyl 4-bromo-butanoate), M) | | G.22 | 1.49(e) | 468.2 (M + H)$^+$ |
| 3-{2-Amino-7-[7-benzo[b]thiophen-2-yl-1-(2-trimethylsilanyl-ethoxymeth-yl)-1H-indazol-5-yl]-pyrrolo[3,2-d]pyrimidin-5-yl}-2-methylpropionic acid (Preparation #5, R (methyl 3-bromo 2-methyl propionoate), V | | G.23 | 1.63(e) | 469.2 (M + H)$^+$ |

TABLE G-continued

Examples prepared using general procedure G

| Precursor | Product | Example # | HPLC R$_t$(min)(method) | m/z |
|---|---|---|---|---|
| 3-{2-Amino-7-[7-benzo[b]thiophen-2-yl-1-(2-trimethylsilanyl-ethoxymethyl)-1H-indaozl-5-yl]-pyrrolo[3,2-d]pyrimidin-5-yl}-2-methyl-propionic acid methyl ester (Preparation #5, R (using methyl 3-bromo 2-methylpropionate)) | | G.24 | 1.96(e) | 483.3 (M + H)$^+$ |
| 2-Amino-7-[7-benzo[b]thiophen-2-yl-1-(2-trimethylsilanyl-ethoxymethyl)-1H-indazol-5-yl]-pyrrolo[3,2-d]pyrimidine-5-carboxylic acid isopropyl ester (Preparation #5, T (using diisopropyl azodicarboxylate) | | G.25 | 2.22(e) | 469.1 (M + H)$^+$ |

General Procedure H: Acid Cleavage of a TBDMS-Protecting Group

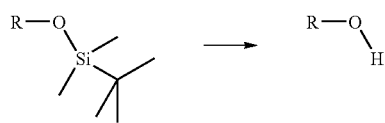

To a mixture of a TBDMS protected substrate in an organic solvent (for example methanol, ethanol, ispropanol, $CH_2Cl_2$, or dioxane, preferably methanol) is added an excess amount of an acid (5-50 equivalents, preferably 20 equivalents) (for example HCl, or TFA, preferably HCl). The reaction mixture is then stirred at about 25-85° C. (preferably about 65° C.) for about 0.5-24 hours (preferably about 1 hour). The solvent is evaporated and the product is isolated by crystallization or by chromatography.

Illustration of General Procedure H

Example #30

(3-[(2-Amino-pyrimidin-4-yl)-(7-benzo[b]thiophen-2-yl-1H-indazol-5-yl)-amino]-propan-1-ol

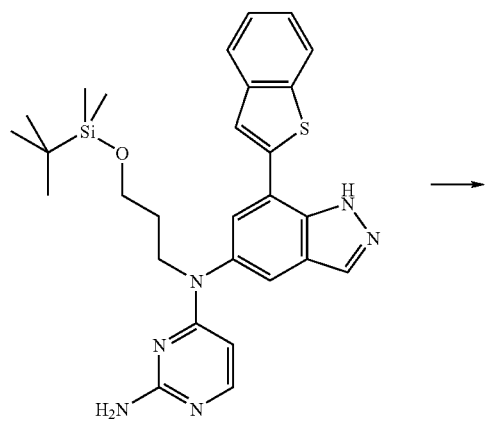

→

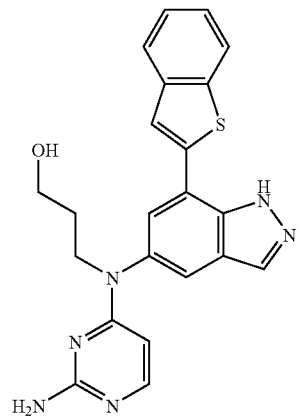

6N hydrochloric acid (1 mL) was added to a mixture of $N^4$-(7-benzo[b]thiophen-2-yl-1H-indazol-5-yl)-$N^4$-[3-(tert-butyl-dimethyl-silanyloxy)-propyl]-pyrimidine-2,4-diamine (prepared from example #F.8.1, via general procedures O then N, 0.179 g, 0.339 mmol) in ethanol (2 mL). The reaction mixture was heated to about 65° C. for about 1 hour then cooled to about ambient temperature. The solvents were evaporated and the residue was purified by reverse phase chromatography (Thermo Hypersil-Keystone 250×21.2 mm 8µ Hypersil® HS C18 column; 5% acetonitrile/0.1 M aqueous ammonium acetate –100% acetonitrile over 20 min, 100% acetonitrile hold 5 minutes, 21 mL/min) to afford (3-[(2-amino-pyrimidin-4-yl)-(7-benzo[b]thiophen-2-yl-1H-indazol-5-yl)-amino]-propan-1-ol (0.022 g, 0.053 mmol) as an off white solid; RP-HPLC (Table 1, Method e) $R_t$ 1.77 min.; m/z: $(M+H)^+$ 417.1.

TABLE H.1

Examples prepared using general procedure H

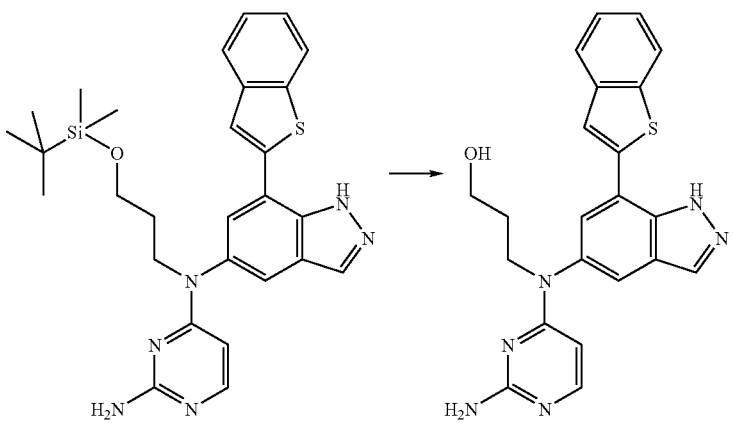

| TBDMS protected alcohol | Product | Example # | R$_t$/min(method) | m/z(ESI+) |
|---|---|---|---|---|
| N'4'-(7-Benzo[b]thiophen-2-yl-1H-indazol-5-yl)-N'4'-[2-(tert-butyl-dimethyl-silanyloxy)-ethyl]-pyrimidine-2,4-diamine (Example #F.8.1, O then N) | | H.1.1 | 1.52(e) | 390 (M + H)⁺ |

General Procedure I: Deprotection of a Benzyl Ether

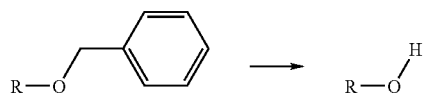

A mixture of a benzyl protected ether (1 equivalent) and a Pd catalyst (for example, 10 wt. % Pd on carbon or palladium (II) oxide, preferably 10 wt. % Pd on carbon) (5-10 mol %, preferably 7 mol %) in a degassed organic solvent (for example MeOH or EtOH, preferably MeOH) is shaken under an atmosphere of hydrogen gas at about 30-50 psi (preferably 40 psi) at about 10-50° C. (preferably about 25° C.) for about 2-24 hours (preferably about 18 hours). The reaction mixture is evacuated, flushed with an inert gas (for example nitrogen or argon, preferably nitrogen) and filtered. The solvents are removed under reduced pressure to afford the product that can be further purified by chromatography or crystallization.

Illustration of General Procedure I:

Example #15

5-[3-(1H-Pyrrol-2-yl)-1H-indazol-5-yl]-pyridin-3-ol

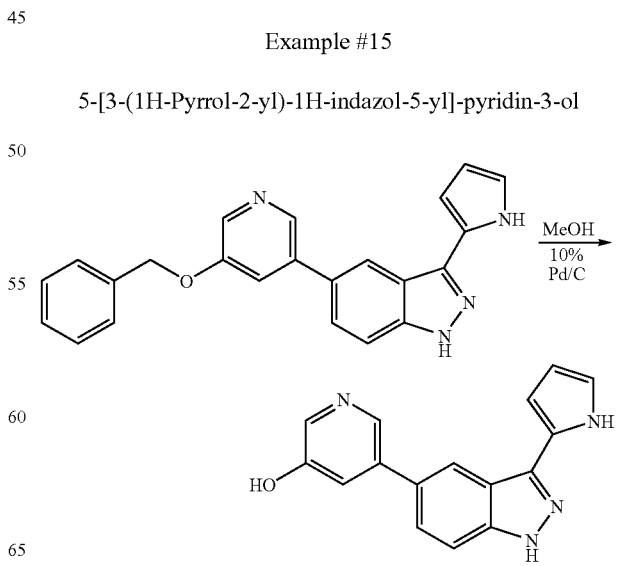

A mixture of 5-(5-benzyloxy-pyridin-3-yl)-3-(1H-pyrrol-2-yl)-1H-indazole (Preparation #16c, E and F (using 5-benzyloxy-3-bromopyridine), 0.015 g, 0.4 mmol) in MeOH (5 mL) and 10 wt. % Pd/C (3 mg) was shaken under an atmosphere of hydrogen (about 40 psi) for about 24 hours. The crude product was filtered and the solvent was removed under reduced pressure to yield 5-[3-(1H-pyrrol-2-yl)-1H-indazol-5-yl]-pyridin-3-ol (0.088 g, 80%); RP-HPLC (Table 1, Method e) $R_t$=1.78 min; m/z: (M+H)$^+$ 277, (M−H)$^−$ 275.

General Procedure J: Reduction of an Aldehyde to an Alcohol

A mixture of an aldehyde (1-1.2 equivalents, preferably 1 equivalent) and a reducing agent (for example borane, borane-pyridine, borane-diemethylsulfide, LiBH$_4$ or NaBH$_4$, preferably NaBH$_4$) (1.0-3.0 equivalents, preferably 2.0 equivalents) in an organic solvent (for example, DMF, dioxane, THF, MeOH or EtOH, preferably MeOH) is stirred at about 5-65° C. (preferably about 25° C.) for about 0.5-24 hours (preferably about 1 hour) under an inert atmosphere. If heated, the mixture is allowed to cool to ambient temperature, and the solvent is removed under reduced pressure. The solid residue can then be purified by chromatography or crystallization.

Illustration of General Procedure J:

Example #16

[3-(7-Benzo[b]thiophen-2-yl-1H-indazol-5-yl)-phenyl]-methanol

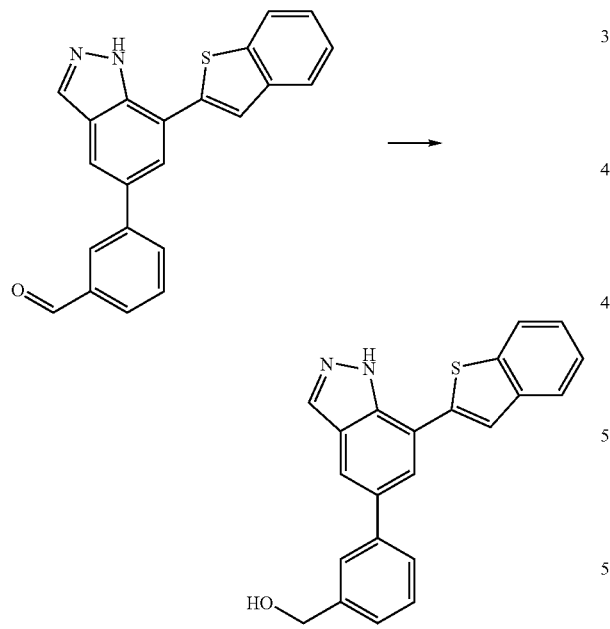

A mixture of 3-(7-benzo[b]thiophen-2-yl-1H-indazol-5-yl)-benzaldehyde (Preparation #25, F (using 3-bromobenzaldehyde), 50 mg, 0.14 mmol), and NaBH$_4$ (0.01 g, 0.26 mmol) in MeOH (2 mL) was stirred at ambient temperature for about 1 hour. The reaction mixture was concentrated under reduced pressure then the residue was purified by reverse phase preparative HPLC (Thermo Hypersil-Keystone 250×21.2 mm 8μ Hypersil® HS C18 column; 5% CH$_3$CN/50 mM aqueous ammonium acetate hold for 5 min; 5-50% CH$_3$CN/50 mM aqueous ammonium acetate over 20 min; 50-100% CH$_3$CN/ 50 mM aqueous ammonium acetate over 1 min; hold at 100% CH$_3$CN for 5 minutes, 21 mL/min) to yield [3-(7-benzo[b]thiophen-2-yl-1H-indazol-5-yl)-phenyl]-methanol (6 mg, 12%); (DMSO-d$_6$, 400 MHz) 8.8 (d, 1H), 8.55 (d, 1H), 8.37 (s, 1H), 8.19 (d, 1H), 8.18 (s, 1H), 8.10 (t, 1H), 8.04 (dd, 1H), 7.93 (dd, 1H), 7.89 (d, 1H, 7.45 (m, 2H), 5.40 (t, 1H), 4.6 (d, 2H); RP-HPLC (Table 1, Method e) $R_t$=1.85 min; m/z: (M−H)$^−$ 355.8.

General Procedure K: Nucleophilic Displacement of an Aryl Sulfone

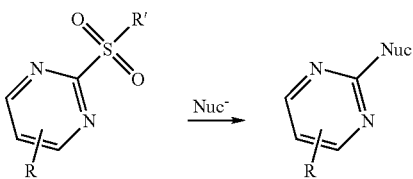

An aryl sulfone is treated with a large excess of a nucleophile (for example an amine or an alcohol, preferably an amine) (100-500 equivalents, preferably 250 equivalents) in the absence of an organic solvent. The mixture is stirred for 5-60 hours (preferably about 16 hours) at about 0-100° C. (preferably about 20° C.). If heated, the mixture is allowed to cool to ambient temperature, filtered, and the solids are further purified by crystallization or chromatography if necessary.

Illustration of General Procedure K

Example #17

(7-Benzo[b]thiophen-2-yl-1H-indazol-5-yl)-(2-hydrazino-pyrimidin-4-yl)-amine

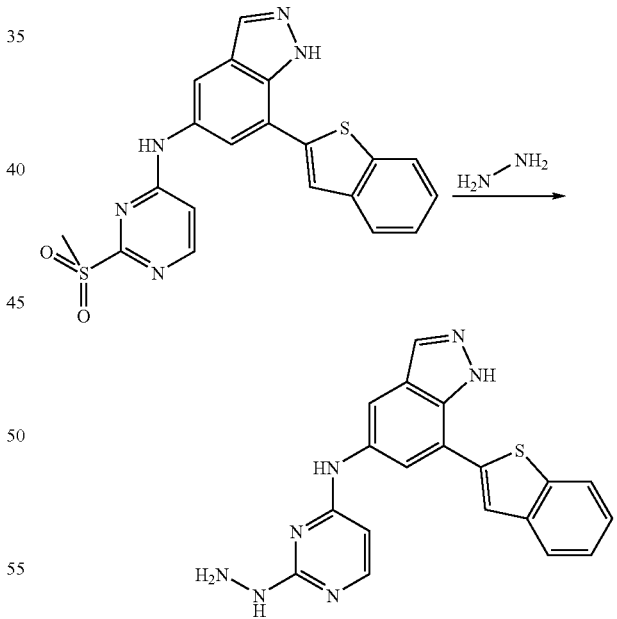

(7-Benzo[b]thiophen-2-yl-1H-indazol-5-yl)-(2-methanesulfonyl-pyrimidin-4-yl)-amine (Preparation #8, 20 mg, 0.048 mmol) was treated with hydrazine (0.4 mL, 12.2 mmol) at ambient temperature for about 5 hours. A solid was filtered off and was further purified by trituration in dichloromethane followed by filtration to yield (7-benzo[b]thiophen-2-yl-1H-indazol-5-yl)-(2-hydrazino-pyrimidin-4-yl)-amine (4 mg, 23% yield); LC/MS (method f) $R_t$ 6.0 min; m/z (ESI−): (M−H)$^+$ 371.7.

TABLE K
Examples using general procedure K prepared from (7-benzo[b]thiophen-2-yl-1H-indazol-5-yl)-(2-methanesulfonyl-pyrimidin-4-yl)-amine (Preparation #8)
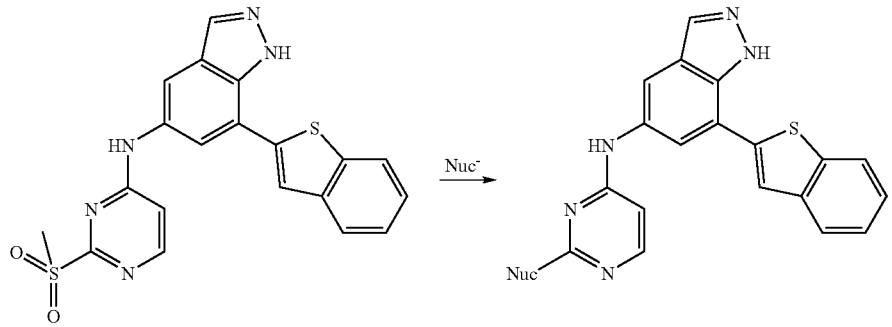
| Nucleophile | Product | Example # | R$_t$(min)(method) | m/z (ESI−): (M − H)$^+$ |
|---|---|---|---|---|
| N',N'-Dimethyl-ethane-1,2-diamine | | K.1.1 | 1.7(e) | 430.1 (M − H)$^+$ |
| Pyrrolidin-3-ol | | K.1.2 | 1.7(e) | 429.1 (M − H)$^+$ |
| 2-Amino-ethanol | | K.1.3 | 1.6(e) | 403.1 (M − H)$^+$ |

TABLE K-continued
Examples using general procedure K prepared from (7-benzo[b]thiophen-2-yl-1H-indazol-5-yl)-(2-methanesulfonyl-pyrimidin-4-yl)-amine (Preparation #8)
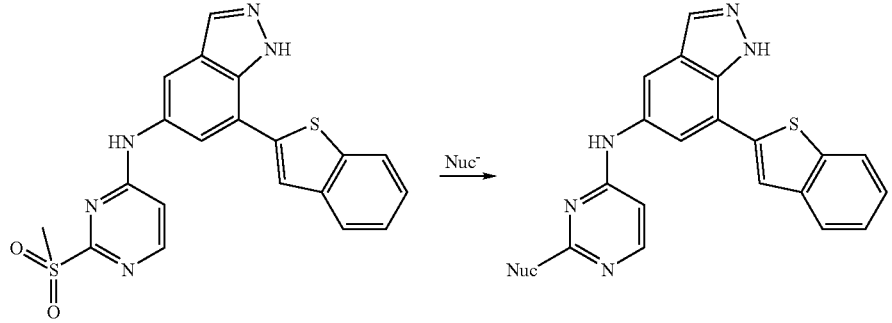
| Nucleophile | Product | Example # | R$_t$(min)(method) | m/z (ESI−): (M − H)$^+$ |
|---|---|---|---|---|
| 2-Methoxy-ethylamine | | K.1.4 | 1.8(e) | 417.1 (M − H)$^+$ |
| 2-Dimethylamino-ethanol | | K.1.5 | 1.9(e) | 431.1 (M − H)$^+$ |
| 2-(2-Hydroxy-ethylamino)-ethanol | | K.1.6 | 1.6(e) | 447.1 (M − H)$^+$ |

General Procedure L: Reduction of a Nitroaromatic Compound to an Aniline

To a solution of a nitroaromatic compound (preferably 1 equivalent) in a solvent (for example, EtOAc, EtOH, HOAc, 9M NH$_4$OH, preferably EtOAc) is added a reducing reagent (for example, hydriodic acid, iron powder, iron sulfate hydrate, tin chloride dehydrate, or palladium on carbon) (0.2-10 equivalents, preferably 3 equivalents). The reaction mixture is stirred at about 20-100° C. (preferably about 90° C.) for about 1-20 hours (preferably about 2 hours). A hydrogen atmosphere (about 15-60 psi, preferably about 40 psi) is when a palladium catalyst is employed. If iron sulfate hydrate is used as the reducing reagent the mixture is filtered hot and then acidified with HOAc to about pH=4, then the product is filtered off and rinsed with water. If tin chloride or iron powder are used the mixture is allowed to cool to ambient temperature and then diluted with an organic solvent (for example, EtOAc or CH$_2$Cl$_2$, preferably CH$_2$Cl$_2$). If palladium is used as the reducing reagent the reaction mixture is filtered through celite and rinsed with organic solvent. If hydriodic acid is used, the organic layer is washed with saturated aqueous sodium thiosulfate. The organic layer is then washed with an aqueous base solution (for example, Na$_2$CO$_3$ or NaOH, preferably NaOH). The organic layer is separated, dried over a desiccant, and concentrated to give the aniline compound.

Illustration of General Procedure L
Preparation #28: 3-Iodo-1H-indazol-5-ylamine

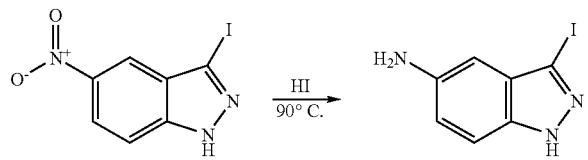

A suspension of 3-iodo-5-nitro-1H-indazole (2.0 g, 6.92 mmol) in stabilized hydroiodic acid (57% wt aqueous solution, 21 mL) was heated at about 90° C. for about 2 hours. The reaction mixture became homogeneous as the reaction progressed. After cooling to ambient temperature, the dark purple mixture was diluted with EtOAc (500 mL) and washed successively with saturated aqueous sodium thiosulfate (200 mL), saturated aqueous NaHCO$_3$ (200 mL) and brine (200 mL). The colorless organic layer was dried over anhydrous magnesium sulfate, and concentrated to dryness to give 3-iodo-1H-indazol-5-ylamine: $^1$H NMR (DMSO-d$_6$, 400 MHz) $\delta$ 13.03 (s, 1H), 7.26 (d, 1H), 6.85 (m, 1H), 6.44 (d, 1H), 5.03 (s, 2H); LC/MS (30% to 95% acetonitrile/0.01M aqueous ammonium acetate over 4.5 min at 0.8 mL/min; $\lambda$=190-700 nm; Genesis C18, 3 µm, 30×4.6 mm column; Electrospray ionization method observing both +ve and -ve ions) R$_t$ 1.25 min.; m/z: 260 (M+H)$^+$.

General Procedure M: Amide Formation from an Ester

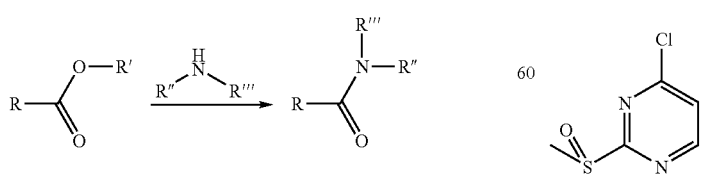

At room temperature, a mixture of an ester (1.0 equivalent) and an amine (for example, ammonia, a primary amine or a second amine) (10-500 equivalents, preferably 20 equivalents) optionally diluted with an alcoholic solvent (MeOH, EtOH or i-PrOH, preferably i-PrOH) is heated at about 60-140° C. (preferably about 100° C.) in a sealed vessel with stirring for about 0.5-7 days (preferably about 1 day). The mixture is cooled to ambient temperature, concentrated and is further purified by chromatography or crystallization, or used in a subsequent step without further purification.

Illustration of General Procedure M:
See Example #1.

General Procedure N: Nucleophilic Substitution of Aromatic Halide with an Amino Compound

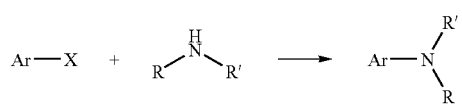

To a solution of an amine (1.0 equivalent) with or without a base (Et$_3$N or DIEA, preferably Et$_3$N) in an organic solvent (for example, EtOH, MeOH, or dioxane, preferably EtOH) is added an aromatic halide (1.0-10 equivalents, preferably 1.0 equivalent). The reaction mixture is heated at about 25-160° C. (preferably about 80° C.) with stirring for about 20 minutes-4 hours (preferably about 30 minutes) or heated in a microwave reactor at about 120-180° C. (preferably about 150° C.) for about 5-30 minutes (preferably about 10 minutes). The mixture is allowed to cool to ambient temperature. Then either the solvent is removed under reduced pressure or the mixture is filtered to give crude product that is then purified directly by chromatography or crystallization or submitted to the following aqueous work up. The crude material is suspended in a basic solution (for example, NH$_4$OH in MeOH, saturated aqueous NaHCO$_3$ or 2M aqueous Na$_2$CO$_3$, preferably saturated aqueous NaHCO$_3$) then filtered and washed with an organic solvent (for example MeOH, EtOAc, or CH$_2$Cl$_2$). If needed, the resulting solid can then be purified by chromatography or crystallization. If a tert-butoxycarbonyl (Boc) protected diamine is used then the material is suspended in a mixture of methanol/6 N hydrochloric acid and heated to about 65° C. for about one hour then cooled, concentrated and purified by chromatography or crystallization Illustration of General Procedure N:

Preparation #46. (7-Benzo[b]thiophen-2-yl-1H-indazol-5-yl)-(2-methanesulfonyl-pyrimidin-4-yl)-amine

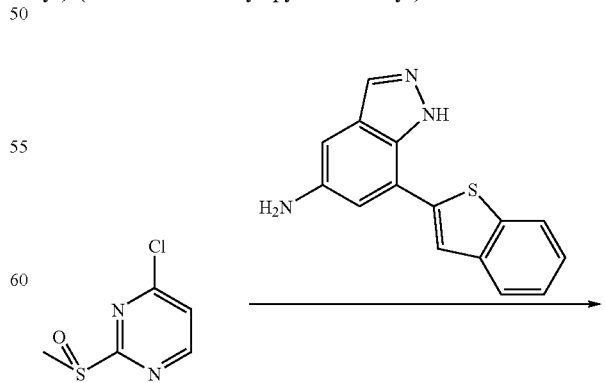

-continued

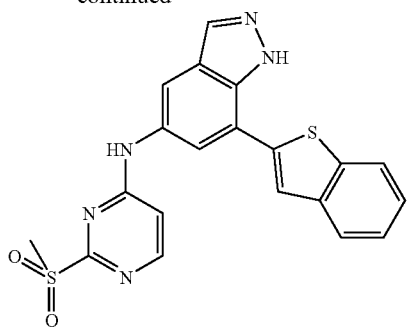

To a mixture of 4-chloro-2-methanesulfonyl-pyrimidine (2.54 g, 13.2 mmol) in DME (20 mL) was added a mixture of 7-benzo[b]thiophen-2-yl-1H-indazol-5-ylamine (Example #F.8.1, 1.95 g, 7.35 mmol) and Et₃N (1.43 mL, 10.3 mmol) in DME (160 mL). The reaction mixture was stirred at room temperature for about 16 hours then filtered, then filtrate was adsorbed onto alumina. The mixture was purified by flash column chromatography over alumina using CH₂Cl₂/MeOH (99:1) as an eluent to yield the initial crop of product. A second crop was obtained by triturating the alumina in CH₂Cl₂/MeOH (8:2) and combined with the first to afford 7-benzo[b]thiophen-2-yl-1H-indazol-5-yl)-(2-methane-sulfonyl-pyrimidin-4-yl)-amine (1.09 g, 36% yield): LC/MS (method e) R$_t$ 1.8 min; m/z (ESI−): (M−H)⁺ 419.9.

TABLE N.1

Examples prepared using general procedure N from Example #F.8.1

| Aryl halide | Product | Ex. # | R$_t$(min)(method) | m/z or ¹H NMR (d₆ DMSO, 400 MHz) |
|---|---|---|---|---|
| 7-Chloro-1H-pyrrolo[2,3-c]pyridine | | N.1.1 | 2.2 min(e) | 382.0(M + H)⁺ |
| 4-Chloro-pyridin-3-ylamine | | N.1.2 | 14 min (b) | 1.87(s, 3H), 4.85 (bs, 2H), 6.85(d, 1H), 7.41(m, 3H), 7.44(s, 1H), 7.57(s, 1H), 7.61(m, 1H), 7.88(m, 2H), 8.00(m, 1H), 8.15(m, 2H) |
| 2-Chloro-4,6-dimethoxy-1,3,5-triazine | | N.1.3 | 2.1 min(e) | 403.0(M + H)⁺ |

TABLE N.1-continued

Examples prepared using general procedure N from Example #F.8.1

| Aryl halide | Product | Ex. # | R$_t$(min)(method) | m/z or $^1$H NMR (d$_6$ DMSO, 400 MHz) |
|---|---|---|---|---|
| 2-Amino-6-chloropurine | | N.1.4 | 1.6 min(e) | 399.0(M + H)$^+$ |
| 6-Chloro-pyrimidine-2,4-diamine | | N.1.5 | 1.5 min(e) | 373.9(M + H)$^+$ |
| 4-Chloro-thieno[3,2-c]pyridine | | N.1.6 | 2.5 min(e) | 398.9(M + H)$^+$ |
| 6-Chloro-pyridazin-3-ylamine | | N.1.7 | 1.7 min(e) | 358.9(M + H)$^+$ |

TABLE N.1-continued

Examples prepared using general procedure N from Example #F.8.1

| Aryl halide | Product | Ex. # | R$_t$(min)(method) | m/z or $^1$H NMR (d$_6$ DMSO, 400 MHz) |
|---|---|---|---|---|
| 2-Chloro-pyrimidine-4,5-diamine | | N.1.8 | 1.6 min(e) | 374.0(M + H)$^+$ |
| 6-Chloro-[1,3,5]triazine-2,4-diamine | | N.1.9 | 1.5 min(e) | 373.1(M − H)$^−$ |
| 4-Chloro-thieno[3,2-d]pyrimidine | | N.1.10 | 2.2 min(e) | 399.8(M + H)$^+$ |

TABLE N.1-continued
Examples prepared using general procedure N from Example #F.8.1
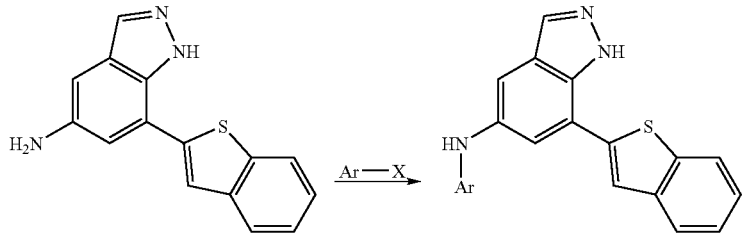
| Aryl halide | Product | Ex. # | R$_t$(min)(method) | m/z or $^1$H NMR (d$_6$ DMSO, 400 MHz) |
|---|---|---|---|---|
| 2-Chloro-6,7-dimethoxy-quinazolin-4-ylamine | | N.1.11 | 2.1 min(e) | 468.9(M + H)$^+$ |
| 1H-Pyrrolo[2,3-d]pyrimidin-4-ylamine | | N.1.12 | 2.0 min(e) | 383.0(M + H)$^+$ |
| 6-Chloro-nicotinamide | | N.1.13 | 2.4 min(e) | 7.10(d, 1H), 7.34 (m, 3H), 7.37(s, 1H), 7.91(d, 1H), 7.97(d, 2H), 8.08 (m, 3H), 8.22(bs, 1H), 8.58(s, 1H), 9.19(s, 1H), 13.27(bs, 1H) |

TABLE N.1-continued

Examples prepared using general procedure N from Example #F.8.1

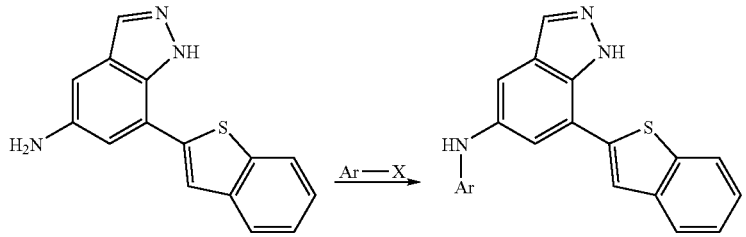

| Aryl halide | Product | Ex. # | R$_t$(min)(method) | m/z or $^1$H NMR (d$_6$ DMSO, 400 MHz) |
|---|---|---|---|---|
| 2-Acetamido-4-chloro pyrimidine | | N.1.14 | 2.50(e) | 353.0 (M − H)$^−$ |

TABLE N.2

Examples using general procedure N from 4-chloro-2-aminopyrimidine

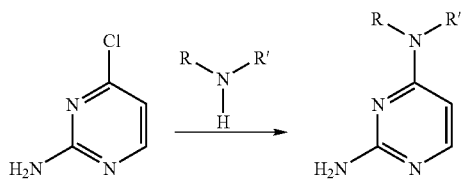

| Amine | Product | Ex. # | R$_t$(min)(method) | m/z |
|---|---|---|---|---|
| (7-Benzo[b]thiophen-2-yl-1H-indazol-5-yl)-(4-imidazo[1,2-α]pyridin-2-yl-benzyl)-amine (Example # F.8.1, then O) | | N.2.1 | 1.6 min(e) | 565.4 (M + H)$^+$ |

TABLE N.2-continued

Examples using general procedure N from 4-chloro-2-aminopyrimidine

| Amine | Product | Ex. # | R$_t$(min)(method) | m/z |
|---|---|---|---|---|
| 3-Iodo-1H-indazol-5-ylamine (FR2836914) | | N.2.2 | 0.8(e) | 261.2 (M − H)− |
| 5-Amino-1H-indazol-3-ol (FR2836914) | | N.2.3 | 0.96(f) | 241.2 (M − H)− |
| 5-Amino-7-benzo[b]thiophen-2-yl-1H-indazol-3-ol (Preparation #50, N, L) | | N.2.4 | 1.26(e) | 375.3 (M − H)− |
| N-(5-Amino-3-chloro-1H-indazol-7-yl)-acetamide(J. Med. Chem., 2003, 46(26), 5663-5673) | | N.2.5 | 0.62(e) | 318.0 (M + H)+ |

TABLE N.2-continued

Examples using general procedure N from 4-chloro-2-aminopyrimidine

| Amine | Product | Ex. # | R$_t$(min)(method) | m/z |
|---|---|---|---|---|
| 3-Iodo-1H-indazol-5-ylamine (Preparation #28) | | N.2.6 | 1.22(a) | 352.8 (M + H)$^+$ |
| 7-Bromo-1H-indazol-5-ylamine (Preparation #6) | | N.2.7 | 1.13(e) | 305.1 (M + H)$^+$ |
| 5-Amino-1H-indazole-3-carboxylic acid | | N.2.8 | 0.40(e) | 270.9 (M + H)$^+$ |
| N-(5-Amino-1H-indazol-3-yl)-benzamide (W, L) | | N.2.9 | 1.08(e) | 346.1 (M + H)$^+$ |

TABLE N.2-continued

Examples using general procedure N from 4-chloro-2-aminopyrimidine

| Amine | Product | Ex. # | R$_t$(min)(method) | m/z |
|---|---|---|---|---|
| N-(5-Amino-1H-indazol-3-yl)-3-methoxy-benzamide (W, L) | | N.2.10 | 0.93(e) | 376.4 (M + H)$^+$ |
| N-(5-Amino-1H-indazol-3-yl)-3-dimethylamino-benzamide (W, L) | | N.2.11 | 1.13(e) | 389.2 (M + H)$^+$ |
| N'3'-Benzyl-1H-indazole-3,5-diamine (O, L) | | N.2.12 | 1.61(e) | 425.3 (M + H)$^+$ |
| 1H-indazol-4-ylamine (L) | | N.2.13 | 0.48(e) | 226.8 (M + H)$^+$ |

TABLE N.2-continued

Examples using general procedure N from 4-chloro-2-aminopyrimidine

| Amine | Product | Ex. # | R$_t$(min)(method) | m/z |
|---|---|---|---|---|
| 6-Methoxy-1H-indazol-5-ylamine (According to Preparation #6) | | N.2.14 | 0.40(e) | 257.3 (M + H)$^+$ |
| 7-Chloro-1H-indazol-5-ylamine (According to Preparation #6) | | N.2.15 | 1.58(e) | 389 (M + H)$^+$ |
| (7-Benzo[b]thiophen-2-yl-1H-indazol-5-yl)-(tetrahydropyran-4-ylmethyl)-amine (Example #F.8.1, O) | | N.2.16 | 2.17(e) | 457.1 (M + H)$^+$ |
| 3-Chloro-1H-indazol-5-ylamine(J. Med. Chem. (2003), 46(26), 5663-5673) | | N.2.17 | 3.03(f) | 261.2 (M + H)$^+$ |

TABLE N.2-continued

Examples using general procedure N from 4-chloro-2-aminopyrimidine

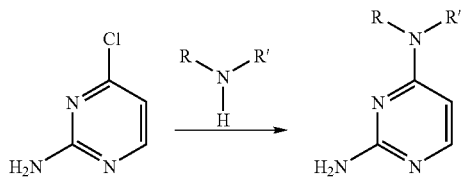

| Amine | Product | Ex. # | R$_t$(min)(method) | m/z |
|---|---|---|---|---|
| 3-Morpholin-4-yl-1H-indazol-5-ylamine (Pharmazie, 33(6), 377-8, 1978, N, L) | | N.2.18 | 2.43(f) | 311.9 (M + H)$^+$ |
| N-(5-Amino-3-chloro-1H-indazol-7-yl)-benzamide(J. Med. Chem., 46(26), 5663-5673, 2003, W, L) | | N.2.19 | 1.47(e) | 380.3 (M + H)$^+$ |
| (5-Amino-3-chloro-1H-indazol-7-yl)-carbamic acid tert-butyl ester (J. Med. Chem., 46(26), 5663-5673, 2003, W, L) | | N.2.20 | 0.52(e) | 276.0 (M + H)$^+$ |
| N-(5-Amino-3-chloro-1H-indazol-7-yl)-methanesulfonamide(J. Med. Chem., 46(26), 5663-5673, 2003, S, L) | | N.2.21 | 2.82(f) | 354.2 (M + H)$^+$ |

Representative NMR Data of Example #N.2.8

¹H NMR (DMSO-d$_6$, 400 MHz); 8.28 (br, 1H), 8.10 (m, 1H), 8.03 (d, 1H), 7.92 (d, 1H), 7.78 (s, 1H), 7.61 (d, 1H), 7.43 (m, 3H), 6.07 (m, 2H), 5.42 (d, 1H), 3.92 (d, 2H), 3.82 (m, 2H), 3.21 (t, 2H), 2.33 (m, 1H), 1.91 (s, 3H), 1.60 (m, 2H), 1.29 (m, 2H).

TABLE N.3

Examples prepared using general procedure N from Preparation #3

| Precursor | Product | Ex # | R$_t$(min) (method) | m/z |
|---|---|---|---|---|
| 1H-Indazol-5-ylamine | (structure shown) | N.3.1 | 3.38(a) | 266 (M + H)⁺ |

TABLE N.4

Examples prepared using general procedure N from Example #F.8.1

| Aryl halide | Product | Ex # | R$_t$(min)(method) | m/z |
|---|---|---|---|---|
| 2,4,6-Trichloro-[1,3,5]triazine | (structure shown) | N.4.1 | 2.35(e) | 411(M − H)⁻ |

TABLE N.4-continued
Examples prepared using general procedure N from Example #F.8.1
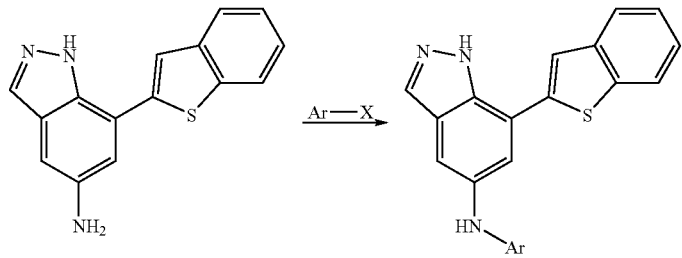
| Aryl halide | Product | Ex # | R$_t$(min)(method) | m/z |
|---|---|---|---|---|
| 2-Amino-6-chloro-pyrimidine-4-carboxylic acid methyl ester (J. Org. Chem., 1961, 26, 2755-2763) | | N.4.2 | 1.77(e) | 417(M + H)$^+$ |
| 4,6-Dichloro-pyrimidin-2-ylamine | | N.4.3 | 2.02(e) | 391(M − H)$^-$ |

TABLE N.4-continued
Examples prepared using general procedure N from Example #F.8.1
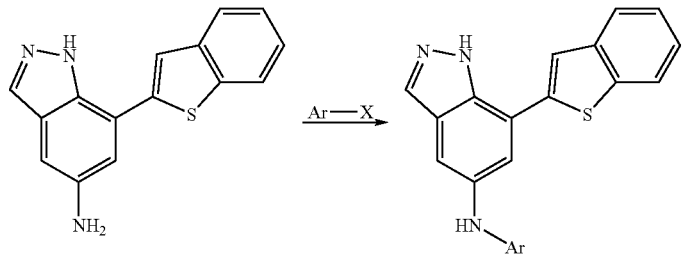
| Aryl halide | Product | Ex # | R$_t$(min)(method) | m/z |
|---|---|---|---|---|
| 4-Chloro-6-isopropyl-pyrimidin-2-yl amine | | N.4.4 | 1.72(e) | 401.3(M + H)$^+$<br>398.9(M − H)$^−$ |
TABLE N.5
Examples prepared using general procedure N from Example #N.4.3
| Amine | Product | Ex # | R$_t$(min)(method) | m/z |
|---|---|---|---|---|
| N',N'-Dimethyl-ethane-1,2-diamine | | N.5.1 | 1.23(e) | 446 (M + H)$^+$ |

TABLE N.5-continued

Examples prepared using general procedure N from Example #N.4.3

| Amine | Product | Ex # | R$_t$(min)(method) | m/z |
|---|---|---|---|---|
| Diethyl-amine | | N.5.2 | 2.21(e) | 431 (M + H)$^+$ |

TABLE N.6

Examples prepared using general procedure N from Example #N.4.1

| Precursor | Product | Ex # | R$_t$(min)(method) | m/z |
|---|---|---|---|---|
| Diethylamine | | N.6.1 | 3.23(a) | 485(M − H)− |

TABLE N.7
Examples prepared using general procedure N from Preparation #22d
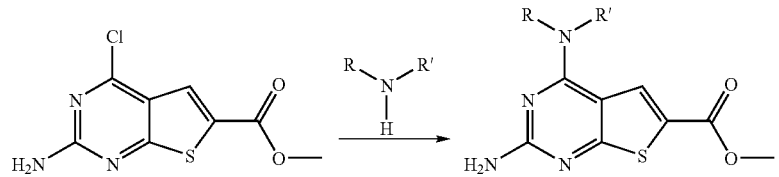
| Amine | Product | Example # | R$_t$(min)(method) | m/z(ESI+) |
|---|---|---|---|---|
| 1H-Indazol-5-ylamine | | N.7.1 | 1.82(a) | 340.9 (M + H)$^+$ |
TABLE N.8
Examples prepared using general procedure N from Preparation #3
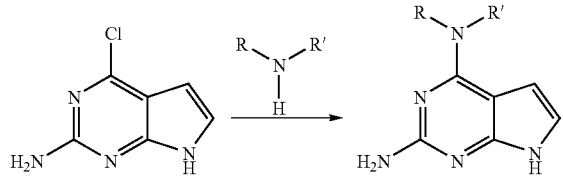
| Amine Precursor | Product | Example # | R$_t$(min)(method) | m/z(ESI+) |
|---|---|---|---|---|
| 7-Benzo[b]thiphen-2-yl-1H-indazol-5-ylamine (Example #F.8.1) | | N.8.1 | 1.80(e) | 398.1 (M + H)$^+$ |

TABLE N.9
Examples prepared using general procedure N from Example N.4.3
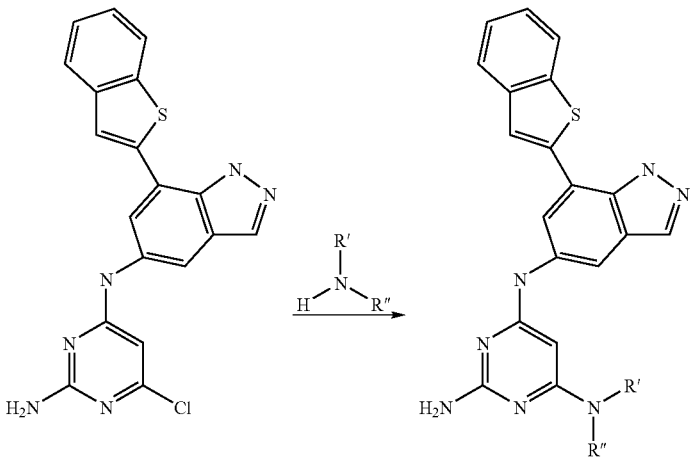
| Amine Precursor | Product | Example # | R$_t$(min)(method) | m/z(ESI+) |
|---|---|---|---|---|
| 2-Methoxy-ethylamine | 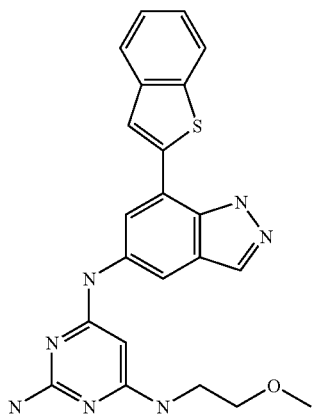 | N.9.1 | 1.54(e) | 432(M + H)$^+$<br>430(M − H)$^−$ |
| 2-Morpholin-4-yl-ethylamine | 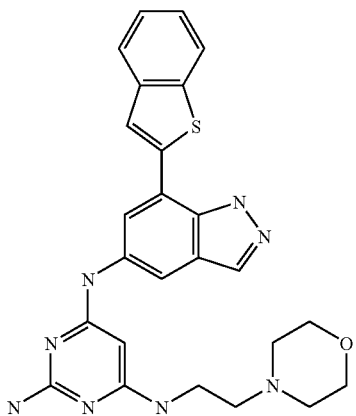 | N.9.2 | 1.03(e) | 487(M + H)+<br>485(M − H)$^−$ |

TABLE N.9-continued
Examples prepared using general procedure N from Example N.4.3
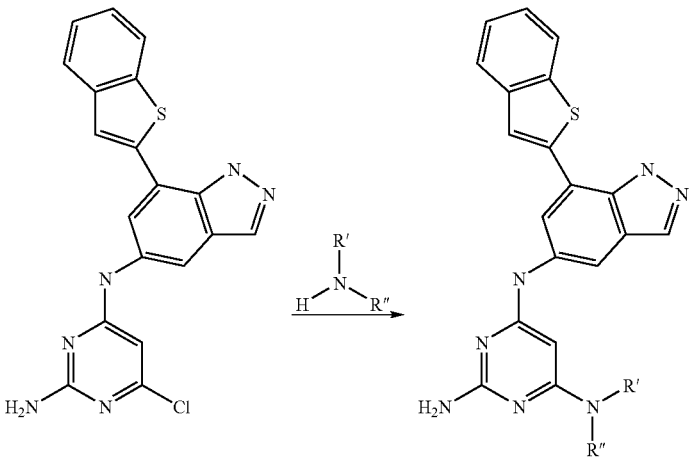
| Amine Precursor | Product | Example # | R$_t$(min)(method) | m/z(ESI+) |
|---|---|---|---|---|
| N*1*,N*1*-Dimethyl-ethane-1,2-diamine | | N.9.3 | 1.11(e) | 445(M + H)$^+$<br>443(M − H)$^-$ |
| Diethyl-amine | | N.9.4 | 1.93(e) | 430(M + H)$^+$<br>428(M − H)$^-$ |

TABLE N.9-continued
Examples prepared using general procedure N from Example N.4.3
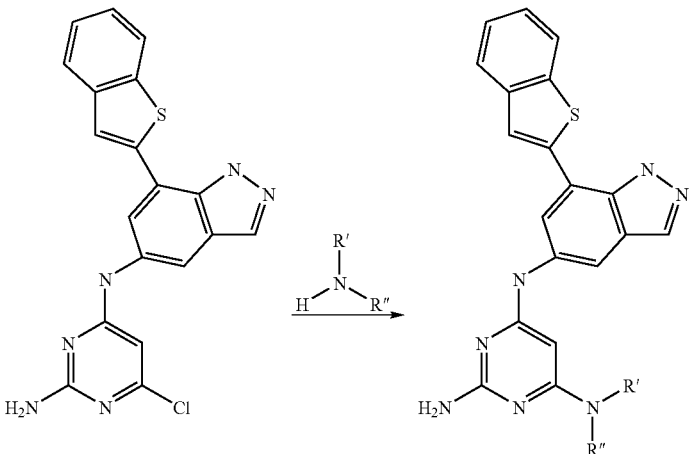
| Amine Precursor | Product | Example # | R$_t$(min)(method) | m/z(ESI+) |
| --- | --- | --- | --- | --- |
| Isopropyl-amine | 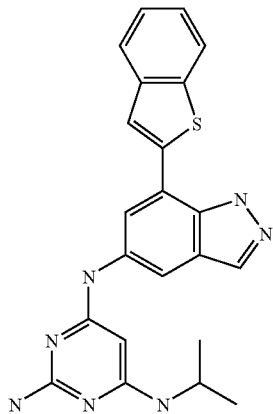 | N.9.5 | 1.69(e) | 416(M + H)$^+$<br>414(M − H)$^-$ |
| 2-(1H-Imidazol-4-yl)-ethylamine | 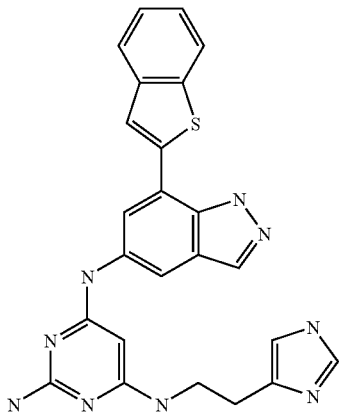 | N.9.6 | 1.10(e) | 468(M − H)$^+$<br>466(M − H)$^-$ |

TABLE N.9-continued
Examples prepared using general procedure N from Example N.4.3
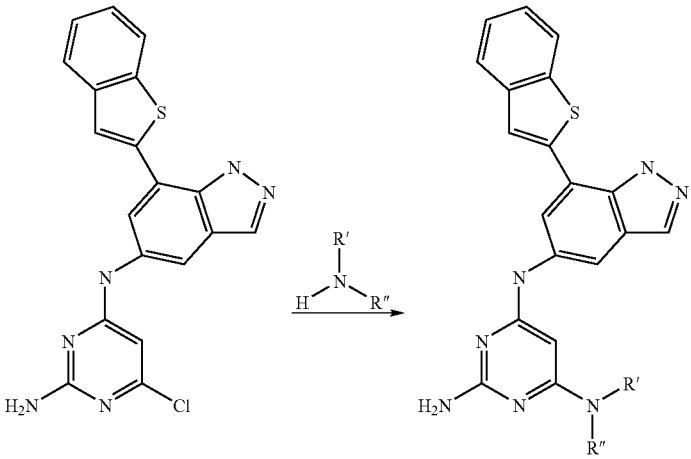
| Amine Precursor | Product | Example # | R$_t$(min)(method) | m/z(ESI+) |
|---|---|---|---|---|
| 2-Amino-ethanol | 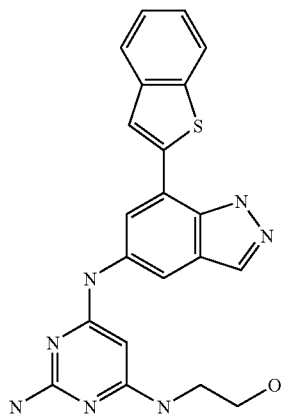 | H.9.7 | 1.28(e) | 418(M + H)$^+$<br>416(M − H)$^−$ |
| 3-Amino-propanol | 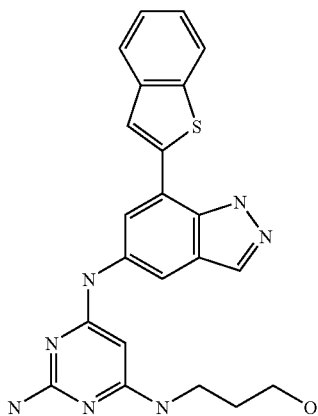 | N.9.8 | 1.44(e) | 432(M + H)$^+$<br>430(M − H)$^−$ |

TABLE N.9-continued
Examples prepared using general procedure N from Example N.4.3
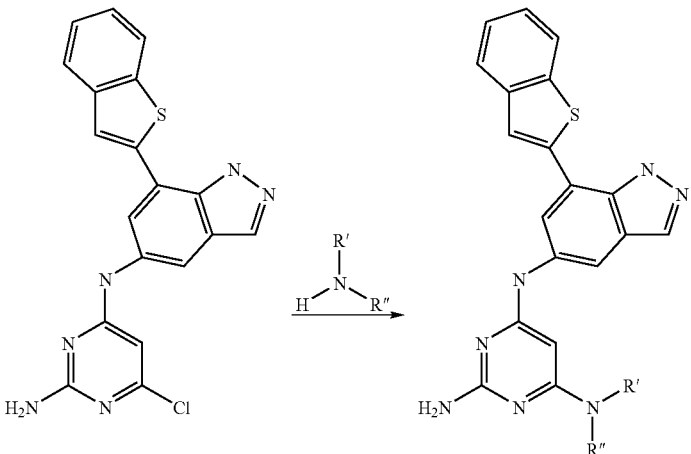
| Amine Precursor | Product | Example # | R$_t$(min)(method) | m/z(ESI+) |
|---|---|---|---|---|
| Ethane-1,2-diamine | | N.9.9 | 1.31(e) | 417(M + H)$^+$<br>415(M − H)$^−$ |
| 2-Pyridin-3-yl-ethylamine | | N.9.10 | 1.53(e) | 479(M + H)$^+$<br>477(M − H)$^−$ |

TABLE N.9-continued

Examples prepared using general procedure N from Example N.4.3

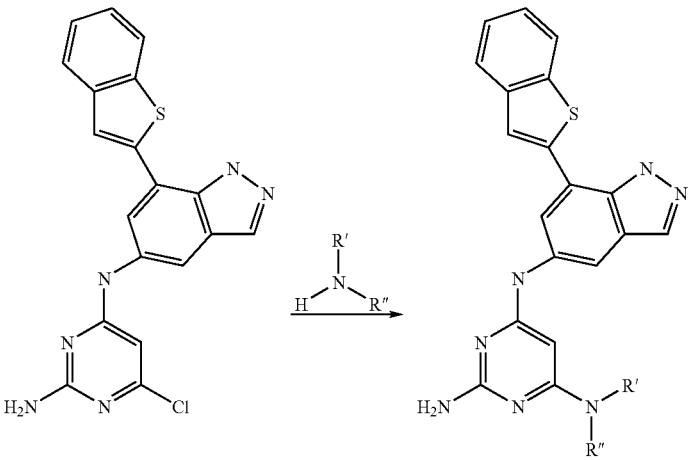

| Amine Precursor | Product | Example # | R_t(min)(method) | m/z(ESI+) |
|---|---|---|---|---|
| Propyl-amine | | N.9.11 | | |
| Phenethylamine | | N.9.12 | 1.78(e) | 478(M + H)+ <br> 476(M − H)− |

General Procedure O: Reductive Alkylation of an Amine with an Aldehyde or a Ketone.

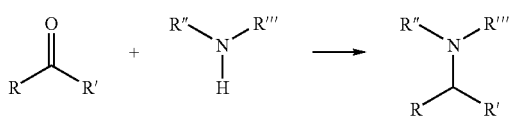

To a suspension of an amine and an aldehyde or a ketone (1-10 equivalents, preferably 1-2 equivalents) in an organic solvent (for example 1,2-dichloroethane, THF, $CH_2Cl_2$, DMF, or EtOAc, preferably 1,2-dichloroethane) with or without acetic acid (1-10 equivalents, preferably 1 equivalent) is added a reducing agent (for example, sodium triacetoxyborohydride or sodium cyanoborohydride, preferably sodium triacetoxyborohydride) (1-10 equivalents, preferably about 2 equivalents). Additional acetic acid (1-10 equivalents, preferably 3 equivalents) is added to progress the reaction when necessary. The resulting mixture is allowed to stir at room temperature for 2-112 hours (preferably 24 hours). The reaction mixture is purified in one of two ways: 1). The reaction solution is treated with an aqueous solution of an appropriate base (for example NaOH, NaHCO₃, or Na₂CO₃, preferably NaHCO₃) and an organic solvent (for example, CH₂Cl₂ or EtOAc, preferably CH₂Cl₂). The two layers are stirred for about 15 minutes then separated. The organic phase is concentrated under reduced pressure. The resulting crude product can be purified by trituration with an appropriate solvent (water, EtOH, toluene, or EtOAc, preferably EtOH) or by chromatography, or 2). The reaction mixture is directly concentrated under reduced pressure and purified by chromatography, trituration, or crystallization.

Illustration of General Procedure O

Example #19a

N-Benzyl-(5-nitro-1H-indazol-3-yl)-amine

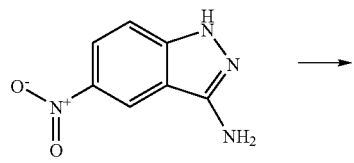

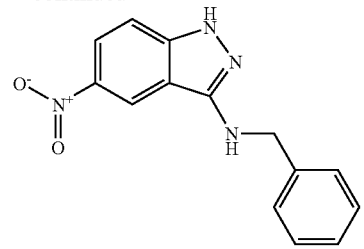

To a suspension of 5-nitro-1H-indazol-3-ylamine (0.025 g, 0.140 mmol) and benzaldehyde (0.067 g, 0.60 mmol) in CH₂Cl₂ (3.0 mL) was added acetic acid (0.024 mL, 0.42 mmol) followed by sodium triacetoxyborohydride (0.059 g, 0.28 mmol). The resulting solution was allowed to stir at room temperature for about 19 hours. The reaction solution was diluted with CH₂Cl₂ (5 mL) and treated with an aqueous solution of NaOH (1N, 5 mL). The two phases were separated and the organic solvent was removed under reduced pressure. The residue was further purified by preparative HPLC (Thermo Hypersil-Keystone 250×21.2 mm 8 Hypersil® HS C18 column; 5% acetonitrile/0.1 M aqueous ammonium acetate-100% acetonitrile over 20 min, 100% acetonitrile hold 5 minutes, 21 mL/min) to give benzyl-(5-nitro-1H-indazol-3-yl)-amine (0.012 g, 0.046 mmol) as an orange solid. RP-HPLC (Table 1, Method e) $R_t$ 2.15 min.; m/z: (M+H)⁺ 269.

TABLE O.1

Examples prepared from using general procedure O from Example #F.1.9

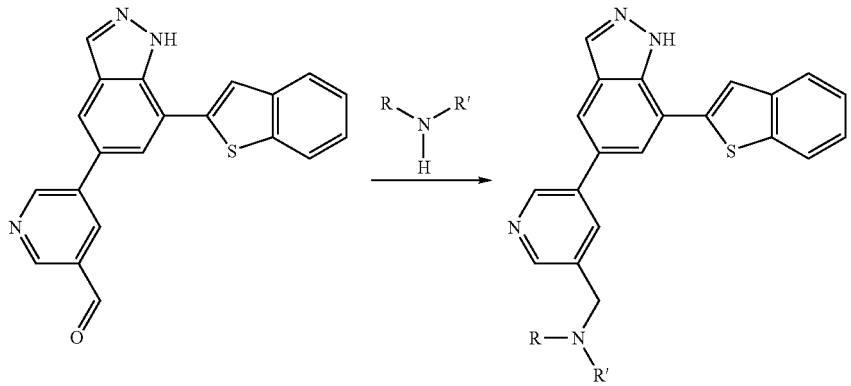

| Amine | Product | Example # | $R_t$/min(method) | m/z(ESI+) |
|---|---|---|---|---|
| Dimethylamine | | O.1.1 | 1.36(e) | 383.4 (M − H)⁻ |

TABLE O.2
Examples prepared using general procedure O from Example #F.8.1
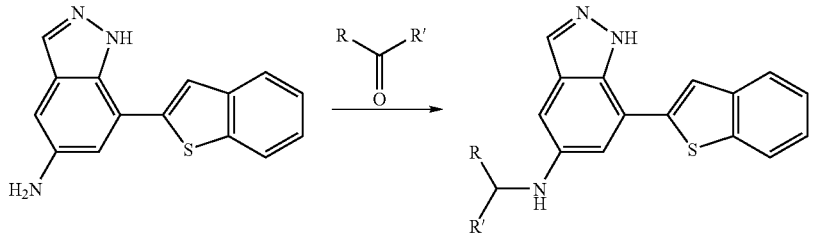
| Aldehyde/Ketone | Product | Example # | $R_t$/min(method) | m/z(ESI+) |
|---|---|---|---|---|
| 4-(Imidazolo[1,2-a]pyridin-4-yl)benzaldehyde | 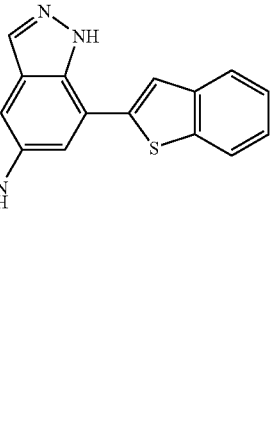 | O.2.1 | 2.1(e) | 472.4 (M + H)+ |

TABLE O.3
Examples prepared using general procedure O from Example #F.5.4
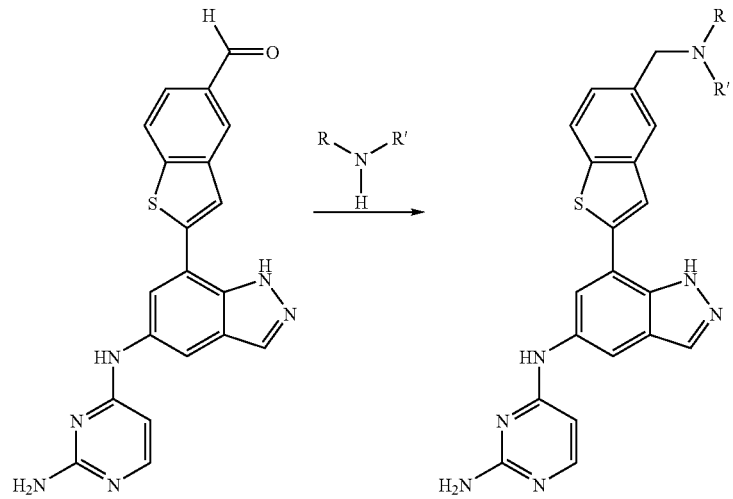
| Amine Precursor | Product | Example # | R$_t$/min(method) | m/z |
|---|---|---|---|---|
| Piperidine | | O.3.1 | 1.24(g) | 456.4 (M + H)$^+$ |

TABLE O.3-continued
Examples prepared using general procedure O from Example #F.5.4
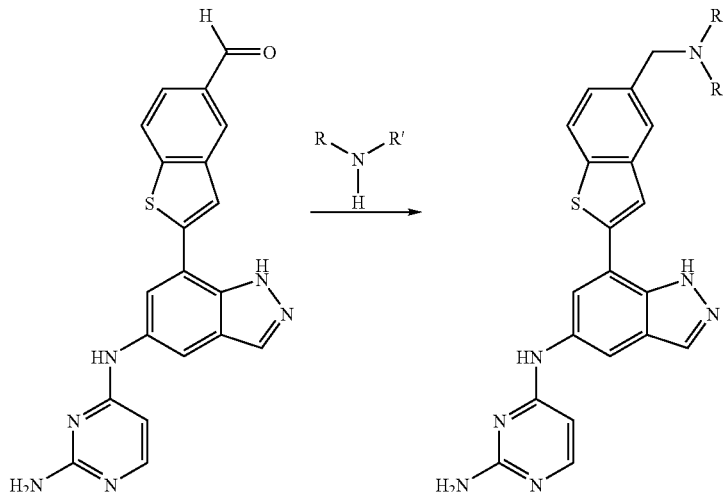
| Amine Precursor | Product | Example # | R$_t$/min(method) | m/z |
|---|---|---|---|---|
| N,N-Dimethyl-1,2-ethanediamine | | O.3.2 | 1.06(g) | 459.3 (M + H)$^+$ |

TABLE O.3-continued
Examples prepared using general procedure O from Example #F.5.4
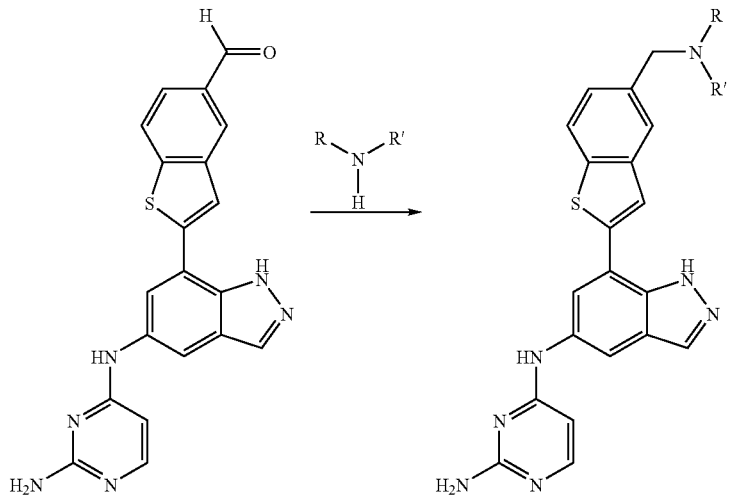
| Amine Precursor | Product | Example # | R$_t$/min(method) | m/z |
|---|---|---|---|---|
| 2-Methoxyethyl amine | | O.3.3 | 1.12(g) | 446.3 (M + H)$^+$ |

TABLE O.3-continued
Examples prepared using general procedure O from Example #F.5.4
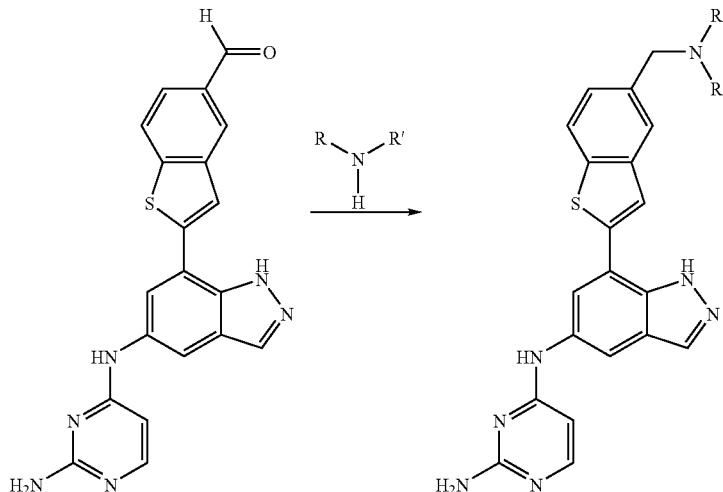
| Amine Precursor | Product | Example # | R$_t$/min(method) | m/z |
|---|---|---|---|---|
| N-(2-Aminoethyl)morpholine | | O.3.4 | 1.12(g) | 501.4 (M + H)$^+$ |

TABLE O.3-continued
Examples prepared using general procedure O from Example #F.5.4
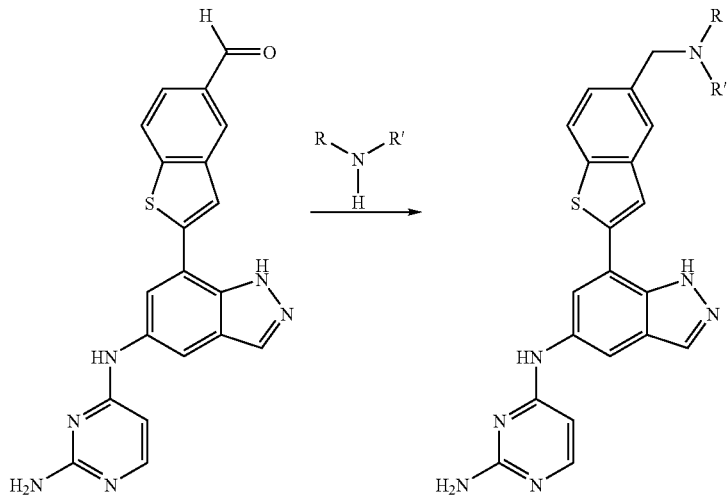
| Amine Precursor | Product | Example # | R$_t$/min(method) | m/z |
|---|---|---|---|---|
| Piperazine | 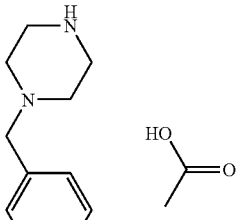 | O.3.5 | 1.13(g) | 457.3 (M + H)$^+$ |

TABLE O.3-continued
Examples prepared using general procedure O from Example #F.5.4
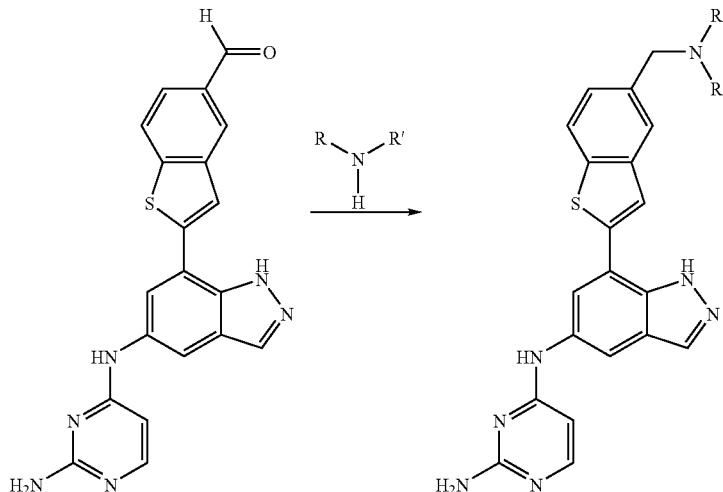
| Amine Precursor | Product | Example # | R$_t$/min(method) | m/z |
|---|---|---|---|---|
| 1-Methylpiperazine | | O.3.6 | 1.14(g) | 471.4 (M + H)$^+$ |

TABLE O.3-continued
Examples prepared using general procedure O from Example #F.5.4
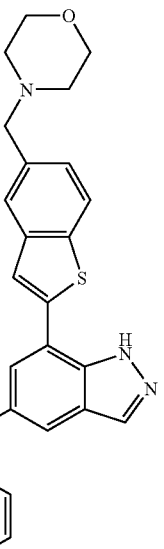
| Amine Precursor | Product | Example # | R$_t$/min(method) | m/z |
|---|---|---|---|---|
| Morpholine | | O.3.7 | 1.13(g) | 458.3 (M + H)⁺ |

TABLE O.3-continued
Examples prepared using general procedure O from Example #F.5.4
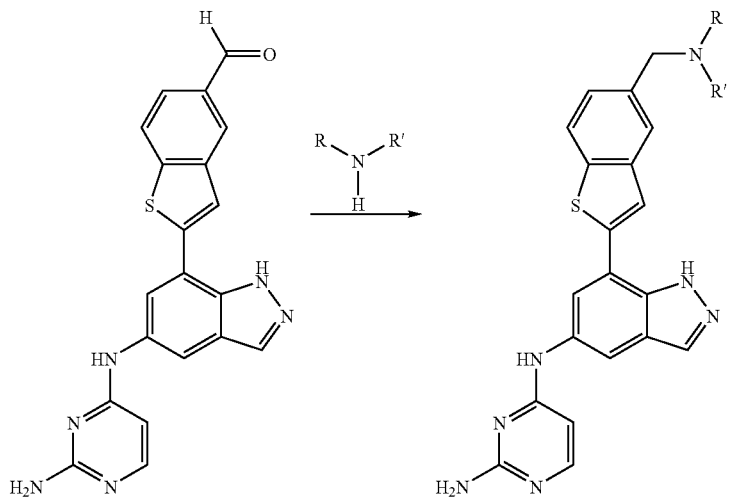
| Amine Precursor | Product | Example # | R$_t$/min(method) | m/z |
|---|---|---|---|---|
| 2-Propen-1-amine | 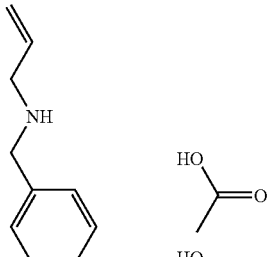 | O.3.8 | 1.13(g) | 428.4 (M + H)$^+$ |

TABLE O.4

Examples prepared using general procedure O from Example #5

| Amine Precursor | Product | Example # | R$_t$/min (method) | m/z |
|---|---|---|---|---|
| 2-Propen-1-amine | | O.4.1 | 1.05 (g) | 409.1 (M − H)$^-$ |

General Procedure P. Deprotection of a Methyl-Protected Alcohol Using Boron Tribromide To a suspension of a methyl-protected alcohol in an organic solvent (1,2-dichloroethane or CH$_2$Cl$_2$, preferably 1,2-dichloroethane) is added a solution of BBr$_3$ (8-20 equivalents, preferably 10 equivalents) in CH$_2$Cl$_2$. The reaction mixture is stirred at about −10 to 5° C. (preferably about 0° C.) for about 0.5-3 hours (preferably about 2 hours), then heated at about 30-100° C. (preferably about 80° C.) for about 2-8 hours (preferably about 3 hours). The reaction mixture can be treated in two different ways: 1). The reaction mixture is allowed to cool to about −10-10° C. (preferably about 0° C.) and quenched with an aqueous solution (for example, saturated aqueous NaHCO$_3$ or Na$_2$CO$_3$, preferably NaHCO$_3$) and extracted with an organic solvent (EtOAc, Et$_2$O, or CH$_2$Cl$_2$, preferably CH$_2$Cl$_2$). The residue is partitioned between water and an organic solvent. The organic layer is separated and the aqueous layer further extracted with the organic solvent. The combined organic extracts are dried over a desiccant and the solvent removed under reduced pressure. 2). The reaction mixture can be cooled down to room temperature and diluted with MeOH then the solvents are removed under reduced pressure. The compound can be further purified by chromatography or crystallization.

Illustration of General Procedure P.

Example #19b

7-[5-(2-Amino-pyrimidin-4-ylamino)-1H-indazol-3-yl]-naphthalen-2-ol diacetate

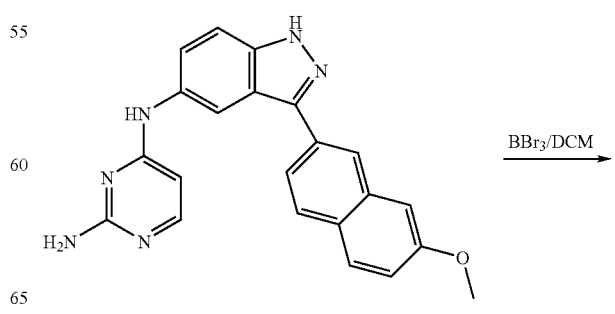

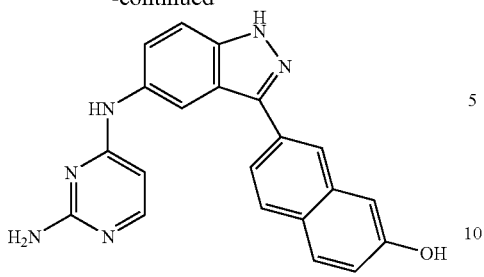

To a suspension of 4-[3-(7-methoxy-naphthalen-2-yl)-1H-indazol-5-ylamino]-pyrimidine-2-amine (Preparation #28 followed by general procedure N and F, 20 mg, 0.05 mmol) in CH$_2$Cl$_2$ (1 mL) was added 1M BBr$_3$ in THF (1 mL). The mixture was stirred for about 2 hours at room temperature then methanol (1 mL) was added and the mixture concentrated under reduced pressure. The residue was purified by preparative reverse phase HPLC to give 7-[5-(2-amino-pyrimidin-4-ylamino)-1H-indazol-3-yl]-naphthalen-2-ol diacetate (12 mg, 60%); (DMSO-d$_6$, 400 MHz) δ9.08 (s, 1H), 8.35 (s, 1H), 8.30 (s, 1H), 8.03 (d, 1H), 7.89 (d, 1H), 7.80 (m, 2H), 7.72 (d, 1H), 7.53 (d, 1H), 7.16 (s, 1H), 7.11 (d, 1H), 6.06 (bs, 2H), 5.99 (d, 1H), 1.87 (s, 6H); RP-HPLC (Table 1, Method e) R$_t$ 1.43 min; m/z: (M+H)$^+$ 369.2.

CH$_2$Cl$_2$/MeOH (9:1), or EtOAc, preferably CH$_2$Cl$_2$). The resulting crude product can be purified by chromatography, trituration, or crystallization.

Illustration of General Procedure Q

Example 19c #48

7-Benzo[b]thiophen-2-yl-1H-indazole-5-carboxylic acid [4-(1H-indol-2-yl)-phenyl]-amide

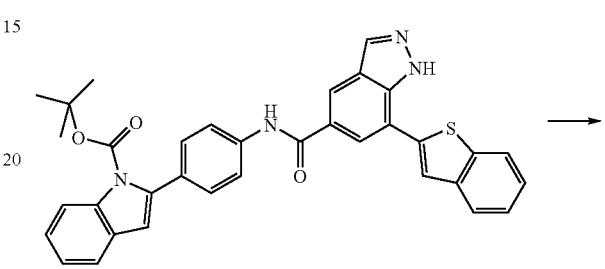

TABLE P.1

Examples synthesized using general procedure P

| Precursor | Product | Example # | R$_t$/min (method) | m/z (ESI+) |
|---|---|---|---|---|
| 4-[3-(5-Methoxy-benzo[b]thiophen-2-yl)-1H-indazol-5-ylamino]-pyrimidine-2-amine (Preparation #28, N, F) | | P.1.1 | 1.19 (e) | 375.3 (M + H)$^+$ |

General Procedure Q: Acid Catalyzed Cleavage of Esters, Amidines, and Carbamates An acid (HCl or TFA, preferably HCl) was added to an amine protected with a carbamate or amidine moiety optionally dissolved in an organic solvent (MeOH, CH$_2$Cl$_2$ or dioxane, preferably MeOH) at about 0-100° C., preferably 40° C. The reaction mixture is stirred for about 5 minutes to 24 hours (preferably 16 h) until the reaction had proceeded to completion as judged by TLC or HPLC analysis. Where necessary, additional acid is added to achieve complete conversion. The solvents are then removed under reduced pressure. The crude product can be treated in two different ways. 1) The material is purified by chromatography, trituration, or crystallization. 2) The material is treated with an aqueous solution of an appropriate base (for example NaOH, NaHCO$_3$, or Na$_2$CO$_3$, preferably NaHCO$_3$) and either collected by filtration or extracted into an organic solvent (for example, CH$_2$Cl$_2$,

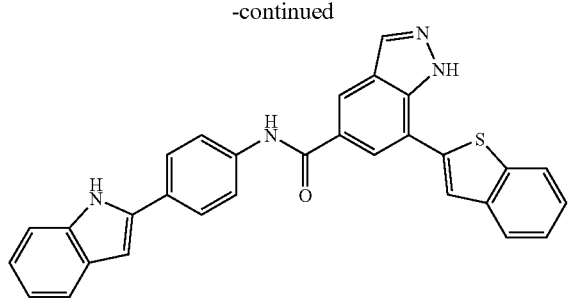

TFA (0.078 g, 0.68 mmol) was added to a solution of 2-4-[(7-benzo[b]thiophen-2-yl-1H-indazole-5-carbonyl)-amino]-phenyl-indole-1-carboxylic acid tert-butyl ester (Preparation #7 then B, 0.100 g, 0.137 mmol) in CH$_2$Cl$_2$ (2.5 mL, 0.039 mol) at about 0° C. The reaction mixture was stirred at about 0° C. for about 30 min then additional TFA (80 uL) was added. After about 30 min the reaction was allowed to warm to room temperature and stirred for about 16 hours, prior to the addition of more TFA (150 uL). After 2 hours the mixture was concentrated under reduced pressure and the crude product was purified by RP-HPLC to yield 7-benzo[b]thiophen-2-yl-1H-indazole-5-carboxylic acid [4-(1H-indol-2-yl)-phenyl]-amide (13 mg, 20% yield): RP-HPLC (Table 1, Method e) $R_t$=2.4 min MS m/z: (M−H)⁻ 483.2.

TABLE Q.1

Examples prepared using general procedure Q

| Ester/Carbamate Precursor | Product | Example # | $R_t$/min (method) | m/z (ESI+) |
|---|---|---|---|---|
| 4-{[(2-Amino-pyrimidin-4-yl)-(7-benzo[b]thiophen-2-yl-1H-indazol-5-yl)-amino]-methyl}-piperidine-1-carboxylic acid tert-butyl ester (Example #F.8.1, O, N) | | Q.1.1 | 1.78 (e) | 416 (M + H)⁺ |
| 7-(1-tert-Butoxycarbonyl-1H-indazol-5-yl)-4-dimethylamino-2-(dimethylamino-methyleneamino)-pyrrolo[3,2-d]pyrimidine-5-carboxylic acid tert-butyl ester (J. Med. Chem., 2003, 46, 3060-3071, F) | | Q.1.2 | 0.82 (e) | 294.1 (M + H)⁺ |
| 4-(7-Benzol[b]thiophen-2-yl-1H-indazol-5-yl)-pyrazole-1-carboxylic acid tert-butyl ester (Preparation #26, F) | | Q.1.3 | 2.00 (e) | 315.1 (M + H)⁺ |

TABLE Q.1-continued

Examples prepared using general procedure Q

| Ester/Carbamate Precursor | Product | Example # | R<sub>t</sub>/min (method) | m/z (ESI+) |
|---|---|---|---|---|
| (3-{5-[5-(2-Aminopyrimidin-4-ylamino)-1H-indazol-7-yl]-indol-1-yl}-propyl)-carbamic acid tert-butyl ester (Example #F.11.5, R) | | Q.1.4 | 1.15 (g) | 399.3 (M + H)+ |
| (2-{5-[5-(2-Aminopyrimidin-4-ylamino)-1H-indazol-7-yl]-indol-1-yl}-ethyl)-carbamic acid tert-butyl ester (Example #F.11.5, R) | | Q.1.5 | 1.10 (g) | 385.3 (M + H)+ |
| (3-{6-[5-(2-Aminopyrimidin-4-ylamino)-1H-indazol-7-yl]-indol-1-yl}-propyl)-carbamic acid tert-butyl ester (Example #F.5.2, R) | | Q.1.6 | 1.09 (g) | 399.5 (M + H)+ |

515

General Procedure R: Base-Promoted Amine Alkylation

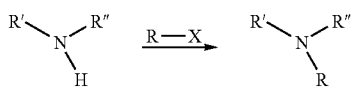

A mixture of an amine substrate and a base (for example, NaH, K$_2$CO$_3$, Cs$_2$CO$_3$, t-BuOK or Na$_2$CO$_3$, preferably Na$_2$CO$_3$) (2-6 equivalents, preferably 2 equivalents) in an organic solvent (for example, THF, DME or DMF, preferably DMF) is stirred at about −10-25° C. (preferably about 0° C.), for about 0-60 minutes (preferably 40 minutes) under an inert atmosphere. An organic halide (for example an organic bromide or an organic chloride, preferably an organic bromide) (2-6 equivalents, preferably 3 equivalents) is added and the reaction is stirred for about 4-96 hours (preferably about 24 hours) at about 20-100° C. (preferably about 60° C.). The solvent is removed under reduced pressure and the crude product can be purified by chromatography, crystallization or used in the next step without further purification.

Illustration of General Procedure R:

Example #20

3-[7-[7-Benzo[b]thiophen-2-yl-1-(2-trimethylsilanyl-ethoxymethyl)-1H-indazol-5-yl]-2-(dimethylamino-methyleneamino)-pyrrolo[3,2-d]pyrimidin-5-yl]-propionic acid methyl ester

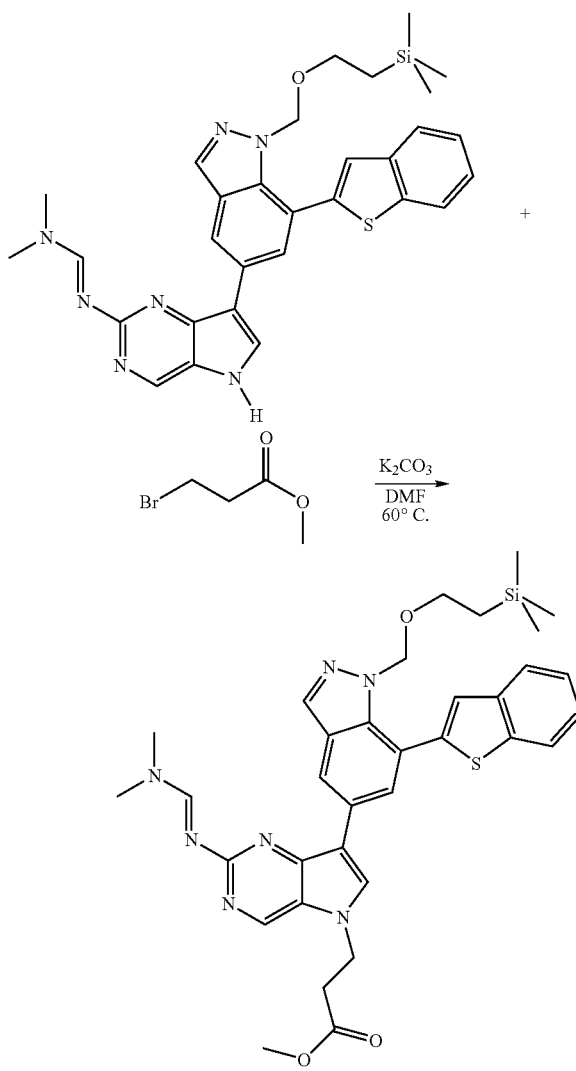

516

To a mixture of {7-[7-benzo[b]thiophen-2-yl-1-(2-trimethylsilanyl-ethoxymethyl)-1H-indazol-5-yl]-5H-pyrrolo[3,2-d]pyrimidin-2-yl}-N,N-dimethyl-formamidine (Preparation #5, 240 mg, 0.42 mmol) in DMF (3 mL) at about 0° C. and under an inert atmosphere was added K$_2$CO$_3$ (140 mg, 1.02 mmol). The reaction mixture was stirred at about 0° C. for about 40 minutes, then 3-bromo-propionic acid methyl ester (0.12 mL, 1.02 mmol) was added. The reaction mixture was stirred at about 60° C. for about 24 hours, then the solvent was removed under reduced pressure and the residual material was used in the next step without further purification. LC/MS (Table 1, Method h) R$_t$ 3.29 min; ESI–MS [M+H]$^+$= 654.4.

General Procedure S: Formation of a Sulfonamide from an Amine:

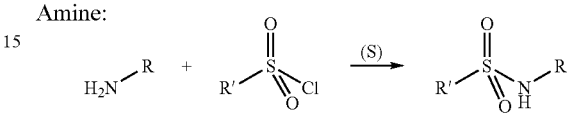

To a mixture of an amine and a base (for example, pyridine, Et$_3$N, or ethyl-diisopropyl-amine, preferably ethyl-diisopropyl-amine) (1-5 equivalents, preferably 1.5 equivalents) in an organic solvent (for example, CH$_2$Cl$_2$, DME, or DMF, preferably DMF) at about 0-50° C. (preferably about 20° C.) and under an inert atmosphere is added a sulfonylchloride (1-5 equivalents, preferably 1.05 equivalents). The reaction mixture is stirred for about 1-6 hours (preferably 2 hours), then concentrated under reduced pressure and purified by chromatography, crystallization or it can be used in the next step without further purification.

Illustration of General Procedure S:

Example #21

3-Oxo-3,4-dihydro-2H-benzo[1,4]oxazine-6-sulfonic acid (7-benzo[b]thiophen-2-yl-1H-indazol-5-yl)-amide

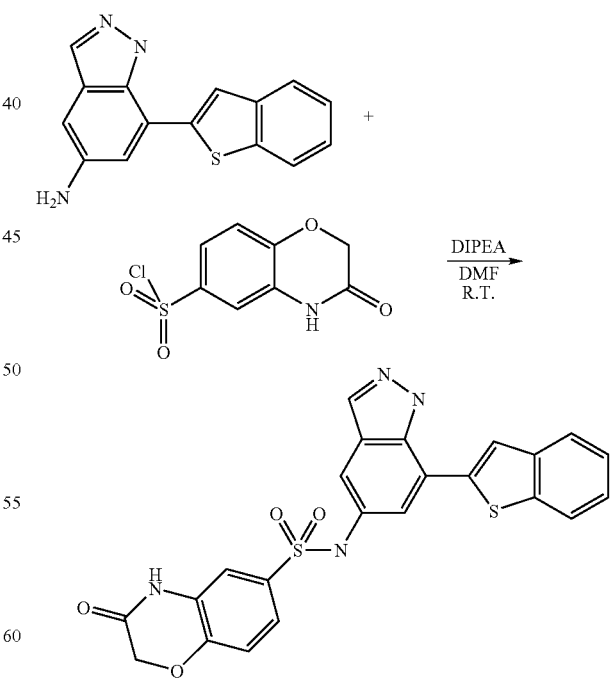

To a mixture of 7-benzo[b]thiophen-2-yl-1H-indazol-5-ylamine (Example #F.8.1, 32 mg, 0.12) and ethyl-diisopropylamine (0.032 mL, 0.18 mmol) in DMF (1 mL) at room temperature and under an inert atmosphere was added 3-oxo-3,4-dihydro-2H-benzo[1,4]oxazine-6-sulfonyl chloride (33 mg, 0.13 mmol). The reaction mixture was stirred at room temperature for 2 hours then concentrated under reduced pressure. The crude material was purified by preparative HPLC (20% to 80% acetonitrile/0.05 M aqueous ammonium acetate, buffered to pH 4.5 over 30 min at 20 mL/min; Hyper- prep C18, 300 Å, 8 μm, 250×21.1 mm column) to afford 3-oxo-3,4-dihydro-2H-benzo[1,4]oxazine-6-sulfonic acid (7-benzo[b]thiophen-2-yl-1H-indazol-5-yl)-amide as a white solid (34 mg, 58%). LC/MS (Table 1, Method e) R$_t$ 1.75 min; ESI–MS [M+H]$^+$=475.3.

TABLE S.1

Examples synthesized using general procedure S from Example #F.8.1

| Precursor | Product | Example # | HPLC R$_t$ (Method) | m/z (ESI+) |
|---|---|---|---|---|
| Benzo[1,2,5]thiadiazole-4-sulfonyl chloride | | S.1.1 | 2.00 (e) | 362.1 (M − H)$^+$ |
| 5-Pyridin-2-yl-thiophene-2-sulfonyl chloride | | S.1.2 | 2.11 (e) | 487.2 (M − H)$^+$ |
| Thiophene-2-sulfonyl chloride | | S.1.3 | 1.98 (e) | 410.2 (M − H)$^+$ |

TABLE S.1-continued

Examples synthesized using general procedure S from Example #F.8.1

| Precursor | Product | Example # | HPLC R$_t$ (Method) | m/z (ESI+) |
|---|---|---|---|---|
| 5-Chloro-1,3-dimethyl-1H-pyrazole-4-sulfonyl chloride | | S.1.4 | 1.89 (e) | 456.2 (M − H)+ |
| 4-Methoxy-benzene-sulfonyl chloride | | S.1.5 | 2.07 (e) | 134.2 (M − H)+ |
| 1-Methyl-1H-imidazole-4-sulfonyl chloride | | S.1.6 | 1.57 (e) | 408.0 (M − H)+ |

TABLE S.1-continued
Examples synthesized using general procedure S from Example #F.8.1
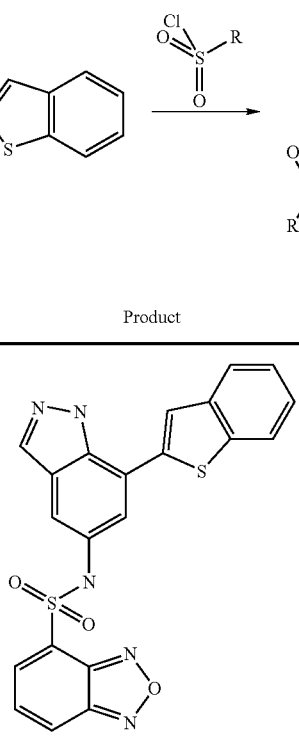
| Precursor | Product | Example # | HPLC R$_t$ (Method) | m/z (ESI+) |
|---|---|---|---|---|
| Benzo[1,2,5]oxadiazole-4-sulfonyl chloride | | S.1.7 | 2.01 (e) | 446.0 (M − H)$^+$ |
| Benzo[1,2,5]thiadiazole-5-sulfonyl chloride | | S.1.8 | 2.06 (e) | 462.2 (M − H)$^+$ |
| Quinoline-8-sulfonyl chloride | | S.1.9 | 2.05 (e) | 455.1 (M − H)$^+$ |

TABLE S.1-continued

Examples synthesized using general procedure S from Example #F.8.1

| Precursor | Product | Example # | HPLC R$_t$ (Method) | m/z (ESI+) |
|---|---|---|---|---|
| 4-Amino-benzene-sulfonyl chloride | | S.1.10 | 1.80 (e) | 419.2 (M − H)$^+$ |
| Isoquinoline-5-sulfonyl chloride | | S.1.11 | 1.89 (e) | 455.2 (M − H)$^+$ |
| 2-Amino-4-methyl-thiazole-5-sulfonyl chloride | | S.1.12 | 1.77 (e) | 439.4 (M − H)$^+$ |

TABLE S.1-continued
Examples synthesized using general procedure S from Example #F.8.1
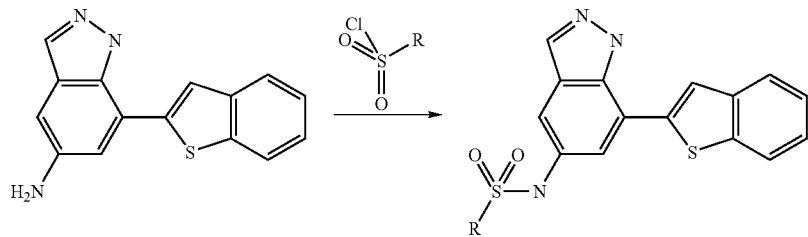
| Precursor | Product | Example # | HPLC R$_t$ (Method) | m/z (ESI+) |
|---|---|---|---|---|
| 3,5-Dimethyl-isoxazole-4-sulfonyl chloride | | S.1.13 | 2.00 (e) | 423.0 (M − H)+ |
| 5-(2-Methyl-thiazol-4-yl)-thiophene-2-sulfonyl chloride | | S.1.14 | 2.13 (e) | 507.2 (M − H)+ |
| 3-Oxo-3,4-dihydro-2H-benzo[1,4]oxazine-6-sulfonyl chloride | | S.1.15 | 1.75 (e) | 475.3 (M − H)+ |

TABLE S.1-continued

Examples synthesized using general procedure S from Example #F.8.1

| Precursor | Product | Example # | HPLC R$_t$ (Method) | m/z (ESI+) |
|---|---|---|---|---|
| 1,2-Dimethyl-1H-imidazole-4-sulfonyl chloride | | S.1.16 | 1.59 (e) | 422.0 (M − H)+ |
| 4-Acetylamino-benzene-sulfonyl chloride | | S.1.17 | 1.72 (e) | 461.3 (M − H)+ |
| 2-Acetylamino-4-methyl-thiazole-5-sulfonyl chloride | | S.1.18 | 1.75 (e) | 482.1 (M − H)+ |

General Procedure T: Mitsunobu Coupling

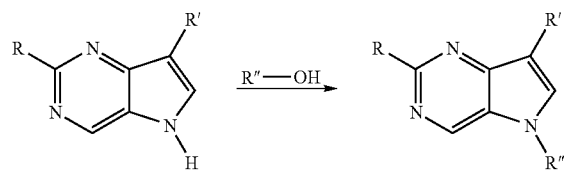

To a mixture of an alcohol (1-5 equivalents, preferably 3 equivalents) and PPh₃ (1-5 equivalents, preferably 2 equivalents) in an organic solvent (for example, THF, DME or CH₂Cl₂, preferably THF) at about −10 to 20° C. (preferably about 0° C.) under an inert atmosphere is added a pyrrolo[3,2-d]pyrimidine (preferably 1 equivalent) followed by slow addition of a Mitsunobu coupling reagent (for example, diisopropyl azodicarboxylate, 1,1'-azobis(N,N-dimethylformamide) or diethyl azodicarboxylate, preferably diisopropyl azodicarboxylate) (2-4 equivalents, preferably 2 equivalents). The reaction mixture is stirred at about 0 to 60° C. (preferably at 20° C.) for about 1-6 hours (preferably 2 hours). The reaction mixture is then concentrated under reduced pressure and the residual crude product is purified by chromatography, crystallization or can be used in the next step without further purification.

Illustration of General Procedure T:

Example #23

N'-{7-[7-Benzo[b]thiophen-2-yl-1-(2-trimethylsilanyl-ethoxymethyl)-1H-indazol-5-yl]-5-isopropyl-5H-pyrrolo[3,2-d]pyrimidin-2-yl}-N,N-dimethylformamidine

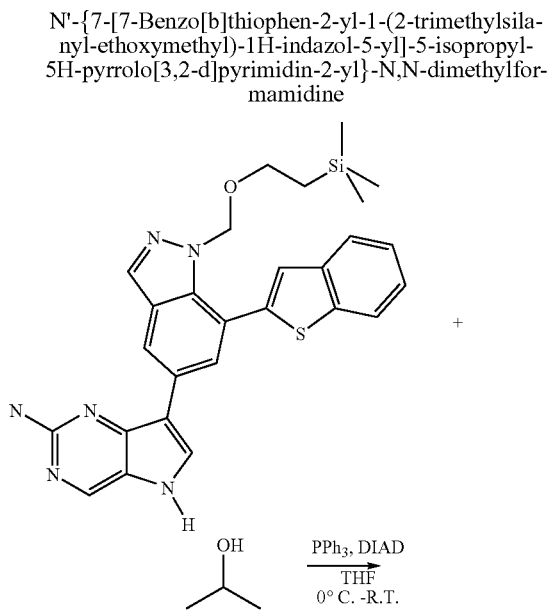

To a mixture of i-PrOH (0.023 uL, 0.3 mmol) and PPh₃ (52.4 mg, 0.2 mmol) in THF at about 0° C. under an inert atmosphere was added {7-[7-benzo[b]thiophen-2-yl-1-(2-trimethylsilanyl-ethoxymethyl)-1H-indazol-5-yl]-5H-pyrrolo[3,2-d]pyrimidin-2-yl}-N,N-dimethylformamidine (Preparation 5a, 50 mg, 0.1 mmol) followed by the slow addition of diisopropyl azodicarboxylate (0.04 mL, 0.2 mmol). The reaction mixture was stirred at about 20° C. for about 4 hours. The reaction mixture was then concentrated, and utilized in the next step without further purification. LC/MS (Table 1, Method e) $R_t$ 2.80 min; ESI–MS [M+H]⁺= 555.4.

General Procedure U: Sonogashira Coupling of a Halide with an Acetylene Compound

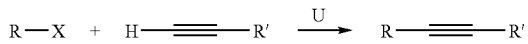

To a solution of a halide (preferably 1.0 equivalent) in an organic solvent (for example, DMF or piperidine, preferably DMF) is added a terminal acetylene (1.0-12.0 equivalents, preferably 1.2 equivalent), a palladium catalyst (for example, dichlorobis(triphenylphosphine) palladium(II), tetrakis (triphenylphosphine) palladium(0), preferably dichlorobis (triphenylphosphine) palladium(II)) (0.02-0.05 equivalent, preferably 0.05 equivalent), a base (for example, piperidine, triethylamine, preferably triethylamine) (0.03-0.06 equivalent, preferably 0.05 equivalent), and copper salt (for example copper (I) bromide, copper (I) iodide, preferably copper (I) iodide) (0.03-0.15 equivalent, preferably 0.10 equivalent). The reaction mixture is heated in a microwave reactor at about 80-130° C. (preferably about 120° C.) for about 2-40 minutes (preferably about 5 minutes). The mixture is allowed to cool to ambient temperature. The insoluble residue is removed by filtration, and the filtrate is concentrated under reduced pressure. The residual crude product is purified by chromatography or crystallization.

Illustration of General Procedure U

Example #24

4-(7-Phenylethynyl-1H-indazol-5-ylamino)-pyrimidine-2-amine

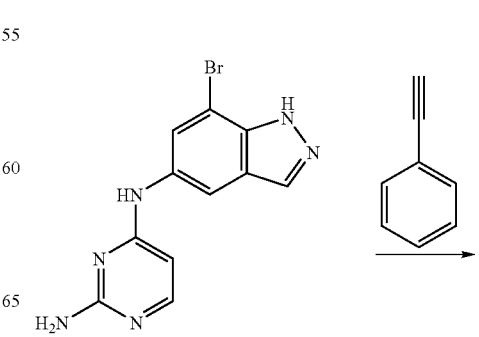

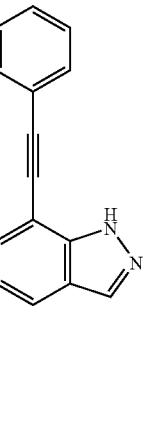

To a solution of N'4'-(7-bromo-1H-indazol-5-yl)-pyrimidine-2,4-diamine (Example #N.2.7, 0.060 g, 0.197 mmol) in DMF (1 mL) in a microwave tube was added phenylacetylene (0.028 ml, 0.256 mmol), copper (I) iodide (0.004 g, 0.020 mmol) and tetrakis (triphenylphosphine) palladium(0) (0.011 g, 0.009 mmol). The tube was sealed and the reaction mixture was heated in a microwave at about 120° C. for about 5 minutes. The mixture was allowed to cool to ambient temperature. The insoluble residue was removed by filtration and washed with DMF (2 mL). The filtrate was purified by preparative RP-HPLC (Rainin C18, 8 mm, 300 Å, 35 cm; 5-100% acetonitrile/0.1 M ammonium acetate over 20 min, 100% acetonitrile hold 10 minutes, 21 mL/min) to obtain 4-(7-phenylethynyl-1H-indazol-5-ylamino)-pyrimidine-2-amine as a white solid (0.015 g, 0.046 mmol); RP-HPLC (Table 1, Method e) $R_t$ 1.70 min; m/z: (M+H)$^+$ 327.2.

TABLE U.1

Examples prepared using General Procedure U using 3-iodo-5-(2-aminopyrimidin-4-yl)amino-1H-indazole

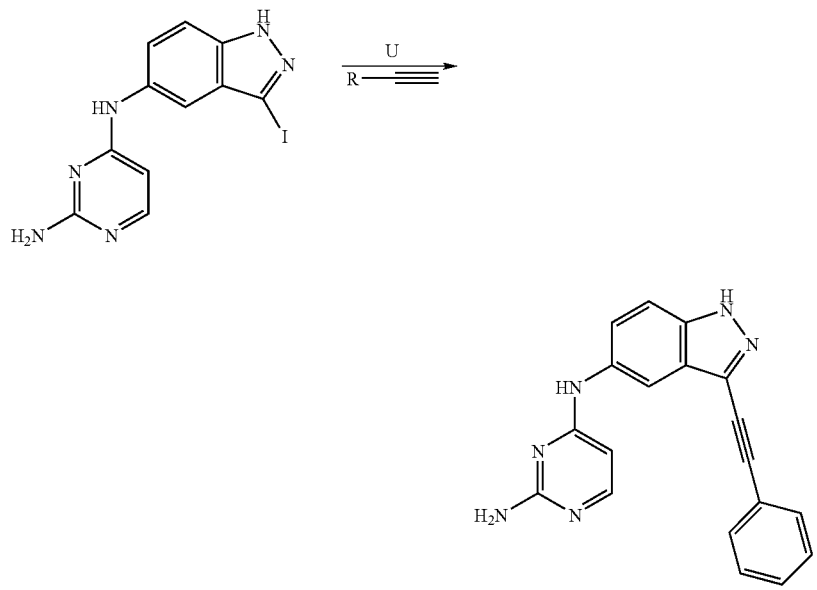

3-Iodo-5-(2-aminopyrimidin-4-yl)amino-1H-indazole was prepared from Preparation #28 via general procedure N using 2-amino-4-chloropyrimdine.

| Acetylene | Product | Example # | HPLC Rt (Method) | m/z |
|---|---|---|---|---|
| Ethynyl-benzene | | U.1.1 | 2.20 (a) | 327 (M + H)$_+$ |

TABLE U.1-continued
Examples prepared using General Procedure U using 3-iodo-5-(2-aminopyrimidin-4-yl)amino-1H-indazole
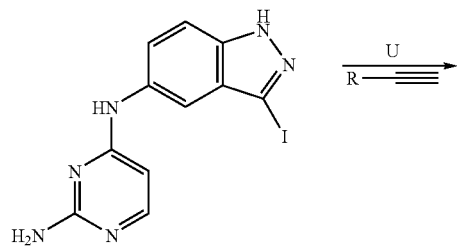
3-Iodo-5-(2-aminopyrimidin-4-yl)amino-1H-indazole was prepared from Preparation #28 via general procedure N using 2-amino-4-chloropyrimdine.
| Acetylene | Product | Example # | HPLC Rt (Method) | m/z |
|---|---|---|---|---|
| 3,3-Dimethyl-but-1-yne | 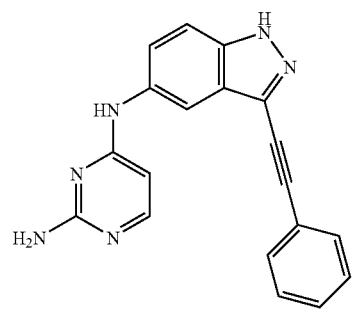 | U.1.2 | 2.10 (a) | 307 (M + H)+ |

TABLE U.2
Examples prepared using General Procedure U from Example #N.2.7
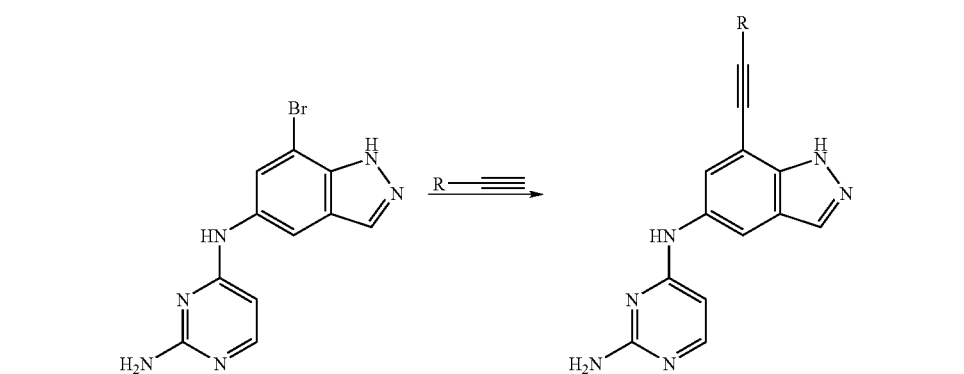
| Acetylene Precursor | Product | Example # | R$_t$/min (method) | m/z (ESI+) |
|---|---|---|---|---|
| Hex-5-ynenitrile | 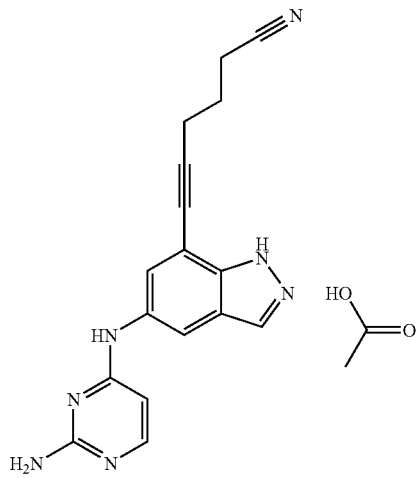 | U.2.1 | 1.27 (e) | 318.2 (M + H)$^+$ |
| Pent-4-yn-1-ol | 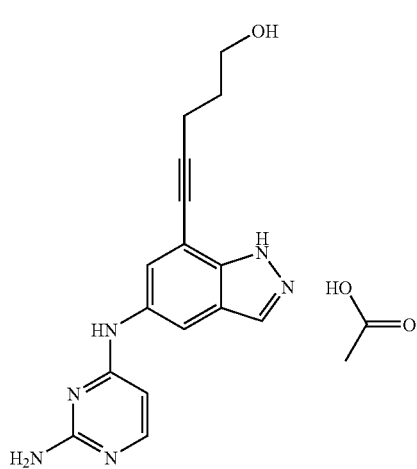 | U.2.2 | 0.70 (e) | 309.0 (M + H)$^+$ |

TABLE U.2-continued

Examples prepared using General Procedure U from Example #N.2.7

| Acetylene Precursor | Product | Example # | R<sub>t</sub>/min (method) | m/z (ESI+) |
|---|---|---|---|---|
| Dimethyl-prop-2-ynyl-amine | | U.2.3 | 1.05 (e) | 308.0 (M + H)+ |
| 2-Methyl-but-3-yn-2-ol | | U.2.4 | 0.73 (e) | 307.0 (M + H)+ |

TABLE U.2-continued

Examples prepared using General Procedure U from Example #N.2.7

| Acetylene Precursor | Product | Example # | R$_t$/min (method) | m/z (ESI+) |
|---|---|---|---|---|
| Prop-2-yn-1-ol | | U.2.5 | 0.53 (e) | 278.9 (M + H)+ |
| Ethynyl-benzene | | U.2.6 | 1.70 (e) | 327.2 (M + H)+ |

TABLE U.2-continued

Examples prepared using General Procedure U from Example #N.2.7

| Acetylene Precursor | Product | Example # | R$_t$/min (method) | m/z (ESI+) |
|---|---|---|---|---|
| Methyl-prop-2-ynyl-amine | | U.2.7 | 0.53 (e) | 294.0 (M + H)$^+$ |
| 3-Ethynyl-phenol | | U.2.8 | 1.20 (e) | 343.0 (M + H)$^+$ |

General Procedure V: Hydrolysis of an Ester to a Carboxylic Acid

To a solution of an ester in an organic solvent (for example, THF, MeOH, or 1,4-dioxane, preferably 1,4-dioxane) at about 10-50° C. (preferably about 25° C.) is added an aqueous base solution (for example, Na$_2$CO$_3$, NaOH or KOH, preferably Na$_2$CO$_3$) (3-20 equivalents, preferably 5 equivalents). The mixture is stirred at about 10-80° C. (preferably about 25° C.) for about 0.5-2 hours (preferably about 1 hour). The mixture is acidified with an acid (preferably 1M HCl solution) to about pH 3. If a precipitation is formed it is filtered off and washed with water. If no precipitation is formed the solvent is removed under reduced pressure and the residue is partitioned between an aqueous acidic solution (for example HCl) and an organic solvent (for example EtOAc or CH$_2$Cl$_2$, preferable CH$_2$Cl$_2$). The organic layer is separated and the aqueous layer is further extracted with an organic solvent. The combined organic extracts are dried over a desiccant. The solvents are removed under reduced pressure to afford the product which can be further purified by crystallization or chromatography.

Illustration of General Procedure V

Example #25

{[5-(2-Amino-pyrimidin-4-ylamino)-1H-indazole-3-carbonyl]-amino}-acetic acid

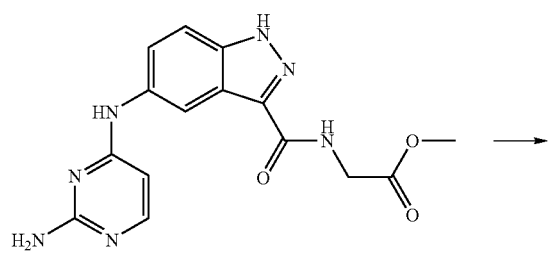

A solution of {[5-(2-amino-pyrimidin-4-ylamino)-1H-indazole-3-carbonyl]-amino}acetic acid methyl ester (was prepared from Example N.2.8, B, 0.014 g, 0.043 mmol) and 2M aqueous NaOH solution (1.0 mL, 2.0 mmol) in 1,4-dioxane (2 mL) was stirred at ambient temperature for about 30 minutes. The reaction mixture was acidified with 1M aqueous HCl solution until pH 3. The white precipitation was filtered off, washed with water (3 mL) and dried under reduced pressure to give {[5-(2-amino-pyrimidin-4-ylamino)-1H-indazole-3-carbonyl]-amino}-acetic acid (0.001 g, 0.003 mmol); RP HPLC (Table 1, Method a) R$_t$=0.42 min; m/z: (M+H)$^+$ 328.2.

TABLE V.1

Examples prepared using general procedure V

| Ester Precursor | Product | Example # | R$_t$/min (method) | m/z (ESI+) or NMR (400 MHz) (d$_6$-DMSO) |
|---|---|---|---|---|
| 3-{[5-(2-Amino-pyrimidin-4-ylamino)-1H-indazole-3-carbonyl]-amino}-benzoic acid ethyl ester (Example #N.2.8, B) | | V.1.1 | 6.90 (j) | 13.8 (br, 1H), 10.51 (s, 1H), 9.67 (m, 1H), 8.58 (s, 1H), 8.22 (m, 1H), 8.08 (d, 1H), 7.89 (d, 1H), 7.82 (d, 1H), 7.64 (m, 2H), 7.47 (t, 1H), 6.62 (m, 2H), 6.11 (d, 1H). |
| 5-Bromo-1H-indazole-7-carboxylic acid methyl ester | | V.1.2 | 0.48 (e) | 239/241 (M − H)$^-$ |

TABLE V.1-continued

Examples prepared using general procedure V

| Ester Precursor | Product | Example # | R$_t$/min (method) | m/z (ESI+) or NMR (400 MHz) (d$_6$-DMSO) |
|---|---|---|---|---|
| 2-[5-(2-Amino-pyrimidin-4-ylamino)-1H-indazol-7-yl]-1H-indole-7-carboxylic acid methyl ester (Example #F.5.11) | 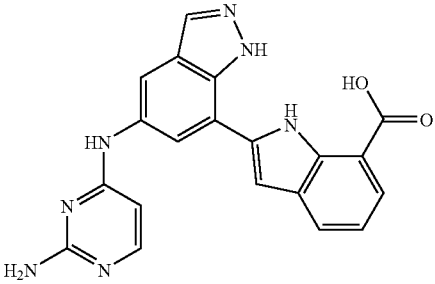 | V.1.3 | 0.8 (e) | 383.9 (M − H)− |
| 2-Amino-6-(7-benzo[b]thiophen-2-yl-1H-indazol-5-ylamino)-pyrimidine-4-carboxylic acid methyl ester (Example #N.4.2) | 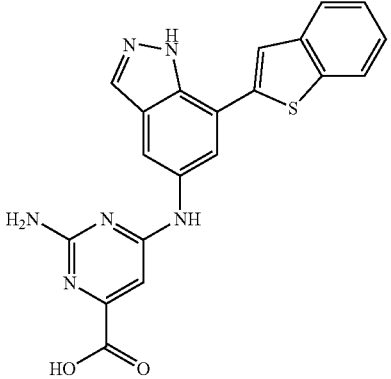 | V.1.4 | 1.32 (e) | 403 (M + H)+ |

General Procedure W: Amide Formation from an Acid Chloride and an Amine

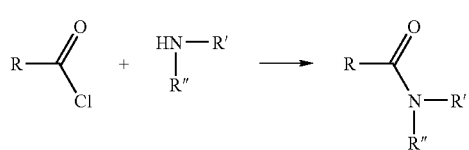

To a solution of an acid chloride and an amine (preferably 1 equivalent) in an organic solvent (for example, pyridine, CH$_2$Cl$_2$ or 1,2-dichloroethane, preferably CH$_2$Cl$_2$) is added a base (for example Et$_3$N or pyridine, preferably pyridine). The reaction mixture is stirred at about 0-50° C. (preferably about 25° C.) for about 0.5-20 hours (preferably about 1 hour). The mixture is diluted with an organic solvent (for example, EtOAc or CH$_2$Cl$_2$, preferably CH$_2$Cl$_2$) and washed with water, then dried under reduced pressure. The product can be further purified by crystallization or chromatography.

Illustration of General Procedure W

Example #26

3-Dimethylamino-N-(5-nitro-1H-indazol-3-yl)-benzamide

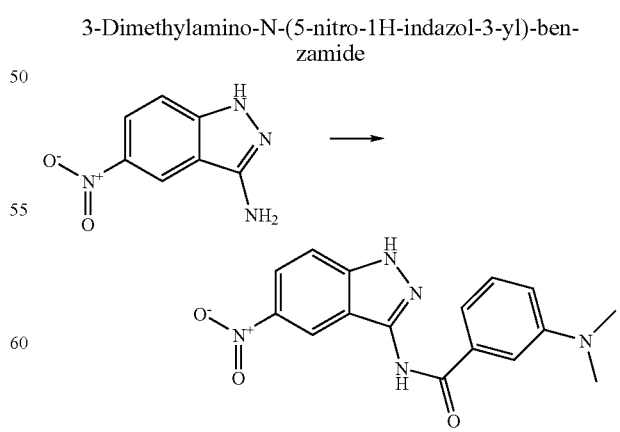

To a solution of 5-nitro-1H-indazol-3-ylamine in pyridine (Ryan Scientific, 0.150 g, 0.838 mmol) cooled to about 0° C. in an ice bath, was added 3-dimethylamino-benzoyl chloride (0.154 g, 0.838 mmol). The reaction mixture was stirred as it warmed to ambient temperature. After about 1 hour it was poured into crushed ice, then extracted with EtOAc (10 mL). The organic solvent portion was washed with a 1M aqueous HCl solution, then concentrated and dried under reduced pressure. The residue was further purified via preparative RP-HPLC (Rainin C18, 8 mm, 300 Å, 35 cm; 5-100% acetonitrile/0.1 M ammonium acetate over 20 min, 100% acetonitrile hold 10 minutes, 21 mL/min) to obtain 3-dimethylamino-N-(5-nitro-1H-indazol-3-yl)-benzamide as a white solid (0.002 g, 0.006 mmol); RP-HPLC (Table 1, Method e) $R_t$ 1.95 min; m/z: (M+H)$^+$ 326.4.

TABLE W.1

Examples prepared from 5-nitro-1H-indazol-3-ylamine using General Procedure W

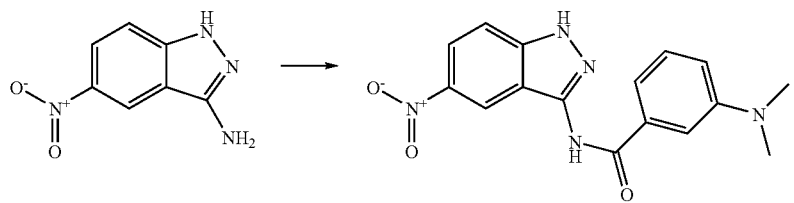

| Acid chloride Precursor | Product | Example # | $R_t$/min (method) | m/z (ESI+) |
|---|---|---|---|---|
| 3-Dimethylamino-benzoyl chloride | | W.1 | 1.95 (e) | 326.4 (M + H)$^+$ |
| Benzoyl chloride | | W.2 | 1.83 (e) | 281 (M − H)$^−$ |

TABLE W.2
Examples prepared from Example #F.2.16 using general procedure W
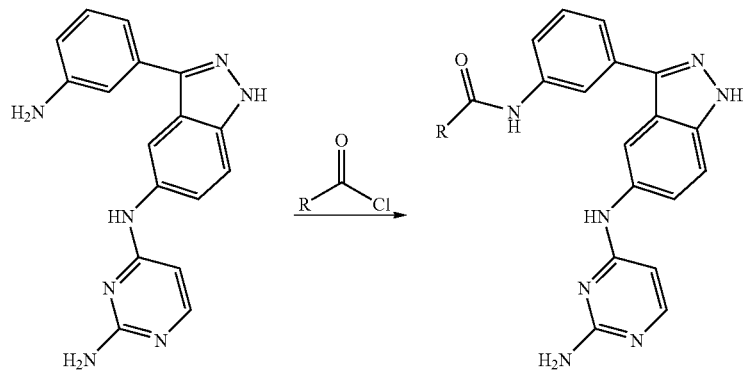
| Acid chloride | Product | Example # | R$_t$/min (method) | m/z (ESI+) |
|---|---|---|---|---|
| Acetyl chloride | | W.2.1 | 0.92 (e) | 360.6 (M + H)$^+$ |
| Benzoyl chloride | | W.2.2 | 1.65 (e) | 422.1 (M + H)$^+$ |
| Cyclobutane carbonyl chloride | | W.2.3 | 1.55 (e) | 400.3 (M + H)$^+$ |

TABLE W.3
Preparation of oxalates from Preparation #15 using general procedure W
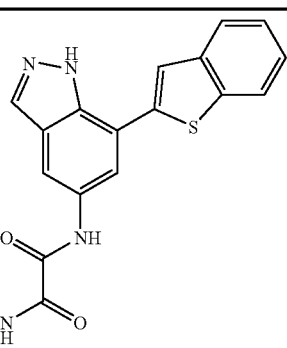
| Amine | Product | Example # | HPLC R$_t$ (Method) | m/z or $^1$H NMR (d$_6$-DMSO, 400 MHz) |
|---|---|---|---|---|
| 2-Methoxy-ethylamine | 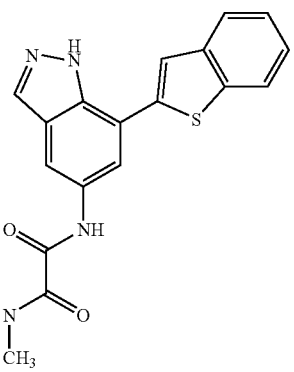 | W.3.1 | 1.84 (e) | 395 (M + H)$^+$ |
| N,N,N'-Trimethyl-ethane-1,2-diamine | 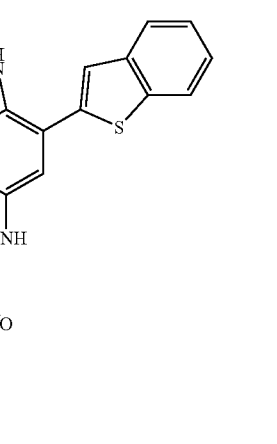 | W.3.2 | 1.34 (a) | 422 (M + H)$^+$ |
| Pyridin-2-ylamine | | W.3.3 | 2.23 (a) | 414 (M + H)$^+$ |

TABLE W.3-continued

Preparation of oxalates from Preparation #15 using general procedure W

| Amine | Product | Example # | HPLC R$_t$ (Method) | m/z or $^1$H NMR (d$_6$-DMSO, 400 MHz) |
|---|---|---|---|---|
| Aniline | | W.3.4 | 2.44 (a) | 411 (M − H)$^-$ |
| Ammonia | | W.3.5 | 1.66 (a) | 337 (M + H)$^+$ |
| Morpholine | | W.3.6 | 1.80 (a) | 407 (M + H)$^+$ |

TABLE W.3-continued

Preparation of oxalates from Preparation #15 using general procedure W

| Amine | Product | Example # | HPLC R$_t$ (Method) | m/z or $^1$H NMR (d$_6$-DMSO, 400 MHz) |
|---|---|---|---|---|
| Methylamine | | W.3.7 | 1.86 (a) | 351 (M + H)$^+$ |
| Dimethyl-amine | | W.3.8 | 1.74 (a) | 363 (M − H)$^−$ |
| 1-[2-(1-piperidine)-1-oxo-ethyl]piperazine | | W.3.9 | | NMR (DMSO): 1.58-1.41 (m, 8H), 3.21 (s, 2H), 3.40-3.55 (m, 10H), 7.44 (m, 2H), 7.91-8.25 (m, 6H). |

TABLE W.3-continued
Preparation of oxalates from Preparation #15 using general procedure W
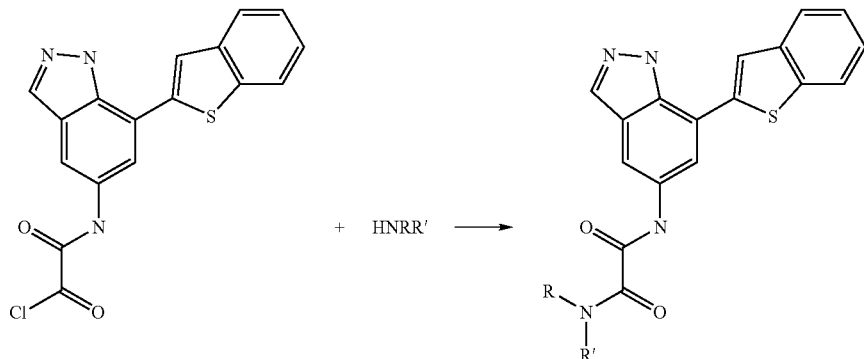
| Amine | Product | Example # | HPLC R$_t$ (Method) | m/z or $^1$H NMR (d$_6$-DMSO, 400 MHz) |
|---|---|---|---|---|
| Cyclohexylamine | | W.3.10 | 2.98 (k) | 417 (M − H)$^-$ |
| 1-(3-Amino-propyl)-pyrrolidin-2-one | | W.3.11 | 2.28 (k) | 460 (M − H)$^-$ |
| Cyclopropyl-methylamine | | W.3.12 | 2.65 (k) | 389 (M − H)$^-$ |

TABLE W.3-continued

Preparation of oxalates from Preparation #15 using general procedure W

| Amine | Product | Example # | HPLC R$_t$ (Method) | m/z or $^1$H NMR (d$_6$-DMSO, 400 MHz) |
|---|---|---|---|---|
| Tetrahydro-pyran-4-ylamine | | W.3.13 | 2.35 (k) | 419 (M − H)$^-$ |
| [2,2']-Bithiophenyl-5-yl-methylamine | | W.3.14 | 3.09 (k) | 513 (M − H)$^-$ |
| Pyridin-4-ylamine | | W.3.15 | 2.48 (k) | 412 (M − H)$^-$ |

TABLE W.3-continued

Preparation of oxalates from Preparation #15 using general procedure W

| Amine | Product | Example # | HPLC R$_t$ (Method) | m/z or $^1$H NMR (d$_6$-DMSO, 400 MHz) |
|---|---|---|---|---|
| Pyridin-3-ylamine | | W.3.16 | 2.42 (k) | 412 (M − H)$^-$ |
| Naphthalen-2-yl-methylamine | | W.3.17 | 3.02 (k) | 475 (M − H)$^-$ |

TABLE W.3-continued
Preparation of oxalates from Preparation #15 using general procedure W
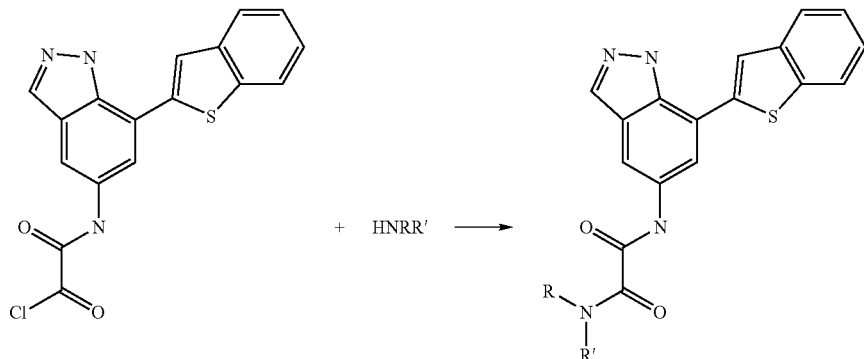
| Amine | Product | Example # | HPLC R$_t$ (Method) | m/z or $^1$H NMR (d$_6$-DMSO, 400 MHz) |
|---|---|---|---|---|
| Pyrimidin-5-ylamine | | W.3.18 | 2.27 (k) | 413 (M − H)$^-$ |
| 2-Ethoxy-ethylamine | | W.3.19 | 1.93 (k) | 407 (M − H)$^-$ |
| 1-Pyrazin-2-yl-piperazine | | W.3.20 | 2.28 (k) | 482 (M − H)$^-$ |

TABLE W.3-continued
Preparation of oxalates from Preparation #15 using general procedure W
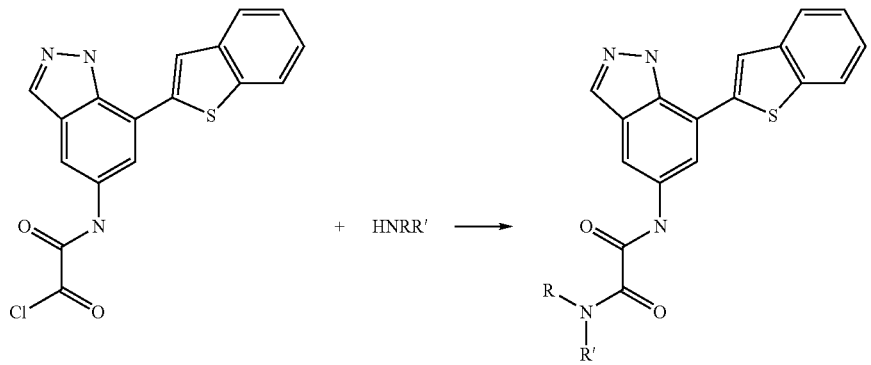
| Amine | Product | Example # | HPLC R$_t$ (Method) | m/z or $^1$H NMR (d$_6$-DMSO, 400 MHz) |
|---|---|---|---|---|
| 1-Isopropyl-piperazin-2-one | | W.3.21 | 2.22 (k) | 460 (M − H)$^-$ |
| 4-Pyrimidin-2-yloxy-piperidine | | W.3.22 | 2.62 (k) | 497 (M − H)$^-$ |
| 3-Imidazol-1-yl-propylamine | | W.3.23 | 2.45 (k) | 443 (M − H)$^-$ |

TABLE W.3-continued
Preparation of oxalates from Preparation #15 using general procedure W
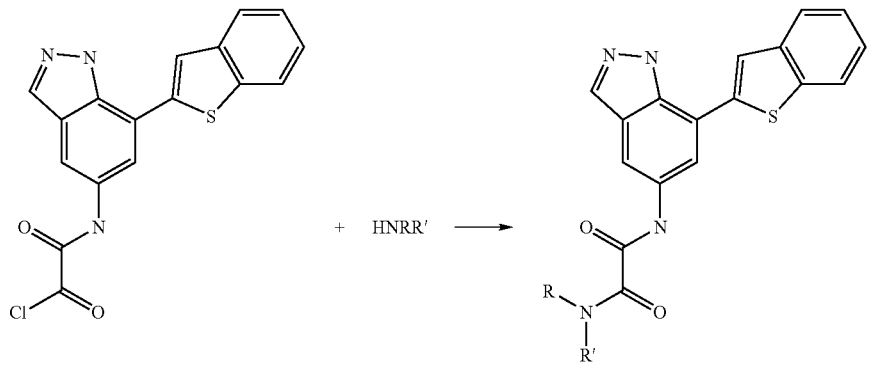
| Amine | Product | Example # | HPLC R$_t$ (Method) | m/z or $^1$H NMR (d$_6$-DMSO, 400 MHz) |
|---|---|---|---|---|
| (1-Methyl-1H-pyrrol-2-yl)-methylamine | | W.3.24 | 2.63 (k) | 428 (M − H)$^-$ |
| 1-Methyl-piperazine | | W.3.25 | 2.19 (k) | 418 (M − H)$^-$ |
| N-Methyl-(2-pyridin-2-yl)ethylamine | | W.3.26 | 2.28 (k) | 454 (M − H)$^-$ |

TABLE W.3-continued

Preparation of oxalates from Preparation #15 using general procedure W

| Amine | Product | Example # | HPLC R$_t$ (Method) | m/z or $^1$H NMR (d$_6$-DMSO, 400 MHz) |
|---|---|---|---|---|
| N,N-Diethyl-piperidine-3-carboxamide | | W.3.27 | 2.32 (k) | 502 (M − H)$^−$ |
| 2-(2-Methyl-benzimidazol-1-yl)-ethylamine | | W.3.28 | 2.35 (k) | 493 (M − H)$^−$ |
| 5-Methyl-pyrazin-2-ylmethylamine | | W.3.29 | 2.27 (k) | 441 (M − H)$^−$ |

TABLE W.3-continued

Preparation of oxalates from Preparation #15 using general procedure W

| Amine | Product | Example # | HPLC R$_t$ (Method) | m/z or $^1$H NMR (d$_6$-DMSO, 400 MHz) |
|---|---|---|---|---|
| Pyrazin-2-ylamine | | W.3.30 | 2.48 (k) | 413 (M − H)$^-$ |
| N,N-Dimethyl-ethane-1,2-diamine | | W.3.31 | 2.36 (k) | 406 (M − H)$^-$ |
| 1-Morpholin-4-yl-2-piperazin-1-yl-ethanone | | W.3.32 | 2.09 (k) | 531 (M − H)$^-$ |

TABLE W.3-continued

Preparation of oxalates from Preparation #15 using general procedure W

| Amine | Product | Example # | HPLC R$_t$ (Method) | m/z or $^1$H NMR (d$_6$-DMSO, 400 MHz) |
|---|---|---|---|---|
| 2-(1-Methyl-1H-pyrrol-2-yl)-ethylamine | | W.3.33 | 2.69 (k) | 442 (M − H)$^−$ |
| Pyridin-2-yl-methylamine | | W.3.34 | 2.37 (k) | 426 (M − H)$^−$ |
| Pyridin-3-yl-methylamine | | W.3.35 | 2.28 (k) | 426 (M − H)$^−$ |

TABLE W.3-continued

Preparation of oxalates from Preparation #15 using general procedure W

| Amine | Product | Example # | HPLC R$_t$ (Method) | m/z or $^1$H NMR (d$_6$-DMSO, 400 MHz) |
|---|---|---|---|---|
| Benzo[1,3]dioxol-5-yl-methylamine | | W.3.36 | 2.67 (k) | 469 (M − H)$^-$ |
| Benzothiazol-6-ylamine | | W.3.37 | 2.70 (k) | 468 (M − H)$^-$ |
| 2,5-Dimethyl-2H-pyrazol-3-ylamine | | W.3.38 | 2.33 (k) | 429 (M − H)$^-$ |

TABLE W.3-continued

Preparation of oxalates from Preparation #15 using general procedure W

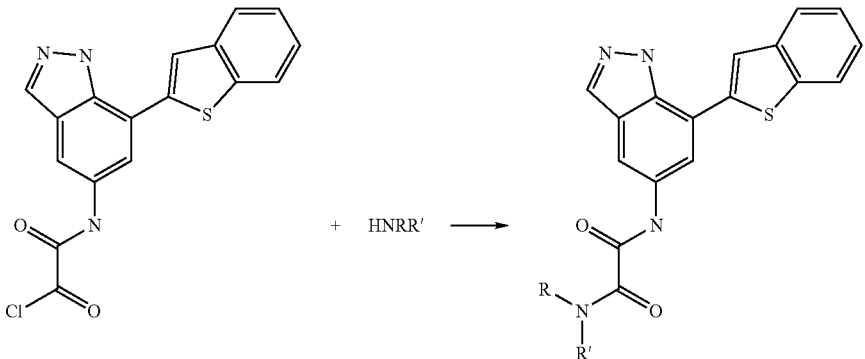

| Amine | Product | Example # | HPLC R$_t$ (Method) | m/z or $^1$H NMR (d$_6$-DMSO, 400 MHz) |
|---|---|---|---|---|
| Pyridin-4-yl-methylamine | | W.3.39 | 2.28 (k) | 426 (M − H)$^-$ |

General Procedure X: Indazole Formation Using Hydrazine

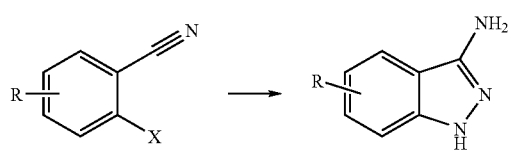

A mixture of an ortho-halobenzonitrile (1 equivalent) in 30% aqueous hydrazine (1-10 equivalents, preferably about 3 equivalents) is heated in a sealed tube to about 50-200° C. (preferably about 120° C.) for about 30-120 minutes (preferably about 45 minutes). The mixture is cooled to ambient temperature and the precipitation is filtered off, washed with water and dried under reduced pressure to yield the desired indazole.

Illustration of General Procedure X
Preparation # 49. 7-Nitro-1H-indazol-3-ylamine

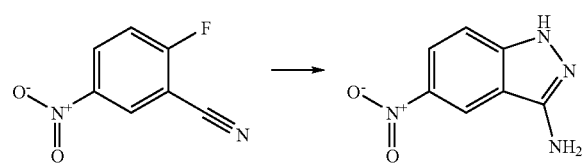

A mixture of 5-nitro-2-fluoro-benzonitrile (Aldrich, 1.00 g, 6.02 mmol) in 30% aqueous hydrazine (5.00 mL, 18.1 mmol) was heated to about 120° C. in a sealed tube for about 40 minutes. The mixture was cooled to ambient temperature and the precipitate was filtered off, washed with water (10 mL) and dried under reduced pressure to yield 7-nitro-1H-indazol-3-ylamine (0.470 g, 26.4 mmol); (DMSO-d$_6$, 400 MHz) δ 12.16 (br, 1H), 8.90 (m, 1H), 8.05 (dd 1H), 7.35 (d, 1H), 5.98 (br, 2H); RP-HPLC (Table 1, Method j) R$_t$ 8.07 min.

TABLE X.1.

Examples prepared using general procedure X

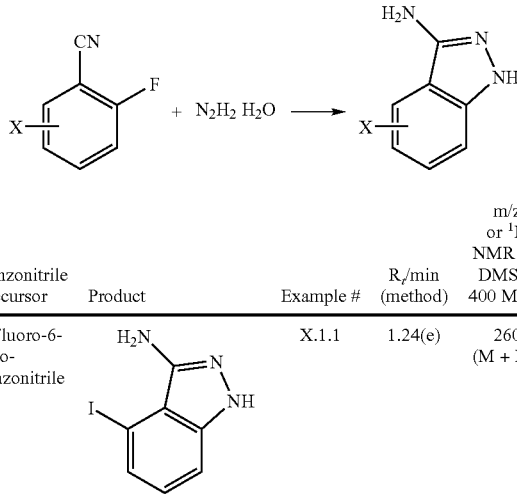

| Benzonitrile Precursor | Product | Example # | R$_t$/min (method) | m/z or $^1$H NMR (d$_6$ DMSO, 400 MHz) |
|---|---|---|---|---|
| 2-Fluoro-6-iodo-benzonitrile | | X.1.1 | 1.24(e) | 260 (M + H)$^+$ |

TABLE X.1.-continued

Examples prepared using general procedure X

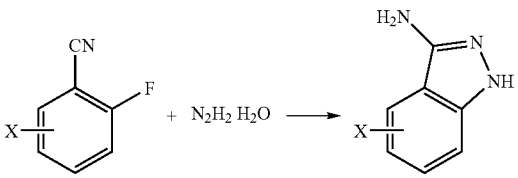

| Benzonitrile Precursor | Product | Example # | R$_t$/min (method) | m/z or $^1$H NMR (d$_6$ DMSO, 400 MHz) |
|---|---|---|---|---|
| 2-Fluoro-5-bromo-benzonitrile | 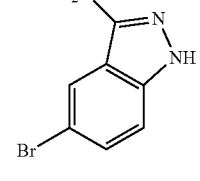 | X.1.2 | 1.78(e) | 210/212 (M − H)$^−$ |
| 2-Fluoro-6-bromo-benzonitrile | 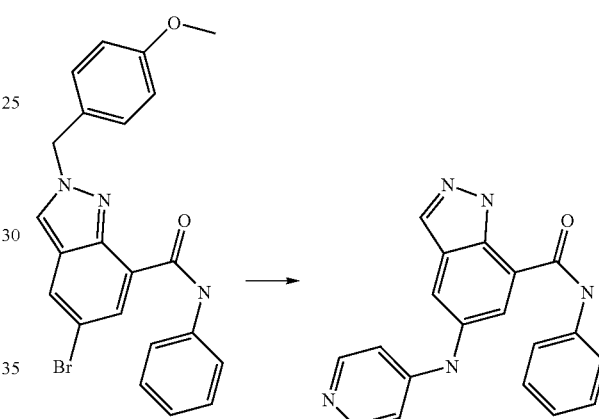 | X.1.3 | 1.82(e) | 210/212 (M − H)$^−$ |

General Procedure Y: Pd Mediated Coupling of an Aryl Halide with an Amine Followed by Acid Deprotection To a mixture of an amine (1-5 equivalents, preferably 1.25 equivalents), an aryl halide (for example, an aryl bromide, aryl chloride or an aryl iodide, preferably an aryl iodide) (0.7-3 equivalents, preferably 1 equivalent) and an inorganic base (for example, KF, Na$_2$CO$_3$ or Cs$_2$CO$_3$, preferably Cs$_2$CO$_3$) (2-16 equivalents, preferably 2.5 equivalents) in a degassed organic solvent (for example THF, DME, DMF, 1,4-dioxane, toluene, preferably 1,4-dioxane) is added a palladium catalyst (for example tris(benzylideneacetone)dipalladium (0) and XANTPHOS, tetrakis(triphenylphosphine)palladium(0), bis(acetato)triphenylphosphinepalladium(II) (~5% Pd) polymer-bound FibreCat™ or [1,1′-bis(diphenylphosphino)ferrocene]dichloropalladium(II), complex with dichloromethane, preferably tris(benzylideneacetone)dipalladium (0) and XANTPHOS) (0.01-0.10 equivalents, preferably 0.05 equivalents). The reaction mixture is heated at about 40-150° C. (preferably about 95° C.) for about 0.5-24 hours (preferably about 2 hours) or at about 100-200° C. (preferably 150° C.) for about 5-60 minutes (preferably about 15 minutes) in a microwave under an inert atmosphere. The reaction mixture is allowed to cool and the crude product is treated with an acid (preferably trifluoroacetic acid) (5-80 M solution, preferably 20M solution) optionally containing a cation scavenger (preferably triisopropyl silane) (0.7-2.5 equivalents, preferably 1.2 equivalents) for about 10-150 minutes (preferably about 15 minutes) at about 70-150° C. (preferably about 100° C.) in a sealed tube, either by conventional heating or by microwave heating. Solvents are removed under reduced pressure to give the product that can be further purified by crystallization or chromatography.

Illustration of General Procedure Y

Example #27

N-Phenyl-5-(pyridin-4-ylamino)-1H-indazole-7-carboxamide

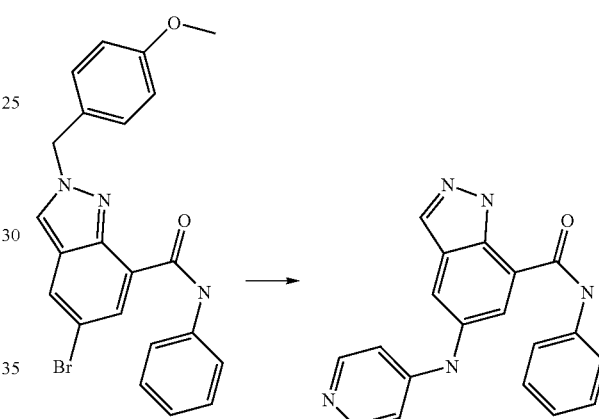

A mixture of 5-bromo-2-(4-methoxy-benzyl)-2H-indazole-7-carboxylic acid, phenylamide (prepared from preparation #12a using general procedures V and B, 75.0 mg, 0.20 mmol), 4-aminopyridine(24.0 mg, 0.25 mmol), cesium carbonate (195 mg, 0.60 mmol), and XANTPHOS (11.6 mg, 0.02 mmol) was suspended in 1,4-dioxane (2.5 mL) at ambient temperature under an inert atmosphere. Tris(dibenzylideneacetone)dipalladium(0) (9.2 mg, 0.01 mmol) was added and nitrogen gas was bubbled through the resulting suspension for about 5 minutes. The reaction mixture was heated at about 95° C. for about 2 hours. The resulting mixture was allowed to cool to ambient temperature and filtered through a celite pad and the solvent was removed under reduced pressure. The residue was dissolved in trifluoroacetic acid (4.0 mL) containing triisopropylsilane (51.0 uL, 0.25 mmol) and the mixture was heated at about 100° C. in a microwave reactor for about 15 minutes. Solvents were removed under reduced pressure and the residue was purified preparative RP-HPLC (Rainin C18, 8 mm, 300 Å, 35 cm; 5-100% acetonitrile/0.1 M ammonium acetate over 20 min, 100% acetonitrile hold 10 minutes, 21 mL/min) to afford N-phenyl-5-(pyridin-4-ylamino)-1H-indazole-7-carboxamide (30 mg, 46%) as an off-white solid, RP HPLC (Table 1, Method e) R$_t$=1.32; MS m/z: (MH)$^+$ 330.

TABLE Y.1.

Examples synthesized using general procedure Y

| Amine | Product | Example # | HPLC R$_t$ (Method) | m/z or $^1$H NMR (d$_6$ DMSO, 400 MHz) |
|---|---|---|---|---|
| 5-Bromo-1-(4-methoxy-benzyl)-1H-indazole-7-carboxylic acid phenylamide (preparation #11d, V and B) | *[structure]* | Y.1.1 | 1.37(e) | 345 (MH)$^+$ |

TABLE Y.2.

Examples prepared using general procedure Y from Preparation #F.8.1 (4-methoxybenzylated using the conditions used to prepare Prepn. 11d and 12a)

| Heterocyclic halide | Product | Example # | HPLC R$_t$ (Method) | m/z or $^1$H NMR (d$_6$ DMSO, 400 MHz) |
|---|---|---|---|---|
| 3-Chloro-5-methyl-isoxazole | *[structure]* | Y.2.1 | 2.1 min (e) | 347.2 (M + H)$^+$ |

General Procedure Z: Acid Cleavage of a THP-Protecting Group

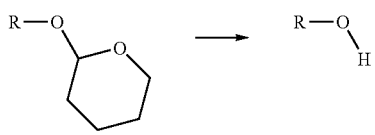

To a mixture of a THP protected alcohol in an organic solvent (for example MeOH, EtOH, i-PrOH or dioxane, preferably MeOH) is added an acid (for example aqueous HCl or PPTS, preferably PPTS) (0.1-1.0 equivalents, preferably 0.5 equivalents). The reaction mixture is stirred at about 10-85° C. (preferably about 25° C.) for about 1-24 hours (preferably about 6 hours). The reaction mixture was diluted with an organic solvent (for example EtOAc, Et$_2$O, or CH$_2$Cl$_2$, preferably EtOAc) and was washed with an aqueous basic solution (for example aqueous Na$_2$CO$_3$ or NaOH, preferably Na$_2$CO$_3$). The solvent is evaporated and the product can be further purified by crystallization or chromatography.

Illustration of General Procedure Z

Example #28

(E)-4-[5-(2-Amino-pyrimidin-4-ylamino)-1H-indazol-7-yl]-but-3-en-1-ol

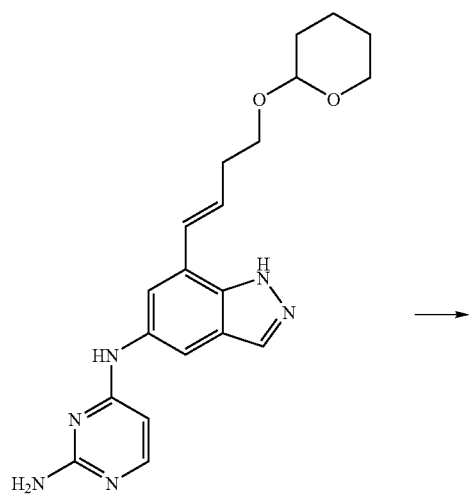

PPTS (0.019 g, 0.075 mmol) was added to a mixture of 4-{7-[(E)-4-(tetrahydro-pyran-2-yloxy)-but-1-enyl]-1H-indazol-5-ylamino}-pyrimidine-2-amine (prepared from Example #N.2.7 reacted with trans-2-[3-(4,4,5,5-tetramethyl-1,3,2-dioxaborolan-2-yl)allyoxy]-tetrahydropyran using general procedure F, 0.037 g, 0.100 mmol) in MeOH (3.0 mL). The reaction mixture was stirred at about 25° C. for about 5 hours. The reaction mixture was diluted with EtOAc (5 mL) and was washed with aqueous Na$_2$CO$_3$ solution (5 mL). The organic portion was evaporated under reduced pressure to afford (E)-4-[5-(2-amino-pyrimidin-4-ylamino)-1H-indazol-7-yl]-but-3-en-1-ol (0.015 g, 0.051 mmol) as an off white solid; RP-HPLC (Table 1, Method e) Rt 0.62 min; m/z: (M+H)$^+$ 297.0.

General Procedure AA: Deprotection of a Cbz-Protected Amino Group

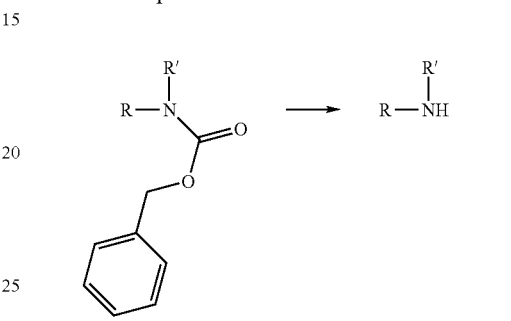

A solution of a Cbz protected amine substrate and formic acid (5-20 equivalents, preferably 10 equivalents) in an organic solvent (for example methanol or ethanol, preferably methanol) is added dropwise to a suspension of Palladium black (1-10 equivalents, preferably 2 equivalents) in an organic solvent (for example methanol or ethanol, preferably methanol). The resulting mixture is allowed to stir at room temperature for about 2-20 hours (preferably 16 hours). The suspension is filtered though a plug of celite and the solvent is removed under reduced pressure. The resulting crude product can be purified by titration with an appropriate solvent (water, ethanol, toluene or ethyl acetate, preferably ethanol) or by chromatography.

Illustration of General Procedure AA

Example # 29

N$^4$-(3-amino-propyl)-N$^4$-(7-benzo[b]thiophen-2-yl-1H-indazol-5-yl)-pyrimidine-2,4-diamine

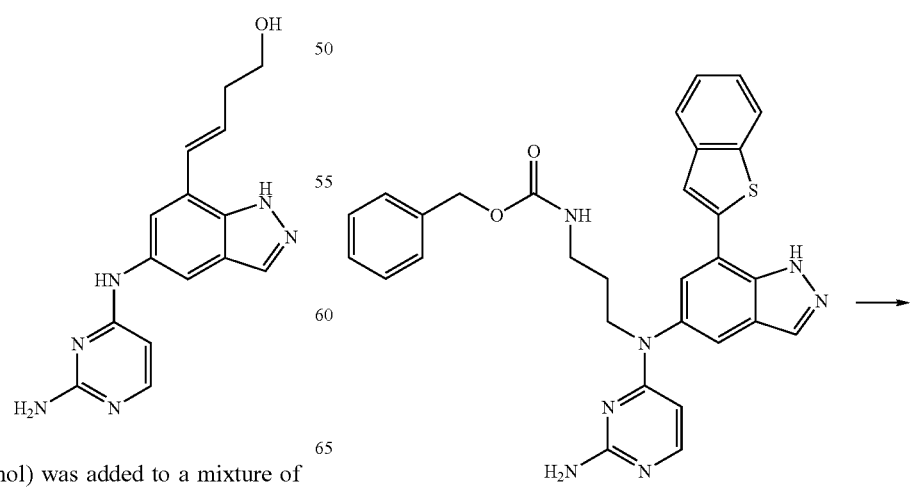

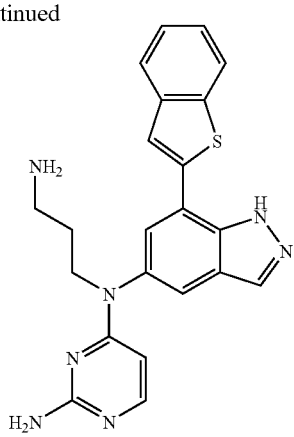

A solution of {3-[(2-amino-pyrimidin-4-yl)-(7-benzo[b]thiophen-2-yl-1H-indazol-5-yl)-amino]-propyl}-carbamic acid benzyl ester (prepared from Example #F.8.1 using general procedures O and N, 0.169 g, 0.308 mmol) and formic acid (0.116 mL, 3.08 mmol) in methanol (2 mL) was added dropwise to a suspension of Palladium black (0.080 g, 0.752 mmol) in methanol (1.5 mL). The resulting mixture was allowed to stir at ambient temperature for about 19 hours. The resulting suspension was filtered though celite and the solvent was removed under reduced pressure. The resulting crude product was purified by reverse chromatography (Thermo Hypersil-Keystone 250×21.2 mm 8μ Hypersil® HS C18 column; 5% acetonitrile/0.1 M aqueous ammonium acetate –100% acetonitrile over 20 min, 100% acetonitrile hold 5 minutes, 21 mL/min) to afford $N^4$-(3-amino-propyl)-$N^4$-(7-benzo[b]thiophen-2-yl-1H-indazol-5-yl)-pyrimidine-2,4-diamine (0.021 g, 17% yield) as a green solid. RP-HPLC (Table 1, Method e) $R_t$ 1.62 min.; m/z: (M+H)$^+$ 416.1.

Specific Examples and Intermediate Preparations

Example #1

2-Amino-4-(1H-indazol-5-ylamino)-thieno[2,3-d]pyrimidine-6-carboxylic acid amide

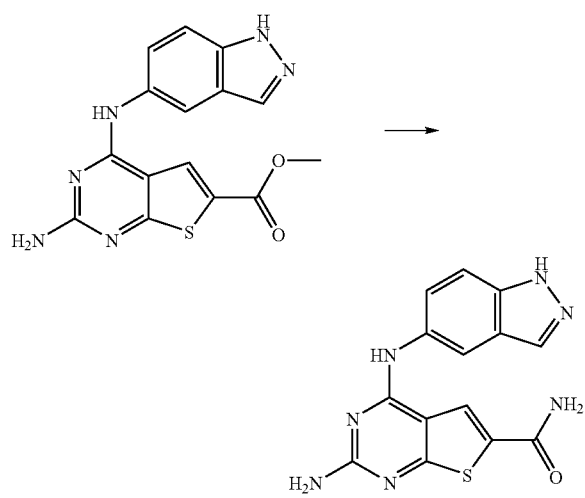

A mixture of 2-amino-4-(1H-indazol-5-ylamino)-thieno[2,3-d]pyrimidine-6-carboxylic acid methyl ester (Example #N.7.1, 0.050 g, 0.15 mmol) and ammonia (ca. 7N in methanol, 1.0 mL) was heated at about 60° C. in a sealed vessel for about 1.5 hours. The mixture was allowed to cool to ambient temperature and additional ammonia (ca. 7N in methanol, 5.0 mL) was added. The reaction mixture was then heated at about 75° C. for about 18 hours, cooled to ambient temperature, additional ammonia (ca. 7N in methanol, 2.0 mL) was added, and heating at about 75° C. was continued for about another 3 days. The mixture was concentrated under reduced pressure and the residue was purified by preparative HPLC (Thermo Hypersil-Keystone 250×21.2 mm 8μ Hypersil® HS C18 column; 5% CH$_3$CN/50 mM aqueous ammonium acetate hold for 5 min, 5-100% CH$_3$CN/50 mM aqueous ammonium acetate over 30 min, hold at 100% CH$_3$CN for 5 minutes, 21 mL/min) to give 2-amino-4-(1H-indazol-5-ylamino)-thieno[2,3-d]pyrimidine-6-carboxylic acid amide (0.015 g, 31%) as a beige solid; RP-HPLC (Table 1, Method a) $R_t$ 0.68 min, m/z (ESI+) 325.9 (M+H)$^+$.

Example #2

1-Benzyl-3-(3-iodo-1H-indazol-5-yl)-urea

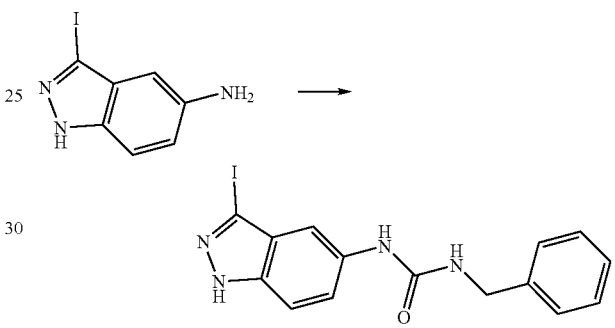

Benzyl isocyanate (0.25 mL, 2.0 mmol) was added to 3-iodo-1H-indazol-5-ylamine (Preparation #28, 0.50 g, 1.9 mmol) in THF (10 mL). After stirring at ambient temperature for about 2.5 hours, the mixture was filtered and washed with Et$_2$O to give 1-benzyl-3-(3-iodo-1H-indazol-5-yl)-urea (0.41 g, 55%) as an ivory solid; RP-HPLC (Table 1, Method e) $R_t$ 0.98 min, m/z (ESI$^+$) 393.0 (M+H)$^+$.

Example #3

2-Amino-4-(7-benzo[b]thiophen-2-yl-1H-indazol-5-ylamino)-7H-pyrrolo[2,3-d]pyrimidine-5-carboxamide

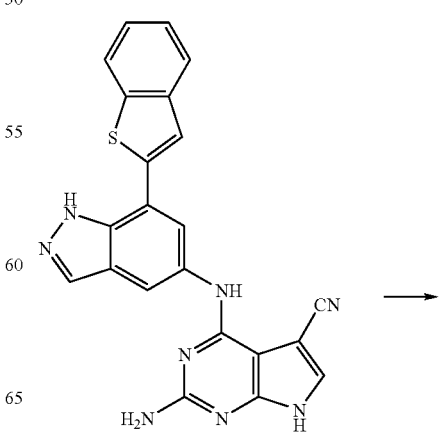

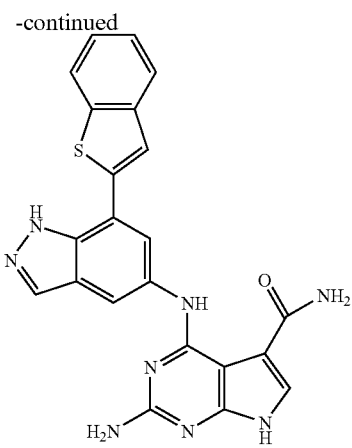

Sodium percarbonate (0.040 g, 0.25 mmol) was added to a mixture of 2-amino-4-(7-benzo[b]thiophen-2-yl-1H-indazol-5-ylamino)-7H-pyrrolo[2,3-d]pyrimidine-5-carbonitrile (prepared via General Procedure N from the reaction of Example #F.8.1 with 6-amino-4-chloro-3-cyano-pyrrolo[2,3-d]pyrimidine [prepared by chlorination of the 4-oxo derivative (*J. Med. Chem.*, 2001, 44(12), 1993-2003) using POCl$_3$ (*Tet.*, 2004, 60, 943-959), 0.10 g, 0.24 mmol) in 1N KOH (2.4 mL) at ambient temperature. After about 21 hours, the reaction mixture was acidified with 5N HCl and filtered. The resulting solid was purified by preparative HPLC (Thermo Hypersil-Keystone 250×21.2 mm 8µ Hypersil® HS C18 column; 5% CH$_3$CN/50 mM aqueous ammonium acetate hold for 5 min, 5-100% CH$_3$CN/50 mM aqueous ammonium acetate over 30 min, hold at 100% CH$_3$CN for 5 minutes, 21 mL/min) to give an impure solid that was triturated with heptane and filtered to give 2-amino-4-(7-benzo[b]thiophen-2-yl-1H-indazol-5-ylamino)-7H-pyrrolo[2,3-d]pyrimidine-5-carboxamide (6.9 mg, 7%); RP-HPLC (Table 1, Method e) R$_t$ 1.64 min; m/z (ESI$^+$): 441.0 (M+H)$^+$.

Example #4

3-(7-Benzo[b]thiophen-2-yl-1H-indazol-5-ylamino)-4-methoxy-cyclobut-3-ene-1,2-dione

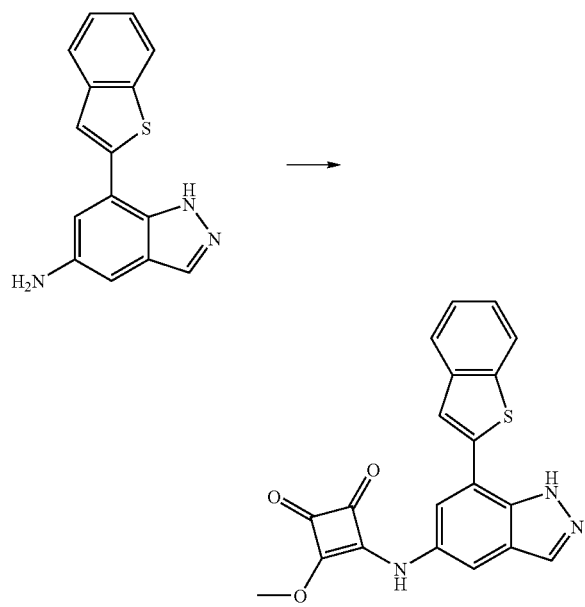

A vial containing a solution of 7-benzo[b]thiophen-2-yl-1H-indazol-5-ylamine (Example #F.8.1, 0.020 g, 0.075 mmol), 3,4-dimethoxy-3-cyclobutene-1,2-dione (0.011 g, 0.077 mmol), N,N-diisopropylethylamine (14 µL, 0.080 mmol) and MeOH (1.5 mL) was shaken at ambient temperature for about 16 hours then filtered to give 3-(7-benzo[b]thiophen-2-yl-1H-indazol-5-ylamino)-4-methoxy-cyclobut-3-ene-1,2-dione (0.022 g, 78%) as a tan solid; RP-HPLC (Table 1, Method e) R$_t$ 1.80 min, m/z (ESI$^+$) 375.9 (M+H)$^+$.

Example #5

5-[5-(2-Amino-pyrimidin-4-ylamino)-1H-indazol-7-yl]-1H-indole-3-carboxaldehyde diacetate

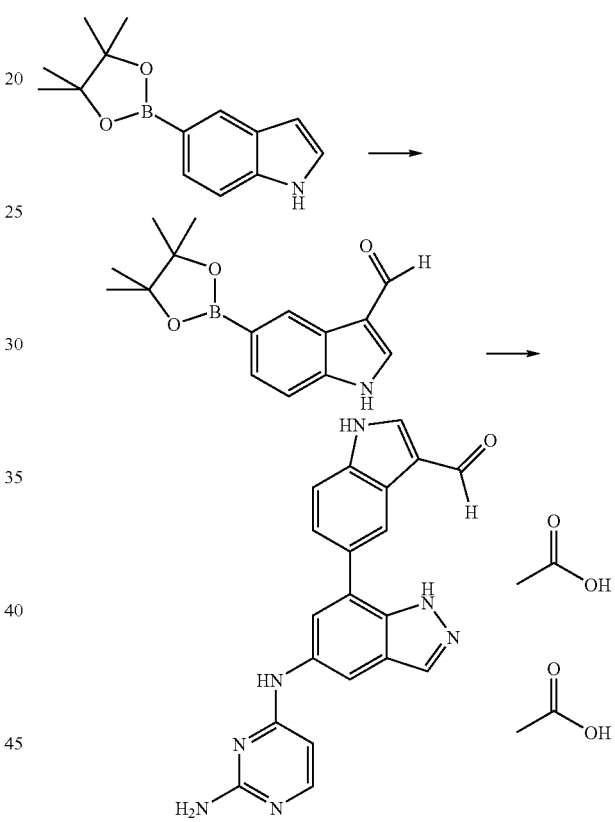

Phosphoryl chloride (43 µL, 0.46 mmol) was added dropwise to DMF (0.17 mL) at about 0° C. After about 20 min, a solution of 5-(4,4,5,5-tetramethyl-[1,3,2]dioxaborolan-2-yl)-1H-indole (Aldrich, 0.10 g, 0.42 mmol) in DMF (0.70 mL) was added dropwise. The reaction was allowed to warm slowly to ambient temperature. After about 7.5 hours, the reaction mixture was concentrated under reduced pressure to give a crude mixture containing 5-(4,4,5,5-tetramethyl-[1,3,2]dioxaborolan-2-yl)-1H-indole-3-carboxaldehyde. The mixture was dissolved in DME (3.0 mL) and transferred to a microwave vial. N$^4$-(7-bromo-1H-indazol-5-yl)-pyrimidine-2,4-diamine (Example #N.2.7, 0.10 g, 0.34 mmol), Pd(PPh$_3$)$_4$ (0.039 g, 0.034 mmol), and Na$_2$CO$_3$ (2.0 M in water, 2.1 mL, 4.2 mmol) were added and the vial was heated in CEM microwave at about 150° C. for about 10 min. The reaction was diluted with water then extracted with EtOAc (3×15 mL). The precipitate present at the layer interface was kept with the organics. The combined organic layers were washed with brine, dried over Na$_2$SO$_4$, decanted, and concentrated. The crude product was triturated with CH$_2$Cl$_2$ and filtered to give a solid which was dissolved in DMSO and purified by preparative HPLC (Thermo Hypersil-Keystone 250×21.2 mm 8μ Hypersil® HS C18 column; 5% CH$_3$CN/50 mM aqueous ammonium acetate hold for 5 min; 5-50% CH$_3$CN/50 mM aqueous ammonium acetate over 15 min; 50-100% CH$_3$CN/50 mM aqueous ammonium acetate over 1 min; hold at 100% CH$_3$CN for 5 minutes, 21 mL/min). The combined fractions containing impure product were concentrated under reduced pressure, lyophilized, dissolved in DMSO, and further purified by preparative HPLC (Thermo Hypersil-Keystone 250× 21.2 mm 8μ Hypersil® HS C18 column; 5% CH$_3$CN/50 mM aqueous ammonium acetate hold for 5 min; 5-50% CH$_3$CN/ 50 mM aqueous ammonium acetate over 20 min; 50-100% CH$_3$CN/50 mM aqueous ammonium acetate over 1 min; hold at 100% CH$_3$CN for 5 minutes, 21 mL/min) to afford 5-[5-(2-amino-pyrimidin-4-ylamino)-1H-indazol-7-y 1]-1H-indole-3-carbaldehyde diacetate (12.3 mg, 6%); RP-HPLC (Table 1, Method e) R$_t$ 1.18 min, m/z (ESI$^+$) 370.3 (M+H)$^+$.

Example #6

N$^4$-(7-Piperidin-3-yl-1H-indazol-5-yl)pyrimidine-2, 4-diamine diacetate

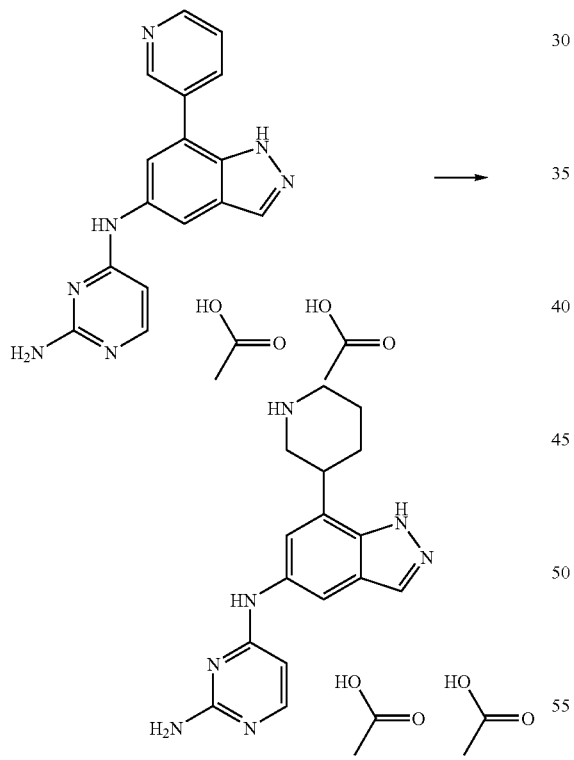

To a vial containing N$^4$-7-pyridin-3-yl-1H-indazol-5-yl)-pyrimidine-2,4-diamine diacetate (Example #F.5.5, 0.040 g, 0.090 mmol) was added L-Selectride® (1.0 M in THF, 0.45 mL, 0.45 mmol). Heated at about 130° C. for about 16 hours Cooled to room temperature and added L-Selectride® (1.0 M in THF, 1.0 mL, 1.0 mmol). Heating at about 130° C. was resumed for about 24 hours. Cooled to room temperature and added L-Selectride® (1.0 M in THF, 0.5 mL, 0.5 mmol). Heating at about 130° C. was resumed for about another 24 hours. The reaction was then cooled to room temperature, quenched with MeOH, and concentrated. The crude product was dissolved in DMSO and purified by preparative HPLC (Thermo Hypersil-Keystone 250×21.2 mm 8μ Hypersil® HS C18 column; 5% CH$_3$CN/50 mM aqueous ammonium acetate hold for 5 min; 5-50% CH$_3$CN/50 mM aqueous ammonium acetate over 20 min; 50-100% CH$_3$CN/50 mM aqueous ammonium acetate over 1 min; hold at 100% CH$_3$CN for 5 minutes, 21 mL/min) to give N$^4$-(7-Piperidin-3-yl-1H-indazol-5-yl)pyrimidine-2,4-diamine diacetate (9.1 mg, 23%) as a white solid; RP-HPLC (Table 1, Method g) R$_t$ 0.94 min, m/z (ESI$^+$) 310.3 (M+H)$^+$.

Example #7

N$^4$-{7-[5-(Aminomethyl)-1-benzothien-2-yl]-1H-indazol-5-yl}pyrimidine-2,4-diamine acetate

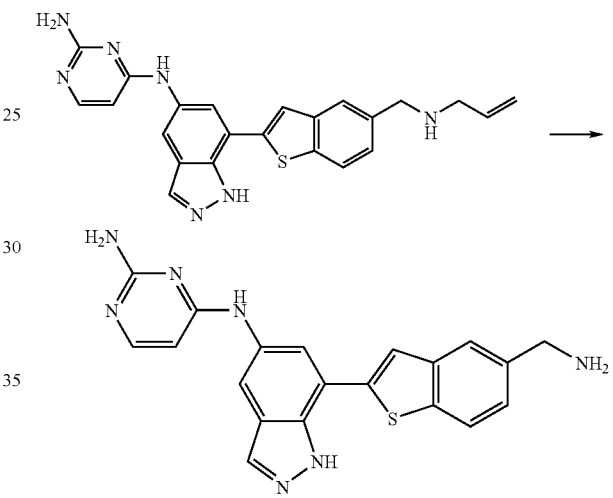

A microwave vial containing N$^4$-(7-5-[(allylamino)methyl]-1-benzothien-2-yl-1H-indazol-5-yl)pyrimidine-2,4-diamine triacetate (Example #O.3.8, 0.022 g, 0.036 mmol), chlorotris(triphenylphosphine)-rhodium(I) (8.4 mg, 0.0090 mmol), CH$_3$CN (0.84 mL), and H$_2$O (0.16 mL) was heated in a CEM microwave at about 120° C. for about 30 min. The reaction was diluted with CH$_3$CN (5 mL), filtered, and washed with CH$_3$CN and EtOAc, to give N$^4$-7-[5-(aminomethyl)-1-benzothien-2-yl]-1H-indazol-5-yl}pyrimidine-2,4-diamine acetate (12.8 mg, 76%) as a tan solid; RP-HPLC (Table 1, Method g) R$_t$ 1.05 min, m/z (ESI$^+$) 388.3 (M+H)$^+$.
Preparation #1: 4-Chloro-2-methanesulfonyl-pyrimidine

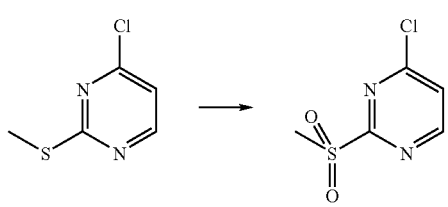

A solution of 4-chloro-2-methylsulfanyl-pyrimidine (Aldrich, 41.37 g, 0.252 mol) in DCM (800 mL) at about 0° C. was treated with 3-chloroperbenzoic acid (75% by weight, 127.76 g, 0.555 mol) in small portions. The reaction mixture was warmed up to ambient temperature and stirred for about 2.5 hours. The insoluble residue was collected by filtration and washed with dichloromethane (100 mL). The filtrate and washings were washed with saturated aqueous sodium bicarbonate solution (3×150 mL) and saturated aqueous sodium chloride solution (200 mL), dried over anhydrous magnesium sulfate, and concentrated to dryness to give 4-chloro-2-methanesulfonyl-pyrimidine (41.83 g, 86%): $^1$H NMR (DMSO-d$_6$, 400 MHz) δ9.08 (d, 1H), 8.10 (d, 1H), 3.44 (s, 3H); LC/MS (Table 1, Method a) R$_t$ 0.70 min.; m/z: (M+H)$^+$ 193.

Preparation #2: 4-Chloro-pyrimidin-2-ylamine

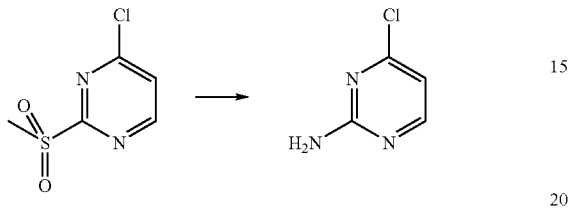

A suspension of 4-chloro-2-methanesulfonyl-pyrimidine (Preparation #1, 41.83 g, 0.217 mol) in ethanol (30 mL) was treated with a solution of saturated ammonia gas in ethanol (300 mL). It was stirred at ambient temperature for about 2 hours, and the white precipitate was collected, washed with methanol (100 mL), and dried under reduced pressure to give 4-chloro-pyrimidin-2-ylamine (15.99 g, 57%): $^1$H NMR (DMSO-d$_6$, 400 MHz), δ8.18 (d, 1H), 7.13 (br, 2H), 6.65 (d, 1H); LC/MS (Table 1, Method a) R$_t$ 1.18 min.

Preparation # 3: 4-Chloro-7H-pyrrolo[2,3-d]pyrimidin-2-ylamine

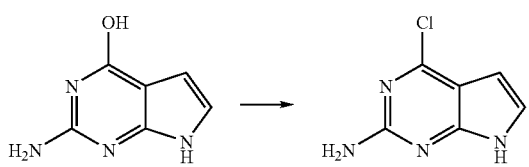

A mixture of 2-amino-7H-pyrrolo[2,3-d]pyrimidin-4-ol (Sigma, 150 mg, 1.0 mmol) in phosphorus oxychloride (1.5 mL) was heated at about 110° C. for about 30 minutes. Phosphorus oxychloride was carefully removed under reduced pressure and the reaction mixture was quenched by slow addition of ice water (10 mL). The resulting mixture was neutralized with saturated aqueous sodium carbonate (about 5 mL) to pH 7. The crude product was extracted into dichloromethane (20 mL) and washed with water (15 mL). The organic layer was separated and the aqueous phase was further extracted with dichloromethane (3×30 mL). The combined organic extracts were dried over anhydrous sodium sulfate and concentrated to give 4-chloro-7H-pyrrolo[2,3-d]pyrimidin-2-ylamine (0.036 g, 0.21 mmol) as a light yellow solid; LC/MS (Table 1, Method a) R$_t$ 1.17 min; MS m/z: (M+H)$^+$ 169.

Preparation #4: tert-Butyl-1,2-(dimethylaminomethylene-amino)-7-iodo-pyrrolo[3,2-d]pyrimidine-5-methanoate

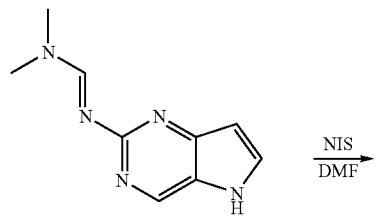

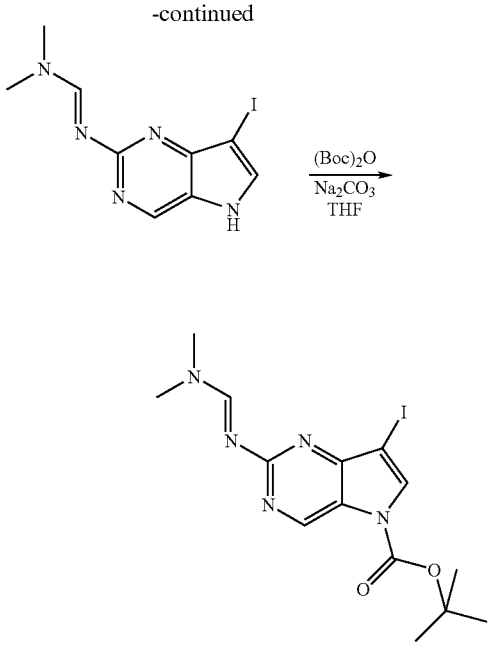

Step 1.

Preparation # 4a. N'-(7-iodo-5H-pyrrolo[3,2-d]pyrimidin-2-yl)-N,N-dimethyl-formamidine N-Iodosuccinimide (3.2 g, 14.2 mmol) was added portionwise to an ice-cold stirred suspension of N,N-dimethyl-N'-(5H-pyrrolo[3,2-d]pyrimidin-2-yl)-formamidine (*Journal of Medicinal Chemistry*, 2003, 46(14), 3060-3071, 2.68 g, 14.2 mmol) in DMF (50 mL). After stirring at ambient temperature overnight, the reaction was concentrated, dissolved in DCM (40 mL) and the product was precipitated using EtOAc (250 mL). After filtration, the pale yellow powder was collected, washed with EtOAc (2×20 mL) and dried under a vacuum overnight to afford N'-(7-iodo-5H-pyrrolo[3,2-d]pyrimidin-2-yl)-N,N-dimethyl-formamidine (3.8 g, 85%) as a yellow powder; $^1$H NMR (DMSO-d$_6$, 400 MHz) δ 12.38 (s, 1H), 8.74 (s, 1H), 8.04 (s, 1 H), 7.93 (s, 1H), 3.29 (s, 3H), 3.19 (s, 3H); ESI–MS [M+H]$^+$=316.1.

Step 2.

Preparation #4: tert-Butyl-1,2-(dimethylaminomethylene-amino)-7-iodo-pyrrolo[3,2-d]pyrimidine-5-methanoate Na$_2$CO$_3$ (1.27 g, 12 mmol) was added to a stirred suspension of N'-(7-iodo-5H-pyrrolo[3,2-d]pyrimidin-2-yl)-N,N-dimethyl-formamidine (Preparation #4a, 1 g, 3.17 mmol) in anhydrous THF (20 mL). Di-tert-butyl dicarbonate (2.76 g, 12 mmol) was added portionwise at ambient temperature and the mixture was stirred at ambient temperature for about 16 hours prior to diluting with DCM (150 mL), filtering and concentrating the filtrate to dryness. The product precipitated from the residue using EtOAc/heptane (50:50, 100 mL). The precipitate was filtered and dried to afford tert-butyl-1,2-(dimethylamino-methyleneamino)-7-iodo-pyrrolo[3,2-d]pyrimidine-5-methanoate (0.95 g, 72%) as a pale yellow solid; $^1$H NMR (DMSO-d$_6$, 400 MHz) δ 9.10 (s, 1H), 8.74 (s, 1H), 7.96 (s, 1H), 3.23 (s, 3H), 3.18 (s, 3H), 1.68 (s, 9H); ESI–MS [M+H]$^+$=416.2.

Preparation #5: N'-{7-[7-Benzo[b]thiophen-2-yl-1-(2-trimethylsilanyl-ethoxymethyl)-1H-indazol-5-yl]-5H-pyrrolo[3,2-d]pyrimidin-2-yl}-N,N-dimethyl-formamidine

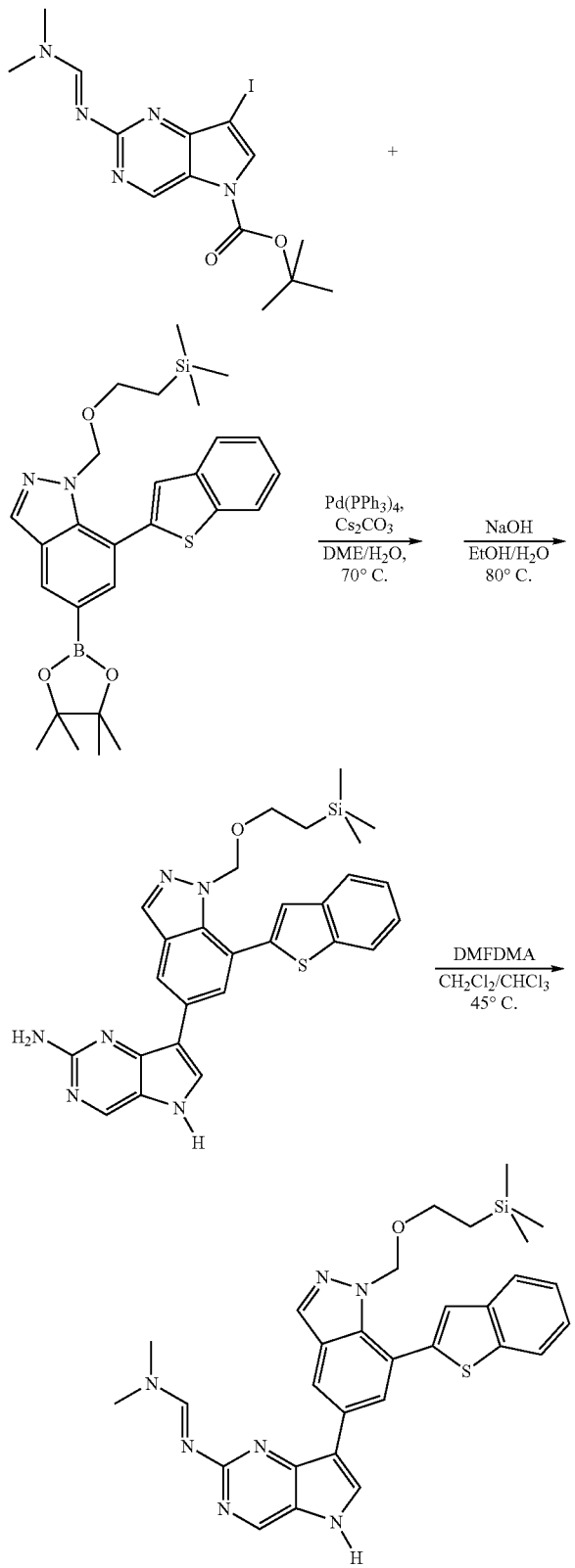

Step 1.

Preparation #5a. 7-[7-benzo[b]thiophen-2-yl-1-(2-trimethylsilanyl-ethoxymethyl)-1H-indazol-5-yl]-5H-pyrrolo[3,2-d]pyrimidin-2-ylamine 2-(Dimethylamino-methyleneamino)-7-iodo-pyrrolo[3,2-d]pyrimidine-5-carboxylic acid tert-butyl ester (Preparation #4, 0.415 g, 1.0 mmoles) was added to a mixture of cesium carbonate (977 mg, 3.0 mmoles), Pd(PPh$_3$)$_4$ (0.12 g, 0.1 mmoles) and 7-(1H-inden-2-yl)-5-(4,4,5,5-tetramethyl-[1,3,2]dioxaborolan-2-yl)-1-(2-trimethylsilanyl-ethoxymethyl)-1H-indazole (Preparation #23 then E, 0.7 g, 1.1 mmoles) in DME (10 mL) and water (0.9 mL) at ambient temperature. The reaction was heated at about 65° C. for about 16 hours then the solvent was evaporated under reduced pressure. EtOH (4 mL) and 30% aqueous NaOH (4 mL) were added and the mixture was heated to about 85° C. for about 1 hour before the EtOH was removed under reduced pressure. The mixture was diluted with EtOAc (150 mL) and washed with water (50 mL) and brine (50 mL), dried over sodium sulfate, filtered, and concentrated under reduced pressure. The crude product was purified by flash column chromatography (0-5% MeOH in CH$_2$Cl$_2$) to afford 7-[7-benzo[b]thiophen-2-yl-1-(2-trimethylsilanyl-ethoxymethyl)-1H-indazol-5-yl]-5H-pyrrolo[3,2-d]pyrimidin-2-ylamine (0.3 g, 60%) as a pale brown solid; LC/MS (Table 1, Method e) R$_t$ 2.66 min; ESI–MS [M+H]$^+$=511.3.

Step 2.

Preparation #5: N'-{7-[7-Benzo[b]thiophen-2-yl-1-(2-trimethylsilanyl-ethoxymethyl)-1H-indazol-5-yl]-5H-pyrrolo[3,2-d]pyrimidin-2-yl}-N,N-dimethyl-formamidine 7-[7-Benzo[b]thiophen-2-yl-1-(2-trimethylsilanyl-ethoxymethyl)-1H-indazol-5-yl]-5H-pyrrolo[3,2-d]pyrimidin-2-ylamine (Preparation #5a, 490 mg, 0.96 mmol) was added to a solution of N,N-dimethylformamide dimethyl acetal (1.27 mL, 9.6 mmoles) in CH$_2$Cl$_2$/CHCl$_3$ (3:2, 5 mL) at ambient temperature. The mixture was heated to about 45° C. for about 16 hours. After concentration, the crude product was purified by flash column chromatography (5-10% MeOH in CH$_2$Cl$_2$) to afford 7'-{7-[7-benzo[b]thiophen-2-yl-1-(2-trimethylsilanyl-ethoxymethyl)-1H-indazol-5-yl]-5H-pyrrolo[3,2-d]pyrimidin-2-yl}-N,N-dimethyl-formamidine (0.4 g, 73%) as a pale brown solid; LC/MS (Table 1, Method h) R$_t$ 2.97 min; ESI–MS [M+H]$^+$=568.4.

Preparation #6: 7-Bromo-1H-indazol-5-ylamine

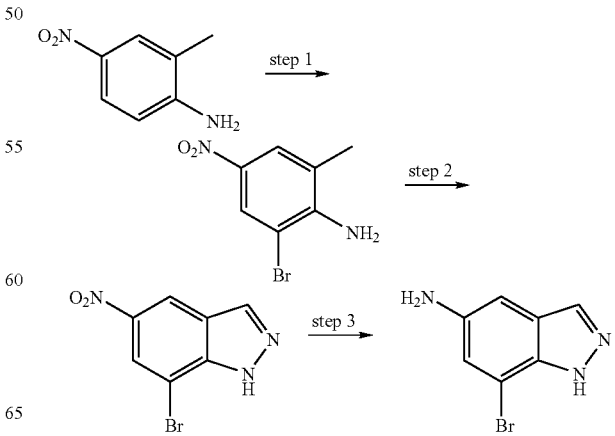

Step 1.

Preparation #6a. 2-Bromo-4-nitro-6-methyl-aniline

Bromine (34.0 mL, 662 mmol) was added dropwise from an addition funnel to a suspension of 2-methyl-4-nitroaniline (100 g, 657 mmol) in glacial HOAc (1 L) at ambient temperature over about 40 min. The reaction mixture was stirred for about an additional 30 min at ambient temperature then diluted with H$_2$O (1 L). The resulting solid was filtered, washed with additional H$_2$O (1 L), and then dried in a vacuum oven overnight (at about 50-60° C.) to give the first crop of material (138.5 g, 91%). Additional precipitate, formed in the filtrate, was collected, washed with H$_2$O (300 mL) then dried in a vacuum oven overnight (at about 50-60° C.) to give an additional batch of 2-bromo-6-methyl-4-nitroaniline (11.4 g, 7%); $^1$H NMR (DMSO-d$_6$, 400 MHz) $\delta$8.14 (d, J=2.4 Hz, 1H), 7.92 (d, J=2.4 Hz, 1H), 6.49 (br s, 2H), 2.23 (s, 3H); LC/MS (Table 1, Method e) R$_t$ 2.02 min; m/z (ESI$^-$) 230.7.

Step 2.

Preparation #6b. 7-Bromo-5-nitro-1H-indazole

NaNO$_2$ (65.00 g, 942.0 mmol) in H$_2$O (140 mL) was added via addition funnel to a 5 L 3-neck round bottom flask, equipped with a mechanical stirrer and a thermometer, containing a mixture of crude 2-bromo-6-methyl-4-nitroaniline (145.0 g, 627.6 mmol) and glacial HOAc (2.5 L). During the addition, the reaction mixture was cooled with an ice bath to to maintain the internal reaction temperature below 25° C. About 1 hour after the addition was complete, additional NaNO$_2$ (21.65 g, 313.8 mmol) in H$_2$O (50 mL) was added to the reaction mixture relatively rapidly (<5 min) with no evidence of an exotherm. After an additional 1 hour, the reaction mixture was concentrated under reduced pressure. The resulting solid was triturated with MeOH/H$_2$O (1:1, 1 L) then filtered, washed with additional MeOH/H$_2$O (1:1, 500 mL), and dried in a vacuum oven at about 50-60° C. for about 16 hours to give 7-bromo-5-nitro-1H-indazole (109.4 g, 72%, 90% pure by HPLC); $^1$H NMR (DMSO-d$_6$, 400 MHz) $\delta$14.28 (br s, 1H), 8.87 (d, J=1.9 Hz, 1H), 8.57 (s, 1H), 8.40 (d, J=1.9 Hz, 1H); LC/MS (Table 1, Method e) R$_t$ 1.75 min; m/z (ESI$^-$) 241.7.

Step 3.

Preparation #6: 7-Bromo-1H-indazol-5-ylamine

A mixture of iron (Aldrich 99.99+%, 13.85 g, 248.0 mmol) and crude 7-bromo-5-nitro-1H-indazole (20.00 g, 82.63 mmol) in glacial acetic acid (100 mL) was heated at about 80° C. in a 2-neck round bottom flask equipped with a mechanical stirrer and a nitrogen line with a bubbler. After about 2.5 hours, MeOH (100 mL) was added, warmed, and filtered hot through Celite®. The Celite® pad was washed with additional MeOH (4×100 mL) and the combined organic layers were concentrated under reduced pressure. The residues were basified to pH ~7 using aqueous Na$_2$CO$_3$ (2M) and the product was extracted into EtOAc (1 L) over about 16 hours. The layers were separated and the aqueous layer was further extracted with additional EtOAc (3×500 mL). The combined organic extracts were washed with brine, dried over anhydrous Na$_2$SO$_4$, decanted, and concentrated. The resulting solid was pre-adsorbed onto silica and purified by silica gel chromatography using heptane/EtOAc (1:1) as the eluent to afford 7-bromo-1H-indazol-5-ylamine (6.92 g, 40%); $^1$H NMR (DMSO-d$_6$, 400 MHz) $\delta$12.92 (br s, 1H), 7.87 (s, 1H), 7.03 (d, J=1.6 Hz, 1H), 6.77 (d, J=1.2 Hz, 1H) 4.96 (br s, 2H); LC-MS (Table 1, Method e) R$_t$ 0.83.

Preparation #7. 7-Benzo[b]thiophen-2-yl-1H-indazole-5-carboxylic acid

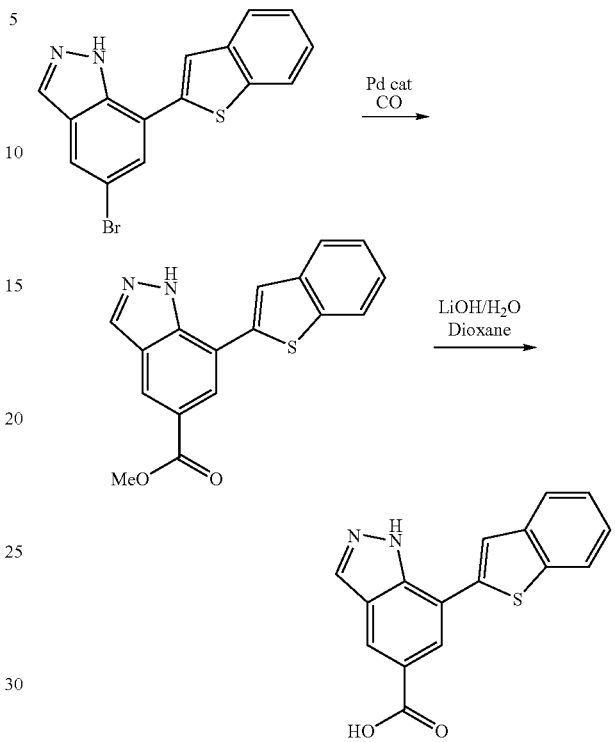

Step 1.

Preparation #7a. Methyl 7-benzo[b]thiophen-2-yl-1H-indazol-5-yl carboxylate

A solution of 7-benzo[b]thiophen-2-yl-5-bromo-1H-indazole (Preparation #26, 4.5 g, 13.7 mmol) in N,N-dimethylformamide (100 mL) was degassed and purged with carbon monoxide. Triethylamine (4.1 g, 41 mmol), methanol (13.1 g, 410 mmol) and dichloro[bis(triphenylphosphine)]palladium (II) (1.45 g, 2.05 mmol) were added and the mixture was heated to about 90° C. for about 15 hours. The mixture was cooled and the solvent was removed under reduced pressure. The residue was triturated with ethyl acetate (75 mL) and water (35 mL) then further purified by flash chromatography over silica gel using dichloromethane/ethyl acetate (95:5) as the eluent to give methyl-7-benzo[b]thiophen-2-yl-1H-indazole-5-methanoate (3.37 g, 80%).

Step 2.

Preparation #7b. 7-Benzo[b]thiophen-2-yl-1H-indazole-5-carboxylic acid

Lithium hydroxide monohydrate (2.25 g, 53.5 mmol) was added to a suspension of methyl-7-benzo[b]thiophen-2-yl-1H-indazole-5-methanoate (3.37 g, 10.71 mmol) in a mixture of 1,4-dioxane (65 mL) and water (9 mL). The mixture was heated to about 65° C. for about 18 hours then cooled to about 40° C. and filtered. The filtrate was acidified with aqueous hydrochloric acid (1N, 54 mL) and the resulting precipitate was collected by filtration and dried under reduced pressure to give 7-benzo[b]thiophen-2-yl-1H-indazole-5-carboxylic acid (3.16 g, 100%); $^1$H NMR (DMSO-d$_6$, 400 MHz) $\delta$ 13.56 (bs, 1H), 8.51 (d, 1H), 8.47 (s, 1H), 8.14 (d, 1H), 8.04 (d, 1H), 7.94 (d, 1H), 7.45 (d, 2H); RP-HPLC (Table 1, Method e) R$_t$=1.06, m/z: (M−H)$^-$ 292.8.

597

Preparation #8. (7-Benzo[b]thiophen-2-yl-1H-indazol-5-yl)-(2-methanesulfonyl-pyrimidin-4-yl)-amine Preparation #9. 4-(7-Benzo[b]thiophen-2-yl-1H-indazol-5-ylamino)-pyrimidin-2-ol

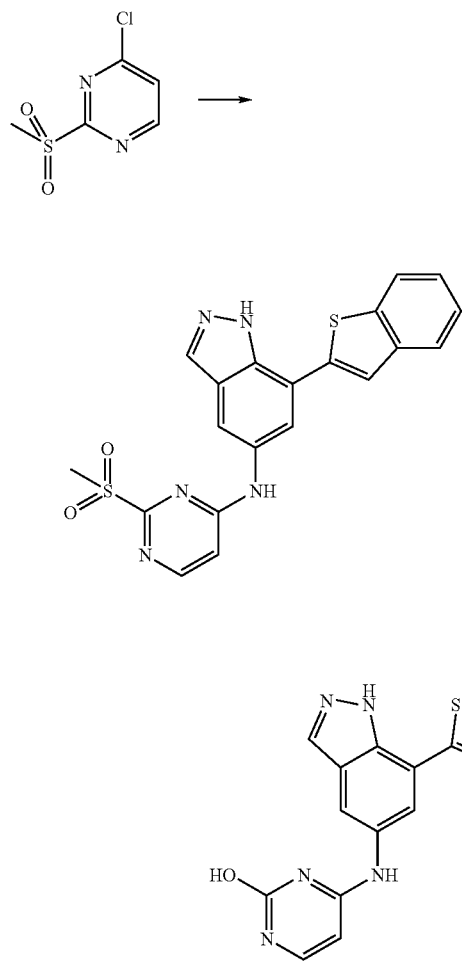

To a mixture of 4-chloro-2-methanesulfonyl-pyrimidine (Preparation #1, 2.54 g, 13.2 mmol) in DME (20 mL) was added 7-benzo[b]thiophen-2-yl-1H-indazol-5-ylamine (Example #F.8.1, 1.95 g, 7.35 mmol) and triethylamine (1.43 mL, 10.3 mmol) in DME (160 mL). After about 16 hours, the mixture was filtered, and the filtrate evaporated and purified by flash column chromatography over alumina using dichloromethane/methanol (99:1) as the eluent to yield product (190 mg, 6% yield). Additional product was obtained by washing the alumina with dichloromethane/methanol (8:2) and concentrating the solution to yield (7-benzo[b]thiophen-2-yl-1H-indazol-5-yl)-(2-methanesulfonyl-pyrimidin-4-yl)-amine (900 mg, 30% yield); LC/MS (Method e) $R_t$ 1.8 min; m/z (ESI–): (M–H)⁺ 419.9.

In an alternate work up, the crude reaction mixture was filtered and the solid was purified by RP-HPLC to yield 4-(7-benzo[b]thiophen-2-yl-1H-indazol-5-ylamino)-pyrimidin-2-ol (2 mg, 0.006 mmol, 0.1% yield): LC/MS $R_t$ (Table 1, Method e) $R_t$ 1.3 min; m/z (ESI–): (M–H)⁺ 358.3.

598

Preparation #10. N'-(1-Benzenesulfonyl-3-bromo-1H-pyrrolo[2,3-c]pyridin-5-yl)-N,N-dimethyl-formamidine

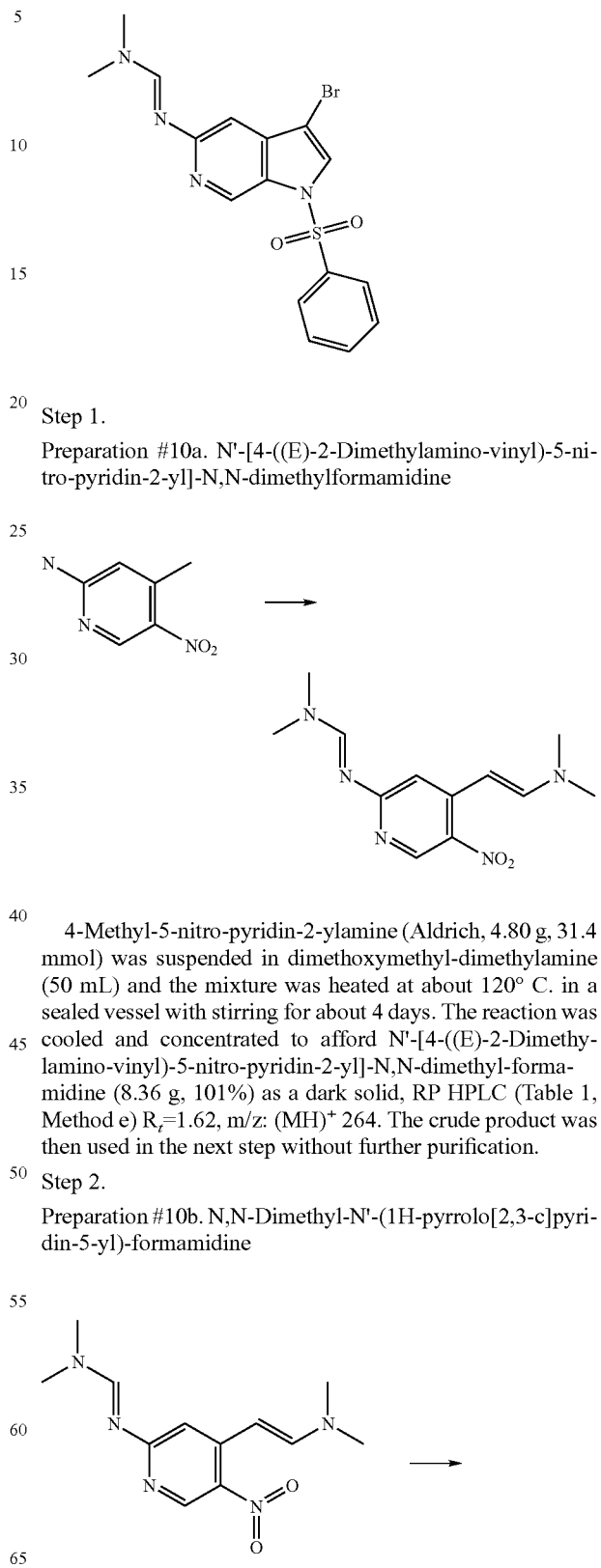

Step 1.

Preparation #10a. N'-[4-((E)-2-Dimethylamino-vinyl)-5-nitro-pyridin-2-yl]-N,N-dimethylformamidine 4-Methyl-5-nitro-pyridin-2-ylamine (Aldrich, 4.80 g, 31.4 mmol) was suspended in dimethoxymethyl-dimethylamine (50 mL) and the mixture was heated at about 120° C. in a sealed vessel with stirring for about 4 days. The reaction was cooled and concentrated to afford N'-[4-((E)-2-Dimethylamino-vinyl)-5-nitro-pyridin-2-yl]-N,N-dimethyl-formamidine (8.36 g, 101%) as a dark solid, RP HPLC (Table 1, Method e) $R_t$=1.62, m/z: (MH)⁺ 264. The crude product was then used in the next step without further purification.

Step 2.

Preparation #10b. N,N-Dimethyl-N'-(1H-pyrrolo[2,3-c]pyridin-5-yl)-formamidine

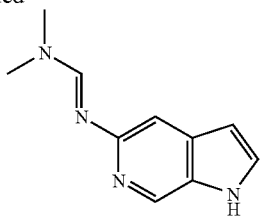

A suspension of N'-[4-((E)-2-dimethylamino-vinyl)-5-nitro-pyridin-2-yl]-N,N-dimethyl-formamidine (Preparation #10a, 8.36 g, 31.4 mmol) and 10% Pd on carbon (800 mg) in ethanol (120 mL) was shaken in a hydrogenation vessel under an atmosphere of 10-55 psi $H_2$ for about 24 hours. The reaction was filtered through Celite® and concentrated to yield N,N-dimethyl-N'-(1H-pyrrolo[2,3-c]pyridin-5-yl)-formamidine (6.19 g, 105%) as a dark solid. RP HPLC (Table 1, Method e) $R_t$=0.84, m/z: $(MH)^+$ 189. The crude product was used in the next step without further purification.

Step 3.

Preparation #10. N'-(1-Benzenesulfonyl-3-bromo-1H-pyrrolo[2,3-c]pyridin-5-yl)-N,N-dimethyl-formamidine

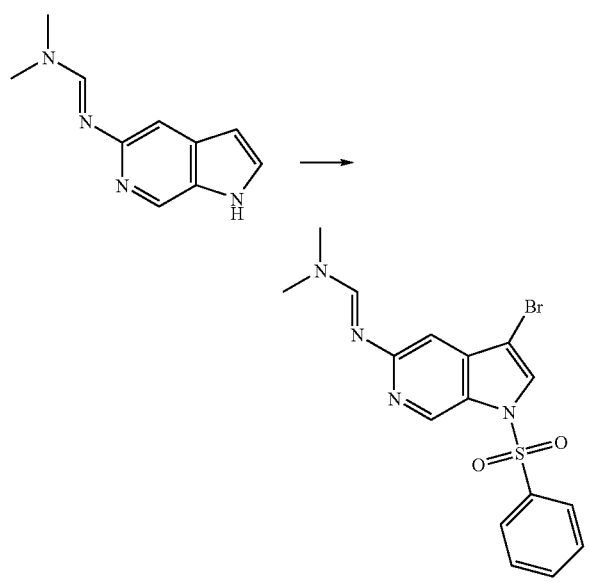

1-Bromo-pyrrolidine-2,5-dione (5.34 g, 30 mmol) was added to a stirred solution of N,N-dimethyl-N'-(1H-pyrrolo[2,3-c]pyridin-5-yl)-formamidine (Preparation #10b, 6.00 g, 31.9 mmol) in DMF (200 mL) at about 0° C. The reaction was allowed to warm to ambient temperature then stirred for about 1 hour. Benzenesulfonyl chloride (3.83 mL, 30.0 mmol) and $Na_2CO_3$ (6.36 g, 60.0 mmol) were added and the mixture was warmed at about 60° C. for about 1 hour. The reaction mixture was concentrated under reduced pressure and the dark solids were triturated with EtOAc (2×100 mL) and filtered. The combined EtOAc layers were passed through a 6 inch silica gel column, eluting with EtOAc. The product fractions were combined and concentrated to yield N'-(1-benzenesulfonyl-3-bromo-1H-pyrrolo[2,3-c]pyridin-5-yl)-N,N-dimethylformamidine (4.29 g, 35%) as a tan solid. RP HPLC (Table 1, Method e) $R_t$=2.18, m/z: $(MH)^+$ 407/409.

Preparation #11. Methyl 1-(4-Methoxy-benzyl)-5-(4,4,5,5-tetramethyl-[1,3,2]dioxaborolan-2-yl)-1H-indazole-7-carboxylate Preparation #12. Methyl 2-(4-Methoxy-benzyl)-5-(4,4,5,5-tetramethyl-[1,3,2]dioxaborolan-2-yl)-2H-indazole-7-carboxylate

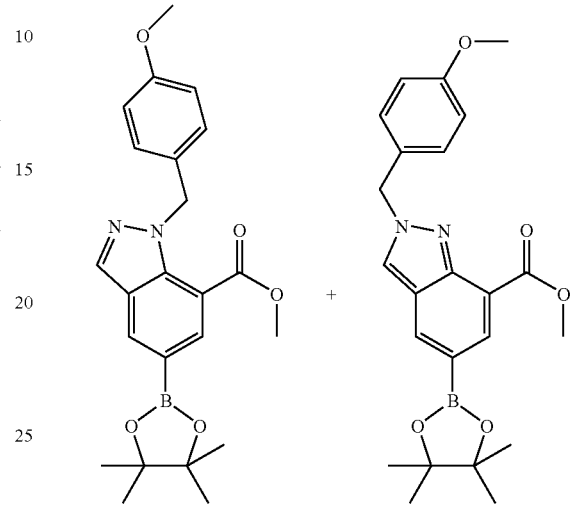

Step 1.

Preparation #11a. Methyl 2-amino-5-bromo-3-iodo-benzoate

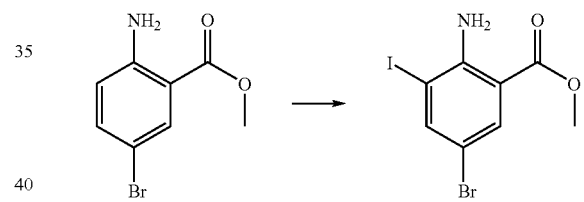

1-Iodo-pyrrolidine-2,5-dione (10.35 g, 46.0 mmol) was added in one portion to a solution of methyl 2-amino-5-bromo-benzoate (10.35 g, 45.0 mmol) in trifluoroacetic acid (90 mL) at ambient temperature. The reaction was stirred for about 1 hour at ambient temperature then concentrated under reduced pressure. The residue was dissolved in $CH_2Cl_2$ (150 mL), washed with saturated $Na_2CO_3$ solution (2×150 mL) and a 10% aqueous solution of $Na_2S_2O_4$ (2×100 mL), dried over anhydrous $MgSO_4$, filtered and concentrated to yield methyl 2-amino-5-bromo-3-iodo-benzoate (15.5 g, 97%) as a yellow solid; RP HPLC (Table 1, Method e) $R_t$=2.45, $^1H$ NMR (DMSO-$d_6$, 400 MHz) δ 3.83 (s, 3H), 7.74 (broad s, 2H), 7.86-7.88 (d, 2H), 8.00-8.02 (d, 1H).

Step 2.

Preparation #11b. Methyl 2-amino-5-bromo-3-methylbenzoate

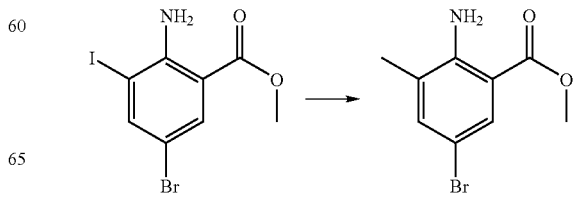

2,4,6-Trimethyl-cyclotriboroxane (6.99 ml, 50.0 mmol) was added to a stirred suspension of methyl 2-amino-5-bromo-3-iodo-benzoate (Preparation #11a, 15.5 g, 43.6 mmol), [1,1'-bis(diphenylphosphino)-ferrocene)dichloropalladium(II) 1:1 complexed with dichloromethane (1.67 g, 2.05 mmol) and cesium carbonate (42.9 g, 132 mmol) in 1,4-dioxane (200 mL) under N$_2$. After about 4 hours at about 90° C. additional 2,4,6-trimethyl-cyclotriboroxane (1.00 ml, 7.15 mmol) was added and the reaction was continued with heating for about 2 more hours. The reaction was cooled, filtered through a short pad of silica gel and concentrated to afford an oil. The crude product was purified by flash chromatography over silica gel using heptane:EtOAc (92:8) as the eluent to yield methyl 2-amino-5-bromo-3-methyl-benzoate (5.9 g, 55%) as a pale yellow solid; RP HPLC (Table 1, Method e) R$_t$=2.72, m/z: (MH)$^+$ 244/246.

Step 3.

Preparation #11c. Methyl 5-bromo-1H-indazole-7-carboxylate

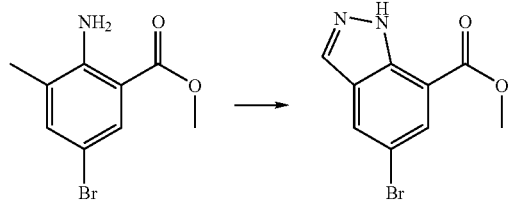

3-Methyl-1-nitrosooxy-butane (3.39 ml, 25.2 mmol) was added to a solution of 2-methyl amino-5-bromo-3-methyl-benzoate (5.38 g, 22.0 mmol) in glacial acetic acid (300 mL) cooled to about 17° C. The reaction was stirred for about 10 minutes at about 17° C. then transferred over about 1 hour to a mixture of acetic acid (60 mL) and potassium acetate (20.0 g, 0.20 mol) held at 60° C. with stirring. The mixture was stirred about 1 hour then cooled to ambient temperature and concentrated under reduced pressure. The residue was dissolved in EtOAc (about 350 mL) and washed with water (3×150 mL) and saturated aqueous NaCl solution (100 mL), then dried over anhydrous MgSO$_4$. The residues were triturated with ether (50 mL), filtered, washed with additional ether (2×10 mL), and dried to yield 5-bromo-1H-indazole-7-carboxylic acid methyl ester (4.42 g, 79%) as a tan solid, RP HPLC (Table 1, Method e) R$_t$=2.43, m/z: (MH)$^+$ 255/257.

Step 4.

Preparation #11d. Methyl 1-(4-methoxy-benzyl)-5-bromo-1H-indazole-7-carboxylate, and, Preparation #12a. Methyl 2-(4-methoxy-benzyl)-5-bromo-2H-indazole-7

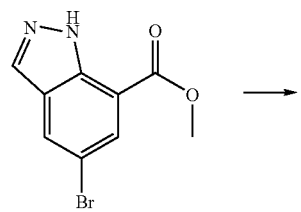

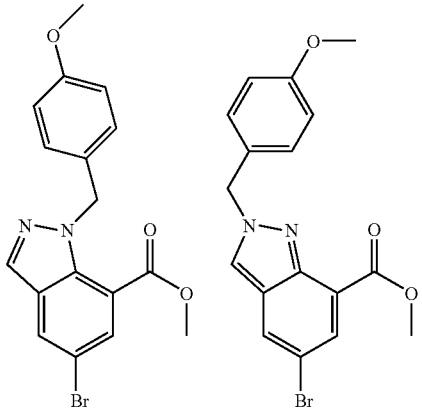

A mixture of methyl 5-bromo-1H-indazole-7-carboxylate (Preparation #11c, 2.60 g, 10.2 mmol), potassium carbonate 3.31 g, 24.0 mmol) and 4-methoxy-benzyl chloride (1.62 ml, 12.0 mmol) in N,N-dimethylformamide (40 mL) was warmed at about 60° C. for about 4 hours. The reaction was filtered, concentrated under reduced pressure and the residue was partitioned between EtOAc (100 mL) and water (50 mL). The layers were separated and the organic layer was washed with water (2×50 mL), dried over anhydrous MgSO$_4$, filtered and concentrated to yield a mixture of methyl 1-(4-methoxy-benzyl)-5-bromo-1H-indazole-7-carboxylate and methyl 2-(4-methoxy-benzyl)-5-2H-indazole-7-carboxylate as an oil (4.07 g, 106%). RP HPLC (Table 1, Method e) R$_t$=2.17, m/z: (MH)$^+$ 244/246, and R$_t$=2.46, m/z: (MH)$^+$ 244/246. The crude product was used without further purification.

Step 5.

Preparation #11. Methyl 1-(4-methoxy-benzyl)-5-(4,4,5,5-tetramethyl-[1,3,2]dioxaborolan-2-yl)-1H-indazole-7-carboxylate Preparation #12. Methyl 2-(4-methoxy-benzyl)-5-(4,4,5,5-tetramethyl-[1,3,2]dioxaborolan-2-yl)-2H-indazole-7-carboxylate

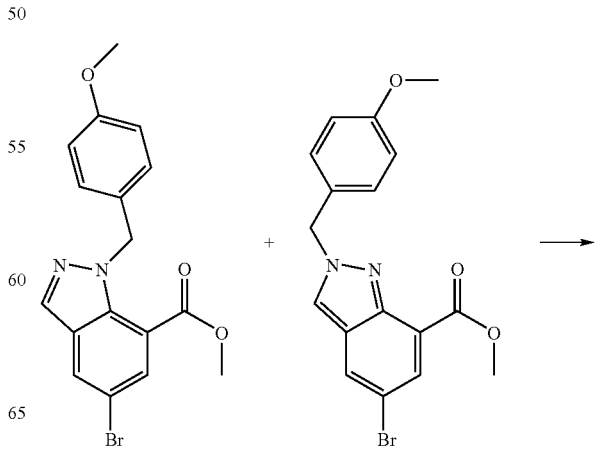

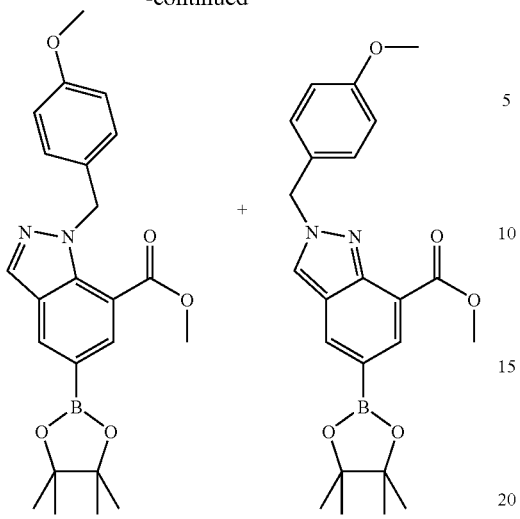

[1,1'-Bis(diphenylphosphino)-ferrocene)dichloropalladium(II) 1:1 complex with dichloromethane (408 mg, 0.50 mmol) was added to a mixture of methyl 1-(4-methoxy-benzyl)-5-bromo-1H-indazole-7-carboxylate and methyl 2-(4-methoxy-benzyl)-5-2H-indazole-7-carboxylate (Preparations #11d and 12a, 3.70 g, 9.87 mmol), 4,4,5,5,4',4',5',5'-octamethyl-[2,2']bi[[1,3,2]dioxaborolanyl] (7.62 g, 30.0 mmol) and potassium acetate (5.88 g, 60.0 mmol) in dimethylformamide (50 mL) under a nitrogen atmosphere. The mixture was sealed and heated at about 80° C. for about 1 hour then cooled to ambient temperature, filtered, and concentrated. The mixture was purified on a silica gel column using CH$_2$Cl$_2$ as the eluent to elute fractions containing the first isomer. These combined fractions were triturated with heptane (about 15 mL), filtered and dried to yield isomer A (2.06 g, 94% purity, 46% yield), RP HPLC (Table 1, Method e) R$_t$=2.50, m/z: (MH)$^+$ 423. The second isomer was eluted using EtOAc and again the fractions were combined, concentrated, and dried to yield isomer B (2.31 g, 55%), RP HPLC (Table 1, Method e) R$_t$=2.24, m/z: (MH)$^+$ 423.

Preparation #13. 5-(5-Amino-1H-pyrrolo[2,3-c]pyridin-3-yl)-1H-indazole-7-carboxylic acid monohydrochloride

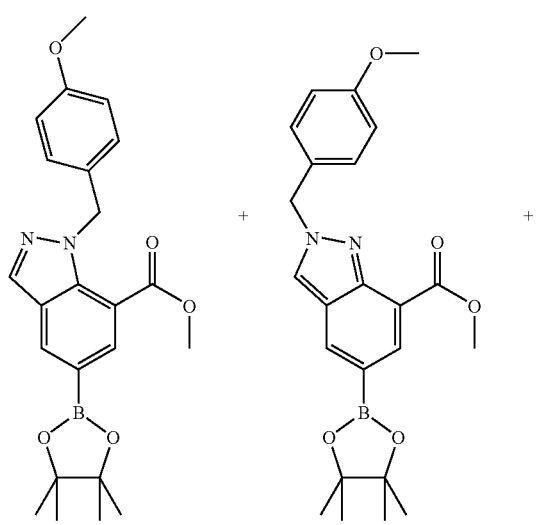

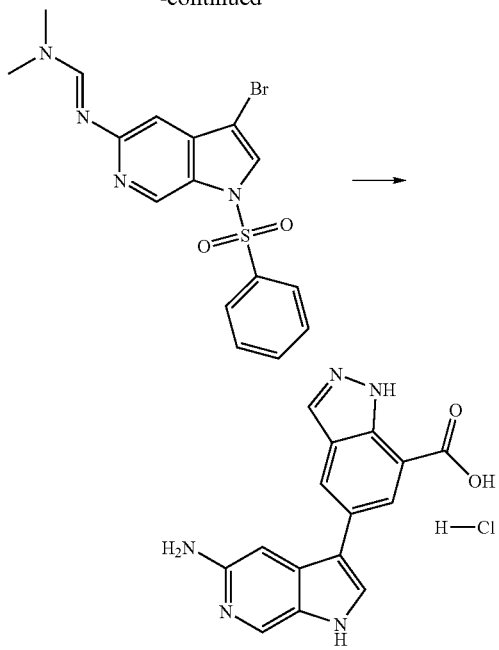

[1,1'-Bis(diphenylphosphino)-ferrocene)dichloropalladium(II) 1:1 complex with dichloromethane (408 mg, 0.50 mmol) was added to a mixture of methyl 5-bromo-1-(4-methoxy-benzyl)-1H-indazole-7-carboxylate ester and methyl 5-bromo-2-(4-methoxy-benzyl)-2H-indazole-7-carboxylate (Preparations #11 and 12, 1:1, 3.99 g, 9.45 mmol), cesium carbonate (9.75 g, 30.0 mmol) and N'-(1-benzenesulfonyl-3-bromo-1H-pyrrolo[2,3-c]pyridin-5-yl)-N,N-dimethyl-formamidine (Preparation #10, 3.85 g, 9.45 mmol) in 1,2-dimethoxyethane (100 mL) and water (25 mL) under an atmosphere of N$_2$. The reaction mixture was heated at about 90° C. for about 4 hours. The reaction was cooled to ambient temperature and the layers separated. The organic layer was filtered through a silica gel pad, eluting with 5% MeOH/EtOAc and the filtrate was concentrated under reduced pressure. The residue was dissolved in trifluoroacetic acid (50 mL) containing triisopropylsilane (2.05 ml, 10.0 mmol) and the mixture was heated in a sealed tube at about 100° C. for about 30 minutes then cooled to ambient temperature and concentrate under reduced pressure. The residue was triturated with ether (100 mL) and the resulting solid was collected by filtration. The solid was then dissolved in methanol (75 mL), treated with aqueous sodium hydroxide (2N, 50 ml, 100 mmol) and heated at reflux for about 6 hours. The reaction was filtered hot, then cooled and acidified with acetic acid to about pH 5.5. The product was filtered off, washed with water (2×10 mL) and dried to yield 5-(5-amino-1H-pyrrolo[2,3-c]pyridin-3-yl)-1H-indazole-7-carboxylic acid (2.60 g, 78%) as the acetate salt. The acetate salt was dissolved in methanol (300 mL) and aqueous HCl (2N, 25 mL) was added. The mixture was concentrated and dried to yield 5-(5-amino-1H-pyrrolo[2,3-c]pyridin-3-yl)-1H-indazole-7-carboxylic acid monohydrochloride (2.35 g, 75%) as a pale yellow solid. RP HPLC (Table 1, Method e) R$_t$=1.31, m/z: (MH)$^+$ 294.

Preparation #14: (7-Benzo[b]thiophen-2-yl-1H-indazol-5-yl)-thiocarbamic acid S-methyl ester

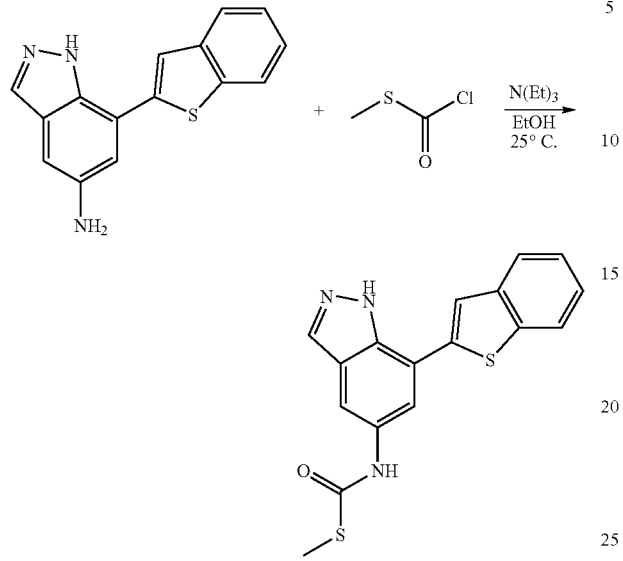

To a solution of 7-benzo[b]thiophen-2-yl-1H-indazol-5-ylamine (Example #F.8.1, 530 mg, 2.0 mmol) and methyl chlorothioformate (0.25 mL, 2.8 mmol) in ethanol (10 mL) was added triethylamine (0.56 mL, 4.0 mmol). The reaction mixture was stirred at ambient temperature for about 16 hours and the resulting solid was collected by filtration, washed with water (3×50 mL), and dried to yield (7-benzo[b]thiophen-2-yl-1H-indazol-5-yl)-thiocarbamic acid S-methyl ester (448 mg, 66%); LC/MS (Table 1, Method e) $R_t$ 2.14 min; m/z: [M−H]⁻ 338.

Preparation #15: 2-(7-Benzo[b]thiophen-2-yl-1H-indazol-5-ylamino)-2-oxalyl chloride

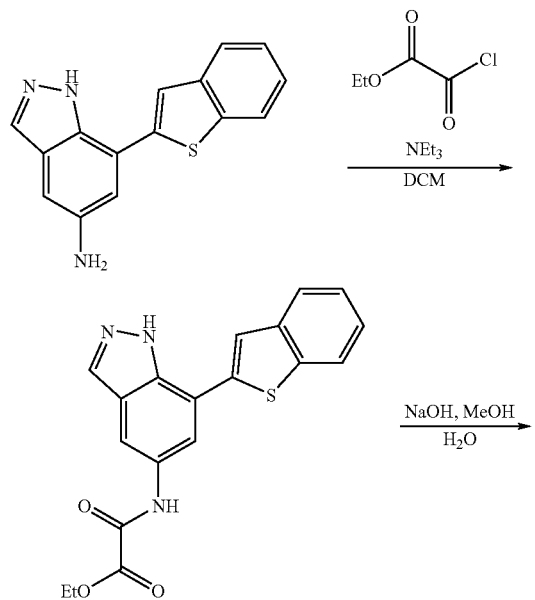

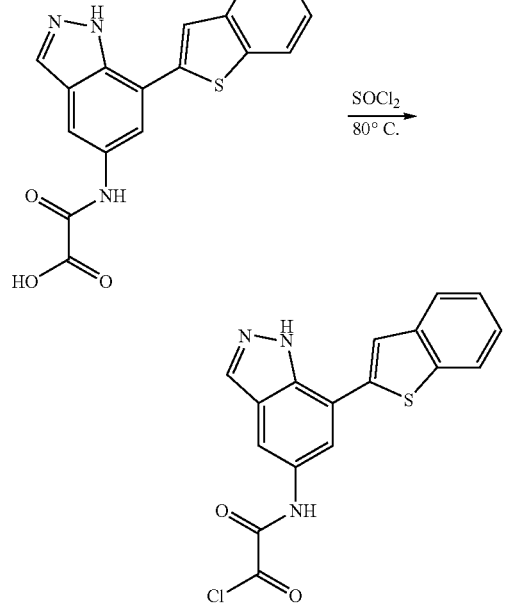

Step 1.
Preparation #15a. Ethyl-N-(7-benzo[b]thiophen-2-yl-1H-indazol-5-yl)-oxamate To a suspension of 7-benzo[b]thiophen-2-yl-1H-indazol-5-ylamine (Example #F.8.1, 151 mg, 0.57 mmol) in dichloromethane (6 mL) was added triethylamine (0.088 mL, 0.63 mmol). The reaction mixture was stirred at about −5° C. for about 10 minutes and ethyl oxalyl chloride (0.064 mL, 0.57 mmol) was added dropwise. The reaction mixture was stirred at about −5° C. for about 90 minutes prior to quenching the reaction with water (about 10 mL). The suspension was extracted with EtOAc (3×50 mL), washed with brine solution (100 mL), and dried over anhydrous magnesium sulfate. The solvent was removed in vacuo and the crude product was purified by flash chromatography over silica gel using heptane:EtOAc (30:70) as the eluent to yield ethyl-N-(7-benzo[b]thiophen-2-yl-1H-indazol-5-yl)-oxamate (169 mg, 81%) as a pale yellow solid, RP HPLC (Table 1, Method e) $R_t$=2.03, m/z: (M−H)⁻ 364.

Step 2.
Preparation #15b. N-(7-benzo[b]thiophen-2-yl-1H-indazol-5-yl)-oxamate

Sodium hydroxide solution (2% aqueous solution, 2 mL) was added to a suspension of ethyl-N-(7-benzo[b]thiophen-2-yl-1H-indazol-5-yl)-oxamate (Preparation #15a, 83 mg, 0.23 mmol) in methanol (3 mL) and the reaction mixture was refluxed at 100° C. for about 1 hour. The solvent was removed in vacuo, and water was added to the residue. The aqueous layer was acidified using aqueous hydrochloric acid solution (1 N) and the resulting solid was collected by filtration, washed with water (3×5 mL), and dried to yield the N-(7-benzo[b]thiophen-2-yl-1H-indazol-5-yl)-oxamate (76 mg, 99%); LC/MS (Table 1, Method e) $R_t$ 0.89 min; m/z: [M−H]⁻ 336.

Step 3.
Preparation #15: 2-(7-Benzo[b]thiophen-2-yl-1H-indazol-5-ylamino)-2-oxalyl chloride A mixture of N-(7-benzo[b]thiophen-2-yl-1H-indazol-5-yl)-oxamate (Preparation #15b, 30 mg, 0.089 mmol) and thionyl chloride (0.5 mL, 6.7 mmol) was stirred at about 80°

C. for about 1 hour. The excess thionyl chloride was removed in vacuo and the 2-(7-benzo[b]thiophen-2-yl-1H-indazol-5-ylamino)-2-oxalyl chloride (31 mg, 98%) was used without further purification.

Preparation #16. 5-Pyridin-3-yl-3-(1H-pyrrol-2-yl)-1H-indazole

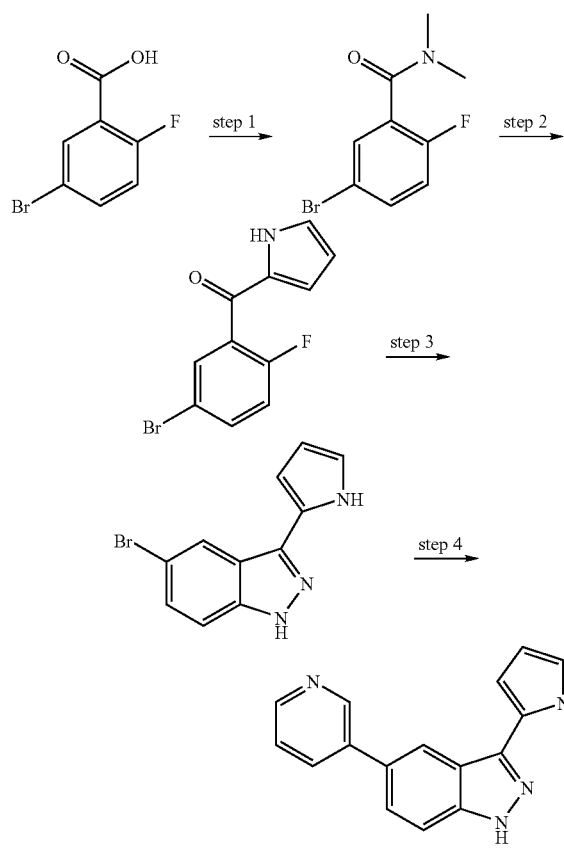

Step 1.
Preparation #16a. 5-Bromo-2-fluoro-N,N-dimethylbenzamide

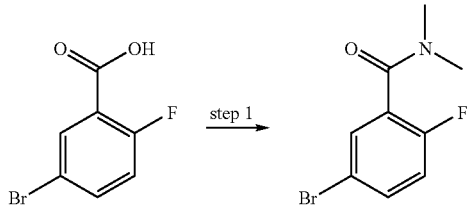

Thionyl chloride (19.8 mL, 228 mmol) was added to a mixture of 5-bromo-2-fluoro-benzoic acid (Aldrich, 5.0 g, 22.8 mmol) in toluene (45 mL). The resulting mixture was heated at reflux for about 3 hours, cooled to ambient temperature and the solvents were removed under reduced pressure. The residue was stirred in THF (40 mL) at about 0° C. and then the reaction was treated with gaseous dimethylamine. The mixture was stirred for about 15 min, concentrated, dissolved in EtOAc (100 mL), washed with 2N HCl solution (2×50 mL), 2N NaOH solution (2×50 mL), and finally with saturated NaCl solution (50 mL). The organic layer was dried over anhydrous MgSO₄, filtered, concentrated, and dried to yield 5-bromo-2-fluoro-N,N-dimethyl-benzamide (4.82 g, 86%) of as an oil, RP HPLC (Table 1, Method e) $R_t$=2.33, m/z: (MH)⁺ 246/248

Step 2.
Preparation #16b. (5-Bromo-2-fluoro-phenyl)-(1H-pyrrol-2-yl)-methanone

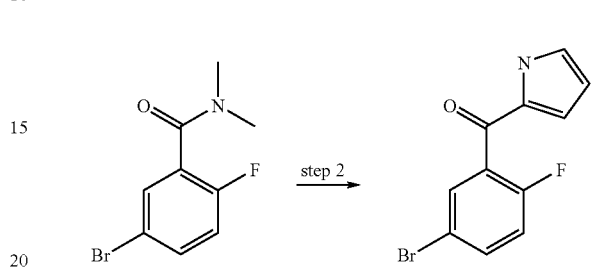

5-Bromo-2-fluoro-N,N-dimethyl-benzamide (Preparation #16a, 4.75 g, 19.3 mmol) and phosphorus oxychloride (5.46 ml, 40.5 mmol) were combined and warmed at about 35° C. for about 28 hours. The mixture was cooled to ambient temperature and a mixture of pyrrole (1.38 mL, 20.0 mmol) in CH₂Cl₂ (40 mL) was added and the reaction was stirred for about 3 hours at ambient temperature. The reaction was quenched by cautious addition of aqueous Na₂CO₃ solution (10% w/v, ~150 mL) and the resulting mixture was heated at reflux for about 2 hours. The product was extracted with CH₂Cl₂ (3×50 mL), dried over anhydrous MgSO₄, filtered and concentrated. The crude product was further purified on silica gel using EtOAc:heptane (1:1) as the eluent to yield 5-bromo-2-fluoro-N,N-dimethyl-benzamide (2.57 g, 50%) as an oil which solidifies on standing. RP HPLC (Table 1, Method e) $R_t$=2.57; m/z: (M–H)⁻ 266/268

Step 3.
Preparation #16c. 5-Bromo-3-(1H-pyrrol-2-yl)-1H-indazole

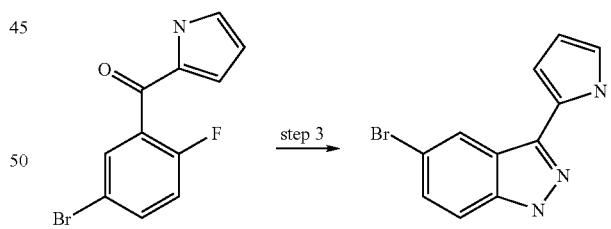

A slurry containing (5-bromo-2-fluoro-phenyl)-(1H-pyrrol-2-yl)-methanone (Preparation #16b, 2.40 g, 8.96 mmol) and hydrazine hydrate (35 mL) was sealed and heated by microwave iat about 150° C. for about 1 hour. The reaction was cooled to ambient temperature and diluted with water (150 mL). The product was extracted with EtOAc (150 mL), washed with 2N HCl solution (50 mL), saturated NaHCO₃ solution (50 mL) and finally a saturated NaCl solution. The EtOAc layer was dried over anhydrous MgSO₄, filtered and concentrated under reduced pressure to yield 5-bromo-3-(1H-pyrrol-2-yl)-1H-indazole (2.38 g, 99%) as an oil. RP HPLC (Table 1, Method e) $R_t$=2.95; m/z: (MH)⁺ 262/264

Step 4.

Preparation #16. 5-Pyridin-3-yl-3-(1H-pyrrol-2-yl)-1H-indazole

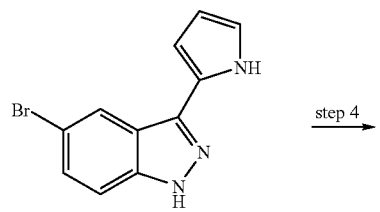

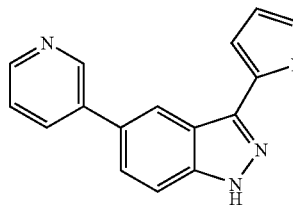

[1,1′-Bis(diphenylphosphino)-ferrocene)dichloropalladium(II) 1:1 complex with dichloromethane (40.8 mg, 0.05 mmol) was added to a mixture containing 5-bromo-3-(1H-pyrrol-2-yl)-1H-indazole (Preparation #16c, 105 mg, 0.40 mmol), aqueous pyridine-3-boronic acid (1M, 1.0 mL), and $Cs_2CO_3$ (391 mg, 1.20 mmol) in DMF (2.0 mL) under a nitrogen atmosphere was added and the mixture was purged with $N_2$ again, then heated at reflux for about 3 days. The reaction was cooled to ambient temperature and the organic layer was filtered through silica gel and concentrated under reduced pressure. The residue was further purified by preparative HPLC (Thermo Hypersil-Keystone 250×21.2 mm 8μ Hypersil® HS C18 column; 5% $CH_3CN$/50 mM aqueous ammonium acetate hold for 5 min; 5-50% $CH_3CN$/50 mM aqueous ammonium acetate over 20 min; 50-100% $CH_3CN$/50 mM aqueous ammonium acetate over 1 min; hold at 100% $CH_3CN$ for 5 minutes, 21 mL/min). Product fractions were combined and concentrated to remove organic solvents and the lyophilized to yield 5-pyridin-3-yl-3-(1H-pyrrol-2-yl)-1H-indazole (44 mg, 42%) as an off-white powder. RP HPLC (Table 1, Method e) $R_t$=2.23; m/z: (MH)+ 261.

Preparation #17. 5-Pyridin-3-yl-1H-indazole

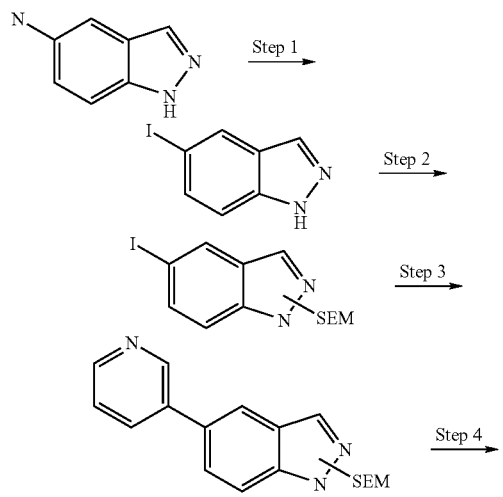

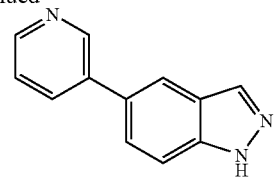

Step 1.

Preparation #17a. 5-Iodo-1H-indazole

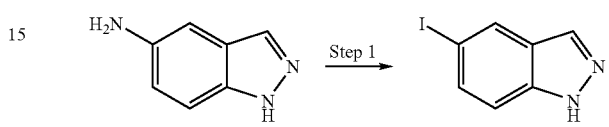

A solution of $NaNO_2$ (6.24 g, 90.0 mmol) in water (36 mL) was added dropwise to a mixture of 1H-indazol-5-ylamine (Aldrich, 12.0 g, 90.1 mmol), water (36 mL), acetonitrile (12 mL) and concentrated HCl (14.4 mL) that was pre-cooled to about −10° C., maintaining the reaction temperature below about −5° C. during the addition. The mixture was stirred for about 10 minutes at about −5° C. after the addition was complete then a solution of KI (15.0 g, 90.0 mmol) in cold water (30 mL) was added, followed by cold acetonitrile (50 mL). The cold bath was removed and the reaction was allowed to warm to ambient temperature with stirring overnight. The organic solvent was removed under reduced pressure and the solid product was filtered off, then re-dissolved in acetonitrile (125 mL) and stirred in the presence of charcoal (about 5 g) for about 30 min. The mixture was filtered and concentrated to yield 5-iodo-1H-indazole (13.1 g, 60%) as a light brown solid. RP HPLC (Table 1, Method e) $R_t$=2.38; m/z: (MH)+ 245.

Step 2.

Preparation #17b. 5-Iodo-1-(2-trimethylsilanyl-ethoxymethyl)-1H-indazole

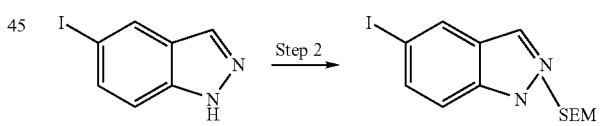

1H-Indazol-5-ylamine (Preparation #17a, 12.9 g, 52.9 mmol) was dissolved in $CHCl_3$ (66 mL), cooled to about 0° C. and treated with a solution of KOH (66.0 g, 1.18 mol) in water (66 mL) and tetrabutylammonium bromide (175 mg, 0.54 mmol). (2-chloromethoxy-ethyl)-trimethyl-silane (10.5 ml, 59.3 mmol) was added over about 5 minutes at about 0° C. with vigorous stirring. The reaction was then stirred for about 30 minutes at about 0° C., diluted with water (100 mL) and extracted with $CHCl_3$ (3×100 mL). The $CHCl_3$ layer was dried over anhydrous $MgSO_4$, filtered, and concentrated to give an oil. The crude product was further purified over silica gel using EtOAc:heptane (95:5) as the eluent to yield 5-iodo-1-(2-trimethylsilanyl-ethoxymethyl)-1H-indazole (11.2 g, 56%) as an oil. RP HPLC (Table 1, Method e) $R_t$=3.04; NMR ($d_6$-DMSO, 400 MHz) δ −0.12 (s, 9H), 0.77-0.80 (t, 2H), 3.47-3.51 (t, 2H), 5.74 (s, 2H), 7.60-7.63 (d, 1H), 7.67-7.70 (d,d 1H), 8.09-8.10 (d, 1H), 8.21-8.22 (m, 1H).

Step 3.
Preparation #17c. 5-Pyridin-3-yl-1-(2-trimethylsilanyl-ethoxymethyl)-1H-indazole

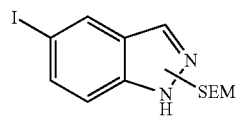

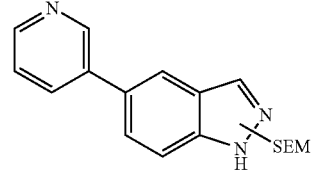

[1,1'-Bis(diphenylphosphino)-ferrocene)dichloropalladium(II) 1:1 complex with dichloromethane (204 mg, 0.25 mmol) was added to a mixture of 5-iodo-1-(2-trimethylsilanyl-ethoxymethyl)-1H-indazole (Preparation #17a, 1.87 g, 5.00 mmol), pyridine-3-boronic acid (737 mg, 6.00 mmol), and Cs$_2$CO$_3$ (4.89 g, 15.0 mmol) in 1,2-dimethoxy-ethane (16 mL) and water (3.2 mL) under a nitrogen atmosphere. The reaction was heated at about 100° C. overnight, cooled, concentrated and extracted with CH$_2$Cl$_2$ (about 30 mL). The extracts were adsorbed onto silica and purified over a silica gel column eluting first with heptane:EtOAc (85:15) and then with heptane:EtOAc (3:2) to yield 5-pyridin-3-yl-1-(2-trimethylsilanyl-ethoxymethyl)-1H-indazole (857 mg, 53%) as an oil. RP HPLC (Table 1, Method e) R$_t$=3.04, m/z: (MH)$^+$ 326.

Step 4.
Preparation #17. 5-Pyridin-3-yl-1H-indazole

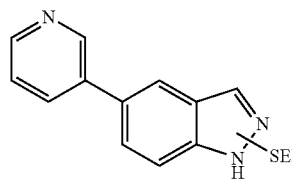

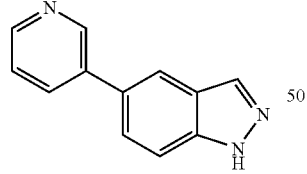

5-Pyridin-3-yl-1-(2-trimethylsilanyl-ethoxymethyl)-1H-indazole (Preparation #17c, 100 mg, 0.31 mmol) and ethylenediamine (133 μL, 2.00 mmol) were dissolved in 1M tetrabutylammonium fluoride in THF (4.0 mL) and the mixture was heated at reflux for about 2 hours. The reactions was cooled to ambient temperature and concentrated under reduced pressure. The residue was dissolved in EtOAc (25 mL), washed with water (2×10 mL) and concentrated under reduced pressure. The crude product was further purified by reverse phase preparative HPLC (Thermo Hypersil-Keystone 250×21.2 mm 8μ Hypersil® HS C18 column; 5% CH$_3$CN/50 mM aqueous ammonium acetate hold for 5 min; 5-50% CH$_3$CN/50 mM aqueous ammonium acetate over 20 min; 50-100% CH$_3$CN/50 mM aqueous ammonium acetate over 1 min; hold at 100% CH$_3$CN for 5 minutes, 21 mL/min) to yield 5-pyridin-3-yl-1H-indazole (61 mg, 64%) as an off-white solid. RP HPLC (Table 1, Method e) R$_t$=1.65, m/z: (MH)$^+$ 196.

Preparation #18. Indole-1,4-dicarboxylic acid 1-tert-butyl ester 4-methyl ester

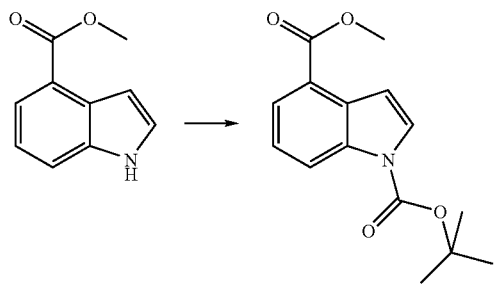

Di-tert-butyldicarbonate (0.068 g, 0.31 mmol) was added to a solution of 1H-indole-4-carboxylic acid methyl ester (Aldrich, 0.050 g, 28 mmol) and 4-dimethylaminopyridine (0.7 mg, 0.006 mmol) in methylene chloride (1.0 mL, 0.016 mol). After 45 minutes, the mixture was quenched and acidified with 1N HCl to about a pH 4. Methylene chloride was added and the layers were separated. The aqueous layer was further extracted with methylene chloride and the combined organics were dried over anhydrous MgSO$_4$ and concentrated to yield indole-1,4-dicarboxylic acid 1-tert-butyl ester 4-methyl ester (0.072 g, 92% yield); (DMSO-d$_6$, 400 MHz) δ 8.37 (d, 1H), 7.91 (d, 1H), 7.86 (d, 1H), 7.46 (t, 1H), 7.21 (d, 1H), 3.92 (s, 3H), 1.65 (s, 10H); RP-HPLC (Table 1, Method e) R$_t$=2.7, m/z: (M+H)$^+$ 276.3.

Preparation #19. Indole-1,7-dicarboxylic acid 1-tert-butyl ester 7-methyl ester

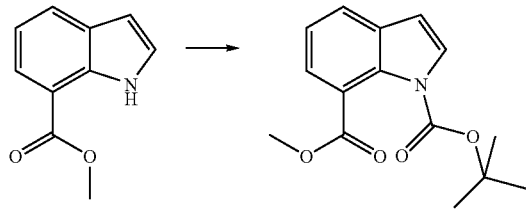

Di-tert-butyldicarbonate (16 g, 0.071 mol) was added to a solution of 1H-indole-7-carboxylic acid methyl ester (Acros chemicals, 5.0 g, 0.028 mol) and 4-dimethylaminopyridine (0.3 g, 0.003 mol) in methylene chloride (100 mL). The mixture was heated at about 45° C. for about 16 hours. The mixture was quenched and acidified with 1N HCl to about a pH 4. Methylene chloride was added and the layers were separated. The aqueous layer was further extracted with methylene chloride and the combined organics were dried over anhydrous MgSO$_4$ and concentrated to yield indole-1,7-dicarboxylic acid 1-tert-butyl ester 7-methyl ester (9.5 g, 97% yield); RP-HPLC (Table 1, Method e) R$_t$=2.5, m/z: (M+H)$^+$ 276.2.

Preparation #20. Indole-2-boronic-1,7-dicarboxylic acid 1-tert-butyl ester 7-methyl ester

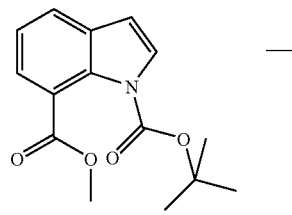  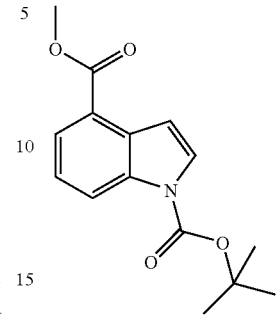

To a mixture of indole-1,7-dicarboxylic acid 1-tert-butyl ester 7-methyl ester (Preparation #19, 9.5 g, 0.028 mol) in tetrahydrofuran (39 mL, 0.48 mol) was added triisopropyl borate (9.5 mL, 0.041 mol). The heterogeneous mixture was cooled to about 0-5° C. and lithium diisopropylamide in tetrahydrofuran (2.0M, 25 mL) was added slowly. After about 2 hours the mixture was quenched with 1N HCl and the layers were separated. The aqueous layer was washed with DCM and the combined organics were dried over anhydrous MgSO₄ and concentrated. Trituration in ether/heptane gave 3 crops of indole-2-boronic-1,7-dicarboxylic acid 1-tert-butyl ester 7-methyl ester (4.10 g, 1.6 g and 3.0 g respectively) as a yellow solid; RP-HPLC (Table 1, Method e) $R_t$ 1.7 min; m/z (M+H)⁺ 378.4.

Preparation #21. Indole-2-boronic-1,4-dicarboxylic acid 1-tert-butyl ester 4-methyl ester

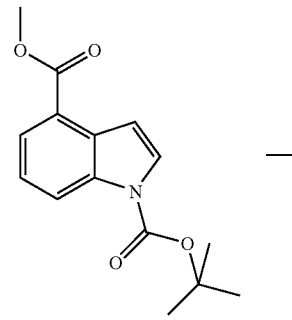 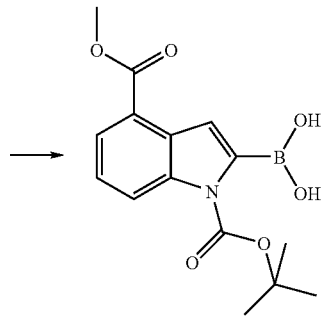

To a solution of indole-1,4-dicarboxylic acid 1-tert-butyl ester 4-methyl ester (Preparation #18, 0.207 g, 0.752 mmol) in THF (1.1 mL) was added triisopropyl borate (260 µL, 0.0011 mol). The solution was cooled to about 0-5° C. and lithium diisopropylamide in tetrahydrofuran (2.0M, 600 µL) was added slowly over about 1 hour. After about 30 minutes, the mixture was quenched with 1N HCl, and the layers were separated. The aqueous layer was washed with DCM and the combined organics were dried over anhydrous MgSO₄ and concentrated. The mixture was triturated in heptane (50 mL) and ether (5 mL) and filtered to yield indole-2-boronic-1,4-dicarboxylic acid 1-tert-butyl ester 4-methyl ester (175 mg, 51% yield): RP-HPLC (Table 1, Method e) $R_t$ 1.84 min; m/z 377.9 (M–H)⁻.

Preparation #22. 4-Diisopropylcarbamoyl-indole-2-boronic-1-carboxylic acid 1-tert-butyl ester

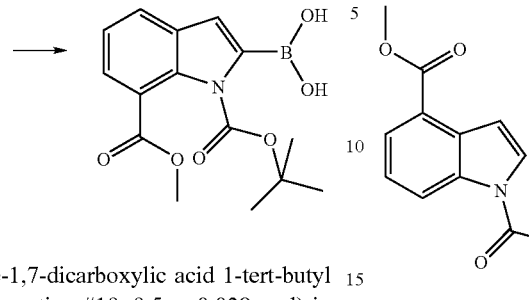

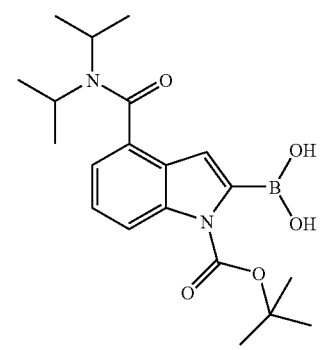

Triisopropyl borate (870 µL, 0.0038 mol) was added to a solution of indole-1,4-dicarboxylic acid 1-tert-butyl ester 4-methyl ester (Preparation #18, 0.70 g, 0.0025 mol) in THF (36 mL). The solution was cooled to about 0-5° C. and lithium diisopropylamide in tetrahydrofuran (2 M, 2.8 mL) was added slowly over about 1 hour. After about another 1.5 hours, the mixture was quenched with 1N HCl, and the layers were separated. The aqueous layer was extracted with DCM, and the combined organics were dried, concentrated, triturated in heptane (50 mL) and ether (5 mL) and filtered. The material was further purified by flash column chromatography using DCM/MeOH (98:2) as the eluent to afford 4-diisopropylcarbamoyl-indole-2-boronic-1-carboxylic acid 1-tert-butyl ester (20 mg, 2% yield): RP-HPLC (Table 1, Method e) $R_t$ 2.0 min; m/z 389.4 (M+H)⁺.

Example #8

4-(7-Benzo[b]thiophen-2-yl-1H-indazol-5-ylamino)-pyrimidin-2-ol

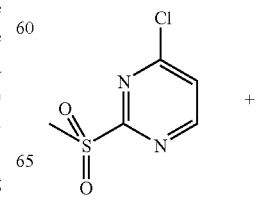 +

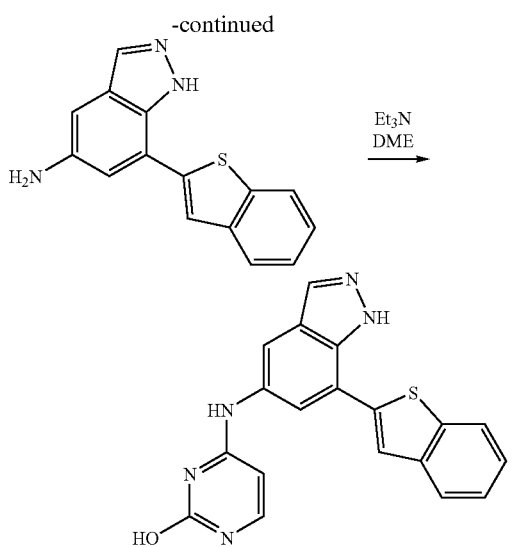

To a mixture of 4-chloro-2-methanesulfonyl-pyrimidine (Preparation #1, 1.35 g, 7.0 mmol) in DME (10 mL) was added a mixture of 7-benzo[b]thiophen-2-yl-1H-indazol-5-ylamine (Example #F.8.1, 1.03 g, 3.9 mmol) and triethylamine (0.76 mL, 5.4 mmol) in DME (70 mL). After about 16 hours at ambient temperature the mixture was filtered, and the solid was purified by reverse phase preparative HPLC (Thermo Hypersil-Keystone 250×21.2 mm 8μ Hypersil® HS C18 column; 5% CH$_3$CN/50 mM aqueous ammonium acetate hold for 5 min; 5-50% CH$_3$CN/50 mM aqueous ammonium acetate over 20 min; 50-100% CH$_3$CN/50 mM aqueous ammonium acetate over 1 min; hold at 100% CH$_3$CN for 5 minutes, 21 mL/min) to yield 4-(7-Benzo[b]thiophen-2-yl-1H-indazol-5-ylamino)-pyrimidin-2-ol (2 mg, 0.006 mmol, 0.1% yield): LC/MS R$_t$ (Method e) 1.3 min; m/z (M–H)⁻ 358.3.

Example #9

{2-[5-(2-Amino-pyrimidin-4-ylamino)-1H-indazol-7-yl]-1H-indol-7-yl}-methanol

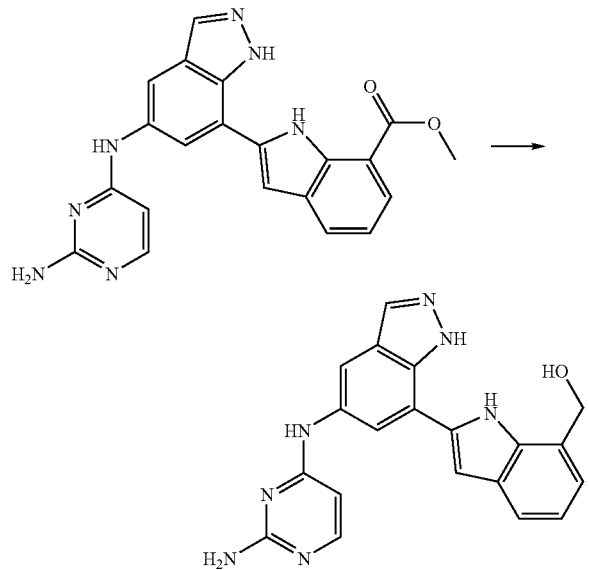

2-[5-(2-Amino-pyrimidin-4-ylamino)-1H-indazol-7-yl]-1H-indole-7-carboxylic acid methyl ester (Preparation #F.8.1, 0.100 g, 0.000250 mol) was added to a solution of lithium aluminum hydride in tetrahydrofuran (1.0M, 1.0 mL) at about 0° C. in 3 portions. Additional THF (1.0 mL) was added after about 10 min., and after about 40 min, the mixture was allowed to warm to ambient temperature. After about a further 60 min, lithium aluminum hydride in THF (1.0M, 1 mL) was added. About 16 hours later, the mixture was quenched with water and neutralized with a saturated aqueous solution of ammonium chloride. The mixture was diluted with EtOAc, and the layers were separated. The aqueous layer was further extracted with EtOAc, and the combined organics were dried over anhydrous MgSO$_4$ and concentrated to yield {2-[5-(2-amino-pyrimidin-4-ylamino)-1H-indazol-7-yl]-1H-indol-7-yl}-methanol (28 mg, 30% yield); LC/MS R$_t$ (Method e) 0.8 min; m/z (M–H)⁻ 370.5.

Example #10

2-[5-(2-Amino-pyrimidin-4-ylamino)-1H-indazol-7-yl]-1H-indole-7-carboxylic acid amide

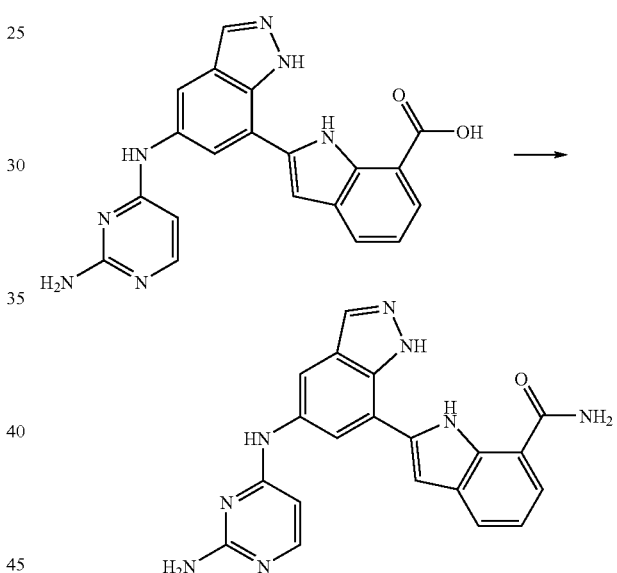

A solution of 2-[5-(2-amino-pyrimidin-4-ylamino)-1H-indazol-7-yl]-1H-indole-7-carboxylic acid (Example #F.5.11, 0.100 g, 0.000259 mol) and N,N-carbonyldiimidazole (0.0842 g, 0.000519 mol) in N,N-dimethylformamide (2.5 mL, 0.032 mol) was heated at about 55° C. for about 45 min. The mixture was cooled with an ice bath and treated with ammonia gas for about 15 min at about 0° C. The mixture was sealed and allowed to warm to ambient temperature. After about 1 hour the mixture was opened to atmosphere, and a 1.2 mL portion of the mixture was purified by reverse phase preparative HPLC (Thermo Hypersil-Keystone 250×21.2 mm 8μ Hypersil® HS C18 column; 5% CH$_3$CN/50 mM aqueous ammonium acetate hold for 5 min; 5-50% CH$_3$CN/50 mM aqueous ammonium acetate over 20 min; 50-100% CH$_3$CN/50 mM aqueous ammonium acetate over 1 min; hold at 100% CH$_3$CN for 5 minutes, 21 mL/min) then filtered to remove the remaining acid. The filtrate was then lyophilized to yield 2-[5-(2-amino-pyrimidin-4-ylamino)-1H-indazol-7-yl]-1H-indole-7-carboxylic acid amide (2 mg, 2% yield): LC/MS R$_t$ (Method e) 0.7 min; m/z (M+H)⁺ 385.4.

Preparation #22a. 5-Bromo-7-iodo-1H-indazole

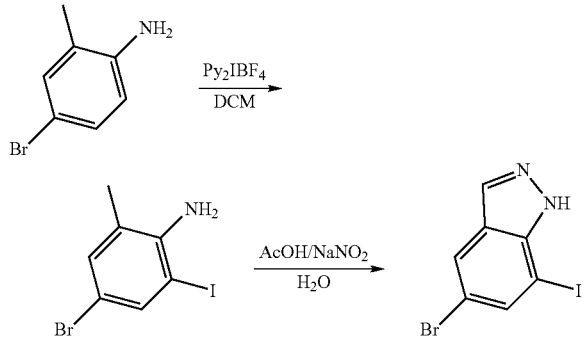

A 1 L round bottom flask equipped with a stir bar was charged with 4-bromo-2-methylaniline (Aldrich, 24.3 g, 0.130 mmol) and dichloromethane (250 mL). bis(pyridine)iodonium(I)tetrafluoroborate (50.0 g, 0.13 mmol) was added in four portions over approximately 10 minutes. The mixture was stirred for about 30 min at ambient temperature then two additional portions of the bis(pyridine)iodonium(I)tetrafluoroborate (2.5 g each) were added and the reaction was continued for about 1 h. Water (150 mL) was added and after stirring for about 10 minutes the mixture was transferred to a separatory funnel and the layers separated. The organic solution was then washed with saturated aqueous Na$_2$S$_2$O$_3$ (100 mL) then water (50 mL). The organic solution was dried over anhydrous magnesium sulfate then filtered and evaporated to give an oil (51.4 g) which was applied to a silica gel column (400 g) and eluted with heptane/dichloromethane/ethyl acetate (12:7:1) to give 4-bromo-2-iodo-6-methyl-phenylamine (31.08 g, 76.6%) as a dark solid.

4-bromo-2-iodo-6-methyl-phenylamine (31.08 g, 99.6 mmol) was dissolved in glacial acetic acid (400 mL) in a 1 L round bottom flask equipped with a stir bar. The flask was then charged in one portion with sodium nitrite (7.56 g, 109.6 mmol) dissolved in water (18.7 mL). The mixture was stirred for about 15 minutes then the solvents were removed by evaporation on a rotovap at a bath temperature of about 35° C. The residue was stirred with water (200 mL) for 15 minutes and the resulting solid was collected by filtration and dried to yield 5-bromo-7-iodo-1H-indazole (30.6 g, 95%) as a brownish-tan solid; (DMSO-d$_6$, 400 MHz) δ 13.6 (bs, 1H), 8.24 (s, 1H), 8.04 (d, J=1.54 Hz, 1H), and 7.88 (d, J=1.54 Hz, 1H); RP-HPLC (Table 1, Method e) R$_t$=3.63 min; m/z: (M−H)$^-$ 322.8.

Preparation #22b: N,N-Dimethyl-1-[5-(4,4,5,5-tetramethyl-1,3,2-dioxaborolan-2-yl)-1H-indol-3-yl]methanamine

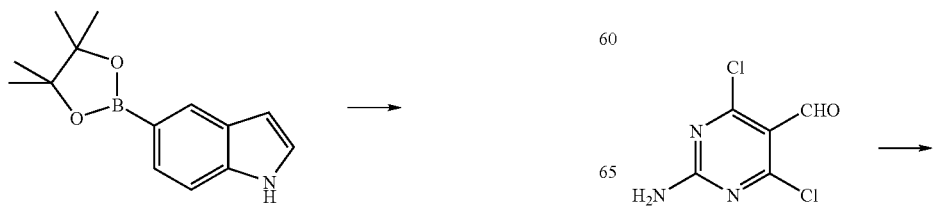

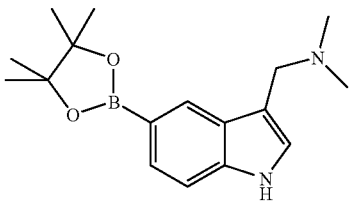

To a suspension of Eschenmoser's salt (0.91 g, 4.9 mmol) in CH$_3$CN (3 mL) and HOAc (1.5 mL) at rt was added a solution of 5-(4,4,5,5-tetramethyl-[1,3,2]dioxaborolan-2-yl)-1H-indole (1.0 g, 4.1 mmol) in CH$_3$CN (3 mL) dropwise over about 10 min. After about 2 hours, the reaction was quenched with saturated aqueous NaHCO$_3$ and extracted with CH$_2$Cl$_2$ (3×15 mL). The combined organic layers were washed with brine, dried over Na$_2$SO$_4$, decanted, and concentrated to give crude N,N-Dimethyl-1-[5-(4,4,5,5-tetramethyl-1,3,2-dioxaborolan-2-yl)-1H-indol-3-yl]methanamine (0.60 g, 50%); RP-HPLC (Table 1, Method g) R$_t$ 1.39 min; $^1$H NMR (d$_6$-DMSO, 400 MHz) δ11.26 (br s, 1H), 8.07 (s, 1H), 7.44 (d, J=8.2 Hz, 1H), 7.37 (m, 2H), 3.92 (s, 2H), 2.40 (s, 6H), 1.31 (s, 12H).

Preparation #22c: Thieno[2,3-b]pyridin-2-ylboronic acid.

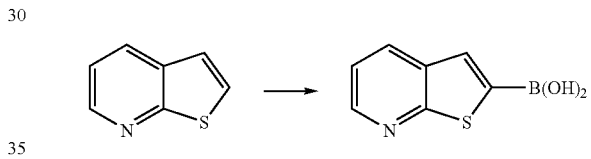

To a solution of thieno[2,3-b]pyridine (0.50 g, 3.7 mmol) in THF (25 mL) at about −78° C. was added n-BuLi (1.6 M in hexane, 2.5 mL, 4.1 mmol) dropwise over about 10 min. After about 45 min, added triisopropyl borate (0.93 mL, 4.1 mol). Stirred for about 1 hour at about −78° C. then at about 0° C. for about 30 min. 10% aqueous HCl (10 mL) was added and the ice bath was removed. After about 30 min, EtOAc (30 mL) was added. The reaction mixture was filtered to remove a precipitate that was washed with additional water and EtOAc. The combined layers were separated and the aqueous layer was extracted with additional EtOAc (2×30 mL). The combined organic layers were washed with brine, dried over anhydrous Na$_2$SO$_4$, decanted, and concentrated to get a solid that was triturated with EtOAc and heptane then filtered to give thieno[2,3-b]pyridin-2-ylboronic acid (0.043 g, 6%); RP-HPLC (Table 1, Method g) R$_t$ 1.67 min, m/z (ESI+) 180.1 (M+H)$^+$.

Preparation #22d: 2-Amino-4-chloro-thieno[2,3-d]pyrimidine-6-carboxylic acid methyl ester

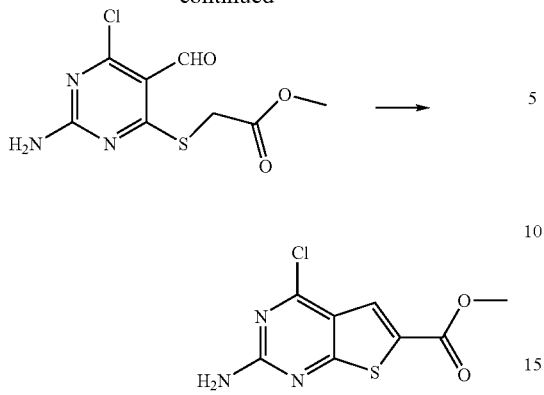

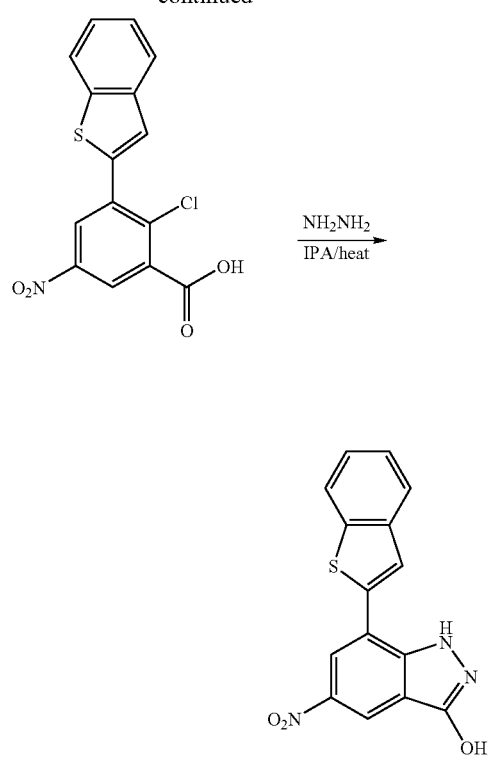

Step 1.

Preparation #22e. (2-amino-6-chloro-5-formyl-pyrimidin-4-ylsulfanyl)-acetic acid methyl ester To a mixture of 2-amino-4,6-dichloro-5-pyrimidinecarbaldehyde (Apin, 2.00 g, 10.4 mmol) in dioxane (20 mL) was added triethylamine (1.60 mL, 11.5 mmol) and methyl thioglycolate (1.90 mL, 21.2 mmol). After about 3 hours, the reaction mixture was diluted with water (30 mL) and then filtered, washed with additional water to give (2-amino-6-chloro-5-formyl-pyrimidin-4-ylsulfanyl)-acetic acid methyl ester (1.801 g, 66%) as a yellow solid; RP-HPLC (Table 1, Method a) $R_t$ 1.85 min, m/z (ESI+) 262.0 (M+H)$^+$.

Step 2.

Preparation #22d: 2-Amino-4-chloro-thieno[2,3-d]pyrimidine-6-carboxylic acid methyl ester To a mixture of (2-amino-6-chloro-5-formyl-pyrimidin-4-ylsulfanyl)-acetic acid methyl ester (Preparation #22e, 0.20 g, 0.76 mmol) in dioxane (7.6 mL) was added $K_2CO_3$ (0.21 g, 1.5 mmol). The resulting mixture was heated at about 100° C. overnight, cooled to room temperature and water (1 mL) added to dissolve base. The remaining solid was filtered and washed with MeOH to give 2-amino-4-chloro-thieno[2,3-d]pyrimidine-6-carboxylic acid methyl ester (0.16 g, 84%) as a pale yellow solid; RP-HPLC (Table 1, Method a) $R_t$ 2.38 min; $^1$H NMR ($d_6$-DMSO, 400 MHz) δ 7.82 (s, 1H), 7.72 (br s, 2H), 3.86 (s, 3H).

Preparation #50. 7-Benzo[b]thiophen-2-yl-5-nitro-1H-indazol-3-ol

A mixture of 3-Benzo[b]thiophen-2-yl-2-chloro-5-nitro-benzoic acid (0.11 g, 0.33 mmol), hydrazine (0.35 mL) and isopropyl alcohol (3 mL) was heated to about 90° C. for about 1 hour. The mixture was cooled then the solvents were evaporated under reduced pressure. The residue was treated with 6N aqueous hydrochloric acid (5 mL) the mixture was extracted with ethyl acetate (3×30 mL). The organic extracts were combined then concentrated to give 7-Benzo[b]thiophen-2-yl-5-nitro-1H-indazol-3-ol RP-HPLC (Table 1, Method e) Rt 1.41 min; m/z: (M−H)$^-$ 310.24.

Example #51

2-(7-Bromo-1H-indazol-5-ylamino)-2-methyl-propan-1-ol

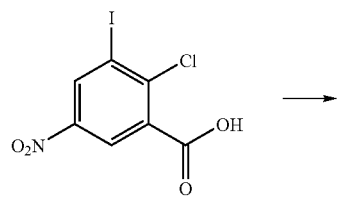

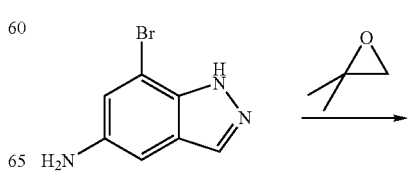

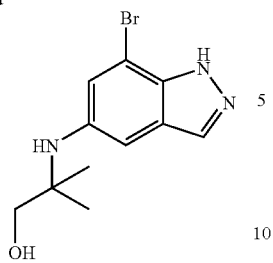

To a solution of 2,2-dimethyl-oxazine (0.100 mL, 1.13 mmol) in THF (5.0 mL) was added 7-bromo-1H-indazol-5-ylamine (Preparation #6, 0.100 g, 0.472 mmol) and samarium chloride (0.012 g, 0.047 mmol). The reaction mixture was stirred at ambient temperature for about 20 hours followed by removal of THF in vacuo. The crude reaction mixture was purified by reverse phase chromatography (RP-HPLC (Rainin C18, 8 mm, 300 Å, 35 cm; 5-100% acetonitrile/0.1 M ammonium acetate over 20 min, 100% acetonitrile hold 10 minutes, 21 mL/min) to afford 2-(7-bromo-1H-indazol-5-ylamino)-2-methyl-propan-1-ol (0.033 g, 0.116 mmol). RP-HPLC (Table 1, Method e) R$_t$ 1.18 min; m/z: (M+H)$^+$ 286.1.

Preparation #52. (7-Benzo[b]thiophen-2-yl-1H-indazol-5-yl)-phenyl-methanone

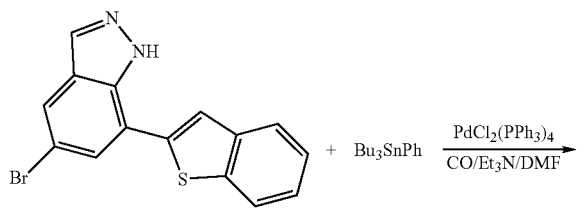

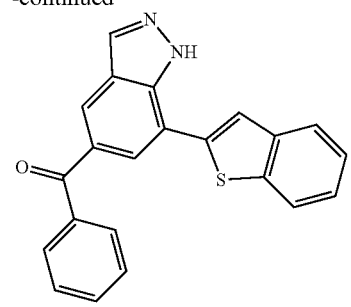

A mixture of 7-benzo[b]thiophen-2-yl-5-bromo-1H-indazole (Preparation #26, 0.25 g, 0.76 mol), tributylphenyltin (0.56 g, 1.52 mmol), triethylamine (0.23 g, 2.28 mmol) and trans-dichloro[bis(triphenylphosphine)]palladium (II) (0.08 g, 0.114 mmol) in N,N-dimethylformamide (4 mL) was purged with carbon monoxide then stirred under an atmosphere of carbon monoxide at about 90° C. in an oil bath for about 2 hours. The solvent was removed in vacuo and the residue was applied to a silica gel column then eluted with dichloromethane/methanol (95:5). The fractions that contained product were combined and triturated with heptane then the solids were collected by filtration and purified by preparative reverse phase HPLC to give (7-Benzo[b]thiophen-2-yl-1H-indazol-5-yl)-phenyl-methanone(23 mg, 8.5%); (DMSO-d$_6$, 400 MHz) δ 13.85 (bs, 1H), 8.49 (bs, 1H), 8.27 (s, 1H), 8.18 (bs, 1H), 8.06 (m, 2H), 7.93 (m, 1H), 7.81 (m, 2H), 7.71 (m, 1H), 7.61 (m, 2H), 7.45 (m, 2H); RP-HPLC (Table 1, Method e) Rt 2.50 min; m/z: (M+H)$^+$ 353.0.

Preparation #53. (7-Benzo[b]thiophen-2-yl-1H-indazol-3-yl)-pyridin-2-yl-methanone

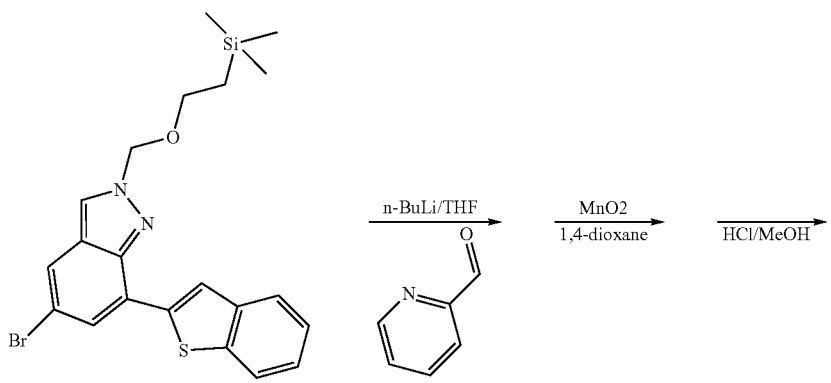

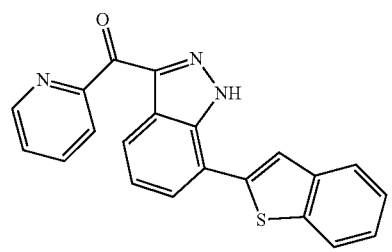

A mixture of 7-benzo[b]thiophen-2-yl-5-bromo-2-(2-trimethylsilanyl-ethoxymethyl)-2H-indazole (Preparation #23, 0.15 g, 0.326 mmol) in tetrahydrofuran (2 mL) was cooled to about −65° C. then a solution of n-butyllithium (1.6 M, 0.36 mL, 0.36 mmol) was added dropwise. After about 30 minutes, 2-pyridinecarboxaldehyde (0.042 g, 0.39 mmol) was added. The mixture was quenched with methanol (1 mL) then warmed to room temperature. The solvent was removed in vacuo and the residue was purified by preparative reverse phase HPLC chromatography (RP-HPLC (Rainin C18, 8 mm, 300 Å, 35 cm; 5-100% acetonitrile/0.1 M ammonium acetate over 20 min, 100% acetonitrile hold 10 minutes, 21 mL/min) to give the intermediate [7-benzo[b]thiophen-2-yl-2-(2-trimethylsilanyl-ethoxymethyl)-2H-indazol-3-yl-pyridin-2-yl-methanol (50 mg) which was suspended in a mixture of 1,4-dioxane (2 mL) and manganese dioxide (90 mg, 31%). The mixture was heated to about 90° C. for 15 minutes then filtered and evaporated. The residue was purified by reverse phase HPLC (RP-HPLC (Rainin C18, 8 mm, 300 Å, 35 cm; 5-100% acetonitrile/0.1 M ammonium acetate over 20 min, 100% acetonitrile hold 10 minutes, 21 mL/min) to give (7-Benzo[b]thiophen-2-yl-1H-indazol-3-yl)-pyridin-2-yl-methanone (22 mg, 44%); (DMSO-$d_6$, 400 MHz) δ 8.8 (bs, 1H), 8.31 (d, 1H), 8.09 (m, 4H), 7.93 (d, 1H), 7.78 (bs, 1H), 6.96 (bs, 1H), 7.51 (t, 1H), 7.43 (m, 2H); RP-HPLC (Table 1, Method e) Rt 2.60 min; m/z: (M−H)⁻ 353.8.

Starting with 7-benzo[b]thiophen-2-yl-5-bromo-1-(2-trimethylsilanyl-ethoxymethyl)-1H-indazole (Preparation #23, 0.2 g, 0.435 mmol) and using the procedure for the preparation of (7-benzo[b]thiophen-2-yl-1H-indazol-3-yl)-pyridin-2-yl-methanone (Preparation #52 above) provided (7-benzo[b]thiophen-2-yl-1H-indazol-5-yl)-pyridin-2-yl-methanone (17 mg, 11%); (DMSO-$d_6$, 400 MHz) δ 8.79 (d, 1H), 8.65 (s, 1H), 8.54 (s, 1H), 8.27 (s, 1H), 8.24 (s, 1H), 8.11 (m, 1H), 8.05 (m, 2H), 7.95 (m, 1H), 7.72 (m, 1H), 7.45 (m, 2H); RP-HPLC (Table 1, Method e) Rt 2.28 min; m/z: (M−H)⁻ 354.1.

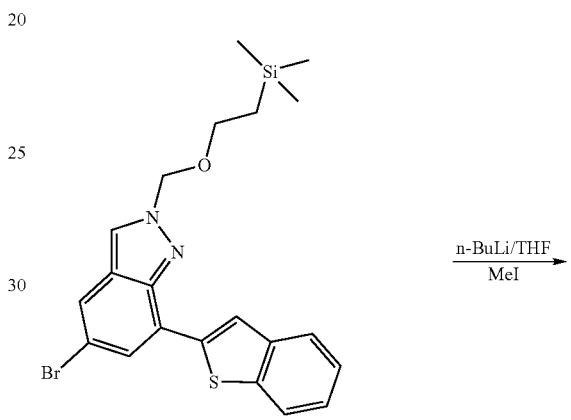

Preparation #54. (7-Benzo[b]thiophen-2-yl-1H-indazol-5-yl)-pyridin-2-yl-methanone

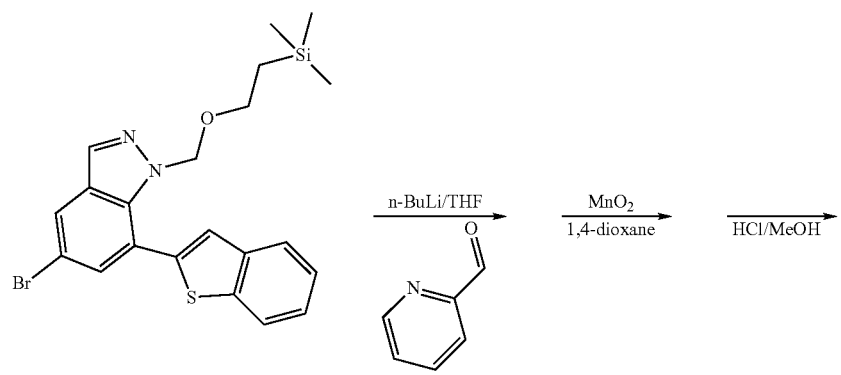

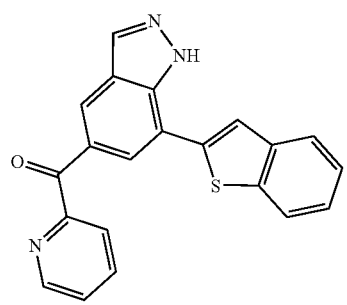

-continued
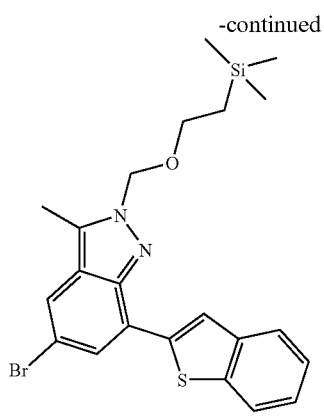
626
Preparation #55. 7-(7-Benzo[b]thiophen-2-yl-3-methyl-1H-indazol-5-yl)-5H-pyrrolo[3,2-d]pyrimidin-2-ylamine
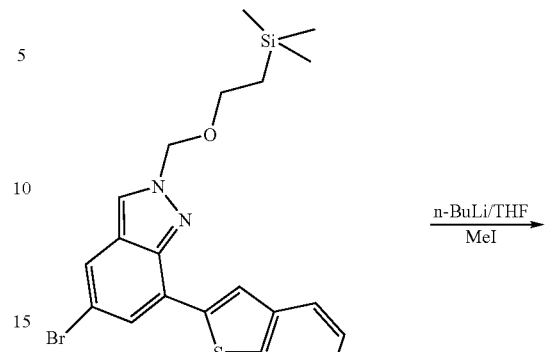
(general method E)
n-BuLi/THF
MeI
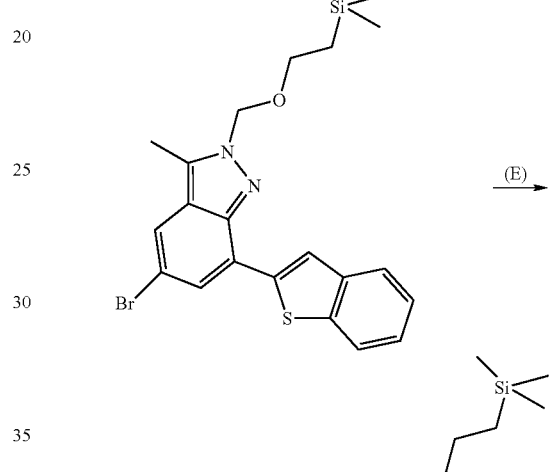
(E)
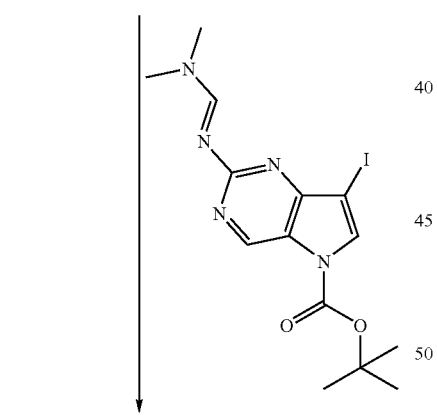
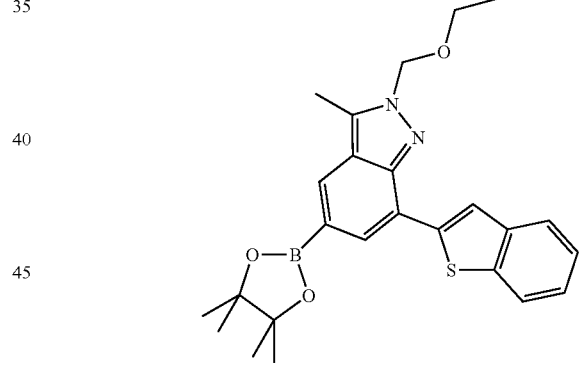
Preparation #4
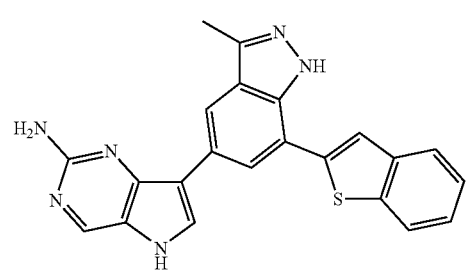

-continued

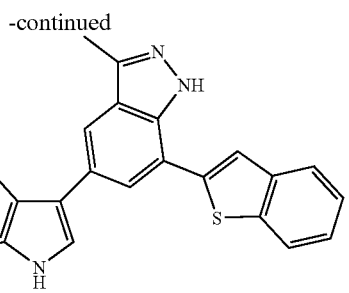

A mixture of 7-benzo[b]thiopen-2-yl-5-bromo-2-(2-trimethylsilanyl-ethoxymethyl)-2H-indazole (Preparation #24, 1.0 g, 2.18 mmol) in tetrahydrofuran (15 mL) was cooled to about −65° C. then a solution of n-butyllithium (1.6 M, 1.5 mL, 2.4 mmol) was added dropwise. After about 5 minutes methyliodide (0.37 g, 2.6 mmol) was added then the solution was warmed to about −20° C. Saturated ammonium chloride (1 mL) was added then the mixture was diluted with ethyl acetate (25 mL) and water (10 mL). The layers were separated then the organic layer was dried over magnesium sulfate, filtered and evaporated to give the crude 7-benzo[b]thiophen-2-yl-5-bromo-3-methyl-2-(2-trimethylsilanyl-ethoxymethyl)-2H-indazole which was converted to 7-benzo[b]thiophen-2-yl-3-methyl-5-(4,4,5,5-tetramethyl-[1,3,2]dioxaborolan-2-yl)-2-(2-trimethylsilanyl-ethoxymethyl)-2H-indazole (0.29 g, 25% over 2 steps) using general procedure E. The boronate (200 mg, 0.385 mmol) was coupled with 2-(dimethylamino-methyleneamino)-7-iodo-pyrrolo[3,2-d]pyrimidine-5-carboxylic acid tert-butyl ester (0.135 g, 0.32 mmol) using general procedure F and the resulting product deprotected using general procedure G to give 7-(7-benzo[b]thiophen-2-yl-3-methyl-1H-indazol-5-yl)-5H-pyrrolo[3,2-d]pyrimidin-2-ylamine (24 mg, 19%); (DMSO-$d_6$, 400 MHz) δ 12.48 (bs, 1H), 11.44 (s, 1H), 8.50 (m, 3H), 8.18 (d, 1H), 8.07 (bs, 1H), 8.02 (d, 1H), 7.90 (d, 1H), 7.43 (m, 2H), 5.94 (bs, 2H), 2.61 (s, 3H); RP-HPLC (Table 1, Method e) Rt 1.76 min; m/z: (M−H)⁻ 394.9.

What is claimed is:
1. A compound of Formula (I)

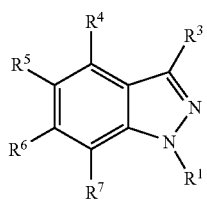

wherein
R¹ is selected from the group consisting of H, benzyl substituted with $OCH_3$, optionally substituted ($C_1$-$C_3$)alkyl, pyrimidine substituted with $NH_2$ and amino($C_1$-$C_3$) alkyl;
R³ is selected from the group consisting of H, halogen, $NH_2$, OH, COOH, —C(O)—NH—$CH_2$—C(O)—$OCH_3$, —NH—$CH_2$-phenyl, —C(O)-pyridinyl, —NH—C(O)-cyclobutyl and —NH—C(O)-phenyl wherein phenyl is optionally substituted with either $N(CH_3)_2$ or $OCH_3$; or
R³ is selected from the optionally substituted group consisting of ($C_1$-$C_6$)alkyl, benzo[b]thienyl, 2,3-dihydrobenzofuranyl, indolyl, isoquinolinyl, morpholinyl, naphthyl, phenyl, piperazinyl, pyrazolyl, pyridinyl, pyrimidinyl, pyrrolyl, quinolinyl and thienyl;
wherein the substituent is selected from one or more $CH_3$, $NH_2$, Cl, F, dimethylamino, OH, $CH_2OH$, —C(O)$NH_2$, COOH, $CF_3$, isopropyl, $OCF_3$, $OCH_3$, —O—$CH_2$-phenyl, CN, $OCH_2CH_3$, —NH—C(O)-cyclobutyl, —NH—C(O)-phenyl, NH—C(O)—$CH_3$, NHC(O)$CH_3$, $N(CH_3)_2$, $S(O)_2CH_3$ and C(O)NH-phenyl; or
R³ is —C(O)—$NY^{100}$—$(C(Y^{100})_2)_x$—$R^a$ wherein
x is 0, 1, 2 or 3;
$Y^{100}$ is independently H or ($C_1$-$C_3$)alkyl; and
$R^a$ is —C(O)—$CH_3$ or is selected from the optionally substituted group ($C_1$-$C_3$)alkyl, amino, aminoalkyl, benzimidazolyl, benzo[b]thienyl, benzotriazolyl, biphenyl, 1,3-dihydrobenzimidazolyl, 1,3-dihydrobenzimidazolyl-2-one, imidazolyl, indolyl, naphthyl, phenyl, pyrazolyl, pyridinyl, pyrimidinyl, tetrahydropyranyl and thiazolyl; or
R³ is A-B wherein A is connected to the indazole and
A is selected from the group consisting of —C≡C, —C≡C phenyl indazolyl, phenyl, pyridinyl and thienyl;
B is selected from the group consisting of benzyloxy, morpholinyl, phenyl, thienyl, t-butyl, —NH—C(O)-cyclobutyl and —NH—C(O)-phenyl;
R⁴ is H or $NH_2$;
R⁵ is selected from the optionally substituted group consisting of benzimidazolyl, 3,4-dihydrobenzo[1,4]thiazinyl, furo[3,2-c]pyridine, indazolyl, indolyl, isoquinolinyl, pyrazolo[3,4-d]pyrimidine, pyrrolo[2,3-b]pyridinyl, pyrrolo[2,3-c]pyridinyl, pyrrolo[2,3-d]pyridinyl, pyrrolo[3,2-d]pyridine, pyrrolo[2,3-d]pyrimidinyl, quinolinyl, quinazolinyl, thieno[2,3-c]pyridinyl, thieno[2,3-d]pyrimidine, thieno[3,2-c]pyridine, 7-azaindolinyl and 7-azaindolyl;
R⁶ is H or R⁶ is selected from the optionally substituted group consisting of ($C_1$)alkoxy, ($C_1$-$C_3$)alkyl, benzo[b]thienyl, NH pyrimidinyl —NH—$S(O)_2$-phenyl-NH-pyrimidinyl, —NH—C(O)-benzo[b]thienyl, pyrrolo[2,3-b]pyrimidinyl and pyridinyl; and
R⁷ is selected from optionally substituted group consisting of benzofuranyl, benzothiazolyl, benzo[b]thienyl, indolyl, isoquinolinyl, quinolinyl, quinoxalinyl, and thieno[2,3-b]pyridinyl; or
R⁷ is Y—Z wherein Y is attached to the indazole; and
Y is benzo[b]thienyl; and
Z is selected from the group consisting of phenyl, thienyl, $CH_2NHCH_2CH_2$-morpholinyl and substituted piperazinyl.

2. The compound of claim 1 wherein
R¹ is H or pyrimidinyl substituted with $NH_2$;
R³ is selected from the group consisting of H, $CH_3$, OH, Cl, benzo[b]thienyl, 2,3-dihydrobenzofuranyl, indolyl, naphthyl, phenyl, pyrazolyl, pyridinyl, pyrimidinyl, pyrrolyl, quinolinyl, thienyl, —NH—C(O)— cyclobutyl and —NH—C(O)-phenyl; wherein
the indolyl is optionally substituted with $CH_3$;
the naphthyl is optionally substituted with $OCH_3$ or OH; and
the phenyl optionally substituted with one or more substituents selected from the group consisting of $CH_3$, $NH_2$, Cl, F, $N(CH_3)_2$, OH, $CH_2OH$, $C(O)NH_2$, COOH, $CF_3$, $OCF_3$, $OCH_3$, CN, $OCH_2CH_3$, NHC(O)$CH_3$, —$S(O)_2CH_3$ and —C(O)—NH-pheny; or $R^3$ is —C(O)—NY$^{100}$—(C(Y$^{100}$)$_2$)$_x$—R$^a$ wherein
  x is 0 or 1;
  Y$^{100}$ is H;
  R$^a$ is selected from the optionally substituted group consisting of benzo[b]thienyl, benzimidazolyl, 1,3-dihydrobenzimidazolyl-2-one, benzotriazolyl, biphenyl, 1,3-dihydrobenzimidazolyl, indolyl, naphthyl and phenyl; wherein
    the naphthyl is substituted with OH or OCH$_3$;
    the phenyl is optionally substituted with one or more Cl, F, OH, CH$_2$OH, CH$_2$CH$_2$OH, COOH, C(O)NH$_2$, N(CH$_3$)$_2$ or methyl; or
$R^3$ is A-B wherein
  A is selected from the group consisting of —C≡C, —C≡C-phenyl, phenyl and thienyl; and
  B is selected from the group consisting of benzyloxy, phenyl, thienyl, —NH—C(O)-cyclobutyl and —NH—C(O)-phenyl;
$R^4$ is H;
$R^5$ is selected from the group consisting of

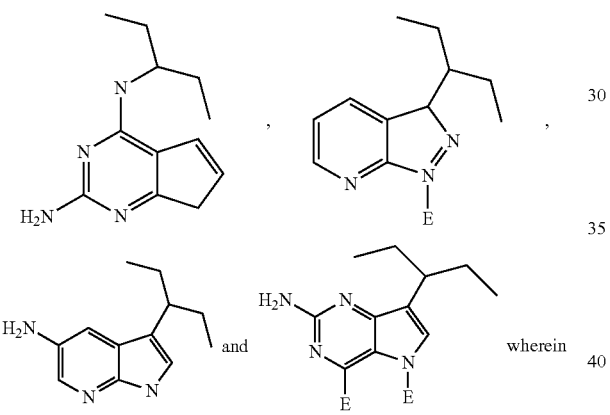

E is selected from the group consisting of H, OH, CH$_3$, —CH$_2$CH$_2$NH$_2$, CH$_2$CH$_2$CH$_2$OH, CH$_2$CH$_2$OCH$_3$, CH$_2$CH$_2$CH$_2$NH$_2$, CH$_2$C(O)OH, CH$_2$CH$_2$C(O)OH, CH$_2$CH$_2$C(O)NH$_2$, CH$_2$CH$_2$C(O)OCH$_3$, CH$_2$CH$_2$CH$_2$OCH$_3$, NHCH$_2$CH$_2$CH$_3$, CH$_2$CH$_2$C(O)NH(CH$_3$), CH$_2$CH$_2$C(O)N(CH$_3$)$_2$, C(O)NHCH$_2$CH$_2$NH(CH$_3$), NHCH$_2$CH$_2$OCH$_3$, NHCH$_2$CH$_2$OH, NHCH$_2$CH$_2$N(CH$_3$)$_2$, isopropyl, CH$_2$C(O)NH$_2$, CH$_2$CH(CH$_3$)C(O)OH, CH$_2$CH$_2$CH$_2$C(O)OH, CH$_2$CH(CH$_3$)C(O)OCH$_3$, CH$_2$CH$_2$CH$_2$CH$_2$NH$_2$, CH$_2$CH$_2$CH$_2$C(O)NH$_2$, N(CH$_3$)$_2$, morpholinylethyl, piperidinylethyl,

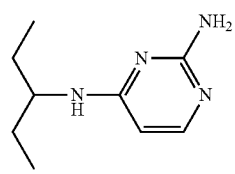

and 4-methylpiperazinylcyclohexyl;

$R^6$ is selected from the group consisting of H, pyrrolo[2,3-b]pyrimidinyl and

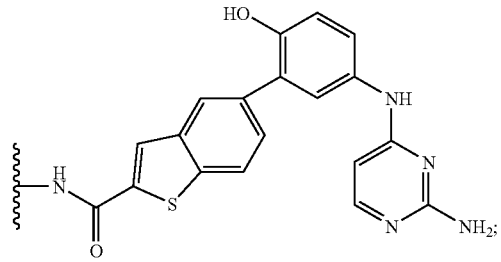

and
$R^7$ is selected from the optionally substituted group consisting of benzofuranyl, benzo[b]thienyl, indolyl, pyrrolyl, quinolinyl, quinoxalinyl, and thieno[2,3-b]pyridinyl, wherein
  the benzo[b]thienyl is optionally substituted with OH, CH$_3$, OCH$_3$, N(CH$_3$)$_2$, OH, CH$_2$=CHNHCH$_3$, CH$_2$NH$_2$, CH$_2$CH$_2$NH$_2$ or CH$_2$NHCH$_2$CH$_2$N(CH$_3$)$_2$; and
  the indolyl is substituted with C(O)N(CH(CH$_3$)$_2$)$_2$, CH$_2$OH, CH$_2$C(O)NH$_2$, COOH, C(O)NH$_2$, N(CH$_3$)$_2$ or S(O)$_2$CH$_3$;
$R^7$ is Y—Z wherein
  Y is benzo[b]thienyl; and
  Z is selected from the optionally substituted group consisting of CH=CHNHCH$_3$, NHCH$_3$, CH$_2$NH$_2$, CH$_2$CH$_2$NH$_2$, CH$_2$NHCH$_3$, CH$_2$NHCH$_2$CH$_2$N(CH$_3$)$_2$, N(CH$_3$)$_2$, CH$_2$NHCH$_2$CH$_2$-morpholinyl, benzo[b]thienyl, morpholinylmethyl, piperazinylmethylphenyl and thienyl.

3. The compound of claim 2 wherein
$R^1$ is H or pyrimidinyl substituted with NH$_2$;
$R^3$ is selected from the group consisting of H, CH$_3$, OH, Cl, benzo[b]thienyl, 2,3-dihydrobenzofuranyl, indolyl, naphthyl, phenyl, pyrazolyl, pyridinyl, pyrimidinyl, pyrrolyl, quinolinyl, thienyl, —NH—C(O)—cyclobutyl and —NH—C(O)-phenyl; wherein
  the indolyl is optionally substituted with CH$_3$;
  the naphthyl is optionally substituted with OH; and
  the phenyl optionally substituted with one or more substituents selected from the group consisting of OH, F, CH$_3$, CF$_3$, CN, —C(O)NH$_2$, NH$_2$, NHC(O)CH$_3$, OCH$_3$, OCF$_3$, OCH$_2$CH$_3$, N(CH$_3$)$_2$, —C(O)—NH-phenyl and —S(O)$_2$CH$_3$; or
$R^3$ is —C(O)—NY$^{100}$—(C(Y$^{100}$)$_2$)$_x$—R$^a$ wherein
  Y$^{100}$ is H;
  x is 0;
  R$^a$ is selected from the optionally substituted group consisting of benzimidazolyl, 1,3-dihydrobenzimidazolyl-2-one, benzotriazolyl, biphenyl, indolyl, naphthyl and phenyl; wherein
    the naphthyl is substituted with OH or OCH$_3$;
    the phenyl is optionally substituted with one or more Cl, F, OH, CH$_2$OH, CH$_2$CH$_2$OH, C(O)NH$_2$, N(CH$_3$)$_2$ or methyl; or
$R^3$ is A-B wherein
  A is selected from the group consisting of phenyl and thienyl; and
  B is selected from the group consisting of benzyloxy, phenyl, thienyl, —NH—C(O)-cyclobutyl and —NH—C(O)-phenyl;

631

R⁵ is selected from the group consisting of

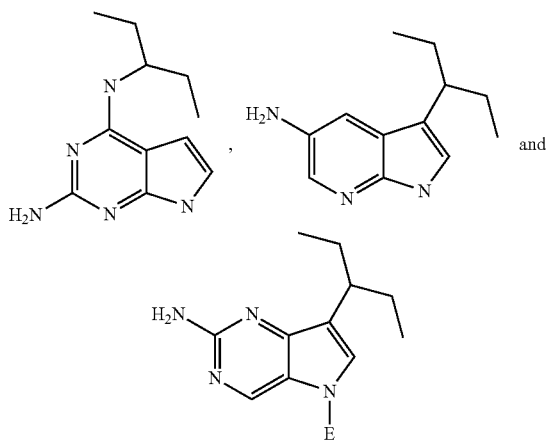

wherein

E is selected from the group consisting of H, CH₃, CH₂C(O)OH, CH₂CH₂CH₂OH, CH₂CH₂CH₂NH₂, CH₂CH₂C(O)OH, CH₂CH₂C(O)NH₂, CH₂CH₂C(O)OCH₃, CH₂CH₂CH₂OCH₃, NHCH₂CH₂CH₃, CH₂CH₂C(O)NH(CH₃), NHCH₂CH₂OCH₃, NHCH₂CH₂OH, isopropyl, CH₂C(O)NH₂, CH₂CH(CH₃)C(O)OH, morpholinylethyl, piperidinylethyl, CH₂CH₂CH₂C(O)OH, CH₂CH(CH₃)C(O)OCH₃, CH₂CH₂NH₂, CH₂CH₂CH₂CH₂NH₂, CH₂CH₂CH₂C(O)NH₂, CH₂CH₂C(O)N(CH₃)₂, and N(CH₃)₂;

R⁶ is H or

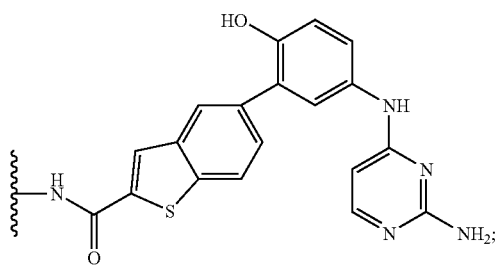

and

R⁷ is selected from the optionally substituted group consisting of benzofuranyl, benzo[b]thienyl, indolyl, quinolinyl, quinoxalinyl, and thieno[2,3-b]pyridinyl, wherein the benzo[b]thienyl is optionally substituted with OH, CH₃, OCH₃, N(CH₃)₂, CH₂=CHNHCH₃, CH₂NH₂, CH₂CH₂NH₂ or CH₂NHCH₂CH₂N(CH₃)₂; and the indolyl is substituted with methyl, CN, C(O)H, CH₂CH₂CH₂NH₂, CH₂NHCH₂CH=CH₂, C(O)CH₃, C(O)OCH₃, OCH₃, C(O)N(CH(CH₃)₂)₂, CH₂OH, CH₂C(O)NH₂, C(O)NH₂, CH₂NHCH₂CH₂N(CH₃)₂ or piperidinylmethyl; or R⁷ is Y—Z wherein Y is benzo[b]thienyl; and Z is selected from the optionally substituted group consisting of CH=CHNHCH₃, NHCH₃, CH₂NH₂, CH₂CH₂NH₂, CH₂NHCH₃, CH₂NHCH₂CH₂N(CH₃)₂, N(CH₃)₂, CH₂NHCH₂CH₂-morpholinyl, benzo[b]thienyl, morpholinylmethyl and piperazinylmethyl; wherein the piperazinyl is optionally substituted with methyl.

632

4. The compound of claim 3 wherein

R¹ and R⁴ are H;

R³ is selected from the optionally substituted group consisting of H, OH, 2,3-dihydrobenzofuranyl, naphthyl, pyrazolyl and pyrrolyl; wherein R³ is —C(O)—NY¹⁰⁰—(C(Y¹⁰⁰)₂)ₓ—Rᵃ wherein Y¹⁰⁰ is H;

x is 0;

Rᵃ is selected from the optionally substituted group consisting of naphthyl and phenyl; wherein the naphthyl is optionally substituted with OH;

the phenyl is optionally substituted with OH; or

R³ is selected from the group consisting of —NH—C(O)-cyclobutyl and —NH—C(O)-phenyl;

R³ is A-B wherein

A is selected from the group consisting of phenyl and thienyl; and

B is selected from the group consisting of benzyloxy, phenyl and thienyl;

R⁵ is

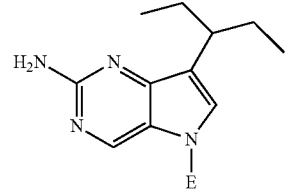

wherein

E is selected from the group consisting of H, CH₂C(O)NH₂, CH₂CH(CH₃)C(O)OCH₃, CH₂CH₂CH₂OH, CH₂CH₂C(O)OCH₃, CH₂CH₂CH₂OCH₃, CH₂CH₂NH₂, CH₂CH₂CH₂NH₂, CH₂CH₂C(O)OH, CH₂CH₂C(O)NH₂, CH₂CH₂CH₂CH₂NH₂, CH₂CH₂CH₂OCH₃, CH₂CH₂CH₂C(O)OH, CH₂CH₂CH₂C(O)NH₂, CH₂CH(CH₃)C(O)OH, CH₂CH₂C(O)NH(CH₃), CH₂CH₂C(O)N(CH₃)₂, N(CH₃)₂, isopropyl, morpholinylethyl and piperidinylethyl;

R⁶ is H or

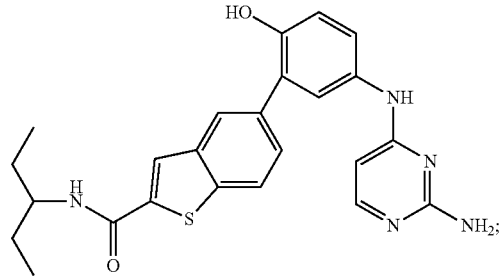

and

R⁷ is selected from the optionally substituted group consisting of benzofuranyl, benzo[b]thienyl, indolyl, and quinolinyl, wherein the benzo[b]thienyl is optionally substituted with OH, CH₃, OCH₃, N(CH₃)₂, CH₂=CH₂NHCH₃, CH₂NH₂, CH₂CH₂NH₂, CH₂NHCH₂CH₂N(CH₃)₂, piperidinylmethyl or CH₂NHCH₂N(CH₃)₂; and the indolyl is optionally substituted with methyl, CN, C(O)H, CH₂CH₂CH₂NH₂, CH₂NHCH₂CH=CH₂, C(O)CH₃, C(O)OCH₃, or OCH₃; methyl, CN, C(O)H, CH₂CH₂CH₂NH₂, CH₂NHCH₂CH=CH₂, C(O)CH₃, C(O)OCH₃, or OCH₃;

or

R⁷ is Y—Z wherein

Y is benzo[b]thienyl; and

Z is selected from the group consisting of CH=CHNHCH₃, NHCH₃, CH₂NH₂, CH₂CH₂NH₂, CH₂NHCH₃, CH₂NHCH₂CH₂N(CH₃)₂, N(CH₃)₂, CH₂NHCH₂CH₂-morpholinyl, benzo[b]thienyl, morpholinylmethyl and piperazinylmethyl;

wherein the piperazinyl is optionally substituted with methyl.

5. The compound of claim 4 wherein

R¹ and R⁴ are H;

R³ is selected from the group consisting of H, OH, 2,3-dihydrobenzofuranyl, pyrrolyl and optionally substituted napthyl; or R³ is —C(O)—NY¹⁰⁰—(C(Y¹⁰⁰)₂)ₓ—Rᵃ wherein Y¹⁰⁰ is H;

x is 0; and

Rᵃ is phenyl substituted with OH;

R⁵ is

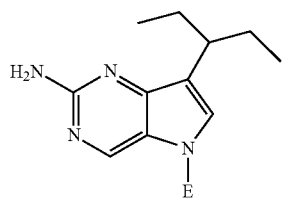

wherein

E is selected from the group consisting of H, CH₂C(O)NH₂, CH₂CH₂NH₂, CH₂CH₂CH₂NH₂, CH₂CH₂CH₂CH₂NH₂, CH₂CH₂CH₂OCH₃, CH₂CH₂CH₂OH, CH₂CH₂C(O)OH, CH₂CH₂CH₂C(O)OH, CH₂CH₂C(O)NH₂, CH₂CH₂CH₂C(O)NH₂, CH₂CH(CH₃)C(O)OCH₃, CH₂CH(CH₃)C(O)OH, CH₂CH₂C(O)OCH₃, CH₂CH₂C(O)NH(CH₃), CH₂CH₂C(O)N(CH₃)₂, N(CH₃)₂, isopropyl, morpholinylethyl and piperidinylethyl;

R⁶ is H or

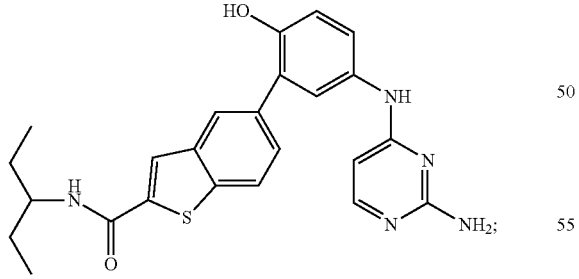

and

R⁷ is selected from the optionally substituted group consisting of benzofuranyl, benzo[b]thienyl, indolyl, and quinolinyl;

wherein the benzo[b]thienyl optionally substituted with OH, CH₃, OCH₃, CH₂=CH₃—NHCH₃, CH₂NH₂, CH₂CH₂NH₂, CH₂NHCH₂CH₂N(CH₃)₂, N(CH₃)₂ or piperidinylmethyl; and the indolyl is optionally substituted with methyl, CN, C(O)H, CH₂CH₂CH₂NH₂, CH₂NHCH₂CH=CH₂, C(O)CH₃, C(O)OCH₃, or OCH₃;

or

R⁷ is Y—Z wherein

Y is benzo[b]thienyl; and

Z is selected from the group consisting of CH₂NHCH₂CH₂-morpholinyl, morpholinylmethyl and piperazinylmethyl wherein the piperazinyl is optionally substituted with methyl.

6. The compound of claim 5 wherein

R¹, R³, R⁴ and R⁶ are H;

R⁵ is

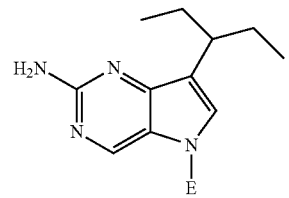

wherein

E is selected from the group consisting of H, —CH₂CH₂NH₂, CH₂CH₂CH₂NH₂, CH₂CH₂CH₂OH, CH₂CH₂C(O)OH and CH₂CH₂C(O)NH₂; and R⁷ is selected from the group consisting of benzo[b]thienyl, and indolyl, wherein the benzo[b]theinyl is optionally substituted by piperidinylmethyl; and the indolyl is optionally substituted by CN, methyl or C(O)H.

7. The compound of claim 6 wherein

R¹, R³, R⁴ and R⁶ are H;

R⁵ is

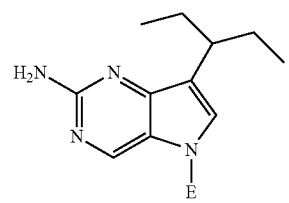

wherein

E is selected from the group consisting of H, —CH₂CH₂NH₂, CH₂CH₂CH₂NH₂, CH₂CH₂CH₂OH, CH₂CH₂C(O)OH and CH₂CH₂C(O)NH₂; and R⁷ is benzo[b]thienyl or indolyl wherein the benzo[b]theinyl is optionally substituted by piperidinylmethyl;

the indolyl is optionally substituted by CN, methyl or C(O)H.

8. The compound of claim 7 wherein R¹, R³, R⁴ and R⁶ are H;

$R^5$ is
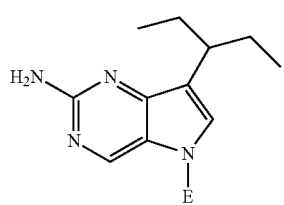
wherein
E is selected from the group consisting of —$CH_2CH_2NH_2$, $CH_2CH_2CH_2NH_2$, $CH_2CH_2CH_2OH$, $CH_2CH_2C(O)OH$ and $CH_2CH_2C(O)NH_2$; and
$R^7$ is benzo[b]thienyl.
* * * * *

UNITED STATES PATENT AND TRADEMARK OFFICE
CERTIFICATE OF CORRECTION

PATENT NO.       : 8,008,481 B2
APPLICATION NO.  : 11/731950
DATED            : August 30, 2011
INVENTOR(S)      : Ericsson et al.

It is certified that error appears in the above-identified patent and that said Letters Patent is hereby corrected as shown below:

Column 628, line 03, claim 1: "one or more" to read as --one or more of--

Column 628, line 23, claim 1: "—C≡C phenyl indazolyl," to read as -- —C≡C—phenyl, indazolyl,--

Column 628, line 41, claim 1: "NH pyrimidinyl" to read as -- —NH—pyrimidinyl,--

Column 628, line 67, claim 2: "—C(O)—NH—pheny" to read as -- —C(O)—NH—phenyl--

Column 629, line 12, claim 2: "one or more" to read as --one or more of--

Column 629, line 30, claim 2:

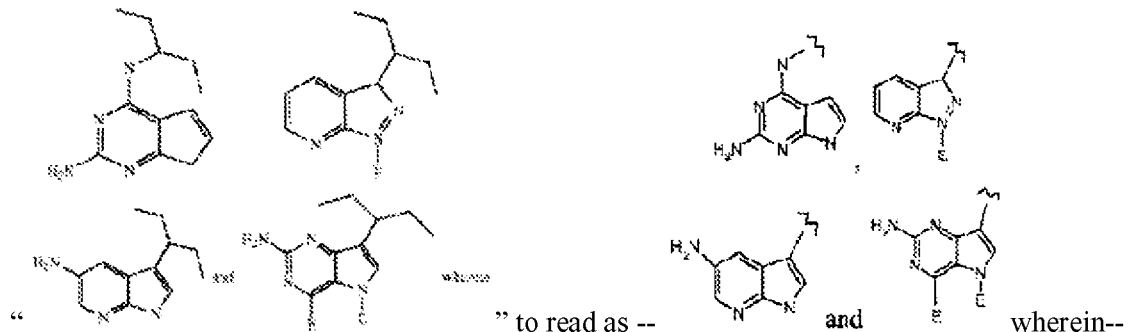

" to read as -- and wherein--

Column 629, line 60, claim 2:

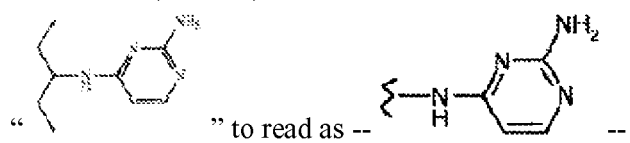

" to read as -- --

Signed and Sealed this
Seventeenth Day of July, 2012

David J. Kappos
*Director of the United States Patent and Trademark Office*

Column 630, line 28, claim 2: "S(O)₂CH₃;" to read as --S(O)₂CH₃; or--
Column 630, line 59, claim 3: "one or more" to read as --one or more of--
Column 631, line 05, claim 3:
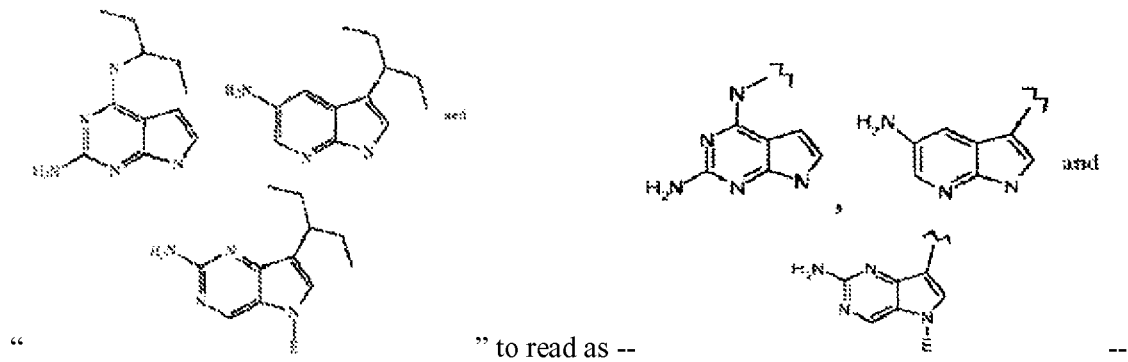
" to read as -- --
Column 632, line 25, claim 4:
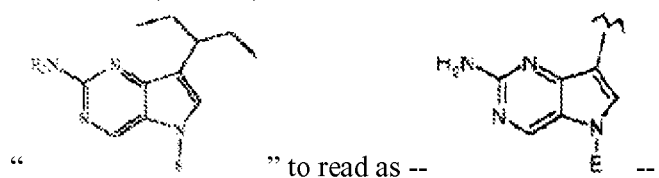
" to read as -- --
Column 632, line 50, claim 4:
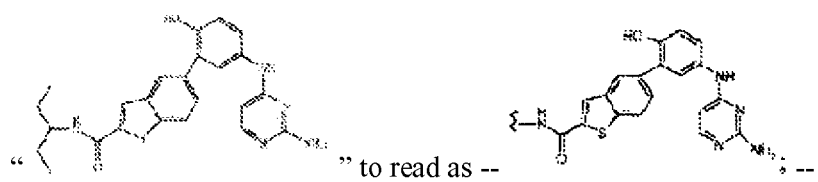
" to read as -- --
Column 633, line 18, claim 5: "napthyl;" to read as --naphthyl;--
Column 633, line 25, claim 5:
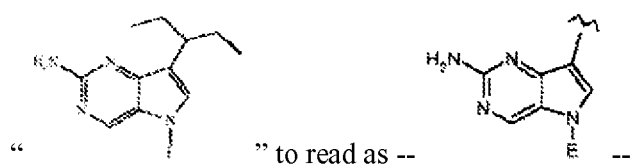
" to read as -- --
Column 633, line 40, claim 5: "CH₂CH(CH₃)C(O)OCH₃" to read as --CH₂CH(CH₃)C(O)OCH₃,--

CERTIFICATE OF CORRECTION (continued)
U.S. Pat. No. 8,008,481 B2

Column 633, line 50, claim 5:

" 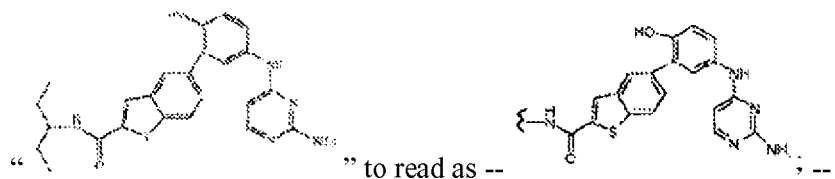 " to read as --  ; --

Column 634, line 20, claim 6:

" 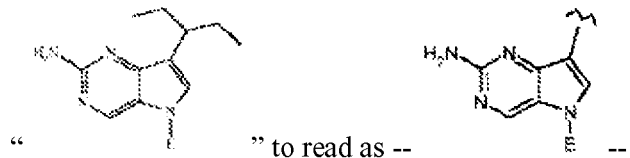 " to read as -- --

Column 634, line 45, claim 7:

" 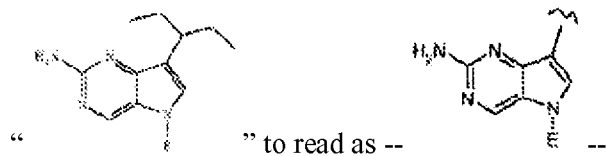 " to read as -- --

Column 635, line 05, claim 8:

" 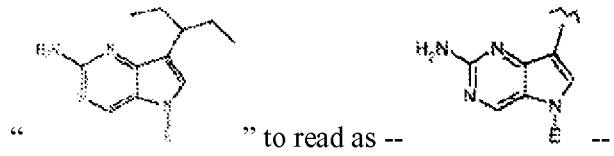 " to read as -- --